United States Patent
Satijn et al.

(10) Patent No.: US 11,970,544 B2
(45) Date of Patent: Apr. 30, 2024

(54) ANTIBODIES

(71) Applicant: GENMAB A/S, Valby (DK)

(72) Inventors: David Satijn, Utrecht (NL); Esther C. W. Breij, Utrecht (NL); Bart E. C. G. De Goeij, Utrecht (NL); Kristel Kemper, Utrecht (NL); Patrick Engelberts, Copenhagen V (DK); Edward N. Van Den Brink, Halfweg (NL); Rik Rademaker, Utrecht (NL); Dennis Verzijl, Amstelveen (NL); Sjeng Horbach, Oss (NL); Paul Parren, Odijk (NL)

(73) Assignee: GENMAB A/S, Valby (DK)

( * ) Notice: Subject to any disclaimer, the term of this patent is extended or adjusted under 35 U.S.C. 154(b) by 494 days.

(21) Appl. No.: 17/353,087

(22) Filed: Jun. 21, 2021

(65) Prior Publication Data

US 2022/0049013 A1 Feb. 17, 2022

Related U.S. Application Data

(60) Division of application No. 16/813,167, filed on Mar. 9, 2020, which is a continuation of application No. PCT/EP2019/056197, filed on Mar. 12, 2019.

(30) Foreign Application Priority Data

Mar. 12, 2018 (EP) ..................... 18161293
May 31, 2018 (EP) ..................... 18175347

(51) Int. Cl.
*C07K 16/30* (2006.01)
*A61P 35/00* (2006.01)
*C12N 15/79* (2006.01)
*A61K 39/00* (2006.01)

(52) U.S. Cl.
CPC .............. *C07K 16/30* (2013.01); *A61P 35/00* (2018.01); *C12N 15/79* (2013.01); *A61K 2039/505* (2013.01); *C07K 2317/31* (2013.01); *C07K 2317/51* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 9,150,663 B2 | 10/2015 | Labrijn et al. |
| 9,212,230 B2 | 12/2015 | Schuurman et al. |
| 10,344,050 B2 | 7/2019 | Gramer et al. |
| 10,407,501 B2 | 9/2019 | Van Den Brink et al. |
| 10,434,184 B2 | 10/2019 | Dengl et al. |
| 10,465,006 B2 | 11/2019 | Van Den Brink et al. |
| 10,590,206 B2 | 3/2020 | Labrijn et al. |
| 10,597,464 B2 | 3/2020 | Labrijn et al. |
| 10,906,991 B2 | 2/2021 | Schuurman et al. |
| 11,008,399 B2 | 5/2021 | Satijn et al. |
| 11,130,819 B2 | 9/2021 | Satijn et al. |
| 2006/0088522 A1 | 4/2006 | Boghaert et al. |
| 2010/0105874 A1 | 4/2010 | Schuurman et al. |
| 2013/0039913 A1 | 2/2013 | Labrijn et al. |
| 2014/0303356 A1 | 10/2014 | Gramer et al. |
| 2015/0337049 A1 | 11/2015 | Labrijn et al. |
| 2016/0046727 A1 | 2/2016 | Labrijn et al. |
| 2016/0159930 A1 | 6/2016 | Schuurman et al. |
| 2016/0168247 A1 | 6/2016 | Van Den Brink et al. |
| 2016/0333095 A1 | 11/2016 | Van Den Brink et al. |
| 2017/0233497 A1 | 8/2017 | Labrijn et al. |
| 2019/0284278 A1 | 9/2019 | Rademaker et al. |
| 2020/0048304 A1 | 2/2020 | Gramer et al. |
| 2020/0123255 A1 | 4/2020 | Van Den Brink et al. |
| 2020/0199229 A1 | 6/2020 | Van Den Brink et al. |
| 2020/0262932 A1 | 8/2020 | Labrijn et al. |
| 2020/0277397 A1 | 9/2020 | Satijn et al. |
| 2020/0332022 A1 | 10/2020 | Labrijn et al. |
| 2021/0070877 A1 | 3/2021 | Satijn et al. |
| 2021/0230296 A1 | 7/2021 | Satijn et al. |
| 2023/0257479 A1* | 8/2023 | Satijn ..................... A61P 35/00 424/133.1 |

FOREIGN PATENT DOCUMENTS

| | | |
|---|---|---|
| WO | 1998/55607 A2 | 12/1998 |
| WO | 2001/036486 A2 | 5/2001 |
| WO | 03038098 A2 | 5/2003 |
| WO | 2006/031653 A2 | 3/2006 |
| WO | 2007/106744 A2 | 9/2007 |
| WO | 2008/119353 A1 | 10/2008 |

(Continued)

OTHER PUBLICATIONS

Abdiche YN, et al. "Antibodies Targeting Closely Adjacent or Minimally Overlapping Epitopes Can Displace One Another," PLoS ONE, vol. 12(1): e0169535. doi:10.1371/journal.pone.0169535 (2017).
Abdiche, Y. et al., "Exploring blocking assays using Octet, ProteOn, and Biacore biosensors," Anal Biochem., vol. 386(2): 172-180 (2009).
Carsberg, C. et al., "Metastasis-associated 5T4 antigen disrupts cell-cell contacts and induces cellular motility in epithelial cells ," Int J Cancer, vol. 68: 84-92 (1996).
Damelin, M. et al., "Delineation of a cellular hierarchy in lung cancer reveals an oncofetal antigen expressed on tumor-initiating cells ," Cancer Res., vol. 71: 4236-4246 (2011).
Edwards, B. et al., "The Remarkable Flexibility of the Human Antibody Repertoire; Isolation of Over One Thousand Different Antibodies to a Single Protein, BLyS," J Mol Biol., vol. 334:103-118 (2003).

(Continued)

Primary Examiner — Jessica H Roark
(74) Attorney, Agent, or Firm — Nelson Mullins Riley & Scarborough LLP; Jane E. Remillard, Esq.; Christopher L. Frank

(57) ABSTRACT

The present invention relates to antibodies binding to 5T4, including bispecific antibodies binding to 5T4 and CD3. The invention further provides pharmaceutical compositions comprising the antibodies and use of the antibodies for therapeutic and diagnostic procedures, in particular in cancer therapy.

31 Claims, 30 Drawing Sheets

Specification includes a Sequence Listing.

(56) References Cited

FOREIGN PATENT DOCUMENTS

| WO | 2011048369 | A1 | 4/2011 |
|---|---|---|---|
| WO | 2011/131746 | A2 | 10/2011 |
| WO | 2011/147986 | A1 | 12/2011 |
| WO | 2013/041687 | A1 | 3/2013 |
| WO | 2013/060867 | A2 | 5/2013 |
| WO | 2014108483 | A1 | 7/2014 |
| WO | 2014/137931 | A1 | 9/2014 |
| WO | 2015/001085 | A1 | 1/2015 |
| WO | 2015/104346 | A1 | 7/2015 |
| WO | 2015/155345 | A1 | 10/2015 |
| WO | 2016/022939 | A1 | 2/2016 |
| WO | 2017/009442 | A1 | 1/2017 |
| WO | 2017/072207 | A1 | 5/2017 |
| WO | 2017/072208 | A1 | 5/2017 |
| WO | 2017/089447 | A1 | 6/2017 |
| WO | 2017/107973 | A1 | 6/2017 |
| WO | 2017/182672 | A1 | 10/2017 |
| WO | 2018/127175 | A1 | 7/2018 |
| WO | 2018/167486 | A1 | 9/2018 |
| WO | 2018/184558 | A1 | 10/2018 |
| WO | 2019/016402 | A1 | 1/2019 |
| WO | 2019/109047 | A1 | 6/2019 |
| WO | 2019/160904 | A1 | 8/2019 |

OTHER PUBLICATIONS

Eisen, T. et al., "Naptumomab estafenatox: targeted immunotherapy with a novel immunotoxin," Curr Oncol Rep., vol. 16:370 (2014).
Gershoni J. M et al., "Epitope mapping—The first step in developing epitope-based vaccines," Biodrugs, vol. 21(3):145-156 (2007).
Gramer, M. et al., "Production of stable bispecific IgG1 by controlled Fab-arm exchange: scalability from bench to large-scale manufacturing by application of standard approaches," MAbs, vol. 5: 962-973 (2013).
Kagermeier-Schenk, B. et al., "Waif1/5T4 inhibits Wnt/?-catenin signaling and activates noncanonical Wnt pathways by modifying LRP6 subcellular localization," Dev Cell, vol. 21:1129-1143 (2011).
Labrijn, A. et al., "Efficient generation of stable bispecific IgG1 by controlled Fab-arm exchange," PNAS, vol. 110:5145-5150 (2013).
Marchalonis, J. et al., "The antibody repertoire in evolution: Chance, selection, and continuity," Dev & Comp Immunol., vol. 30:223-247 (2006).
Scurr, M. et al., "Effect of Modified Vaccinia Ankara-5T4 and Low-Dose Cyclophosphamide on Antitumor Immunity in Metastatic Colorectal Cancer: A Randomized Clinical Trial," JAMA Oncol., vol. 12:10 (2017).
Shapiro, G. et al., "First-in-human trial of an anti-5T4 antibody-monomethylauristatin conjugate, PF-06263507, in patients with advanced solid tumors," Invest New Drugs, vol. 35:315-323 (2017).
Shaw, D. et al., "Glycosylation and epitope mapping of the 5T4 glycoprotein oncofoetal antigen," Biochem. J., vol. 363: 137-45 (2002).
Shields, R. et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., vol. 276(9):6591-6604 (2001).
Southall, P. J. et al., "Immunohistological distribution of 5T4 antigen in normal and malignant tissues," Br J Cancer, vol. 61: 89-95 (1990).
Stern, P. et al., "5T4 oncofoetal antigen: an attractive target for immune intervention in cancer," Cancer Immunol Immunother., vol. 66: 415-426 (2017).
Van Schouwenburg, P. et al., "Functional Analysis of the Anti-adalimumab Response Using Patient-derived Monoclonal Antibodies," J Biol Chem. vol. 289:34482-34488 (2014).
Zhao, Y. et al., "Structural insights into the inhibition of Wnt signaling by cancer antigen 5T4/Wnt-activated inhibitory factor 1," Structure, vol. 22:612-620 (2014).

* cited by examiner

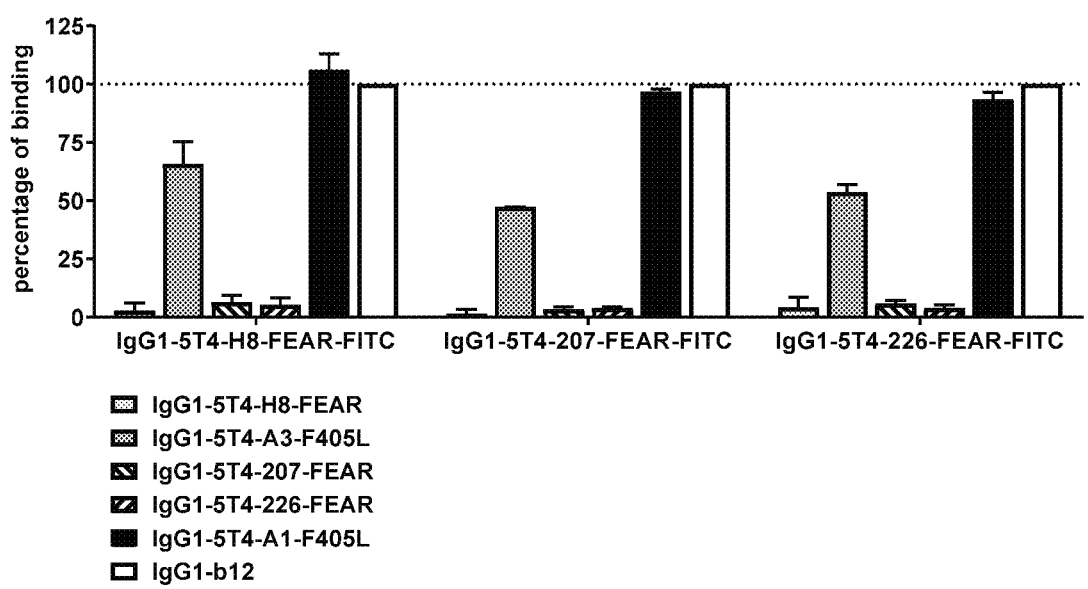

FIG. 6A
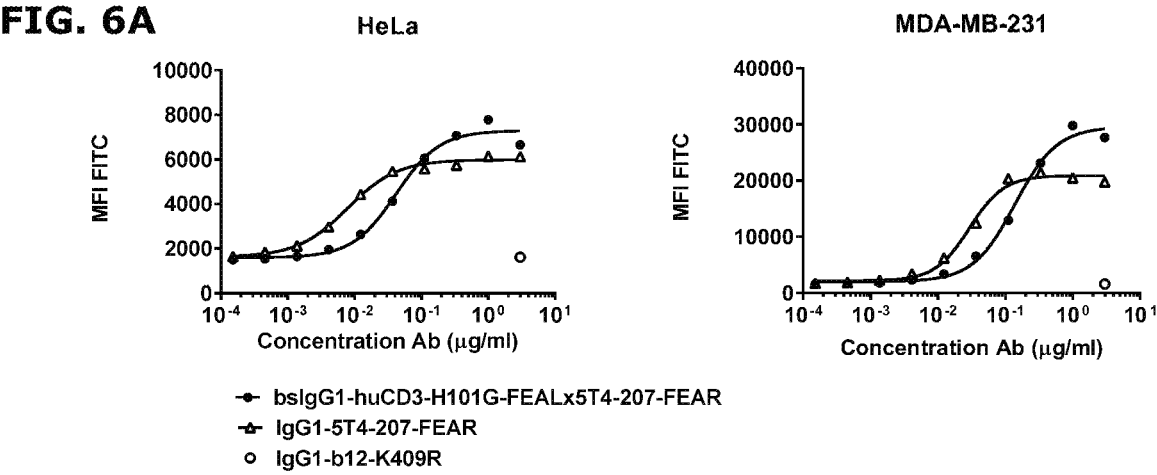
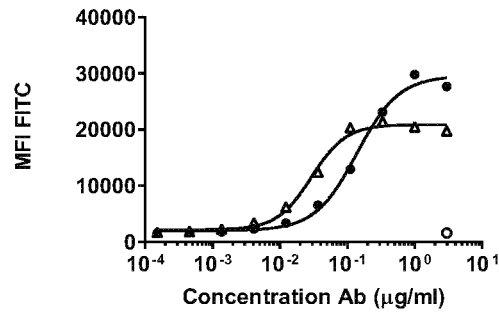
- bsIgG1-huCD3-H101G-FEALx5T4-207-FEAR
- IgG1-5T4-207-FEAR
- IgG1-b12-K409R
FIG. 6B
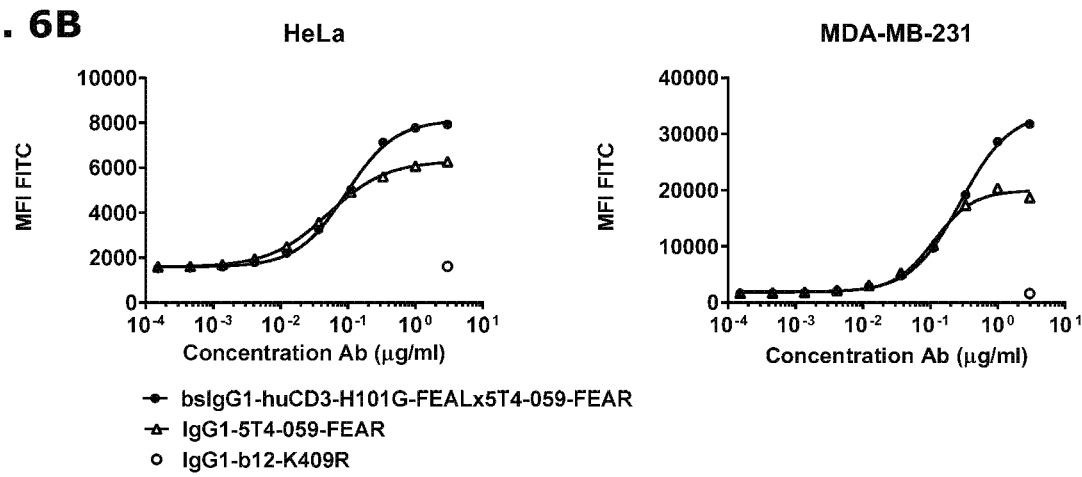
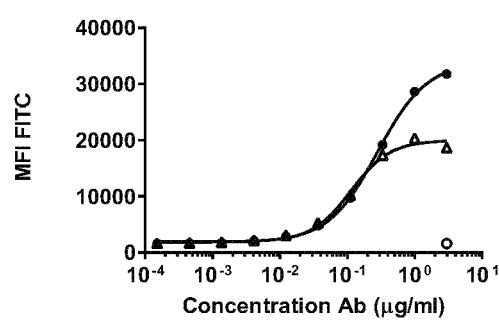
- bsIgG1-huCD3-H101G-FEALx5T4-059-FEAR
- IgG1-5T4-059-FEAR
- IgG1-b12-K409R
FIG. 6C
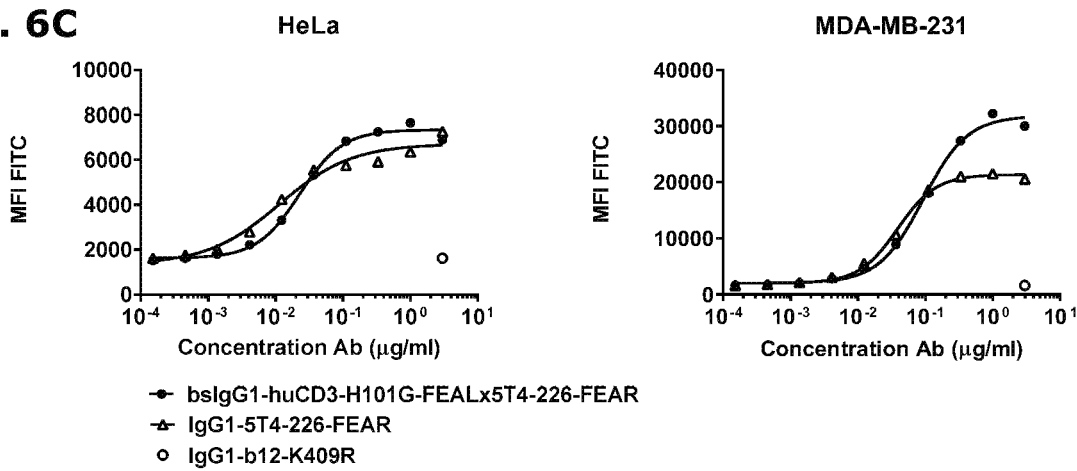
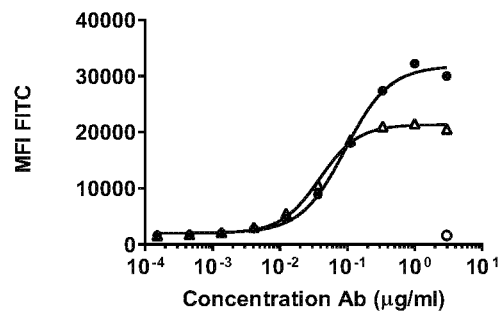
- bsIgG1-huCD3-H101G-FEALx5T4-226-FEAR
- IgG1-5T4-226-FEAR
- IgG1-b12-K409R

FIG. 7A
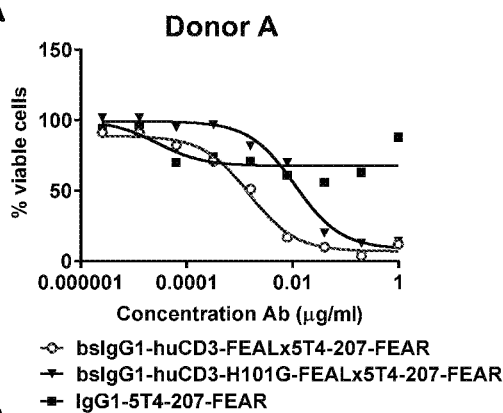
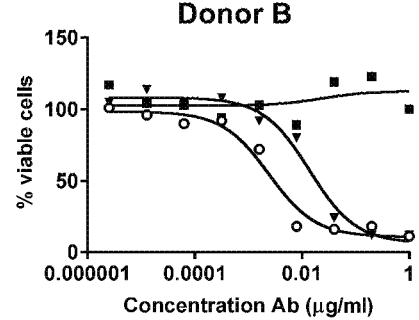
- bsIgG1-huCD3-FEALx5T4-207-FEAR
- bsIgG1-huCD3-H101G-FEALx5T4-207-FEAR
- IgG1-5T4-207-FEAR
FIG. 7B
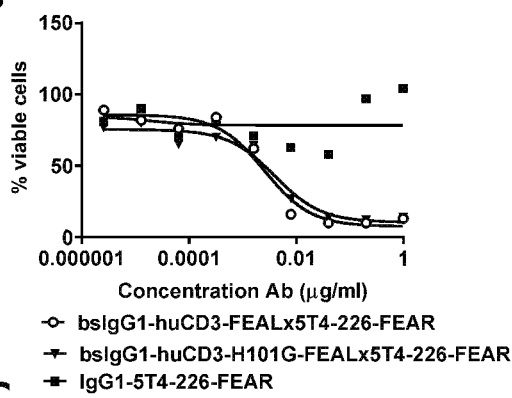
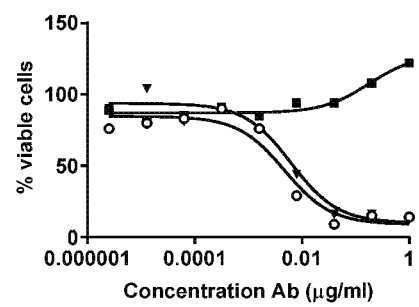
- bsIgG1-huCD3-FEALx5T4-226-FEAR
- bsIgG1-huCD3-H101G-FEALx5T4-226-FEAR
- IgG1-5T4-226-FEAR
FIG. 7C
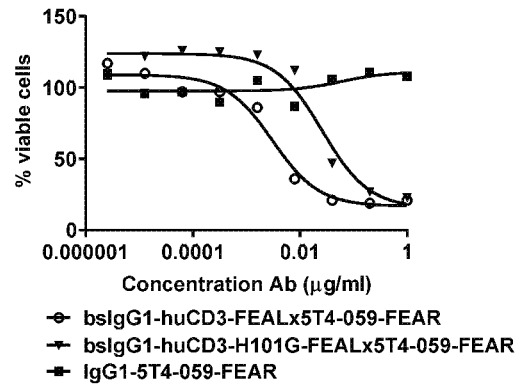
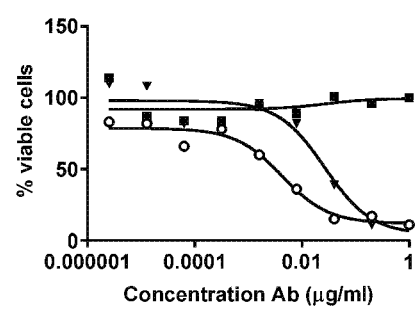
- bsIgG1-huCD3-FEALx5T4-059-FEAR
- bsIgG1-huCD3-H101G-FEALx5T4-059-FEAR
- IgG1-5T4-059-FEAR

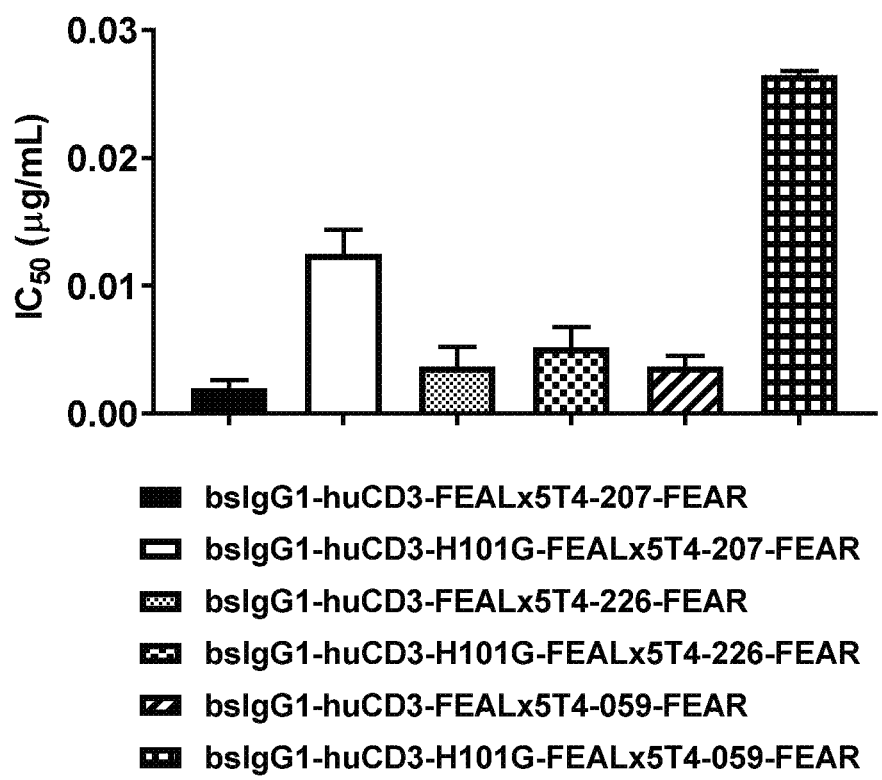

- BsIgG1-huCD3-FEALx5T4-207-FEAR
- BsIgG1-huCD3-H101G-FEALx5T4-207-FEAR
- IgG1-5T4-207-FEAR

- BsIgG1-huCD3-FEALx5T4-226-FEAR
- BsIgG1-huCD3-H101G-FEALx5T4-226-FEAR
- IgG1-5T4-226-FEAR

- BsIgG1-huCD3-FEALx5T4-059-FEAR
- BsIgG1-huCD3-H101G-FEALx5T4-059-FEAR
- IgG1-5T4-059-FEAR

- BsIgG1-huCD3-FEALx5T4-106-FEAR
- BsIgG1-huCD3-H101G-FEALx5T4-106-FEAR
- IgG1-5T4-106-FEAR

- BsIgG1-huCD3-FEALx5T4-A1-FEAR
- BsIgG1-huCD3-H101G-FEALx5T4-A1-FEAR
- IgG1-5T4-A1-FEAR

- BsIgG1-huCD3-FEALx5T4-A3-FEAR
- BsIgG1-huCD3-H101G-FEALx5T4-A3-FEAR
- IgG1-5T4-A3-FEAR

FIG. 10A
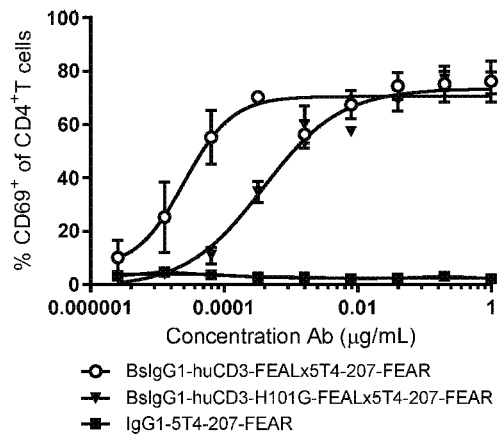
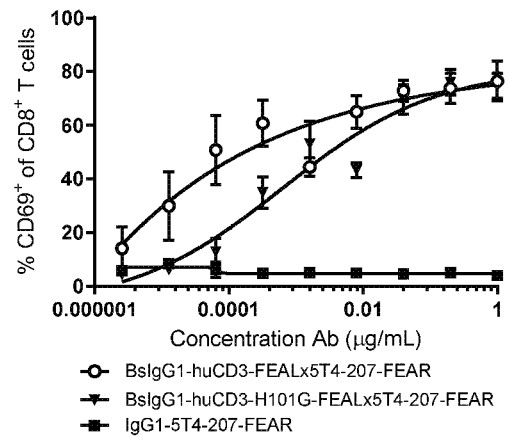
FIG. 10B
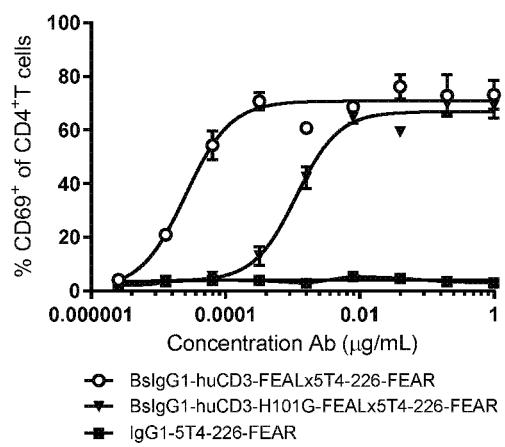
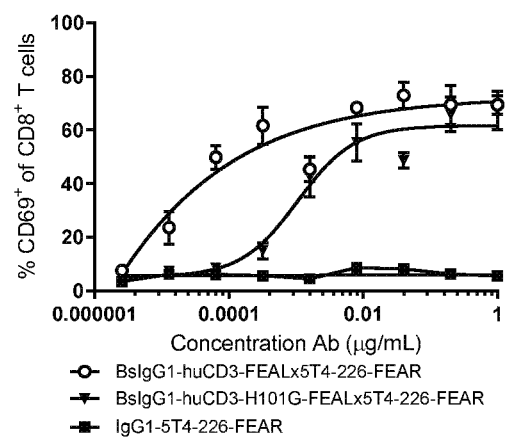
FIG. 10C
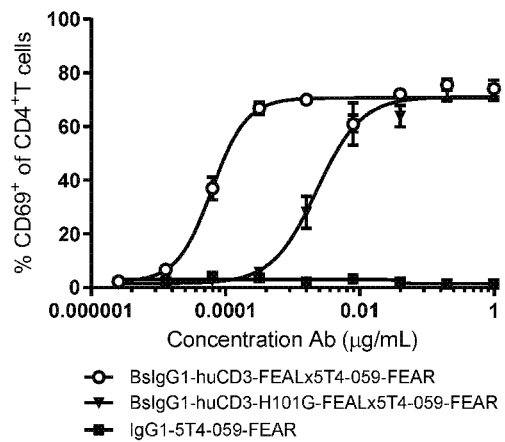
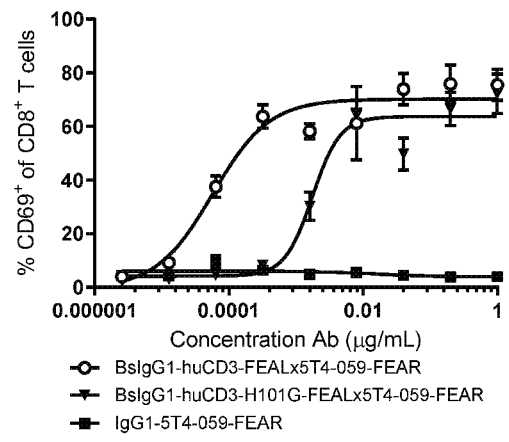

FIG. 10D
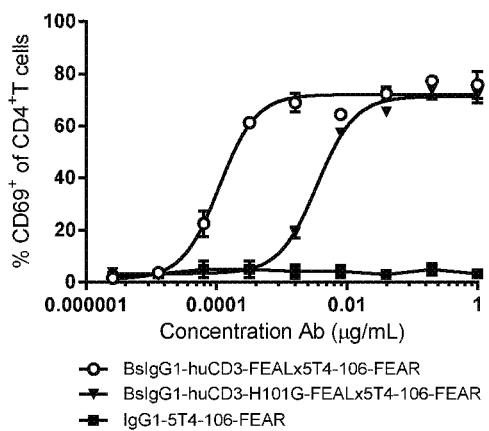 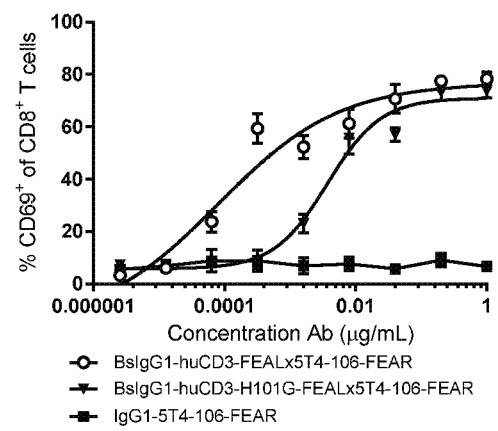
FIG. 10E
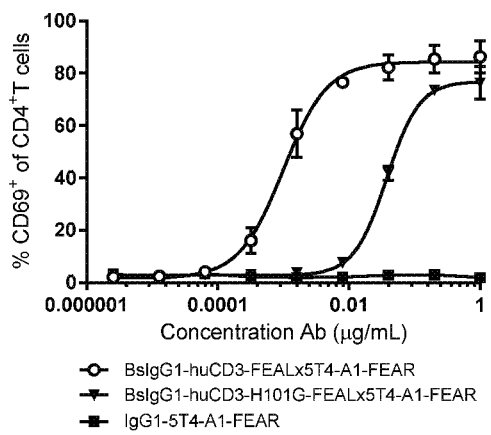 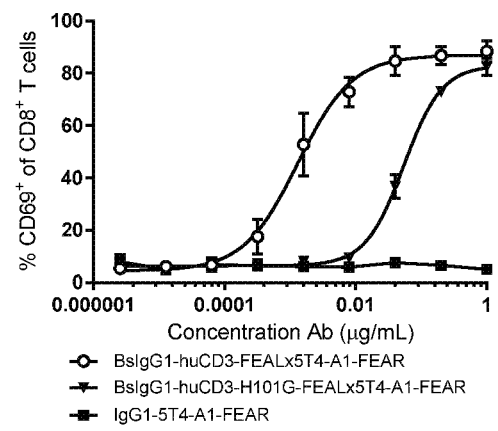
FIG. 10F
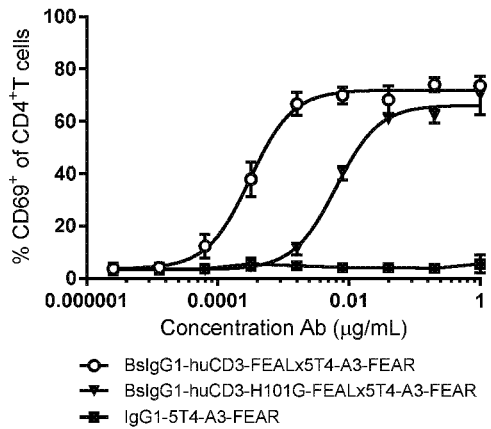 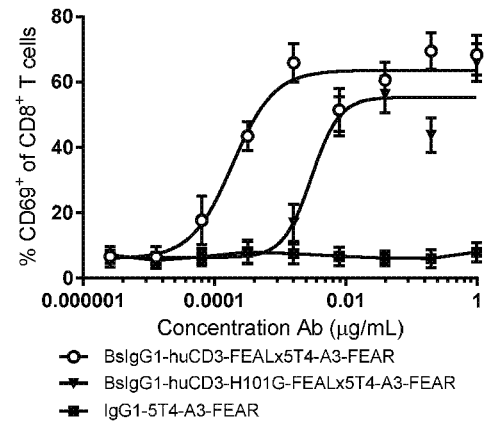

FIG. 13A
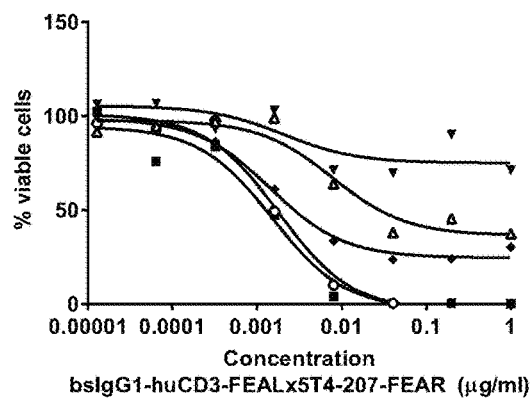
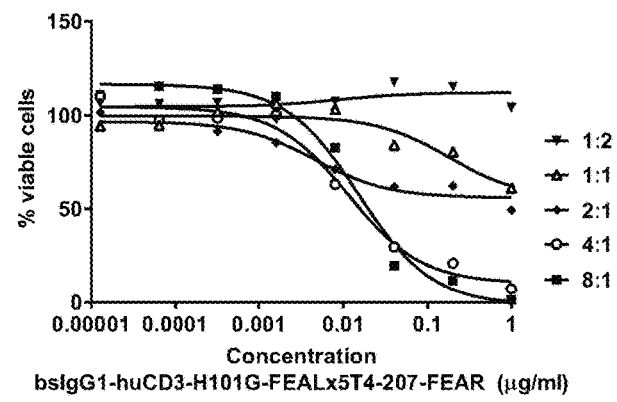
FIG. 13B
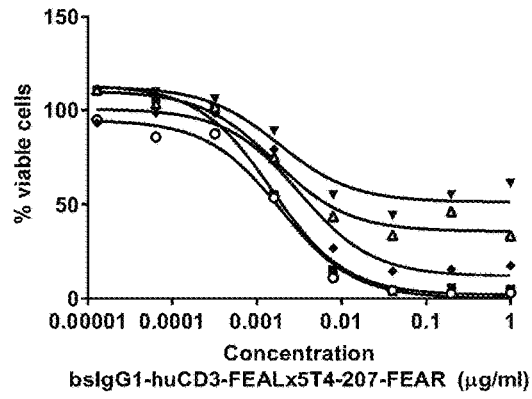
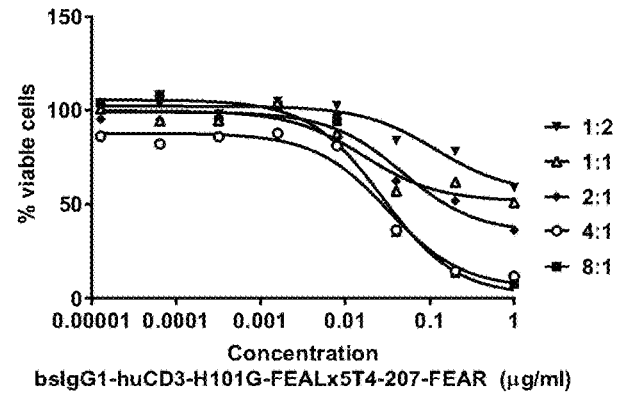

- ○- PBS
- △- 0.5 mg/kg bsIgG1-huCD3-FEALx5T4-207-FEAR
- ▲- 0.5 mg/kg bsIgG1-huCD3-H101G-FEALx5T4-207-FEAR
- ▽ Treatment under US 11,970,544 B2

ANTIBODIES

RELATED APPLICATIONS

This application is a divisional of U.S. patent application Ser. No. 16/813,167, filed Mar. 9, 2020, which is a continuation of International Application No. PCT/EP2019/056197, filed Mar. 12, 2019, which claims priority to European Patent Application Nos. 18161293.8 and 18175347.6, filed Mar. 12, 2018, and May 31, 2018, respectively. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 21, 2021, is named GMI_190PCCNCDV_Sequence_Listing.txt and is 90,400 bytes in size.

FIELD OF INVENTION

The present invention relates to antibodies binding to 5T4, including bispecific antibodies binding to 5T4 and CD3. The invention further provides pharmaceutical compositions comprising the antibodies and use of the antibodies for therapeutic and diagnostic procedures, in particular in cancer therapy.

BACKGROUND

5T4 (also known as trophoblast glycoprotein [TPBG] or Wnt-activated inhibitory factor 1 [WAIF1]) is a 72 kDa, single-pass transmembrane protein that contains 8 leucine-rich repeats (LRR) and 7 potential N-glycosylation sites (Zhao et al., 2014 Structure 22, 612-620).

5T4 expression is limited in normal adult tissues, except for placenta (Southall et al., 1990 Br J Cancer 61, 89-95). 5T4 is expressed in many human cancers, including renal, cervical, ovarian, lung, prostate and colon cancer (Stern and Harrop, 2017 Cancer Immunol Immunother 66, 415-426; Southall et al., 1990 Br J Cancer 61, 89-95). 5T4 expression in tumor cells drives tumor development by 1) facilitating epithelial-to-mesenchymal transition (Damelin et al., 2011 Cancer Res 71, 4236-4246; Carsberg et al., 1996 Int J Cancer 68, 84-92), and 2) inhibition of the canonical Wnt/beta-catenin signaling pathway and activation of the non-canonical Wnt pathway (Kagermeier-Schenk et al., 2011 Dev Cell 21, 1129-1143).

5T4-targeting antibodies and 5T4-targeting therapies have clinical activity in several cancers known to express 5T4 (including colorectal, lung and renal cancer). For example, naptumomab estafenatox is a recombinant fusion protein that consist of the 5T4-Fab moiety genetically fused to the engineered superantigen variant SEA/E-120. It is currently in clinical trials as an immunotherapy for non-small cell lung cancer (NSCLC), renal cell (RCC) and pancreatic cancer (see e.g. Eisen, et al., 2014 Curr Oncol Rep 16, 370). Furthermore, TroVax® is a modified vaccinia Ankara that expresses 5T4 constructs (MVA-5T4), which shows clinical benefit in colorectal, prostate and renal cancer (see e.g. Stern and Harrop, 2017 Cancer Immunol Immunother 66, 415-426; Scurr et al., 2017 JAMA Oncol 12, 10). Further anti-5T4 antibodies have been described in WO2007106744, WO03038098, WO2011048369, WO2013041687, WO2017072207.

While significant progress has been made on eradication of cancer, there is still a need for further improvement of antibody-based cancer therapy.

SUMMARY OF INVENTION

It is an object of the present invention to provide an antibody comprising at least one antigen-binding region capable of binding to 5T4 (Trophoblast glycoprotein), wherein the antibody is able to block binding to 5T4 of an antibody comprising a variable heavy chain (VH) region comprising the sequence set forth in SEQ ID NO: 5, and a variable light chain (VL) region comprising the sequence set forth in SEQ ID NO: 9 [059].

The antibody may in particular be a bispecific antibody and may further comprise an antigen binding region of an antibody that binds to CD3, such as human CD3ε (epsilon), such as human CD3ε (epsilon) as specified in SEQ ID NO: 4.

In another aspect, the present invention relates to a nucleic acid construct comprising
a) a nucleic acid sequence encoding a heavy chain sequence of an antibody comprising an antigen-binding region capable of binding to 5T4 as defined herein, and/or
b) a nucleic acid sequence encoding a light chain sequence of an antibody comprising an antigen-binding region capable of binding to 5T4 as defined herein.

In another aspect, the present invention relates to an expression vector comprising
a) a nucleic acid sequence encoding a heavy chain sequence of an antibody comprising an antigen-binding region capable of binding to 5T4 as defined herein, and/or
b) a nucleic acid sequence encoding a light chain sequence of an antibody comprising an antigen-binding region capable of binding to 5T4 as defined herein.

In another aspect, the present invention relates to a cell comprising a nucleic acid construct or an expression vector as defined herein.

In another aspect, the present invention relates to a composition comprising an antibody according to the invention.

In another aspect, the present invention relates to a pharmaceutical composition comprising an antibody as defined herein and a pharmaceutically acceptable carrier.

In another aspect, the present invention relates to an antibody as defined herein for use as a medicament, such as for use in the treatment of a disease.

In another aspect, the present invention relates to a method of treating a disease or disorder, the method comprising administering an antibody, a composition or pharmaceutical composition as defined herein, to a subject in need thereof.

In another aspect, the present invention relates to methods for producing an antibody as defined herein.

In another aspect, the present invention relates to a kit-of-parts, comprising an antibody as defined herein; and instructions for use of said kit.

In another aspect, the present invention relates to an anti-idiotypic antibody, which binds to the antigen-binding region capable of binding to 5T4 of the antibody as defined herein.

BRIEF DESCRIPTION OF FIGURES

FIGS. 1A-1C. IgG1-5T4-A3-F405L showed no binding to the immobilized IgG1-5T4-A3-F405L-5T4ECDHis complex, indicating cross-block (self-block) with IgG1-5T4-A3-F405L. IgG1-5T4-H8-FEAR antibodies showed an increase in mass (indicating binding to the immobilized IgG1-5T4-A3-F405L-5T4ECDHis complex) and hence no cross-block with IgG1-5T4-A3-F405L. FIG. 1A. IgG1-5T4-059-FEAR, FIG. 1B. IgG1-5T4-207-FEAR and FIG. 1C. IgG1-5T4-226-FEAR all showed an initial increase in mass (indicating binding of the antibodies to the immobilized IgG1-5T4-A3-F405L-5T4ECDHis complex) followed by a rapid decrease in mass. This behavior of the antibodies is indicative of antibody displacement (Abdiche Y N, et al. (2017) Antibodies Targeting Closely Adjacent or Minimally Overlapping Epitopes Can Displace One Another. PLoS ONE 12(1): e0169535. doi:10.1371/journal.pone.0169535).

FIG. 2: Simultaneous binding of 5T4 antibodies to membrane-bound 5T4 measured with flow cytometry. 5T4 antibodies IgG1-5T4-H8-FEAR, IgG1-5T4-207-FEAR and IgG1-5T4-226-FEAR were conjugated to fluorescein isothiocyanate (FITC) and added at a concentration of 2 µg/mL to 5T4-expressing SK-OV-3 cells in presence of 10 µg/mL unconjugated IgG1-5T4-H8-FEAR, IgG1-5T4-A1-F405L, IgG1-5T4-A3-F405L, IgG1-b12, IgG1-5T4-207-FEAR or IgG1-5T4-226-FEAR. Percentage binding of FITC-labeled antibodies was calculated and depicted as mean percentage binding±standard deviation (SD).

FIG. 5A. Binding of bsIgG1-huCD3-H101G-FEAL×5T4-207-FEAR and IgG1-5T4-207-FEAR. FIG. 5B. Binding of bsIgG1-huCD3-H101G-FEAL×5T4-226-FEAR and IgG1-5T4-226-FEAR. FIG. 5C. Binding of bsIgG1-huCD3-H101G-FEAL×5T4-059-FEAR and IgG1-5T4-059-FEAR. FIG. 5D. Binding of bsIgG1-huCD3-H101G-FEAL×5T4-H8-FEAR and IgG1-5T4-H8-FEAR.

FIG. 5E. Binding of bsIgG1-huCD3-H101G-FEAL×5T4-207-FEAR and IgG1-5T4-207-FEAR; FIG. 5F. Binding of bsIgG1-huCD3-H101G-FEAL×5T4-226-FEAR and IgG1-5T4-226-FEAR; FIG. 5G. Binding of bsIgG1-huCD3-H101G-FEAL×5T4-059-FEAR and IgG1-5T4-059-FEAR; FIG. 5H. Binding of bsIgG1-huCD3-H101G-FEAL×5T4-106-FEAR and IgG1-5T4-106-FEAR; FIG. 5I. Binding of bsIgG1-huCD3-H101G-FEAL×5T4-076-FEAR and IgG1-5T4-076-FEAR; FIG. 5J. Binding of bsIgG1-huCD3-H101G-FEAL×5T4-085-FEAR and IgG1-5T4-085-FEAR; FIG. 5K. Binding of bsIgG1-huCD3-H101G-FEAL×5T4-127-FEAR and IgG1-5T4-127-FEAR; FIG. 5L. Binding of bsIgG1-huCD3-H101G-FEAL×5T4-A1-FEAR and IgG1-5T4-A1-FEAR; FIG. 5M. Binding of bsIgG1-huCD3-H101G-FEAL×5T4-A3-FEAR and IgG1-5T4-A3-FEAR.

FIGS. 6A-6C: Binding of CD3×5T4 bispecific and 5T4 monospecific antibodies to 5T4-positive human tumor cells. Mono- and bivalent binding of 5T4 antibodies to HeLa cells (left panels) or MDA-MB-231 cells (right panels) was determined by flow cytometry. Cells were incubated with increasing concentrations of antibodies. After secondary labelling with FITC-conjugated goat-anti-human IgG F(ab')2, the MFI was determined by flow cytometry. FIG. 6A. Binding of bsIgG1-huCD3-H101G-FEAL×5T4-207-FEAR and IgG1-5T4-207-FEAR antibodies to HeLa cells (left panel) or MDA-MB-231 cells (right panel). FIG. 6B. Binding of bsIgG1-huCD3-H101G-FEAL×5T4-059-FEAR and IgG1-5T4-059-FEAR antibodies to HeLa cells (left panel) or MDA-MB-231 cells (right panel). FIG. 6C. Binding of bsIgG1-huCD3-H101G-FEAL×5T4-226-FEAR and IgG1-5T4-226-FEAR antibodies to HeLa cells (left panel) or MDA-MB-231 cells (right panel). IgG1-b12-K409R (3 µg/mL) was included as negative control (open circles).

FIG. 6D. Binding of bsIgG1-huCD3-H101G-FEAL×5T4-207-FEAR and IgG1-5T4-207-FEAR;

FIG. 6E. Binding of bsIgG1-huCD3-H101G-FEALx5T4-226-FEAR and IgG1-5T4-226-FEAR; FIG. 6F. Binding of bsIgG1-huCD3-H101G-FEALx5T4-059-FEAR and IgG1-5T4-059-FEAR; FIG. 6G. Binding of bsIgG1-huCD3-H101G-FEALx5T4-106-FEAR and IgG1-5T4-106-FEAR; FIG. 6H. Binding of bsIgG1-huCD3-H101G-FEALx5T4-085-FEAR and IgG1-5T4-085-FEAR; FIG. 6I. Binding of bsIgG1-huCD3-H101G-FEALx5T4-127-FEAR and IgG1-5T4-127-FEAR; FIG. 6J. Binding of bsIgG1-huCD3-H101G-FEALx5T4-A1-FEAR and IgG1-5T4-A1-FEAR; FIG. 6K. Binding of bsIgG1-huCD3-H101G-FEALx5T4-A3-FEAR and IgG1-5T4-A3-FEAR FIG. 6L. Binding of bsIgG1-huCD3-H101G-FEALx5T4-207-FEAR and IgG1-5T4-207-FEAR; FIG. 6M. Binding of bsIgG1-huCD3-H101G-FEALx5T4-226-FEAR and IgG1-5T4-226-FEAR; FIG. 6N. Binding of bsIgG1-huCD3-H101G-FEALx5T4-059-FEAR and IgG1-5T4-059-FEAR; FIG. 6O. Binding of bsIgG1-huCD3-H101G-FEALx5T4-106-FEAR and IgG1-5T4-106-FEAR; FIG. 6P. Binding of bsIgG1-huCD3-H101G-FEALx5T4-085-FEAR and IgG1-5T4-085-FEAR; FIG. 6Q. Binding of bsIgG1-huCD3-H101G-FEALx5T4-127-FEAR and IgG1-5T4-127-FEAR; FIG. 6R. Binding of bsIgG1-huCD3-H101G-FEALx5T4-A1-FEAR and IgG1-5T4-A1-FEAR; FIG. 6S. Binding of bsIgG1-huCD3-H101G-FEALx5T4-A3-FEAR and IgG1-5T4-A3-FEAR.

FIGS. 7A-7C: Induction of cytotoxicity in vitro by CD3x5T4 bispecific antibodies in MDA-MB-231 cells using purified T cells as effector cells. MDA-MB-231 cells were incubated with increasing concentrations of CD3x5T4 bispecific antibodies or monospecific, bivalent 5T4 antibodies and isolated T cells as effector cells in an Effector:Target cell (E:T) ratio of 8:1. Purified T cells obtained from two different donors were used for this experiment, donor A (left panels) and donor B (right panels). Cytotoxicity was determined by measuring the percentage of viable MDA-MB-231 cells after 72 hrs of incubation (% viable cells=[absorbance sample−absorbance staurosporine-treated target cells]/[absorbance untreated target cells−absorbance staurosporine-treated target cells]×100). FIG. 7A. Cytotoxicity induced in the presence of bsIgG1-huCD3-FEALx5T4-207-FEAR, bsIgG1-huCD3-H101G-FEALx5T4-207-FEAR and IgG1-5T4-207-FEAR; FIG. 7B. Cytotoxicity induced in the presence of bsIgG1-huCD3-FEALx5T4-226-FEAR, bsIgG1-huCD3-H101G-FEALx5T4-226-FEAR and IgG1-5T4-226-FEAR; FIG. 7C. Cytotoxicity induced in the presence of bsIgG1-huCD3-FEALx5T4-059-FEAR, bsIgG1-huCD3-H101G-FEALx5T4-059-FEAR and IgG1-5T4-059-FEAR.

FIG. 7D: IC50 values of cytotoxicity induced in vitro by CD3x5T4 bispecific antibodies in MDA-MB-231 cells using purified T cells as effector cells. IC50 values of the T-cell mediated cytotoxicity induced by bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR or bsIgG1-huCD3-H101G-FEALx5T4-059-FEAR in MDA-MB-231 cells were analyzed using GraphPad Prism V7.02 software. Data are presented as mean IC50 values of two different donors±SD.

FIG. 8A. T-cell-mediated cytotoxicity (decrease in survival) induced in the presence of bsIgG1-huCD3-FEALx5T4-207-FEAR, bsIgG1-huCD3-H101G-FEALx5T4-207-FEAR and IgG1-5T4-207-FEAR; FIG. 8B. T-cell-mediated cytotoxicity induced in the presence of bsIgG1-huCD3-FEALx5T4-226-FEAR, bsIgG1-huCD3-H101G-FEALx5T4-226-FEAR and IgG1-5T4-226-FEAR; FIG. 8C. T-cell-mediated cytotoxicity induced in the presence of bsIgG1-huCD3-FEALx5T4-059-FEAR, bsIgG1-huCD3-H101G-FEALx5T4-059-FEAR and IgG1-5T4-059-FEAR; FIG. 8D. T-cell-mediated cytotoxicity induced in the presence of bsIgG1-huCD3-FEALx5T4-106-FEAR, bsIgG1-huCD3-H101G-FEALx5T4-106-FEAR and IgG1-5T4-106-FEAR; FIG. 8E. T-cell-mediated cytotoxicity induced in the presence of bsIgG1-huCD3-FEALx5T4-A1-FEAR, bsIgG1-huCD3-H101G-FEALx5T4-A1-FEAR and IgG1-5T4-A1-FEAR; FIG. 8F. T-cell-mediated cytotoxicity induced in the presence of bsIgG1-huCD3-FEALx5T4-A3-FEAR, bsIgG1-huCD3-H101G-FEALx5T4-A3-FEAR and IgG1-5T4-A3-FEAR.

FIG. 8G. IC50 values of the T-cell-mediated cytotoxicity induced by bsIgG1-huCD3-FEALx5T4-207-FEAR, bsIgG1-huCD3-FEALx5T4-226-FEAR, bsIgG1-huCD3-FEALx5T4-059-FEAR, bsIgG1-huCD3-FEALx5T4-106-FEAR, bsIgG1-huCD3-FEALx5T4-A1-FEAR and bsIgG1-huCD3-FEALx5T4-A3-FEAR; FIG. 8H. IC50 values of the T-cell-mediated cytotoxicity induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, bsIgG1-huCD3-H101G-FEALx5T4-A1-FEAR and bsIgG1-huCD3-H101G-FEALx5T4-A3-FEAR.

FIG. 9A. T-cell activation induced in the presence of bsIgG1-huCD3-FEALx5T4-207-FEAR, bsIgG1-huCD3-H101G-FEALx5T4-207-FEAR and IgG1-5T4-207-FEAR; FIG. 9B. T-cell activation induced in the presence of bsIgG1-huCD3-FEALx5T4-226-FEAR, bsIgG1-huCD3-H101G-FEALx5T4-226-FEAR and IgG1-5T4-226-FEAR; FIG. 9C. T-cell activation induced in the presence of bsIgG1-huCD3-FEALx5T4-059-FEAR, bsIgG1-huCD3-H101G-FEALx5T4-059-FEAR and IgG1-5T4-059-FEAR.

FIGS. 10A-10F: In vitro T-cell activation by CD3×5T4 bispecific antibodies in the presence of MDA-MB-231 cells. MDA-MB-231 cells were incubated with increasing concentrations of CD3×5T4 bispecific antibodies and 5T4 homodimers and isolated T cells as effector cells in an E:T ratio of 8:1. T-cell activation was measured by an increase in % CD69+ cells within the CD4$^+$ (left panels) and CD8$^+$ (right panels) T cell populations. Three different donors were used for this experiment; data shown are mean % CD69 upregulation±SEM of three donors tested. FIG. 10A. T-cell activation induced in the presence of bsIgG1-huCD3-FEAL×5T4-207-FEAR, bsIgG1-huCD3-H101G-FEAL×5T4-207-FEAR and IgG1-5T4-207-FEAR; FIG. 10B. T-cell activation induced in the presence of bsIgG1-huCD3-FEAL×5T4-226-FEAR, bsIgG1-huCD3-H101G-FEAL×5T4-226-FEAR and IgG1-5T4-226-FEAR; FIG. 10C. T-cell activation induced in the presence of bsIgG1-huCD3-FEAL×5T4-059-FEAR, bsIgG1-huCD3-H101G-FEAL×5T4-059-FEAR and IgG1-5T4-059-FEAR; FIG. 10D. T-cell activation induced in the presence of bsIgG1-huCD3-FEAL×5T4-106-FEAR, bsIgG1-huCD3-H101G-FEAL×5T4-106-FEAR and IgG1-5T4-106-FEAR; FIG. 10E. T-cell activation induced in the presence of bsIgG1-huCD3-FEAL×5T4-A1-FEAR, bsIgG1-huCD3-H101G-FEAL×5T4-A1-FEAR and IgG1-5T4-A1-FEAR; FIG. 10F. T-cell activation induced in the presence of bsIgG1-huCD3-FEAL×5T4-A3-FEAR, bsIgG1-huCD3-H101G-FEAL×5T4-A3-FEAR and IgG1-5T4-A3-FEAR.

FIG. 10G. $EC_{50}$ values of the CD69 upregulation induced by bsIgG1-huCD3-FEAL×5T4-207-FEAR, bsIgG1-huCD3-FEAL×5T4-226-FEAR, bsIgG1-huCD3-FEAL×5T4-059-FEAR, bsIgG1-huCD3-FEAL×5T4-106-FEAR, bsIgG1-huCD3-FEAL×5T4-A1-FEAR and bsIgG1-huCD3-FEAL×5T4-A3-FEAR; FIG. 10H. $EC_{50}$ values of the CD69 upregulation induced by bsIgG1-huCD3-H101G-FEAL×5T4-207-FEAR, bsIgG1-huCD3-H101G-FEAL×5T4-226-FEAR, bsIgG1-huCD3-H101G-FEAL×5T4-059-FEAR, bsIgG1-huCD3-H101G-FEAL×5T4-106-FEAR, bsIgG1-huCD3-H101G-FEAL×5T4-A1-FEAR and bsIgG1-huCD3-H101G-FEAL×5T4-A3-FEAR. FIG. 10I. $EC_{50}$ values of the CD25 upregulation induced by bsIgG1-huCD3-FEAL×5T4-207-FEAR, bsIgG1-huCD3-FEAL×5T4-226-FEAR, bsIgG1-huCD3-FEAL×5T4-059-FEAR, bsIgG1-huCD3-FEAL×5T4-106-FEAR, bsIgG1-huCD3-FEAL×5T4-A1-FEAR and bsIgG1-huCD3-FEAL×5T4-A3-FEAR; FIG. 10J. $EC_{50}$ values of the CD25 upregulation induced by bsIgG1-huCD3-H101G-FEAL×5T4-207-FEAR, bsIgG1-huCD3-H101G-FEAL×5T4-226-FEAR, bsIgG1-huCD3-H101G-FEAL×5T4-059-FEAR, bsIgG1-huCD3-H101G-FEAL×5T4-106-FEAR, bsIgG1-huCD3-H101G-FEAL×5T4-A1-FEAR and bsIgG1-huCD3-H101G-FEAL×5T4-A3-FEAR. FIG. 10K. $EC_{50}$ values of the PD1 upregulation induced by bsIgG1-huCD3-FEAL×5T4-207-FEAR, bsIgG1-huCD3-FEAL×5T4-226-FEAR, bsIgG1-huCD3-FEAL×5T4-059-FEAR, bsIgG1-huCD3-FEAL×5T4-106-FEAR, bsIgG1-huCD3-FEAL×5T4-A1-FEAR and bsIgG1-huCD3-FEAL×5T4-A3-FEAR; FIG. 10L. $EC_{50}$ values of the PD1 upregulation induced by bsIgG1-huCD3-H101G-FEAL×5T4-207-FEAR, bsIgG1-huCD3-H101G-FEAL×5T4-226-FEAR, bsIgG1-huCD3-H101G-FEAL×5T4-059-FEAR, bsIgG1-huCD3-H101G-FEAL×5T4-106-FEAR, bsIgG1-huCD3-H101G-FEAL×5T4-A1-FEAR and bsIgG1-huCD3-H101G-FEAL×5T4-A3-FEAR.

FIG. 11A. Concentration of IL-10, IL-13 and TNF in the supernatant of T cell (derived from donor A)-tumor cell co-cultures, after 72 h of incubation with CD3×5T4 bispecific antibodies or 5T4 monospecific antibodies. FIG. 11B. Concentration of IL-10, IL-13 and TNF in the supernatant of T cell (derived from donor B)-tumor cell co-cultures, after 72 h of incubation with CD3×5T4 bispecific antibodies or 5T4 monospecific antibodies.

FIG. 12A. donor C and FIG. 12B. donor D.

FIGS. 13A and 13B: Induction of cytotoxicity in SK-OV-3 cells in vitro by CD3×5T4 bispecific antibodies using T cells as effector cells at varying E:T ratios. SK-OV-3 cells were incubated with increasing concentrations of bsIgG1-huCD3-FEAL×5T4-207-FEAR (left panels) or bsIgG1-huCD3-H101G-FEAL×5T4-207-FEAR (right panels) and isolated T cells as effector cells in an E:T ratio of 1:2, 1:1, 2:1, 4:1 and 8:1. The efficiency of cytotoxicity was determined by measuring the percentage of viable SK-OV-3 cells after 72 h of incubation (% viable cells=[absorbance sample−absorbance staurosporine-treated target cells]/[absorbance untreated target cells−absorbance staurosporine-treated target cells]×100). T cells from two different donors were used for this experiment: FIG. 13A. donor E and FIG. 13B. donor F.

FIG. 14A. Average tumor size in the MDA-MB-231 xenograft model in NSG-HIS mice after treatment with PBS (vehicle control), 0.5 mg/kg bsIgG1-huCD3-FEAL×5T4-207-FEAR or 0.5 mg/kg bsIgG1-huCD3-H101G-FEAL×5T4-207-FEAR. Tumor size was assessed by caliper measurement. Error bars indicate SEM. FIG. 14B. Percentage of NSG-HIS mice injected with MDA-MB-231 cells with a tumor size <500 mm$^3$ after treatment with PBS, bsIgG1-huCD3-FEAL×5T4-207-FEAR or bsIgG1-huCD3-H101G-FEAL×5T4-207-FEAR.

FIG. 16A. Cytotoxicity (decrease in survival) induced in pancreas cancer cell lines; FIG. 16B. Cytotoxicity (decrease in survival) induced in cervical cancer cell lines.

FIG. 17A. T-cell activation induced by CD3×5T4 bispecific antibodies in the presence of pancreas cancer cell line BxPc-3; FIG. 17B. T-cell activation induced by CD3×5T4 bispecific antibodies in the presence of pancreas cancer cell line PANC-1; FIG. 17C. T-cell activation induced by CD3×5T4 bispecific antibodies in the presence of cervical cancer cell line SiHa; FIG. 17D. T-cell activation induced by CD3×5T4 bispecific antibodies in the presence of cervical cancer cell line Ca Ski.

FIG. 17E. EC50 values of CD4+ T-cell activation induced by bsIgG1-huCD3-H101G-FEAL×5T4-207-FEAR in the presence of the indicated tumor cell lines; FIG. 17F. EC50 values of CD8+ T-cell activation induced by bsIgG1-huCD3-H101G-FEAL×5T4-207-FEAR in the presence of the indicated tumor cell lines.

DETAILED DESCRIPTION

Definitions

Figure 1A:
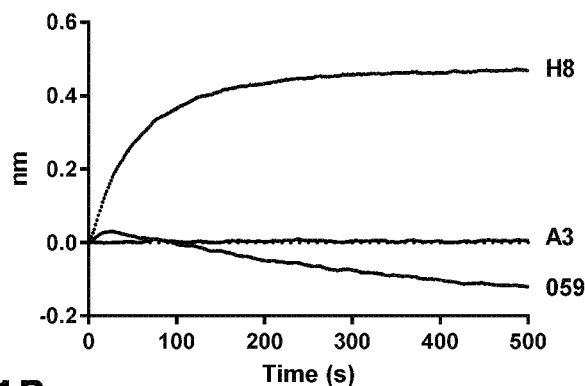
FIGS. 1A-1C: Antibody displacement of IgG1-5T4-059-FEAR, IgG1-5T4-207-FEAR and IgG1-5T4-226-FEAR in combination with IgG1-5T4-A3-F405L. Antibody displacement was determined by biolayer interferometry on an Octet HTX instrument (ForteBio). IgG1-5T4-A3-F405L was immobilized on the biosensor and loaded with human 5T4ECDHis (mature protein of SEQ ID NO. 99). Subsequently, the loaded biosensors were exposed to IgG1-5T4-A3-F405L, IgG1-5T4-H8-FEAR, IgG1-5T4-059-FEAR, IgG1-5T4-207-FEAR or IgG1-5T4-226-FEAR. The figure shows the association responses (500 s) upon exposure to the second antibodies.

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, at least about 24 hours or more, at least about 48 hours or more, at least about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to be internalized). The binding region (or binding domain which may be used herein, both having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells) and components of the complement system such as C1q, the first component in the classical pathway of complement activation.

In the context of the present invention, the term "antibody" includes a monoclonal antibody (mAb), an antibodylike polypeptide, such as a chimeric antibody and a humanized antibody, as well as an 'antibody fragment' or a 'fragment thereof' retaining the ability to specifically bind to the antigen (antigen-binding fragment) provided by any known technique, such as enzymatic cleavage, peptide synthesis, and recombinant techniques, and retaining the ability to be conjugated to a toxin. An antibody as defined according to the invention can possess any isotype unless the disclosure herein is otherwise limited.

As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the light chain variable domain (VL), heavy chain variable domain (VH), light chain constant region (CL) and heavy chain constant region domain 1 (CH1) domains, or a monovalent antibody as described in WO 2007/059782; (ii) F(ab')$_2$ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment Ward et al., Nature 341, 544-546 (1989), which consists essentially of a VH domain and is also called domain antibody Holt et al; Trends Biotechnol. 2003 November; 21(11):484-90; (vi) camelid or nanobodies Revets et al; Expert Opin Biol Ther. 2005 January; 5(1):111-24 and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Revets et al; Expert Opin Biol Ther. 2005 January; 5(1):111-24 and Bird et al., Science 242, 423-426 (1988). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein.

An antibody can be produced in and collected from different in vitro or ex vivo expression or production systems, for example from recombinantly modified host cells, from hybridomas or systems that use cellular extracts supporting in vitro transcription and/or translation of nucleic acid sequences encoding the antibody. It is to be understood that a multitude of different antibodies, the antibodies being as defined in the context of the present invention, is one that can be provided by producing each antibody separately in a production system as mentioned above and thereafter mixing the antibodies, or by producing several antibodies in the same production system.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences are defined according to IMGT (see Lefranc M P. et al., Nucleic Acids Research, 27, 209-212, 1999] and Brochet X. Nucl. Acids Res. 36, W503-508 (2008)).

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by half-molecule exchange, as well as recombining at nucleic acid level and/or through co-expression of two half-molecules in the same cells.

The term "antigen-binding region" or "binding region" as used herein, refers to a region of an antibody which is capable of binding to the antigen. The antigen can be any molecule, such as a polypeptide, e.g. present on a cell, bacterium, or virion. The terms "antigen" and "target" may, unless contradicted by the context, be used interchangeably in the context of the present invention. The terms "antigen-binding region" and "antigen-binding site" may, unless contradicted by the context, be used interchangeably in the context of the present invention.

The term "blocks binding" or "blocking the binding of an antibody" or "cross-blocking binding" or "cross-blocks binding" refers to the situation where one antibody bound to a specific antigen prevents binding of the second antibody to the same antigen and vice versa. In the absence of the other antibody, each antibody has the ability to bind to the antigen as determined by a significant binding response, whereas one of the antibodies lacks a binding response when the other antibody is present. The ability of one antibody to block the binding of another antibody may be determined by biolayer interferometry in a classical sandwich epitope binning assay format, for instance as described in Example 3 in the present application and by Abdiche et al. (Abdiche Y N, Malashock D S, Pinkerton A, Pons J. Exploring blocking assays using Octet, ProteOn, and Biacore biosensors. Anal Biochem. 2009; 386(2): 172-180). Briefly, in a sandwich epitope binning assay, an antibody in solution is tested for binding to its specific antigen that is first captured via an immobilized antibody. In the context of the present invention, one antibody does not block the binding of another antibody if it is capable of "displacing" the other antibody, according to the definition of "displacement" below. The terms "blocks binding" and "blocking the binding of an antibody" and "cross-blocking binding" and "cross-blocks binding" may, unless contradicted by the context, be used interchangeably in the context of the present invention. Preferably, the ability of one antibody to block the binding of another antibody is determined using full-length antibodies.

The term "displacement" or "ability to displace" or "displacing" refers to the situation wherein two antibodies perturb one another's binding to an antigen by kinetically altering one another's binding to their specific antigen via the formation of a transient trimolecular complex, which rapidly collapses by retaining one antibody to the antigen and displacing the other. Antibody displacement is defined in Abdiche et al., 2017 (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi: 10.1371/journal.pone.0169535). Antibody displacement may be determined by biolayer interferometry using real-time label-free biosensors in a classical sandwich assay format as described in Abdiche et al. 2017 and Example 4 in the present application. Preferably, antibody displacement is determined using antibodies which are in the IgG format.

The term "binding" as used herein refers to the binding of an antibody to a predetermined antigen or target, typically with a binding affinity corresponding to a $K_D$ of $1E^{-6}$ M or less, e.g. $5E^{-7}$ M or less, $1E^{-7}$ M or less, such as $5E^{-8}$ M or less, such as $1E^{-8}$ M or less, such as $5E^{-9}$ M or less, or such as $1E^{-9}$ M or less, when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "$K_D$" (M), as used herein, refers to the dissociation equilibrium constant of a particular antibody-antigen interaction, and is obtained by dividing $k_d$ by $k_a$.

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "5T4" as used herein, refers to the protein entitled 5T4, which is also referred to as trophoblast glycoprotein, 5T4 oncofetal antigen, 5T4 oncofetal trophoblast glycoprotein, TPBG, WAIF1 and M6P1. It is 72-80 kDa transmembrane protein with an extensively N-linked glycosylated core. In humans (*Homo sapiens*), the 5T4 protein has the amino acid sequence shown in SEQ ID NO: 1 (Human Trophoblast glycoprotein: Uniprot accession no. Q13641). In the amino acid sequence shown in SEQ ID NO: 1, amino acid residues 1-31 are a signal peptide, and amino acid residues 32-420 are the mature polypeptide. In cynomolgus monkey (*Macaca fascicularis*), the 5T4 protein has the amino acid sequence shown in SEQ ID NO: 2 (Uniprot accession no. Q4R8Y9). In the amino acid sequence shown in SEQ ID NO: 2, amino acid residues 1-34 are a signal peptide, and amino acid residues 35-420 are the mature polypeptide. In chicken (*Gallus gallus*), the 5T4 protein has the amino acid sequence shown in SEQ ID NO: 3 (Uniprot accession no. R4GM46). In the sequence shown in SEQ ID NO: 3, amino acid residues 1-27 are a signal peptide, and amino acid residues 28-379 are the mature polypeptide.

The term "CD3" as used herein, refers to the human Cluster of Differentiation 3 protein which is part of the T-cell co-receptor protein complex and is composed of four distinct chains. CD3 is also found in other species, and thus, the term "CD3" is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766; amino acid residues 1-22 is a signal peptide and amino acid residues 23-207 is the mature CD3ε polypeptide, which is identified herein as SEQ ID NO: 4; cynomolgus monkey CD3ε UniProtKB/Swiss-Prot No Q95LI5; or rhesus monkey CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

The term "antibody binding region" refers to a region of the antigen, which comprises the epitope to which the antibody binds. An antibody binding region may be determined by epitope binning using biolayer interferometry, by alanine scan, or by shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f)) that is encoded by heavy chain constant region genes. Further, each heavy chain isotype can be combined with either a kappa (κ) or lambda (λ) light chain.

The term "full-length antibody" when used herein, refers to an antibody (e.g., a parent or variant antibody) comprising one or two pairs of heavy and light chains, each containing all heavy and light chain constant and variable domains that are normally found in a heavy chain-light chain pair of a wild-type antibody of that isotype. In a full length variant antibody, the heavy and light chain constant and variable domains may in particular contain amino acid substitutions that improve the functional properties of the antibody when compared to the full length parent or wild type antibody. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

The term "human antibody", as used herein, is intended to include antibodies having variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "Fc region" as used herein, refers to a region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat Kabat, E. A. et al., Sequences of proteins of immunological interest. 5th Edition—US Department of Health and Human Services, NIH publication No. 91-3242, pp 662, 680, 689 (1991). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions," as used herein, is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxicity (ADCC), (v) Fc-gamma receptor (FcgR)-binding, (vi) antibody-dependent, FcγR-mediated antigen crosslinking, (vii) antibody-dependent cellular phagocytosis (ADCP), (viii) complement-dependent cellular cytotoxicity (CDCC), (ix) complement-enhanced cytotoxicity, (x) binding to complement receptor of an opsonized antibody mediated by the antibody, (xi) opsonisation, and (xii) a combination of any of (i) to (xi).

The term "inertness", "inert" or "non-activating" as used herein, refers to an Fc region which is at least not able to bind any FcγR, induce Fc-mediated cross-linking of FcγRs, or induce FcγR-mediated cross-linking of target antigens via two Fc regions of individual antibodies, or is not able to bind C1q. The inertness of an Fc region of an antibody, may be tested using the antibody in a monospecific or bispecific format.

The term "full-length" when used in the context of an antibody indicates that the antibody is not a fragment, but contains all of the domains of the particular isotype normally found for that isotype in nature, e.g. the VH, CH1, CH2, CH3, hinge, VL and CL domains for an IgG1 antibody.

The term "monovalent antibody", in the context of the present invention, refers to an antibody molecule that can interact with a specific epitope on an antigen, with only one antigen binding domain (e.g. one Fab arm). In the context of a bispecific antibody, "monovalent antibody binding" refers to the binding of the bispecific antibody to one specific epitope on an antigen with only one antigen binding domain (e.g. one Fab arm).

The term "monospecific antibody" in the context of the present invention, refers to an antibody that has binding specificity to one epitope only. The antibody may be a monospecific, monovalent antibody (i.e. carrying only one antigen binding region) or a monospecific, bivalent antibody (i.e. an antibody with two identical antigen binding regions).

The term "bispecific antibody" refers to an antibody having two non-identical antigen binding domains, e.g. two non-identical Fab-arms or two Fab-arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells.

The term "bivalent antibody" refers to an antibody that has two antigen binding regions, which bind to epitopes on one or two targets or antigens or binds to one or two epitopes on the same antigen. Hence, a bivalent antibody may be a monospecific, bivalent antibody or a bispecific, bivalent antibody.

The term "amino acid" and "amino acid residue" may herein be used interchangeably, and are not to be understood limiting. Amino acids are organic compounds containing amine (—NH$_2$) and carboxyl (—COOH) functional groups, along with a side chain (R group) specific to each amino acid. In the context of the present invention, amino acids may be classified based on structure and chemical characteristics. Thus, classes of amino acids may be reflected in one or both of the following tables:

Main Classification Based on Structure and General Chemical Characterization of R Group

| Class | Amino acid |
|---|---|
| Acidic Residues | D and E |
| Basic Residues | K, R, and H |
| Hydrophilic Uncharged Residues | S, T, N, and Q |

-continued

| Class | Amino acid |
|---|---|
| Aliphatic Uncharged Residues | G, A, V, L, and I |
| Non-polar Uncharged Residues | C, M, and P |
| Aromatic Residues | F, Y, and W |

Alternative Physical and Functional Classifications of Amino Acid Residues

| Class | Amino acid |
|---|---|
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid–position–substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of Lysine with Arginine in amino acid position 409.

Substitution of an amino acid at a given position to any other amino acid is referred to as:

Original amino acid–position; or e.g. "K409"

For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is:

"Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in such embodiments, the Lysine in position 409 has been deleted from the amino acid sequence.

The term "host cell", as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, Expi293F cells, PER.C6 cells, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK-293 cells, Expi293F cells, plant cells, or fungi, including yeast cells.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

The term "internalized" or "internalization" as used herein, refers to a biological process in which molecules such as the antibody according to the present invention, are engulfed by the cell membrane and drawn into the interior of the cell. Internalization may also be referred to as "endocytosis".

Antibodies

In a first aspect, the present invention provides an antibody comprising at least one antigen-binding region capable of binding to 5T4 (Trophoblast glycoprotein), wherein the antibody is able to block binding to 5T4 of an antibody selected from the group consisting of:

a) an antibody comprising a VH region comprising the sequence set forth in SEQ ID NO: 5 and a VL region comprising the sequence set forth in SEQ ID NO: 9 [059], b) an antibody comprising a VH region comprising the sequence set forth in SEQ ID NO: 12 and a VL region comprising the sequence set forth in SEQ ID NO: 16 [076], c) an antibody comprising a VH region comprising the sequence set forth in SEQ ID NO: 19 and a VL region comprising the sequence set forth in SEQ ID NO: 23 [085], d) an antibody comprising a VH region comprising the sequence set forth in SEQ ID NO: 26 and a VL region comprising the sequence set forth in SEQ ID NO: 30 [106], e) an antibody comprising a VH region comprising the sequence set forth in SEQ ID NO: 33 and a VL region comprising the sequence set forth in SEQ ID NO: 37 [127], f) an antibody comprising a VH region comprising the sequence set forth in SEQ ID NO: 40 and a VL region comprising the sequence set forth in SEQ ID NO: 44 [207]; and g) an antibody comprising a VH region comprising the sequence set forth in SEQ ID NO: 47 and a VL region comprising the sequence set forth in SEQ ID NO: 51 [226].

In particular, the invention provides an antibody comprising at least one antigen-binding region capable of binding to 5T4 (Trophoblast glycoprotein), wherein the antibody is able to block binding to 5T4 of an antibody comprising a variable heavy chain (VH) region comprising the sequence set forth in SEQ ID NO: 5, and a variable light chain (VL) region comprising the sequence set forth in SEQ ID NO: 9 [059].

The antibody may in particular be able to block binding to 5T4 of an antibody selected from the group consisting of:

a) an antibody comprising a variable heavy chain (VH) region comprising the sequence set forth in SEQ ID NO: 40 and a variable light chain (VL) region comprising the sequence set forth in SEQ ID NO: 44 [207], b) an antibody comprising a variable heavy chain (VH) region comprising the sequence set forth in SEQ ID NO: 47 and a variable light chain (VL) region comprising the sequence set forth in SEQ ID NO: 51 [226]; and an antibody comprising a variable heavy chain (VH) region comprising the sequence set forth in SEQ ID NO: 5 and a variable light chain (VL) region comprising the sequence set forth in SEQ ID NO: 9 [059].

In particular embodiments of the invention, the antibody is able to block binding to 5T4 of an antibody selected from the group consisting of:

a) an antibody comprising a variable heavy chain (VH) region comprising the sequence set forth in SEQ ID NO: 40 and a variable light chain (VL) region comprising the sequence set forth in SEQ ID NO: 44 [207]; and
b) an antibody comprising a variable heavy chain (VH) region comprising the sequence set forth in SEQ ID NO: 47 and a variable light chain (VL) region comprising the sequence set forth in SEQ ID NO: 51 [226]

The antibodies according to the invention are characterized by having specificity for or having the ability to bind human (*Homo sapiens*) 5T4. Hence, 5T4 as referred to herein may in particular be human 5T4, such as the mature polypeptide of SEQ ID NO: 1.

In further embodiments, the antibodies of the invention are characterized by having specificity for or having the ability to bind to cynomolgus monkey (*Macaca fascicularis*) 5T4, such as specificity for or the ability to bind to both human and cynomolgus monkey 5T4. Cynomolgus monkey 5T4 may in particular be the mature polypeptide of SEQ ID NO: 2.

In still further embodiments, the antibodies according to the invention have specificity for or have the ability to bind to chicken (*Gallus gallus*) 5T4, such as specificity for or the ability to bind to human 5T4 and chicken 5T4 or such as specificity for or the ability to bind to human, cynomolgus monkey and chicken 5T4, wherein chicken 5T4 in particular may have the amino acid sequence of the mature polypeptide of SEQ ID NO: 3.

Accordingly, the antibodies of the invention may have specificity for or be able to bind to human 5T4 such as the mature polypeptide of SEQ ID NO: 1 and cynomolgus monkey 5T4, such as the mature polypeptide of SEQ ID NO: 2.

Further, the antibodies according to the invention may have specificity for or be able to bind to human 5T4, such as the mature polypeptide of SEQ ID NO: 1, cynomolgus monkey 5T4 such as the mature polypeptide of SEQ ID NO: 2 and chicken 5T4, such as the mature polypeptide of SEQ ID NO: 3.

The antibodies according to the invention may be able to bind human 5T4, cynomolgus monkey and/or chicken 5T4, with a binding affinity that corresponds to a $K_D$ value of 1E−7 M or less, such as a $K_D$ value of about 1E−7 M or less, 5E−8 M or less, about 5E−8 M or less, 1E−8 M or less, about 1E−8 M or less, 5E−9 M or less, about 5E−9 M or less, such as 1E−9 M or less or such as about 1E−9 M or less, such as with a binding affinity corresponding to a $K_D$ value which is within the range of 1E−7 to 5E−10 M, such as within the range of about 1E−7 to about 5E−10 M, such as 1E−7 to 1E−9 M, such as about 1E−7 to about 1E−9 M, such as 5E−8 to 5E−10 M, such as about 5E−8 to about 5E−10 M, such as 5E−8 to 1E−9 M, such as about 5E−8 to about 1E−9 M, such as 1E−8 to 5E−10 M, such as about 1E−8 to about 5E−10 M, such as 1E−8 to 1E−9 M, such as about 1E−8 to about 1E−9 M, such as 1E−8 to 5E−9 M or such as about 1E−8 to about 5E−9 M.

While it is within the capacity of the skilled person to determine the affinity of an antibody for binding to its target, the binding affinity of the antibodies according to the invention for 5T4 may in particular be determined by biolayer interferometry, optionally as set forth in Example 2 herein.

More specifically, the binding affinity of an antibody according to the invention may determined using a procedure, such as a biolayer interferometry procedure, comprising the steps of:
I) Immobilizing the antibody at an amount of 1 μg/mL for 600 seconds on an anti-human IgG Fc Capture biosensor;
II) Determining association over a time period of 200 seconds and dissociation over a time period of 1000 seconds of 5T4ECDHis (mature protein of SEQ ID NO: 99) or cynomolgus monkey 5T4 (mature protein of SEQ ID NO: 2, or recombinant cynomolgus monkey 5T4 protein (Cusabio; cat. no. CSB-MP024093MOV), using 2-fold dilution series ranging from 100 nM to 1.56 nM.
III) Referencing the data to a buffer control (0 nM).

The binding affinity of an antibody according to the invention may in particular be determined using an antibody as defined in any one of the preceding claims, which is a monospecific, bivalent antibody, such as an antibody which is a full length IgG1.

In further embodiments of the invention, the antibody recognizes or binds to an epitope or antibody binding region or binding site on 5T4, said binding site or epitope or antibody binding region being recognized by any one of the antibodies selected from the group consisting of:
a) an antibody comprising a VH region comprising the sequence set forth in SEQ ID NO: 5 and a VL region comprising the sequence set forth in SEQ ID NO: 9 [059],
b) an antibody comprising a VH region comprising the sequence set forth in SEQ ID NO: 12 and a VL region comprising the sequence set forth in SEQ ID NO: 16 [076],
c) an antibody comprising a VH region comprising the sequence set forth in SEQ ID NO: 19 and a VL region comprising the sequence set forth in SEQ ID NO: 23 [085],
d) an antibody comprising a VH region comprising the sequence set forth in SEQ ID NO: 26 and a VL region comprising the sequence set forth in SEQ ID NO: 30 [106],
e) an antibody comprising a VH region comprising the sequence set forth in SEQ ID NO: 33 and a VL region comprising the sequence set forth in SEQ ID NO: 37 [127],
f) an antibody comprising a VH region comprising the sequence set forth in SEQ ID NO: 40 and a VL region comprising the sequence set forth in SEQ ID NO: 44 [207]; and
g) an antibody comprising a VH region comprising the sequence set forth in SEQ ID NO: 47 and a VL region comprising the sequence set forth in SEQ ID NO: 51 [226].

In still further embodiments, the antibody according to the invention recognizes or binds to an antibody binding region, a binding site or epitope on 5T4, which is not an antibody binding region, a binding site or epitope bound by, or is different from an antibody binding region, a binding site or epitope bound by, an antibody selected from the group consisting of:
a) an antibody comprising a VH region comprising the sequence set forth in SEQ ID NO: 87 and a VL region comprising the sequence set forth in SEQ ID NO: 88 [H8],
b) an antibody comprising a VH region comprising the sequence set forth in SEQ ID NO: 83 and a VL region comprising the sequence set forth in SEQ ID NO: 84 [A1]; and
c) An antibody comprising a VH region comprising the sequence set forth in SEQ ID NO: 85 and a VL region comprising the sequence set forth in SEQ ID NO: 86 [A3].

In other embodiments, the binding of the antibody according to the invention to 5T4 is blocked by binding to 5T4 of an antibody comprising a variable heavy chain (VH) region comprising the sequence set forth in SEQ ID NO: 85 and a variable light chain (VL) region comprising the sequence set forth in SEQ ID NO: 86 [A3]. An antibody comprising the VH and VL sequences set forth in SEQ ID NOs 85 and 86 respectively, is antibody A3, one of three murine 5T4 antibodies disclosed in WO2007106744. Rephrase: antibody A3 with a single aa substitution. In the CDR sequences?

In still other embodiments, the antibody according to the invention shows displacement of an antibody bound to 5T4 or to His-tagged extracellular domain of 5T4 (e.g. 5T4ECDHis/mature protein of SEQ ID NO: 99), said antibody bound to 5T4 comprising a variable heavy chain (VH) region comprising the sequence set forth in SEQ ID NO: 85 and a variable light chain (VL) region comprising the sequence set forth in SEQ ID NO: 86 [A3]. This displacement behavior indicates that the antibody of the invention binds to an epitope, which is different from the epitope bound by antibody A3, but may be adjacent to or even overlapping with the epitope bound by A3.

"Displacement" or the ability to displace a bound antibody may be determined in a biolayer interferometry assay, such as in an assay performed as described in Example 4 of the present application.

"Cross-blocking", or the ability of an antibody as defined according to the invention to block binding of another antibody to 5T4 may be determined by the use of a fluorescence-activated cell sorting (FACS) assay, such as in an assay performed as described in Example 5.

In particular, "cross-blocking", or the ability of an antibody according to the invention to block binding of another antibody to 5T4, is determined as the ability of an unconjugated antibody to block binding of a conjugated antibody, and is optionally determined in a procedure comprising the steps of:
  i) Providing a set of samples, each sample comprising a mixture of human ovary adenocarcinoma SK-OV-3 cells, an antibody which binds to 5T4 and is conjugated to fluorescein isothiocyanate (FITC), and an excess of unconjugated antibody targeting 5T4,
  ii) Incubating the samples for 30 minutes at 4° C., and thereafter subjecting the samples to centrifugation,
  iii) Removing the supernatant from each sample and resuspending the cells in buffer and determining mean fluorescence intensity (MFI) of FITC using a flow cytometer; and
  iv) Calculating the percentage of binding as following:
    The difference in MFI between cells incubated with a mixture of FITC-conjugated antibodies and unconjugated antibodies and cells incubated without FITC-conjugated or unconjugated antibodies, multiplied by 100, and subsequently divided by the difference in MFI between cells incubated with a mixture of FITC-conjugated antibodies and IgG-b12 antibodies and cells incubated without FITC-conjugated or unconjugated antibodies.

While the skilled person will be familiar with suitable technologies for determining the ability of an antibody to block the binding of another antibody to its target, or to displace another antibody bound to its target, the present application discloses procedures suitable for determining blocking of binding and displacement. Hence, in some embodiments, the ability of an antibody according to the invention to block binding of another antibody to 5T4 or to displace another antibody bound to 5T4, may be determined using biolayer interferometry, such as in biolayer interferometry performed as described in Example 3.

In particular, the ability of an antibody according to the invention to block binding of another antibody to 5T4, or to displace another antibody bound to 5T4 is determined using biolayer interferometry may be determined in a procedure comprising the steps of:
  i) Immobilizing the antibody according to the invention, at an amount of 20 µg/mL in 10 mM sodium acetate buffer to an activated Amine-Reactive $2^{nd}$ Generation biosensor,
  ii) Quenching the biosensor with the immobilized antibody in ethanolamine pH 8.5,
  iii) Immersing the biosensor with the immobilized antibody in a composition comprising 3.6 µg/mL (100 nM) of human 5T4ECDHis (mature protein of SEQ ID NO: 99) for a time period of 500 seconds, and then
  iv) Immersing the biosensor with the immobilized antibody and 5T4ECDHis in a composition comprising 10 µg/mL of the other antibody targeting 5T4 and determining the association response over a time period of 500 seconds;
  wherein steps i)-iv) are performed at a temperature of 30° C. and with shaking at 1000 rpm.

The antibodies provided herein may bind to an epitope or antibody binding region on human 5T4 comprising the amino acid residues R73, Y92 and R94; the numbering of each amino acid residue referring to its position in SEQ ID NO: 1.

Also provided herein are antibodies, which bind to an epitope or antibody binding region on human 5T4 comprising the amino acid residues S69, R73, Y92 and R94; the numbering of each amino acid residue referring to its position in SEQ ID NO: 1.

Further provided herein are antibodies, which bind to an epitope or antibody binding region on human 5T4 comprising the amino acid residues R73, T74, Y92, R94 and N95; the numbering of each amino acid residue referring to its position in SEQ ID NO: 1.

Based on the results provided in Example 16 herein it is hypothesized, without any wish to be bound by theory, that any one or more of these amino acid residues (i.e. S69, R73, T74, Y92, R94 and N95) is/are directly involved in binding of the antibody, such as by way of non-covalent interactions; e.g with amino acid residues within the CDR sequences of the antibody. The hypothesis is supported by the fact that these residues were identified as being surface-exposed on the structure of 5T4 (4cnm; provided in the RCSB PDB Protein Data Bank; DOI: 10.2210/pdb4CNM/pdb) as published in Zhao, Y., Malinauskas, T., Harlos, K., & Jones, E. Y. (2014). Structural insights into the inhibition of Wnt signaling by cancer antigen 5T4/Wnt-activated inhibitory factor 1. Structure, 22(4), 612-620.

One or more of the following additional amino acid residues may be involved binding of the antibody, such as indirectly involved in binding, e.g. by impacting protein folding and/or positioning of one or more amino acid residues directly involved in binding of the antibody: L89, F111, L117, F138, L144, D148, N152; the numbering of each amino acid residue referring to its position in SEQ ID NO: 1. In particular, L89, F111, L117, F138, L144 have been identified as part of a hydrophobic core within 5T4 as described by Zhao et al., Structure, 22(4), 612-620.

Further, the antibody disclosed herein may to an epitope or antibody binding region on human 5T4 within which amino acid residues R73, Y92 and R94 are directly involved in binding the antibody, and wherein one or more of amino acid residues F111, F138, L144 and D148 are indirectly involved in said binding; the numbering of each amino acid residue referring to its position in SEQ ID NO: 1.

The antibody provided herein may bind to an epitope or antibody binding region on human 5T4 within which amino acid residues S69, R73, Y92 and R94 are directly involved in binding the antibody, and wherein one or more of amino acid residues F111, F138, and D148 are indirectly involved in said binding; the numbering of each amino acid residue referring to its position in SEQ ID NO: 1.

Also, the present disclosure provides antibodies which bind to an epitope or antibody binding region on human 5T4 within which amino acid residues R73, T74, Y92, R94 and N95 are directly involved in binding the antibody, and wherein amino acid residue F138 is indirectly involved in said binding; the numbering of each amino acid residue referring to its position in SEQ ID NO: 1.

The amino acid residues comprised by said epitope or antibody binding region and optionally the one or more additional amino acid residues which are indirectly involved in binding may be identified by alanine scanning of human 5T4 having the amino acid sequence set forth in SEQ ID NO: 1 or the mature polypeptide sequence of SEQ ID NO: 1, or by alanine scanning of of a polypeptide comprising amino acid residues 32-355 of SEQ ID NO: 1.

The alanine scanning may in particular be performed as set forth or essentially as set forth in Example 16 herein.

Further, the alanine scanning may be performed by a procedure comprising the steps of:
i) Expressing mutant human 5T4 polypeptides in which all amino acid residues in the extracellular domain of human 5T4 (corresponding to amino acid residues 32-355 of SEQ ID NO: 1), except cysteines and alanines, are individually substituted with alanine, and wild type 5T4 polypeptides (amino acid residues 32-355 of SEQ ID NO: 1) individually in human embryonic kidney cells, e.g. HEK 293 cells, such that for each mutant or wild type 5T4 a sample comprising 70-90,000 cells, such as 80,000 cells is provided,
ii) Incubating the cells in each sample with 20 μL of said antibody conjugated to fluorescein isothiocyanate (FITC)-conjugated antibody (3 μg/mL; in FACS buffer) for 40 minutes at room temperature, and subsequently washing each sample twice in 150-180 μL FACS buffer (phosphate-buffered saline [PBS; Lonza, cat. no. BE17-517]+0.1% [w/v] BSA [Roche, cat. no. 10735086001]+0.02% [w/v] sodium azide [NaN₃; EMELCA Bioscience, cat. no. 41920044-3]) and resuspending the cells in each sample in 30 μL FACS buffer,
iii) Determining, for each sample, the average amount of antibody bound per cell as the geometric mean of the fluorescence intensity (gMFI) for the viable, single cell population in said sample and normalizing the data for each test antibody against the binding intensity of a non-cross blocking 5T4-specific control antibody using the equation:

$$\text{Normalized } gMFI_{aa\, position} = \text{Log}_{10}\left(\frac{gMFI_{Test\, Ab}}{gMFI_{Control\, Ab}}\right)$$

wherein 'aa position' refers to the position that was mutated into an alanine,
wherein the Z-score is calculated to express loss or gain of binding of the antibody, according to the calculation:

$$\text{Z-score(fold change)} = \frac{\text{Normalized } gMFI_{aa\, position} - \mu}{\sigma}$$

wherein μ and σ are the mean and standard deviation, respectively, of the Normalized gMFI calculated from all mutants,
wherein data is excluded from the analysis if the gMFI of the control antibody for a particular 5T4 mutant is lower than the mean $gMFI_{Control\, Ab}$–2.5×SD of the mean $gMFI_{Control\, Ab}$ (from all mutants); and optionally wherein data is excluded from the analysis if a residue binds with a Z-score just below −1.5 (e.g. between −1.5 and −1.8, such as between −1.5 and −1.7 or such as between −1.5 and −1.6) and that residue is predicted to be buried and spatially separated from the majority of residues, which are predicted to be surface-exposed and for which loss of binding or reduced binding is determined.

A suitable non-cross blocking 5T4-specific control antibody to be used in step iii) is a bispecific antibody comprising
an antigen-binding region, which comprises a VH sequence as set forth in SEQ ID NO: 83 and a VL sequence as set forth in SEQ ID NO: 84 [A1]; and
an antigen binding region, which comprises a VH sequence as set forth in SEQ ID NO: 97 and a VL sequence as set forth in SEQ ID NO: 98 [B12].

The present invention provides antibodies which bind to 5T4 such that there is loss of binding or binding is reduced if any one or more of the amino acid residues R73, Y92 and R94 is/are substituted with alanine; the numbering of each amino acid residue referring to its position in SEQ ID NO: 1.

In particular, the antibodies may bind to 5T4 such that there is loss of binding or binding is reduced if any one or more of the amino acid residues S69, R73, Y92 and R94 is/are substituted with alanine; the numbering of each amino acid residue referring to its position in SEQ ID NO: 1.

Further, the antibodies may bind to 5T4 such that there is loss of binding or binding is reduced if any one or more of the amino acid residues R73, T74, Y92, R94 and N95 is/are substituted with alanine; the numbering of each amino acid residue referring to its position in SEQ ID NO: 1.

Also, the antibodies disclosed herein may bind to 5T4 such that there is loss of binding or binding is reduced if any one or more of the amino acid residues: L89, F111, L117, F138, L144, D148, N152 is/are substituted with alanine; the numbering of each amino acid residue referring to its position in SEQ ID NO: 1.

Further, the antibodies may bind to 5T4 such that there is loss of binding or binding is reduced if any one or more of the amino acid residues R73, Y92, R94, F111, F138, L144 and D148 is/are substituted with alanine; the numbering of each amino acid residue referring to its position in SEQ ID NO: 1.

The antibodies may bind to 5T4 such that there is loss of binding or binding is reduced if any one or more of the amino acid residues S69, R73, Y92, R94, F111, F138, and D148 is/are substituted with alanine; the numbering of each amino acid residue referring to its position in SEQ ID NO: 1.

In other embodiments, the antibodies of the invention may bind to 5T4 such that there is loss of binding or binding is reduced if any one or more of the amino acid residues R73, T74, Y92, R94, N95 and F138 is/are substituted with alanine; the numbering of each amino acid residue referring to its position in SEQ ID NO: 1.

The the effect of any of the alanine substitutions provided above may be determined by alanine scanning of a polypeptide comprising amino acid residues 32-355 of SEQ ID NO: 1.

In particular, the effect of the alanine substitutions may be determined by a procedure as set forth or essentially as set forth in Example 16 herein.

Loss of binding may be defined as a Z-score in binding being lower than 1.5; the Z-score optionally being calculated as set forth or essentially as set forth in Example 16 herein.

The effect of any of the alanine substitutions may be determined by a procedure comprising the steps of:
  i) Expressing mutant human 5T4 polypeptides in which all amino acid residues in the extracellular domain of human 5T4 (corresponding to amino acid residues 32-355 of SEQ ID NO: 1), except cysteines and alanines, are individually substituted with alanine, and wild type 5T4 polypeptides individually in human embryonic kidney cells, e.g. HEK 293 cells, such that for each mutant or wild type 5T4 a sample comprising 70-90,000 cells, such as 80,000 cells is provided,
  ii) Incubating the cells in each sample with 20 µL of said antibody conjugated to fluorescein isothiocyanate (FITC)-conjugated antibody (3 µg/mL; in FACS buffer) for 40 minutes at room temperature, and subsequently washing each sample twice in 150-180 µL FACS buffer (phosphate-buffered saline [PBS; Lonza, cat. no. BE17-517]+0.1% [w/v] BSA [Roche, cat. no. 10735086001]+ 0.02% [w/v] sodium azide [NaN$_3$; EMELCA Bioscience, cat. no. 41920044-3]) and resuspending the cells in each sample in 30 µL FACS buffer,
  iii) Determining, for each sample, the average amount of antibody bound per cell as the geometric mean of the fluorescence intensity (gMFI) for the viable, single cell population in said sample and normalizing the data for each test antibody against the binding intensity of a non-cross blocking 5T4-specific control antibody using the equation:

$$\text{Normalized } gMFI_{aa\ position} = \text{Log}_{10}\left(\frac{gMFI_{Test\ Ab}}{gMFI_{Control\ Ab}}\right)$$

wherein 'aa position' refers to the position that was mutated into an alanine,
wherein the Z-score is calculated to express loss or gain of binding of the antibody, according to the calculation:

$$Z\text{-score(fold change)} = \frac{\text{Normalized } gMFI_{aa\ position} - \mu}{\sigma}$$

wherein µ and σ are the mean and standard deviation, respectively, of the Normalized gMFI calculated from all mutants,
wherein data is excluded from the analysis if the gMFI of the control antibody for a particular 5T4 mutant is lower than the mean gMFI$_{Control\ Ab}$−2.5×SD of the mean gMFI$_{Control\ Ab}$ (from all mutants); and optionally wherein data is excluded from the analysis if a residue binds with a Z-score just below −1.5 (e.g. between −1.5 and −1.8, such as between −1.5 and −1.7 or such as between −1.5 and −1.6) and that residue is predicted to be buried and spatially separated from the majority of residues, which are predicted to be surface-exposed and for which loss of binding or reduced binding is determined.

A suitable non-cross blocking 5T4-specific control antibody in step iii) of the procedure above is a bispecific antibody comprising
  an antigen-binding region, which comprises a VH sequence as set forth in SEQ ID NO: 83 and a VL sequence as set forth in SEQ ID NO: 84 [A1]; and
  an antigen binding region, which comprising a VH sequence as set forth in SEQ ID NO: 97 and a VL sequence as set forth in SEQ ID NO: 98 [B12].

The antibody according to the invention may be characterized by having reduced internalization capacity as shown by reduced cytotoxicity when conjugated to a cytotoxic moiety as compared to a likewise conjugated antibody comprising a variable heavy chain (VH) region comprising the sequence set forth in SEQ ID NO: 87 and a variable light chain (VL) region comprising the sequence set forth in SEQ ID NO: 88 [H8]. An antibody comprising the VH and VL sequences set forth in SEQ ID Nos: 87 and 88 respectively, may be murine 5T4 antibody mAb5T4, also called the H8 antibody, (Shaw et al. (2002), Biochem. J. 363: 137-45, WO98/55607). Various chimeric or humanized versions of antibody H8 are disclosed in WO06/031653.

Cytotoxicity or internalization of 5T4 antibodies that monovalently bind 5T4 may be determined using a procedure as set forth in Example 7 in the present application. In particular, cytotoxicity may be determined in an assay comprising the steps of:
  i) Providing an toxin-conjugated bispecific antibody that monovalently binds 5T4, comprising a first-Fab arm of an antibody as defined in any one of the preceding claims and a second Fab arm capable of binding to HIV viral protein gp120 (HIV-1 gp120), wherein the HIV-1 gp120-specific Fab-arm is conjugated to Duostatin-3,
  ii) Incubating 5T4-positive breast cancer cells MDA-MB-468 (ATCC clone HTB-132) or HCC1954 (ATCC clone CRL-1338) with said bispecific antibody that monovalently binds 5T4 for 5 days at 37° C.; and
  iii) Determining the viability of the cells.

IgG-b12 is a HIV-1 gp120 specific antibody (Barbas, C F. J Mol Biol. 1993 Apr. 5; 230(3):812-23). Sequences of the heavy chain (VH) and light chain variable regions (VL) are set forth in SEQ ID NOs: 97 and 98, respectively.

In certain embodiments, the antibody of the invention is one, wherein said antigen-binding region, which is capable of binding to 5T4 comprises a heavy chain variable region (VH) selected from the group consisting of:
  a) a heavy chain variable region (VH) comprising the CDR1, CDR2, and CDR3 sequences of SEQ ID NOs.: 6, 7 and 8 [059],
  b) a heavy chain variable region (VH) comprising the CDR1, CDR2, and CDR3 sequences of SEQ ID NOs.: 13, 14 and 15 [076],
  c) a heavy chain variable region (VH) comprising the CDR1, CDR2, and CDR3 sequences of SEQ ID NOs.: 20, 21 and 22 [085],
  d) a heavy chain variable region (VH) comprising the CDR1, CDR2, and CDR3 sequences of SEQ ID NOs.: 27, 28 and 29 [106],
  e) a heavy chain variable region (VH) comprising the CDR1, CDR2, and CDR3 sequences of SEQ ID NOs.: 34, 35 and 36 [127],
  f) a heavy chain variable region (VH) comprising the CDR1, CDR2, and CDR3 sequences of SEQ ID NOs.: 41, 42 and 43 [207], g) a heavy chain variable region (VH) comprising the CDR1, CDR2, and CDR3 sequences of SEQ ID NOs.: 48, 49 and 50 [226]; and h) a heavy chain variable region (VH) comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to g).

In other embodiments, the antibody according to the invention is one, wherein said antigen-binding region capable of binding to 5T4 comprises a heavy chain variable region (VH) selected from the group consisting of:

a) a heavy chain variable region (VH) comprising the CDR1, CDR2, and CDR3 sequences of SEQ ID NOs.: 6, 7 and 8 [059], b) a heavy chain variable region (VH) comprising the CDR1, CDR2, and CDR3 sequences of SEQ ID NOs.: 41, 42 and 43 [207];

c) a heavy chain variable region (VH) comprising the CDR1, CDR2, and CDR3 sequences of SEQ ID NOs.: 48, 49 and 50 [226]; and d) a heavy chain variable region (VH) comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to c).

In particular, the antibody according to the invention may be one, wherein said antigen-binding region capable of binding to 5T4 comprises a heavy chain variable region (VH) comprising CDR1, CDR2, and CDR3 sequences of SEQ ID NOs.: 6, 7 and 8 [059].

Alternatively, the antibody according to the invention may be one, wherein said antigen-binding region capable of binding to 5T4 comprises a heavy chain variable region (VH) selected from the group consisting of: a heavy chain variable region (VH) comprising CDR1, CDR2, and CDR3 sequences of SEQ ID NOs.: 41, 42 and 43 [207].

Also, the antibody according to the invention may be one, wherein said antigen-binding region capable of binding to 5T4 comprises a heavy chain variable region (VH) selected from the group consisting of: a heavy chain variable region (VH) comprising CDR1, CDR2, and CDR3 sequences of SEQ ID NOs.: 48, 49 and 50 [226].

In other embodiments, the antibody according to the invention is one, wherein said antigen-binding region capable of binding to 5T4 comprises a heavy chain variable region (VH) and a light chain variable region (VL) selected from the group consisting of:

a) a heavy chain variable region (VH) comprising the CDR1, CDR2, and CDR3 sequences of SEQ ID NOs.: 6, 7 and 8, respectively, and a light chain variable region (VL) comprising the CDR1, CDR2, and CDR3 sequences of SEQ ID NO: 10, AAS and SEQ ID NO: 11, respectively [059], b) a heavy chain variable region (VH) comprising the CDR1, CDR2, and CDR3 sequences of SEQ ID NOs.: 13, 14 and 15, respectively; and a light chain variable region (VL) comprising the CDR1, CDR2, and CDR3 sequences of SEQ ID NO: 17, DAS and SEQ ID NO:18, respectively [076], c) a heavy chain variable region (VH) comprising the CDR1, CDR2, and CDR3 sequences of SEQ ID NOs.: 20, 21 and 22, respectively; and a light chain variable region (VL) comprising the CDR1, CDR2, and CDR3 sequences of SEQ ID NO: 24, DAS and SEQ ID NO: 25, respectively [085], d) a heavy chain variable region (VH) comprising the CDR1, CDR2, and CDR3 sequences of SEQ ID NOs.: 27, 28 and 29, respectively; and a light chain variable region (VL) comprising the CDR1, CDR2, and CDR3 sequences of SEQ ID NO: 31, DVS and SEQ ID NO: 32, respectively [106], e) a heavy chain variable region (VH) comprising the CDR1, CDR2, and CDR3 sequences of SEQ ID NOs.: 34, 35 and 36, respectively; and a light chain variable region (VL) comprising the CDR1, CDR2, and CDR3 sequences of SEQ ID NO: 38, DAS and SEQ ID NO: 39, respectively [127], f) a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and SEQ ID NO: 46, respectively [207], g) a heavy chain variable region (VH) comprising the CDR1, CDR2, and CDR3 sequences of SEQ ID NOs.: 48, 49 and 50, respectively, and a light chain variable region (VL) region comprising the CDR1, CDR2, and CDR3 sequences of SEQ ID NO: 52, DAS and SEQ ID NO: 53, respectively [226]; and h) a heavy chain variable region (VH) comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to g).

The antibody according to the invention may be an antibody, wherein the six complementarity-determining regions (CDRs) of the antigen binding region(s) capable of binding to 5T4 comprise, in total, at the most 1, 2, 3, 4, 5, 6, 7, 8, 9 or at the most 10 amino acid substitutions, when compared to i) the CDR sequences of SEQ ID NOs: 6, 7, 8, 10, AAS and SEQ ID NO: 11 [059], ii) the CDR sequences of SEQ ID NOs.: 41, 42, 43, 45, DAS and SEQ ID NO: 46 [207]; or iii) the CDR sequences of SEQ ID NOs.: 48, 49, 50, 52, DAS and SEQ ID NO: 53 [226].

Preferably 1, such as 2, 3, 4, 5, 6, 7, 8, 9 or 10 of the said amino acid substitutions is/are conservative amino acid substitution(s).

The antibody may in particular comprise one or two heavy chain variable regions in which the complementarity-determining region 3 (CDR3) comprises six consecutive amino acid residues of the sequence set forth in SEQ ID NO: 102 (YYGMDV) [059, 207, 226]. These six consecutive amino acid residues may be the most C-terminal amino acid residues within the CDR3.

The antibody according to the invention may be an antibody, wherein said antigen-binding region capable of binding to 5T4 comprises one or two heavy chain variable region(s) (VH) comprising the CDR1 sequence of SEQ ID NO: 41 (GGSFSGYY), the CDR2 sequence of SEQ ID NO: 103 (IDHSX$_1$ST), and the CDR3 sequence of SEQ ID NO: 104 (AX$_2$WFGELX$_3$X$_4$YYYGMDV), and a light chain variable region (VL) comprising the CDR1 sequence of SEQ ID NO: 105 (QSVSSX$_5$), the CDR2 sequence DAS, and the CDR3 sequence of SEQ ID NO: 46 (QQRSNWPLT), and wherein X$_1$ is G or E, X$_2$ is A or G, X$_3$ is W or Y, X$_4$ is D or H and X$_5$ is Y or F [207, 226].

The antibody according to the invention may be one, wherein said antigen-binding region capable of binding to 5T4 comprises a heavy chain variable region (VH) comprising the CDR1, CDR2, and CDR3 sequences of SEQ ID NOs.: 6, 7, and 8, respectively, and a light chain variable region (VL) comprising the CDR1, CDR2, and CDR3 sequences of SEQ ID NO: 10, AAS and SEQ ID NO: 11, respectively [059].

Alternatively, the antibody according to the invention may be one, wherein said antigen-binding region capable of binding to 5T4 comprises a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and SEQ ID NO: 46, respectively [207].

Additionally, the antibody according to the invention may be one, wherein said antigen-binding region capable of binding to 5T4 comprises a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and 53, respectively [226].

In some embodiments, the antibody according to the invention is an antibody, wherein said antigen-binding region capable of binding to 5T4 comprises a heavy chain variable region (VH) selected from the group consisting of:
  a) a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059],
  b) a heavy chain variable region (VH) comprising the sequence of SEQ ID NO: 12 or a sequence having at least 90%, at least 95%, at least 97%, or at least 99% amino acid sequence identity to the sequence of SEQ ID NO: 12 [076],
  c) a heavy chain variable region (VH) comprising the sequence of SEQ ID NO: 19 or a sequence having at least 90%, at least 95%, at least 97%, or at least 99% amino acid sequence identity to the sequence of SEQ ID NO: 19 [085],
  d) a heavy chain variable region (VH) comprising the sequence of SEQ ID NO: 26 or a sequence having at least 90%, at least 95%, at least 97%, or at least 99% amino acid sequence identity to the sequence of SEQ ID NO: 26 [106],
  e) a heavy chain variable region (VH) comprising the sequence of SEQ ID NO: 33 or a sequence having at least 90%, at least 95%, at least 97%, or at least 99% amino acid sequence identity to the sequence of SEQ ID NO: 33 [127],
  f) a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207]; and
  g) a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226].

The antibody according to the invention may in particular be an antibody, wherein said antigen-binding region capable of binding to 5T4 comprises a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059].

Also, the antibody according to the invention may be one, wherein said antigen-binding region capable of binding to 5T4 comprises a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207].

Additionally, the antibody according to the invention may be an antibody, wherein said antigen-binding region capable of binding to 5T4 comprises a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226].

In other embodiments, the antibody according to the invention is an antibody, wherein said antigen-binding region capable of binding to 5T4 comprises a heavy chain variable region (VH) and a light chain variable region (VL) selected from the group consisting of:
  a) a heavy chain variable region (VH) comprising the sequence of SEQ ID NO: 5 or a sequence having at least 90%, at least 95%, at least 97%, or at least 99% amino acid sequence identity to the sequence of SEQ ID NO: 5, and a light chain variable region (VL) comprising the sequence of SEQ ID NO: 9 or a sequence having at least 90%, at least 95%, at least 97%, or at least 99% amino acid sequence identity to the sequence of SEQ ID NO: 9 [059],
  b) a heavy chain variable region (VH) comprising the sequence of SEQ ID NO: 12 or a sequence having at least 90%, at least 95%, at least 97%, or at least 99% amino acid sequence identity to the sequence of SEQ ID NO: 12, and a light chain variable region (VL) comprising the sequence of SEQ ID NO: 16 or a sequence having at least 90%, at least 95%, at least 97%, or at least 99% amino acid sequence identity to the sequence of SEQ ID NO: 16 [076],
  c) a heavy chain variable region (VH) comprising the sequence of SEQ ID NO: 19 or a sequence having at least 90%, at least 95%, at least 97%, or at least 99% amino acid sequence identity to the sequence of SEQ ID NO: 19, and a light chain variable region (VL) comprising the sequence of SEQ ID NO: 23 or a sequence having at least 90%, at least 95%, at least 97%, or at least 99% amino acid sequence identity to the sequence of SEQ ID NO: 23 [085],
  d) a heavy chain variable region (VH) comprising the sequence of SEQ ID NO: 26 or a sequence having at least 90%, at least 95%, at least 97%, or at least 99% amino acid sequence identity to the sequence of SEQ ID NO: 26, and a light chain variable region (VL) comprising the sequence of SEQ ID NO: 30 or a sequence having at least 90%, at least 95%, at least 97%, or at least 99% amino acid sequence identity to the sequence of SEQ ID NO: 30 [106],
  e) a heavy chain variable region (VH) comprising the sequence of SEQ ID NO: 33 or a sequence having at least 90%, at least 95%, at least 97%, or at least 99% amino acid sequence identity to the sequence of SEQ ID NO: 33, and a light chain variable region (VL) comprising the sequence of SEQ ID NO: 37 or a sequence having at least 90%, at least 95%, at least 97%, or at least 99% amino acid sequence identity to the sequence of SEQ ID NO: 37 [127], f) a heavy chain variable region (VH) comprising the sequence of SEQ ID NO: 40 or a sequence having at least 90%, at least 95%, at least 97%, or at least 99% amino acid sequence identity to the sequence of SEQ ID NO: 40, and a light chain variable region (VL) comprising the sequence of SEQ ID NO: 44 or a sequence having at least 90%, at least 95%, at least 97%, or at least 99% amino acid sequence identity to the sequence of SEQ ID NO: 44 [207], g) a heavy chain variable region (VH) comprising the sequence of SEQ ID NO: 47 or a sequence having at least 90%, at least 95%, at least 97%, or at least 99% amino acid sequence identity to the sequence of SEQ ID NO: 47, and a light chain variable region (VL) comprising the sequence of SEQ ID NO: 51 or a sequence having at least 90%, at least 95%, at least 97%, or at least 99% amino acid sequence identity to the sequence of SEQ ID NO: 51 [226].

In one embodiment, the at least one binding region comprises a variable heavy chain (VH) region and a variable light chain (VL) region having at most 10 mutations or substitutions, at most 5 mutations or substitutions, such as at most 4 mutations or substitutions, such as at most 3 mutations or substitutions, such as at most 2 mutations or substitutions, such as at most 1 mutation or substitution, across said heavy chain variable region (VH) and light chain variable region (VL) region selected from the group consisting of:

a) a heavy chain variable region (VH) comprising or consisting of the sequence of SEQ ID NO: 5, and a light chain variable region (VL) comprising or consisting of the sequence of SEQ ID NO: 9 [059], b) a heavy chain variable region (VH) comprising or consisting of the sequence of SEQ ID NO: 12, and a light chain variable region (VL) comprising or consisting of the sequence of SEQ ID NO: 16 [076], c) a heavy chain variable region (VH) comprising or consisting of the sequence of SEQ ID NO: 19, and a light chain variable region (VL) comprising or consisting of the sequence of SEQ ID NO: 23 [085], d) a heavy chain variable region (VH) comprising or consisting of the sequence of SEQ ID NO: 26, and a light chain variable region (VL) comprising or consisting of the sequence of SEQ ID NO: 30 [106], e) a heavy chain variable region (VH) comprising or consisting of the sequence of SEQ ID NO: 33, and a light chain variable region (VL) comprising or consisting of the sequence of SEQ ID NO: 37 [127], f) a heavy chain variable region (VH) comprising or consisting of the sequence of SEQ ID NO: 40, and a light chain variable region (VL) comprising or consisting of the sequence of SEQ ID NO: 44 [207], g) a heavy chain variable region (VH) comprising or consisting of the sequence of SEQ ID NO: 47, and a light chain variable region (VL) comprising or consisting of the sequence of SEQ ID NO: 51 [226].

In some embodiments of the present disclosure, the at most 10 mutations or substitutions, at most 5 mutations or substitutions, such as at most 4 mutations or substitutions, such as at most 3 mutations or substitutions, such as at most 2 mutations or substitutions, such as at most 1 mutation or substitution are allowed across the full length of the variable heavy chain and the entire variable light chain. In other embodiments, the at most 10 mutations or substitutions, at most 5 mutations or substitutions, such as at most 4 mutations or substitutions, such as at most 3 mutations or substitutions, such as at most 2 mutations or substitutions, such as at most 1 mutation or substitution may not be within any of the 6 CDR sequences in the said variable heavy chain and the variable light chain.

The up to 10 mutations or substitutions may be distributed across the full length of the variable heavy chain and the variable light chain of each binding region. Some or all of the mutations or substitutions may be conservative substitutions in which one amino acid residue is substituted with an amino acid residue of the same class as indicated under the definition "amino acid" herein above; for instance an acidic amino acid being substituted for another acidic amino acid residue, and an aromatic residue may be substituted for another aromatic residue. It may be preferred that 35% or more, 50% or more, 60% or more, 70% or more, 75% or more, 80% or more, 85% or more, 90% or more, 92% or more, 93% or more or 94% or more of the substitutions in the variant are conservative amino acid residue replacements.

In particular, some or all of the mutations or substitutions may be with amino acid residue(s) each having the same physical or functional properties as the respective amino acid residue which they substitute. Amino acid residues sharing physical and functional properties are provided under the definition "amino acid" herein above; for instance a under the definition "amino acid" herein above; for instance a hydrophobic residue may be substituted for another hydrophobic amino acid residue or a cycloalkenyl-associated residue may be substituted for another cycloalkenyl-associated residue.

Antibodies comprising substitutions or mutations as disclosed above may in particular be functional variants of the VL regions, VH regions, or one or more CDRs defined above with reference to sequences identifiers. A functional variant of a VL, VH, or CDR used in the context of the antibodies of the present invention still allows the antibody to retain at least a substantial proportion (at least about 50%, 60%, 70%, 80%, 90%, 95%, 99% or more) of the affinity and/or the specificity/selectivity of the parent antibody, and in some cases such an 5T4 antibody may even be associated with greater affinity, selectivity and/or specificity than the parent antibody.

In further embodiments of the invention, the antibody is one, wherein said antigen-binding region capable of binding to 5T4 comprises a heavy chain variable region (VH) and a light chain variable region (VL) selected from the group consisting of:

a) a heavy chain variable region (VH) comprising or consisting of the sequence of SEQ ID NO: 5, and a light chain variable region (VL) comprising or consisting of the sequence of SEQ ID NO: 9 [059], b) a heavy chain variable region (VH) comprising or consisting of the sequence of SEQ ID NO: 12, and a light chain variable region (VL) comprising or consisting of the sequence of SEQ ID NO: 16 [076], c) a heavy chain variable region (VH) comprising or consisting of the sequence of SEQ ID NO: 19, and a light chain variable region (VL) comprising or consisting of the sequence of SEQ ID NO: 23 [085], d) a heavy chain variable region (VH) comprising or consisting of the sequence of SEQ ID NO: 26, and a light chain variable region (VL) comprising or consisting of the sequence of SEQ ID NO: 30 [106], e) a heavy chain variable region (VH) comprising or consisting of the sequence of SEQ ID NO: 33, and a light chain variable region (VL) comprising or consisting of the sequence of SEQ ID NO: 37 [127], f) a heavy chain variable region (VH) comprising or consisting of the sequence of SEQ ID NO: 40, and a light chain variable region (VL) comprising or consisting of the sequence of SEQ ID NO: 44 [207]; and
g) a heavy chain variable region (VH) comprising or consisting of the sequence of SEQ ID NO: 47, and a light chain variable region (VL) comprising or consisting of the sequence of SEQ ID NO: 51 [226].

The antibody of the invention may be a full-length antibody, such as a full length IgG1 antibody.

Further, the antibody of the invention may be a monovalent antibody. Alternatively, the antibody according to the invention may be a bivalent antibody.

In other embodiments, the antibody provided according to the present invention is a monospecific antibody.

Alternatively, the antibody according to the present disclosure may be a bispecific antibody.

It is further within the scope of the present disclosure to provide an antibody as defined above, the antibody comprising an antigen binding region of an antibody that binds to CD3, such as human CD3ε (epsilon), such as human CD3ε (epsilon) as specified in SEQ ID NO: 4.

In particular, the present disclosure provides a bispecific antibody comprising a first antigen binding region of an antibody as disclosed above, and a second binding region which binds to CD3, such as human CD3 as defined above.

Examples of bispecific antibody molecules which may be used in the present invention include but are not limited to (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig™), where each light chain and heavy chain contains two variable domains in tandem through a short peptide linkage Wu et al., Generation and Characterization of a Dual Variable Domain Immunoglobulin (DVD-Ig™) Molecule, In: Antibody Engineering, Springer Berlin Heidelberg (2010); (iv) a chemically-linked bispecific (Fab')2 fragment; (v) a Tandab®, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule (Dock-and-Lock®), based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, such as CrossMabs, or a bispecific antibody obtained via a controlled Fab arm exchange (such as described in WO 2011/131746).

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domains molecules include but are not limited to the Triomab® (Trion Pharma/Fresenius Biotech, WO/2002/020039), the Knobs-into-Holes (Genentech, WO9850431;), CrossMAbs (Roche, WO2011117329) and the electrostatically-matched (Amgen, EP1870459 and WO2009089004; Chugai, US201000155133; Oncomed, WO2010129304), the LUZ-Y (Genentech), DIG-body and PIG-body (Pharmabcine), the Strand Exchange Engineered Domain body (SEEDbody) (EMD Serono, WO2007110205), the Biclonics (Merus), FcΔAdp (Regeneron, WO 2010/015792), bispecific IgG1 and IgG2 (Pfizer/Rinat, WO11143545), Azymetric scaffold (Zymeworks/Merck, WO2012058768), mAb-Fv (Xencor, WO2011028952), bivalent bispecific antibodies (Roche WO 2009/080254) and DuoBody® molecules (Genmab A/S, WO 2011/131746).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), mAb2 (F-Star, WO2008003116), Zybodies™ (Zyngenia), approaches with common light chain (Crucell/Merus, U.S. Pat. No. 7,262,028), κλBodies (NovImmune) and CovX-body (CovX/Pfizer).

Examples of IgG fusion molecules include but are not limited to Dual Variable Domain (DVD)-Ig™ (Abbott, U.S. Pat. No. 7,612,181), Dual domain double head antibodies (Unilever; Sanofi Aventis, WO20100226923), IgG-like Bispecific (ImClone/Eli Lilly), Ts2Ab (MedImmune/AZ) and BsAb (Zymogenetics), HERCULES (Biogen Idec, US007951918), scFv fusion (Novartis), scFv fusion (Changzhou Adam Biotech Inc, CN 102250246) and TvAb (Roche, WO2012025525, WO2012025530).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART™) (MacroGenics, WO2008157379, WO2010/080538) and Dual(ScFv)2-Fab (National Research Center for Antibody Medicine—China).

Examples of Fab fusion bispecific antibodies include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of scFv-, diabody-based and domain antibodies include but are not limited to Bispecific T Cell Engager (BiTE®) (Micromet, Tandem Diabody (Tandab™) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting Nanobodies® (Ablynx), dual targeting heavy chain only domain antibodies.

The antibody according to the present disclosure may in particular be an antibody, wherein the antigen binding region that binds to CD3 comprises
 a heavy chain variable region (VH) comprising the CDR1, CDR2, and CDR3 sequences of SEQ ID NOs:

54, 55 and 56, respectively; [huCD3-H1L1] (WO2015001085 (Genmab A/S));
and, optionally
a light chain variable region (VL) comprising the CDR1, CDR2, and CDR3 sequences of SEQ ID NO: 58, GTN and 59, respectively [huCD3-H1L1].

Also disclosed are antibodies wherein the antigen binding region that binds to CD3 comprises
a heavy chain variable region (VH) comprising the sequence of SEQ ID NO: 57, or a sequence having at least 90%, at least 95%, at least 97%, or at least 99% amino acid sequence identity to the sequence of SEQ ID NO: 57 [huCD3-H1L1];
and, optionally
a light chain variable region (VL) comprising the sequence of SEQ ID NO: 60 or a sequence having at least 90%, at least 95%, at least 97%, or at least 99% amino acid sequence identity to the sequence of SEQ ID NO: 60, [huCD3-H1L1].

The present disclosure further provides an antibody, wherein
the antigen-binding region capable of binding to 5T4 comprises a heavy chain variable region (VH) comprising CDR1, CDR2, and CDR3 sequences of SEQ ID NOs.: 6, 7 and 8, respectively, and a light chain variable region (VL) comprising the CDR1, CDR2, and CDR3 sequences of SEQ ID NO: 10, AAS and 11, respectively [059];
and
the antigen-binding region capable of binding to CD3 comprises a heavy chain variable region (VH) comprising CDR1, CDR2, and CDR3 having the sequences as set forth in SEQ ID NOs: 54, 55 and 56, respectively, and a light chain variable region (VL) comprising CDR1, CDR2, and CDR3 having the sequences as set forth in SEQ ID NO: 58, the sequence GTN, and the sequence as set forth in SEQ ID NO: 59 [huCD3-H1L1], respectively.

Also, the disclosure provides an antibody, wherein
the antigen-binding region capable of binding to 5T4 comprises a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NOs.: 45, DAS and 46, respectively [207];
and
the antigen-binding region capable of binding to CD3 comprises a heavy chain variable region (VH) comprising CDR1, CDR2, and CDR3 having the sequences as set forth in SEQ ID NOs: 54, 55 and 56, respectively, and a light chain variable region (VL) comprising CDR1, CDR2, and CDR3 having the sequences as set forth in SEQ ID NO: 58, the sequence GTN, and the sequence as set forth in SEQ ID NO: 59 [huCD3-H1L1], respectively.

Also, disclosure provides an antibody, wherein
the antigen-binding region capable of binding to 5T4 comprises a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and SEQ ID NO: 53, respectively [226–VH+VL CDR1, -2 and -3 sequences];
and
the antigen-binding region capable of binding to CD3 comprises a heavy chain variable region (VH) comprising CDR1, CDR2, and CDR3 having the sequences as set forth in SEQ ID NOs: 54, 55 and 56, respectively, and a light chain variable region (VL) comprising CDR1, CDR2, and CDR3 having the sequences as set forth in SEQ ID NO: 58, the sequence GTN, and the sequence as set forth in SEQ ID NO: 59 [huCD3-H1L1], respectively.

The antigen binding region that binds to CD3, may bind with an equilibrium dissociation constant $K_D$ within the range of 200-1000 nM, such as within the range of 300-1000 nM, within the range of 400-1000 nM, within the range of 500-1000 nM, within the range of 300-900 nM within the range of 400-900 nM, within the range of 400-700 nM, within the range of 500-900 nM, within the range of 500-800 nM, within the range of 500-700 nM, within the range of 600-1000 nM, within the range of 600-900 nM, within the range of 600-800 nM, or such as within the range of 600-700 nM.

In further embodiments, the antibody disclosed herein has a lower human CD3ε binding affinity than an antibody having an antigen-binding region comprising a VH sequence as set forth in SEQ ID NO: 57, and a VL sequence as set forth in SEQ ID NO: 60 [huCD3-H1L1], preferably wherein said affinity is at least 2-fold lower, e.g. at least 5-fold lower, such as at least 10-fold lower, e.g. at least 20-fold lower, at least 30-fold lower, at least 40-fold lower, at least 45-fold lower, at least 50-fold lower, at least 55-fold lower, or such as at least 60-fold lower.

In particular, the antigen binding region that binds to CD3 may bind with an equilibrium dissociation constant $K_D$ within the range of 1-100 nM, such as within the range of 5-100 nM, within the range of 10-100 nM, within the range of 1-80 nM, within the range of 1-60 nM within the range of 1-40 nM, within the range of 1-20 nM, within the range of 5-80 nM, within the range of 5-60 nM, within the range of 5-40 nM, within the range of 5-20 nM, within the range of 10-80 nM, within the range of 10-60 nM, within the range of 10-40 nM, or such as within the range of 10-20 nM.

The affinity with which the antibody according to the invention bind to CD3 may be determined by biolayer interferometry, using a modification of the procedure described above or as set forth in Example 2 herein, in which the antibody is immobilized on a human IgG Fc Capture biosensor and association and dissociation of the CD3E27-GSKa (mature protein of SEQ ID NO: 101) to the immobilize antibody is determined. Further, the affinity with which the antibody according to the invention bind to CD3 may be determined by biolayer interferometry as provided in Example 9 herein.

Antibodies binding CD3, in particular human CD3, with reduced affinity are provided in WO 2017/009442, and it is to be understood that any of these antibodies may serve as the basis for generating antibodies according to the present invention which in addition to the ability to bind 5T4 also have the ability to bind CD3 with reduced affinity. Hence, in further embodiments, the antibody according to the invention is an antibody, wherein
the antigen binding region that binds to CD3 comprises a heavy chain variable (VH) region comprising a CDR1 sequence, a CDR2 sequence and a CDR3 sequence,
the heavy chain variable (VH) region, when compared to a heavy chain variable (VH) region comprising the sequence set forth in SEQ ID NO: 57, has an amino acid substitution in one of the CDR sequences, the substitution being at a position selected from the group consisting of: T31, N57, H101, G105, S110 and Y114, the positions being numbered according to the sequence of SEQ ID NO: 57; and the wild type light chain variable (VL) region comprises the CDR1, CDR2 and CDR3 sequences set forth in SEQ ID NOs: 58, GTN and SEQ ID NO: 59, respectively.

It is preferred that the CDR1, CDR2 and CDR3 sequences of the heavy chain variable (VH) region of the antigen binding region that binds to CD3 comprise, in total, at the most 1, 2, 3, 4 or 5 amino acid substitutions, when compared to the sequence set forth in SEQ ID NO: 57.

The amino acid sequences of the CDR1, CDR2 and CDR3 of the heavy chain variable (VH) region of the antigen binding region that binds to CD3 may have at least 95% sequence identity, such as at least 96% sequence identity, at least 97% sequence identity, at least 98% sequence identity or at least 99% sequence identity to the amino acid sequences of the CDR1, CDR2 and CDR3 of the wild type heavy chain variable (VH) region, sequence identity being calculated based on an aligning an amino acid sequence consisting of the sequences of the CDR1, CDR2 and CDR3 of the heavy chain variable (VH) region of the antigen binding region that binds to CD3 with an amino acid sequence comprising the sequences of the CDR1, CDR2 and CDR3 of the wild type heavy chain variable (VH) region.

In particular, the antigen binding region that binds to CD3 may comprise a mutation selected from the group consisting of: T31M, T31P, N57E, H101G, H101N, G105P, S110A, S110G, Y114M, Y114R, Y114V, the positions being numbered according to the reference sequence of SEQ ID NO: 57.

In certain embodiments, the antibody according to the invention is an antibody, wherein when said antibody is a bispecific antibody, which is devoid of, or has reduced Fc-mediated effector function ("inert" antibody), and comprises an antigen binding region of an antibody that binds to CD3, then the antibody:
a) is capable of mediating concentration-dependent cytotoxicity of SK-OV-3 cells, when using purified peripheral blood mononuclear cells (PBMCs) or T cells as effector cells e.g. when assayed as described in Example 14 herein,
b) is capable of mediating concentration-dependent cytotoxicity of MDA-MB-231 cells, when using purified T cells as effector cells e.g. when assayed as described in Example 13 herein,
c) is capable of activating T cells in vitro in the presence of MDA-MB-231 tumor cells; e.g. when assayed as described in Example 13 (II) herein
d) is capable of activating T-cells in vitro in the presence of BxPC-3, PANC-1, Ca Ski and/or SiHa tumor cells; e.g. when assayed as described in Example 17 herein,
e) is capable of inducing cytotoxicity of BxPC-3, PANC-1, Ca Ski and/or SiHa tumor cells when using purified T cells as effector cells e.g. when assayed as described in Example 17 herein; and/or
f) shows anti-tumor activity, such as inhibition of tumor growth or delayed tumor outgrowth, in a humanized immune hematopoietic stem cell reconstitution mouse xenograft model, such as NOD.Cg-Prkdc$^{scid}$ Il2rg$^{tm1Wjl}$/SzJ inoculated with human MDA-MB-231 tumor cells; e.g. when determined as described in Example 15; and Further, the antibody according to the invention is an antibody that, when assessed by flow cytometry or ELISA, does not bind leukocyte FcγRs, and does not induce CD3-antibody dependent, FcγR-mediated CD3-crosslinking in absence of target (5T4)-specific tumor cells by binding to C1q.

A more detailed disclosure of antibodies with reduced or no Fc-mediated effector function ("inert" antibodies) can be found herein below.

The ability of the antibody to mediate concentration-dependent cytotoxicity of SK-OV-3 cells is determined in an in vitro cytotoxicity assay comprising the steps of:
i) isolating PBMCs or T cells from healthy human donor buffy coats,
ii) providing
a first set of samples, wherein each sample comprises PBMCs and human ovary adenocarcinoma SK-OV-3 cells, and wherein the ratios PBMCs:SK-OV-3 cells in said samples are 1:2, 1:1, 2:1, 4:1, 8:1, and 12:1; and
a second set of samples, wherein each sample comprises T cells and human ovary adenocarcinoma SK-OV-3 cells and wherein the ratios of T cells:SK-OV-3 cells in said samples are 1:2, 1:1, 2:1, 4:1 and 8:1
iii) adding the antibody to each set of samples at concentrations ranging from 0.0128 ng/mL to 1000 ng/mL and incubating the samples for 72 hours at 37° C.; and then
iv) assessing the viability of the SK-OV-3 cells using Resazurin (7-Hydroxy-3H-phenoxazin-3-one 10-oxide).

The ability to activate T cells in vitro in the presence of MDA-MB-231 tumor cells may be determined in an assay comprising the steps of:
i) Isolating T cells from healthy human donor buffy coats,
ii) Providing a set of samples, wherein each sample comprises T-cells and human breast adenocarcinoma MDA-MB-231 cells and wherein the ratio of T-cells:MDA-MB-231 cells in said samples is 8:1,
iii) adding the antibody to the set of samples at concentrations ranging from 0.0128 ng/mL to 1000 ng/mL and incubating the samples for 72 h at 37° C.,
iv) staining the T cells with fluorescent-labeled antibodies against T-cell activation markers, such as CD69-APC, CD25-PE-Cy7 and CD279/PD 1-BV 604 antibodies, by incubation with said antibodies for 30 min at 4° C.; and
v) analyzing the T cells by flow cytometry.

APC anti-human CD69 (CD69-APC) antibodies are commercially available, for instance from BioLegend (Cat. #s 310909 and 310910). CD25 Monoclonal Antibody, PE-Cyanine7 (CD25-PE-Cy7) is also commercially available, for instance from ThermoFisher Scientific (Cat. #25-0259-42) and from BD Biosciences (Cat. #557741). Finally, CD279/PD 1-BV 604 antibodies may be obtained commercially from Genscript (Cat. #A01828).

The activation of T cells in vitro in the presence of BxPC-3, PANC-1, Ca Ski and/or SiHa tumor cells may be determined in an procedure comprising the steps of:
i) Providing T cells isolated from healthy human donor buffy coats,
ii) Providing a set of samples, wherein each sample comprises said T cells and BxPC-3, PANC-1, Ca Ski or SiHa tumor cells and wherein the ratio of T cells:tumor cells in said samples is 4:1,
iii) adding the antibody to the set of samples at concentrations ranging from 0.0128 ng/mL to 5000 ng/mL (such as 5-fold dilutions) and incubating the samples for 72 hours at 37° C., iv) collecting from each sample 110 μL supernatant containing T cells and staining the T cells with fluorescent-labeled antibodies against T-cell markers, such as CD3-eFluor450, CD4-APC-eFluor780, DC8-AF700, and with antibodies against T-cell markers, such as 69-APC, CD25-PE-Cy7 and CD279/PD1-BV604 antibodies, by incubation with said antibodies for 30 minutes at 4° C.; and v) analyzing the samples by flow cytometry.

The ability to induce cytotoxicity of BxPC-3, PANC-1, Ca Ski and/or SiHa tumor cells may be determined in a procedure comprising the steps of i) Providing T cells isolated from healthy human donor buffy coats, ii) Providing a set of test samples and control samples, wherein each sample comprises said T-cells and BxPC-3, PANC-1, Ca Ski or SiHa tumor cells which have been allowed to adhere to the bottom of a 96-well tissue culture plate and wherein the ratio of T-cells: tumor cells in said samples is 4:1, iii) adding the antibody to the set of test samples at concentrations ranging from 0.0128 ng/mL to 5000 ng/mL (such as 5-fold dilutions), while the control samples remain untreated or are incubated with 5 μM staurosporin, and incubating all samples for 72 hours at 37° C., iv) Incubating the adherent cells in 10% (w/w) 7-hydroxy-3H-phenoxazin-3-one 10-oxide (Resazurin) in RPMI-1640 medium supplemented with 10% (w/w) donor bovine serum with iron and penicillin/streptomycin at 37° C. for 4 hours, v) Measuring the absorbance of the cells; setting the absorbance of the cells incubated with staurosporin as 0% viability and the untreated cells as 100% viability and calculating the percentage viable cells as $$x100\ \%\ \text{viable cells} = \left( \frac{[\text{absorbance sample} - \text{absorbance staurosporine treated cells}]}{[\text{absorbance untreated cells} - \text{absorbance staurosporine treated cells}]} \right)$$

The antibody of the invention may in particular be an antibody, wherein the antigen-binding region capable of binding to CD3 comprises:

a) a heavy chain variable region (VH) comprising CDR1, CDR2, and CDR3 having the sequences as set forth in SEQ ID NOs: 61, 55, and 56 [VH CDR1-T31P+Wild type VH CDRs 2, 3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], or b) a heavy chain variable region (VH) comprising CDR1, CDR2, and CDR3 having the sequences as set forth in SEQ ID NOs: 63, 55, and 56 [VH CDR1-T31M+Wild type VH CDRs 2, 3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively, or c) a heavy chain variable region (VH) comprising CDR1, CDR2, and CDR3 having the sequences as set forth in SEQ ID NOs: 54, 65, and 56 [VH CDR-N57E+Wild type VH CDRs 1, 3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively, or d) a heavy chain variable region (VH) comprising CDR1, CDR2, and CDR3 having the sequences as set forth in SEQ ID NOs: 54, 55, and 67 [Wild type VH CDRs 1, 2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

e) a heavy chain variable region (VH) comprising CDR1, CDR2, and CDR3 having the sequences as set forth in SEQ ID NOs: 54, 55, and 69 [Wild type VH CDRs 1, 2+VH CDR3-H101N], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively;

f) a heavy chain variable region (VH) comprising CDR1, CDR2, and CDR3 having the sequences as set forth in SEQ ID NOs: 54, 55, and 71 [Wild type VH CDRs 1, 2+VH CDR3-G105P], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively;

g) a heavy chain variable region (VH) comprising CDR1, CDR2, and CDR3 having the sequences as set forth in SEQ ID NOs: 54, 55, and 73 [Wild type VH CDRs 1, 2+VH CDR3-S110A], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively, or h) a heavy chain variable region (VH) comprising CDR1, CDR2, and CDR3 having the sequences as set forth in SEQ ID NOs: 54, 55, and 75 [Wild type VH CDRs 1, 2+VH CDR3-S110G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively, i) a heavy chain variable region (VH) comprising CDR1, CDR2, and CDR3 having the sequences as set forth in SEQ ID NOs: 54, 55, and 77 [Wild type VH CDRs 1, 2+VH CDR3-Y114V], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively, or j) a heavy chain variable region (VH) comprising CDR1, CDR2, and CDR3 having the sequences as set forth in SEQ ID NOs: 54, 55, and 79 [Wild type VH CDRs 1, 2+VH CDR3-Y114M], respectively, and a light chain variable region (VL) comprising CDR1, CDR2, and CDR3 having the sequences as set forth in SEQ ID NO:

58, the sequence GTN, and the sequence as set forth in SEQ ID NO: 59, respectively [Wild type VL CDRs 1, 2, 3], respectively, or k) a heavy chain variable region (VH) comprising CDR1, CDR2, and CDR3 having the sequences as set forth in SEQ ID NOs: 54, 55, and 81 [Wild type VH CDRs 1, 2+VH CDR3-Y114R], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

In certain embodiments, the antigen-binding region capable of binding to CD3 a heavy chain variable region (VH) comprising CDR1, CDR2, and CDR3 having the sequences as set forth in SEQ ID NOs: 54, 55, and 67 [Wild type VH CDRs 1, 2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

Further, the present invention provides an antibody as defined above, wherein
the antigen-binding region capable of binding to 5T4 comprises a heavy chain variable region (VH) comprising CDR1, CDR2, and CDR3 sequences of SEQ ID NOs.: 6, 7 and 8, respectively, and a light chain variable region (VL) comprising the CDR1, CDR2, and CDR3 sequences of SEQ ID NO: 10, AAS and SEQ ID NO: 11, respectively [059];
and
the antigen-binding region capable of binding to CD3 comprises a heavy chain variable region (VH) comprising CDR1, CDR2, and CDR3 having the sequences as set forth in SEQ ID NOs: 54, 55, and 67 [Wild type VH CDRs 1, 2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

Also, the invention provides an antibody as defined above, wherein
the antigen-binding region capable of binding to 5T4 comprises a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and 46, respectively [207];
and
the antigen-binding region capable of binding to CD3 comprises a heavy chain variable region (VH) comprising CDR1, CDR2, and CDR3 having the sequences as set forth in SEQ ID NOs: 54, 55, and 67 [Wild type VH CDRs 1, 2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

Further, the invention provides an antibody as defined above, wherein
the antigen-binding region capable of binding to 5T4 comprises a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and 53, respectively [226];
and
the antigen-binding region capable of binding to CD3 comprises a heavy chain variable region (VH) comprising CDR1, CDR2, and CDR3 having the sequences as set forth in SEQ ID NOs: 54, 55, and 67 [Wild type VH CDRs 1, 2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1, 2, 3], respectively.

In the antibody according to the invention, the antigen-binding region capable of binding to human CD3 may comprise a VH sequence and a VL sequence selected from the group consisting of:
a) a VH sequence as set forth in SEQ ID NO: 62 [VH T31P] and a VL sequence as set forth in SEQ ID NO: 60,
b) a VH sequence as set forth in SEQ ID NO: 64 [VH T31M] and a VL sequence as set forth in SEQ ID NO: 60,
c) a VH sequence as set forth in SEQ ID NO: 66 [VH N57E] and a VL sequence as set forth in SEQ ID NO: 60,
d) a VH sequence as set forth in SEQ ID NO: 68 [VH H101G] and a VL sequence as set forth in SEQ ID NO: 60,
e) a VH sequence as set forth in SEQ ID NO: 70 [VH H101N] and a VL sequence as set forth in SEQ ID NO: 60,
f) a VH sequence as set forth in SEQ ID NO: 72 [VH G105P] and a VL sequence as set forth in SEQ ID NO: 60,
g) a VH sequence as set forth in SEQ ID NO: 74 [VH S110A] and a VL sequence as set forth in SEQ ID NO: 60,
h) a VH sequence as set forth in SEQ ID NO: 76 [VH S110G] and a VL sequence as set forth in SEQ ID NO: 60,
i) a VH sequence as set forth in SEQ ID NO: 78 [VH Y114V] and a VL sequence as set forth in SEQ ID NO: 60,
j) a VH sequence as set forth in SEQ ID NO: 80 [VH Y114M] and a VL sequence as set forth in SEQ ID NO: 60; and
k) a VH sequence as set forth in SEQ ID NO: 82 [VH Y114R] and a VL sequence as set forth in SEQ ID NO: 60.

In particular, the antibody according to the invention may be an antibody, wherein the antigen-binding region capable of binding to human CD3 comprises a VH sequence as set forth in SEQ ID NO: 68 [VH H101G] and a VL sequence as set forth in SEQ ID NO: 60.

In some embodiments, the antibody according to the invention is one, wherein
the antigen-binding region capable of binding to 5T4 comprises a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059];

and
the antigen-binding region capable of binding to human CD3 comprises a VH sequence as set forth in SEQ ID NO: 68 [VH H101G] and a VL sequence as set forth in SEQ ID NO: 60.

In other embodiments, the antibody according to the invention is one, wherein
the antigen-binding region capable of binding to 5T4 comprises a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207];
and
the antigen-binding region capable of binding to human CD3 comprises a VH sequence as set forth in SEQ ID NO: 68 [VH H101G] and a VL sequence as set forth in SEQ ID NO: 60.

In still other embodiments, the antibody according to the invention is one, wherein
the antigen-binding region capable of binding to 5T4 comprises a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226];
and
the antigen-binding region capable of binding to human CD3 comprises a VH sequence as set forth in SEQ ID NO: 68 [VH H101G] and a VL sequence as set forth in SEQ ID NO: 60.

As will be well-known to the skilled person, each antigen-binding region of an antibody generally comprises a heavy chain variable region (VH) and a light chain variable region (VL), and each of the variable regions comprises three CDR sequences, CDR1, CDR2 and CDR3, respectively, and four framework sequences, FR1, FR2, FR3 and FR4, respectively. This structure may also be found in the antibodies according to the present invention. Further, the antibodies according to the invention may comprise two heavy chain constant regions (CH), and two light chain constant regions (CL).

In particular embodiments, the antibody according to the invention comprises a first and a second heavy chain, such as a first and second heavy chain each comprising at least a hinge region, a CH2 and CH3 region. Stable, heterodimeric antibodies can be obtained at high yield for instance by so-called Fab-arm exchange as provided in WO 2008/119353 and WO 2011/131746, on the basis of two homodimeric starting proteins containing only a few, asymmetrical mutations in the CH3 regions. Hence, in some embodiments of the invention, the antibody a first heavy chain wherein at least one of the amino acids at the positions corresponding to positions selected from the group consisting of T366, L368, K370, D399, F405, Y407 and K409 in a human IgG1 heavy chain has been substituted, and a second heavy chain wherein at least one of the amino acids in the positions corresponding to a position selected from the group consisting of T366, L368, K370, D399, F405, Y407, and K409 in a human IgG1 heavy chain has been substituted, wherein said substitutions of said first and said second heavy chains are not in the same positions, and wherein the amino acid positions are numbered according to EU numbering.

In particular embodiments, the invention provides an antibody, wherein the amino acid in the position corresponding to K409 in a human IgG1 heavy chain is R in said first heavy chain, and the amino acid in the position corresponding to F405 in a human IgG1 heavy chain is L in said second heavy chain, or vice versa.

In some embodiments, the antibody according to the present invention comprises, in addition to the antigen-binding regions, an Fc region consisting of the Fc sequences of the two heavy chains. The first and second Fc sequence may each be of any isotype, including any human isotype, such as an IgG1, IgG2, IgG3, IgG4, IgE, IgD, IgM, or IgA isotype or a mixed isotype. Preferably, the Fc region is a human IgG1, IgG2, IgG3, IgG4 isotype or a mixed isotype, such as a human IgG1 isotype.

Antibodies according to the present invention may comprise modifications in the Fc region to render the antibody an inert, or non-activating, antibody. Hence, in the antibodies disclosed herein, one or both heavy chains may be modified so that the antibody induces Fc-mediated effector function to a lesser extent relative to an antibody which is identical, except for comprising non-modified first and second heavy chains. The Fc-mediated effector function may be measured by determining Fc-mediated CD69 expression on T cells (i.e. CD69 expression as a result of CD3 antibody-mediated, Fcγ receptor-dependent CD3 crosslinking), by binding to Fcγ receptors, by binding to C1q, or by induction of Fc-mediated cross-linking of FcγRs. In particular, the heavy chain constant sequences may be modified so that the Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. as described in Example 3 of WO2015001085. Modifications of the heavy and light chain constant sequences may also result in reduced binding of C1q to said antibody. As compared to an unmodified antibody the reduction may be by at least 70%, at least 80%, at least 90%, at least 95%, at least 97%, or 100% and the C1q binding may be determined by ELISA. Further, the Fc region which may be modified so that said antibody mediates reduced Fc-mediated T-cell proliferation compared to an unmodified antibody by at least 50%, at least 60%, at least 70%, at least 80%, at least 90%, at least 99% or 100%, wherein said T-cell proliferation is measured in a PBMC-based functional assay.

Examples of amino acid positions that may be modified, e.g. in an IgG1 isotype antibody, include positions L234 and L235. Hence, the antibody according to the invention may comprises a first and a second heavy chain, and wherein in both the first and the second heavy chain, the amino acid residues at the positions corresponding to positions L234 and L235 in a human IgG1 heavy chain according to EU numbering are F and E, respectively.

In addition, a D265A amino acid substitution can decrease binding to all Fcγ receptors and prevent ADCC (Shields et al., 2001, J. Biol. Chem. (276):6591-604). Therefore, the antibody according to the invention may comprise a first and a second heavy chain, wherein in both the first and the second heavy chain, the amino acid residue at the position corresponding to position D265 in a human IgG1 heavy chain according to EU numbering is A. Further embodiments of the invention provide antibodies wherein, in at least one, such as in both, of said first and second heavy chains the amino acids in the positions corresponding to positions L234, L235, and D265 in a human IgG1 heavy chain, are F, E, and A, respectively. In the present application antibodies, which have the combination of three amino acid substitutions L234F, L235E and D265A and in addition the K409R or the F405L mutation disclosed herein above are termed with the suffix "FEAR" or "FEAL", respectively.

The amino acid sequence of the wild type IgG1 heavy chain constant region is identified herein as SEQ ID NO: 89. Consistent with the embodiments disclosed above, the antibody of the invention may comprise an IgG1 heavy chain constant region carrying the F405L substitution and having the amino acid sequence set forth in SEQ ID NO: 90 and/or an IgG1 heavy chain constant region carrying the K409R substitution and having the amino acid sequence set forth in SEQ ID NO: 94.

The amino acid sequence of an IgG1 heavy chain constant region carrying the L234F, L235E and D265A substitutions is identified herein as SEQ ID NO: 91. The amino acid sequence of an IgG1 heavy chain constant region carrying the L234F, L235E, D265A and F405L substitutions is identified herein as SEQ ID NO: 92. The amino acid sequence of an IgG1 heavy chain constant region carrying the L234F, L235E, D265A and K409R substitutions is identified herein as SEQ ID NO: 93.

The present invention further provides an antibody, wherein
a) the antigen-binding region(s) capable of binding to 5T4 is/are humanized, and/or
b) the antigen-binding region capable of binding to CD3, if present, is humanized.

Also, the invention provides an antibody, wherein
a) the antigen-binding region(s) capable of binding to 5T4 is/are human, and/or
b) the antigen-binding region capable of binding to CD3, if present, is human.

Further, the invention provides an antibody, wherein
a) the antigen-binding region(s) capable of binding to 5T4 is/are chimeric, and/or
b) the antigen-binding region capable of binding to CD3, if present, is chimeric.

In some embodiments of the invention, the antibody comprises a kappa (κ) light chain. The sequence of in particular embodiments of the invention concerning bispecific antibodies, the kappa light chain comprises the CDR1, -2 and -3 sequences of a 5T4 antibody light chain as disclosed above.

In further embodiments of the invention, the antibody according to any one of the preceding claims, wherein said antibody comprises a lambda (λ) light chain. In particular embodiments of the invention concerning bispecific antibodies, the lambda light chain comprises the CDR1, -2 and -3 sequences of a CD3 antibody light chain as disclosed above, in particular a the CDR1, -2 and -3 sequences of a CD3 antibody having reduced affinity for CD3 as disclosed above. The amino acid sequence of a kappa light chain constant region is included herein as SEQ ID NO: 95 and the amino acid sequence of a lambda light chain constant region is included herein as SEQ ID NO: 96.

In particular embodiments, the antibody comprises a lambda (λ) light chain and a kappa (κ) light chain; e.g. an antibody with a heavy chain and a lambda light chain which comprise the binding region capable of binding to CD3, and a heavy chain and a kappa light chain which comprise the binding region capable of binding to 5T4.

Immunoconjugates

In another aspect, the invention provides an immunoconjugate or antibody-drug conjugate (ADC) comprising the antibody defined above, and a therapeutic moiety, such as a cytotoxic agent, a chemotherapeutic drug, a cytokine, an immunosuppressant, antibiotic, or a radioisotope. In general, the skilled person will have at his disposition numerous cytotoxic agents, chemotherapeutic drugs, cytokines, immunosuppressants, antibiotics and radioisotopes, the optimal choice of therapeutic moiety depending on the desired application of the immunoconjugate. For certain applications the preferred cytotoxic agent may be a microtubule-disrupting agent, such as a duostatin, e.g. Duostatin-3.

Nucleic Acid Constructs

A further aspect of the invention provides nucleic acid construct comprising
a) a nucleic acid sequence encoding a heavy chain sequence of an antibody comprising an antigen-binding region capable of binding to 5T4 as defined herein before, and/or
b) a nucleic acid sequence encoding a light chain sequence of an antibody comprising an antigen-binding region capable of binding to 5T4 as defined herein before.

The nucleic acid construct may further comprise
a) a nucleic acid sequence encoding a heavy chain sequence of an antibody comprising an antigen-binding region capable of binding to CD3 as defined herein before; and/or
b) a nucleic acid sequence encoding a light chain sequence of an antibody comprising an antigen-binding region capable of binding to CD3 as defined herein before.

Expression Vectors

Another aspect of the invention provides an expression vector comprising nucleic acid sequences encoding heavy and/or light chain sequences of an antibody according to the invention. In particular, the expression vector may comprise:
a) a nucleic acid sequence encoding a heavy chain sequence of an antibody comprising an antigen-binding region capable of binding to 5T4 as defined herein before, and/or
b) a nucleic acid sequence encoding a light chain sequence of an antibody comprising an antigen-binding region capable of binding to 5T4 as defined herein before.

The expression vector may further comprise:
a) a nucleic acid sequence encoding a heavy chain sequence of an antibody comprising an antigen-binding region capable of binding to CD3 as defined herein before; and/or
b) a nucleic acid sequence encoding a light chain sequence of an antibody comprising an antigen-binding region capable of binding to CD3 as defined herein before.

In a further embodiment, the expression vector further comprises a nucleic acid sequence encoding the constant region of a light chain, a heavy chain or both light and heavy chains of an antibody, e.g. a human IgG1,κ monoclonal antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-5T4 antibody-encoding nucleic acid is comprised in a naked DNA or RNA vector, including, for example, a linear expression element (as described in for instance Sykes and Johnston, Nat Biotech 17 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaP04-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the anti-5T4 antibody in a bacterial cell. Examples of such vectors include expression vectors such as BlueScript (Stratagene), pIN vectors Van Heeke & Schuster, J Biol Chem 264, 5503 5509 (1989), pET vectors (Novagen, Madison WI) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

A nucleic acid construct and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like.

In an expression vector of the invention, anti-5T4 antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-5T4-antibody-encoding expression vector may be positioned in and/or delivered to a host cell or host animal via a viral vector.

Cells and Host Cells

In a further aspect, the invention provides a cell comprising a nucleic acid construct as defined herein above, or an expression vector as defined herein above. It is to be understood that the cell may have been obtained by transfecting a host cell with said nucleic acid construct or expression vector, such as a recombinant host cell.

The host cell may be of human origin, such as a human embryonic kidney (HEK) cell, such as a HEK/Expi cell. Alternatively, it may be of rodent origin, such as a Chinese hamster ovary cell, such as a CHO/N50 cell. Further, the host cell may be of bacterial origin.

The cell may comprise a nucleic acid sequence encoding an antibody of the invention or parts thereof stably integrated into the cellular genome. Alternatively, the cell may comprise a non-integrated nucleic acid, such as a plasmid, cosmid, phagemid, or linear expression element, which comprises a sequence coding for expression of an anti-5T4 antibody of the invention or a part thereof. In particular, the host cell may comprise a non-integrated nucleic acid, such as a plasmid, cosmid, phagemid, or linear expression element, which comprises a sequence coding for expression of an anti-5T4 antibody or a part thereof.

Compositions

A still further aspect of the invention provides a composition comprising an antibody; e.g. a bispecific antibody or an immunoconjugate as defined in the above. The composition may be a pharmaceutical composition comprising the antibody, bispecific antibody or immunoconjugate and a pharmaceutically acceptable carrier.

The pharmaceutical compositions may be formulated with the carrier, excipient and/or diluent as well as any other components suitable for pharmaceutical compositions, including known adjuvants, in accordance with conventional techniques such as those disclosed in Remington: The Science and Practice of Pharmacy, 19th Edition, Gennaro, Ed., Mack Publishing Co., Easton, PA, 1995. The pharmaceutically acceptable carriers or diluents as well as any known adjuvants and excipients should be suitable for the antibody or antibody conjugate of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact [10% or less relative inhibition, 5% or less relative inhibition, etc.] upon antigen binding).

A pharmaceutical composition of the present invention may include diluents, fillers, salts, buffers, detergents (e. g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho esters, and polylactic acid alone or with a wax, or other materials well known in the art. Methods for the preparation of such formulations are generally known to those skilled in the art, see e.g. Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except in so far as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one antibody, bispecific antibody or antibody-drug conjugate (ADC) of the present invention, a combination of an antibody, a bispecific antibody or ADC according to the invention with another therapeutic compound, or a combination of compounds of the present invention.

The pharmaceutical composition may be administered by any suitable route and mode. Suitable routes of administering a compound of the present invention in vivo and in vitro are well known in the art and may be selected by those of ordinary skill in the art.

In one embodiment, the pharmaceutical composition of the present invention is administered parenterally; i.e. by a mode of administration other than enteral and topical administration; usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion. In particular, the pharmaceutical composition of the present invention may be administered by intravenous or subcutaneous injection or infusion.

Uses and Therapeutical Applications

The present invention further provides an antibody, such as a bispecific antibody, or an immunoconjugate or antibody-drug conjugate (ADC) as defined herein for use as a medicament. The anti-5T4 antibodies or immunoconjugates of the present invention can be used in the treatment or prevention of a disease or disorder involving cells expressing 5T4. In particular, the bispecific antibodies according to the invention; i.e. antibodies which comprise antigen binding regions capable of binding 5T4 and CD3 may be useful in therapeutic settings in which specific targeting and T cell-mediated killing of cells that express 5T4 is desired, and they may be more efficient compared to a regular anti-5T4 antibody in certain such indications and settings.

In one embodiment, the antibody, such as the bispecific antibody, or immunoconjugate or antibody-drug conjugate (ADC) of the present invention is disclosed herein for use in the treatment of cancer. The antibody, such as the bispecific antibody, or the immunoconjugate or antibody-drug conjugate (ADC) may in particular be use in treatment of a cancer, wherein the cancer is characterized by expression of 5T4 in at least some of the tumor cells.

The cancer may in particular be selected from the group consisting of kidney/renal cancer, breast cancer, colorectal cancer, prostate cancer, ovarian cancer, bladder cancer, uterine/endometrial/cervical cancer, lung cancer, gastro-intestinal cancer, stomach cancer, pancreatic cancer, thyroid cancer, head and neck cancer, lymphoma, acute myeloid leukemia.

Additionally, the invention relates to the use of an antibody according to the invention for the manufacture of a medicament, such as a medicament for the treatment of cancer, e.g. a cancer selected from the group consisting of kidney/renal cancer, breast cancer, colorectal cancer, prostate cancer, ovarian cancer, bladder cancer, uterine/endometrial/cervical cancer, lung cancer, gastro-intestinal cancer, stomach cancer, pancreatic cancer, thyroid cancer, head and neck cancer, lymphoma, acute myeloid leukemia.

In a further aspect, the invention provides method of treating a disease, the method comprising administering an antibody, an immunoconjugate, a composition, such as a pharmaceutical composition or antibody-drug conjugate (ADC) according to the invention to a subject in need thereof.

In particular embodiments of the invention, said method is for treatment of a cancer. The method of the invention may in particular comprise the steps of:
a) selecting a subject suffering from a cancer comprising tumor cells expressing 5T4 and/or a cancer known to express 5T4; and
b) administering to the subject the antibody, such as the bispecific antibody, the pharmaceutical composition or the antibody-drug conjugate (ADC) of the present invention.

The cancer may in particular be selected from the group consisting of kidney/renal cancer, breast cancer, colorectal cancer, prostate cancer, ovarian cancer, bladder cancer, uterine/endometrial/cervical cancer, lung cancer, gastro-intestinal cancer, stomach cancer, pancreatic cancer, thyroid cancer, head and neck cancer, lymphoma, acute myeloid leukemia.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the antibodies depend on the disease or condition to be treated and may be determined by the persons skilled in the art. An exemplary, non-limiting range for a therapeutically effective amount of a compound of the present invention is about 0.001-10 mg/kg, such as about 0.001-5 mg/kg, for example 0.001-2 mg/kg, such as about 0.001-1 mg/kg, for instance about 0.001, about 0.01, about 0.1, about 1 or about 10 mg/kg. Another exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician having ordinary skill in the art may readily determine and prescribe the effective amount of the pharmaceutical composition required. For example, the physician or veterinarian could start doses of the antibody employed in the pharmaceutical composition at levels lower than that required to achieve the desired therapeutic effect and gradually increase the dosage until the desired effect is achieved. In general, a suitable daily dose of an antibody of the present invention will be that amount of the compound which is the lowest dose effective to produce a therapeutic effect. Administration may e.g. be parenteral, such as intravenous, intramuscular or subcutaneous. In one embodiment, the antibodies may be administered by infusion in a weekly dosage of calculated by mg/m2. Such dosages can, for example, be based on the mg/kg dosages provided above according to the following: dose (mg/kg)×70:1.8. Such administration may be repeated, e.g., 1 to 8 times, such as 3 to 5 times. The administration may be performed by continuous infusion over a period of from 2 to 24 hours, such as from 2 to 12 hours. In one embodiment, the antibodies may be administered by slow continuous infusion over a long period, such as more than 24 hours, to reduce toxic side effects.

In one embodiment, the antibodies may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of antibody of the present invention in the blood upon administration by for instance taking out a biological sample and using anti-idiotypic antibodies which target the 5T4 antigen antigen-binding region of the antibodies of the present invention.

In one embodiment, the antibodies may be administered as maintenance therapy, such as, e.g., once a week for a period of 6 months or more.

An antibody may also be administered prophylactically to reduce the risk of developing cancer, delay the onset of the occurrence of an event in cancer progression, and/or reduce the risk of recurrence when a cancer is in remission.

The antibodies of the invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agent.

Antibody Production

Also provided herein is a method for producing the antibody, such as the bispecific antibody of the invention. In particular, there is provided a method for producing the antibody of the invention, comprising the steps of
a) culturing a host cell comprising an expression vector as defined herein; and
b) and purifying said antibody from the culture medium.

In embodiments of the invention, wherein the antibody comprises a binding region capable of binding to 5T4 and a binding region capable of binding to CD3, the antibody may be produced using a method comprising the steps of
a) Providing an antibody capable of binding to 5T4 by culturing a host cell comprising an expression vector as defined herein under conditions allowing expression of the antibody capable of binding to 5T4, and purifying the antibody capable of binding to 5T4 from the culture medium;
b) Providing an antibody capable of binding to CD3 by culturing a host cell comprising an expression vector comprising
  I) a nucleic acid sequence encoding a heavy chain sequence of an antibody comprising an antigen-binding region capable of binding to CD3 as defined herein above; and
  II) a nucleic acid sequence encoding a light chain sequence of an antibody comprising an antigen-binding region capable of binding to CD3 as defined herein above;
under conditions allowing expression of the antibody capable of binding to CD3, and purifying the antibody capable of binding to CD3 from the culture medium;
c) incubating said antibody capable of binding to 5T4 together with said antibody capable of binding to CD3 under reducing conditions sufficient to allow cysteines in the hinge region to undergo disulfide-bond isomerization, and
d) obtaining said antibody.

Kits

The invention further provides a kit-of-parts comprising an antibody as disclosed above, such as a kit for use as a companion diagnostic/for identifying within a population of patients, those patients which have a propensity to respond to treatment with an antibody as defined herein above or an immunoconjugate or antibody-drug conjugate (ADC) as defined herein above, or for predicting efficacy or anti-tumor activity of said antibody or immunoconjugate or ADC when used in treatment of a patient, the kit comprising an antibody as defined above; and instructions for use of said kit.

Anti-Idiotypic Antibodies

In a further aspect, the invention relates to an anti-idiotypic antibody which binds to an antibody comprising at least one antigen-binding region capable of binding to 5T4, i.e. an antibody according to the invention as described herein. In particular embodiments, the anti-idiotypic antibody binds to the antigen-binding region capable of binding to 5T4.

An anti-idiotypic (Id) antibody is an antibody which recognizes unique determinants generally associated with the antigen-binding site of an antibody. An anti-Id antibody may be prepared by immunizing an animal of the same species and genetic type as the source of an anti-5T4 monoclonal antibody with the monoclonal antibody against which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to 5T4-specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parental anti-5T4 antibody.

| SEQ ID NO: | Name | Domain | Sequence |
|---|---|---|---|
| 1 | Human 5T4 | ORF | MPGGCSRGPAAGDGR LRLARLALVLLGWVS SSSPTSSASSFSSSA PFLASAVSAQPPLPD QCPALCECSEAARTV KCVNRNLTEVPTDLP AYVRNLFLTGNQLAV LPAGAFARRPPLAEL AALNLSGSRLDEVRA GAFEHLPSLRQLDLS HNPLADLSPFAFSGS NASVSAPSPLVELIL NHIVPPEDERQNRSF EGMVVAALLAGRALQ GLRRLELASNHFLYL PRDVLAQLPSLRHLD LSNNSLVSLTYVSFR NLTHLESLHLEDNAL KVLHNGTLAELQGLP HIRVFLDNNPWVCDC HMADMVTWLKETEVV QGKDRLTCAYPEKMR NRVLLELNSADLDCD PILPPSLQTSYVFLG IVLALIGAIFLLVLY LNRKGIKKWMHNIRD ACRDHMEGYHYRYEI NADPRLTNLSSNSDV |
| 2 | Cynomolgus monkey 5T4 | ORF | MPGGCSRGPAAGDGR LRLARLALVLLGWVS SSSSTSSASSSSSSA PFLASAASAQPPLPD QCPALCECSEAARTV KCVNRNLTEVPTDLP LYVRNLFLTGNQLAV LPAGAFARRPPLAEL AALNLSGSRLDEVRG GAFEHLPSLRQLDLS HNPLAYLSPFAFSGS NASISAPSPLVELIL NHIVPPDDKRQNRSF EGMVAAALVAGRALQ GLHLLELASNHFLYL PRDVLAQLPSLRYLD LSNNSLVSLTYVSFR NLTHLESLHLEDNAL KVLHNGTLAELQGLP HVRVFLDNNPWVCDC HMADMVTWLKQTGVV QGKDRLTCAFPEKMR |

| SEQ ID NO: | Name | Domain | Sequence |
|---|---|---|---|
|  |  |  | NRVLLELNSADLDCD PILPPSLQTSYVFLG IVLALIGAIFLLVLY LNRKGIKKWMHNIRD ACRDHMEGYHRYEI NADPRLTNLSSNSDV |
| 3 | Chicken 5T4 | ORF | MPGREAERRGALCLG LLLHALLGCGSAQPP AACPAPCECSEAAKT VKCVNKNLTEVPPDL PPYVRNLFITGNRLG RLPAGALSAPRLAEL GSLNLSGNHLRAVEA GALAALPALRQLDLG GNPLAELSPLAFGRA SPLEELALRGALREQ GALLGLADLLQAGAL RNLSRLELADNGLLL LPTGMLGALPALRHL DLSNNSLVGLRNVSF QGLVRLQSLNLSDNS LGVLRNGTLAQWRGL PALRRISLSHNTWVC DCAIEDMVAWLKESD QVEGKEALSCAFPEK MAGRALLKLNTSELN CSAPVDVPSQLQTSY VFLGIVLALIGAIFL LVLYLNRKGIKKWMH NIRDACRDHMEGYHY RYEINADPRLTNLSS NSDV |
| 4 | Mature Human CD3ε (epsilon) | Mature protein | QDGNEEMGGITQTPY KVSISGTTVILTCPQ YPGSEILWQHNDKNI GGDEDDKNIGSDEDH LSLKEFSELEQSGYY VCYPRGSKPEDANFY LYLRARVCENCMEMD VMSVATIVIVDICIT GGLLLLVYYWSKNRK AKAKPVTRGAGAGGR QRGQNKERPPPVPNP DYEPIRKGQRDLYSG LNQRRI |
| 5 | HC_5T4-059 | VH | QVQLVESGGGVVQPG RSLRLSCAVSGFTFS SYDMNWVRQAPGKGL EWVTFISYDGSNKYN ADSVKGRFTISRDNS KNTLYLQMNSLRAED TAVYYCARDSYSRSW YGDYYGMDVWGQGTT VTVSS |
| 6 | HC_5T4-059 | VH_CDR1 | GFTFSSYD |
| 7 | HC_5T4-059 | VH_CDR2 | ISYDGSNK |
| 8 | HC_5T4-059 | VH_CDR3 | ARDSYSRSWYGDYYG MDV |
| 9 | LC_5T4-059 | VL | DIQMTQSPSSLSASV GDRVTITCRASQGIS SWLAWYQQKPEKAPK SLIYAASSLQSGVPS RFSGSGSGTDFTLTI SSLQPEDFATYYCQQ YNSYPLTFGGGTKVE IK |
| 10 | LC_5T4-059 LC_5T4-059 | VL_CDR1 VL_CDR2 | QGISSW AAS |
| 11 | LC_5T4-059 | VL_CDR3 | QQYNSYPLT |
| 12 | HC_5T4-076 | VH | QVQLVQSGAEVKKPG ASVKVSCKASGYTFT SYGISWVRQAPGQGL EWMGWISAYNGNTNY AQKLQGRVTMTTDTS TRTAYMELRSLRSDD TAVYYCARDPGYFDW LYGDYWGQGTLVTVS S |
| 13 | HC_5T4-076 | VH_CDR1 | GYTFTSYG |
| 14 | HC_5T4-076 | VH_CDR2 | ISAYNGNT |
| 15 | HC_5T4-076 | VH_CDR3 | ARDPGYFDWLYGDY |
| 16 | LC_5T4-076 | VL | AIQLTQSPSSLSASV GDRVTITCRASQGIS SALAWYQQKPGKAPK LLIYDASSLESGVPS RFSGSGSGTDFTLTI SSLQPEDFATYYCQQ FNSYPRTFGQGTKVE IK |
| 17 | LC_5T4-076 LC_5T4-076 | VL_CDR1 VL_CDR2 | QGISSA DAS |
| 18 | LC_5T4-076 | VL_CDR3 | QQFNSYPRT |
| 19 | HC_5T4-085 | VH | EVQLLESGGGLVQPG GSLRLSCAASGFTFS SYAMSWVRQAPGKGL EWVSAISGSGGSTYN ADSVKGRFTIFRDNS KNTLYLHMNSLRAED TAVYYCARDPGYNNV EYLDHWGQGTLVTVS S |
| 20 | HC_5T4-085 | VH_CDR1 | GFTFSSYA |
| 21 | HC_5T4-085 | VH_CDR2 | ISGSGGST |
| 22 | HC_5T4-085 | VH_CDR3 | ARDPGYNNVEYLDH |
| 23 | LC_5T4-085 | VL | AIQLTQSPSSLSASV GDRVTITCRASQGIS SALAWYQQKPGKAPK LLIYDASSLESGVPS RFSGSGSGTDFTLTI SSLQPEDFATYYCQQ FNSYPLTFGGGTKVE IK |
| 24 | LC_5T4-085 LC_5T4-085 | VL_CDR1 VL_CDR2 | QGISSA DAS |
| 25 | LC_5T4-085 | VL_CDR3 | QQFNSYPLT |
| 26 | HC_5T4-106 | VH | EVQLVQSGAEVKKPG ESLKISCKGSGYRFT SYWIGWVRQMPGKGL EWMGIIYPGDSDARY SPSFQGQVTISADKS ISTAYLQWSSLKASD TGMYYCARSVLFDYW |

-continued

| SEQ ID NO: | Name | Domain | Sequence |
|---|---|---|---|
| | | | GQGTLVTVSS |
| 27 | HC_5T4-106 | VH_CDR1 | GYRFTSYW |
| 28 | HC_5T4-106 | VH_CDR2 | IYPGDSDA |
| 29 | HC_5T4-106 | VH_CDR3 | ARSVLFDY |
| 30 | LC_5T4-106 | VL | AIQLTQSPSSLSASV GDRVTITCRASQGIS SALAWYQQKPGKAPK LLIYDVSNLESGVPS RFSGSGSGTDFTLTI SSLQPEDFATYYCQQ FNSYPHTFGQGTKLE IK |
| 31 | LC_5T4-106 LC_5T4-106 | VL_CDR1 VL_CDR2 | QGISSA DVS |
| 32 | LC_5T4-106 | VL_CDR3 | QQFNSYPHT |
| 33 | HC_5T4-127 | VH | EVQLLESRGGLVQPG GSLRLSCAASGFTFS SYAMSWVRQAPGKGL EWVSTISGSGGSTYY ADSVKGRFTISRDNS KKTLYLQMNSLRAED TAVYYCAKDWGSGSY PAEYFQHWGQGTLVT VSS |
| 34 | HC_5T4-127 | VH_CDR1 | GFTFSSYA |
| 35 | HC_5T4-127 | VH_CDR2 | ISGSGGST |
| 36 | HC_5T4-127 | VH_CDR3 | AKDWGSGSYPAEYFQ H |
| 37 | LC_5T4-127 | VL | EIVLTQSPATLSLSP GERATLSCRASQSVS SYLAWYQQKPGQAPR LLIYDASNRATGIPA RFSGSGSGTDFTLTI SSLEPEDFAVYYCQQ RSNWLMYTFGQGTKL EIK |
| 38 | LC_5T4-127 LC_5T4-127 | VL_CDR1 VL_CDR2 | QSVSSY DAS |
| 39 | LC_5T4-127 | VL_CDR3 | QQRSNWLMYT |
| 40 | HC_5T4-207 | VH | QVQLQQWGAGLLKPS ETLSLTCAVYGGSFS GYYWTWIRQPPGKGL EWIGEIDHSESTNYN PSLKSRVTISVDTSK NQFSLKLSSVTAADT AVYYCAGWFGELYHY YYGMDVWGQGTTVTV SS |
| 41 | HC_5T4-207 | VH_CDR1 | GGSFSGYY |
| 42 | HC_5T4-207 | VH_CDR2 | IDHSEST |
| 43 | HC_5T4-207 | VH_CDR3 | AGWFGELYHYYYGMD V |
| 44 | LC_5T4-207 | VL | EIVLTQSPATLSLSP GERATLSCRASQSVS SYLAWYQQKPGQAPR LLIYDASNRATGIPA RFSGSGSGTDFTLTI SSLEPEDFAVYYCQQ RSNWPLTFGGGTKVE IK |
| 45 | LC_5T4-207 LC_5T4-207 | VL_CDR1 VL_CDR2 | QSVSSY DAS |
| 46 | LC_5T4-207 | VL_CDR3 | QQRSNWPLT |
| 47 | HC_5T4-226 | VH | QVQLQQWGAGLLKPS ETLSLTCAVYGGSFS GYYWSWIRQPPGKGL EWIGEIDHSGSTNYN PSLKSRVTISVDTSK NQFSLKLSSVTAADT AVYYCAAWFGELWDY YYGMDVWGQGTTVTV SS |
| 48 | HC_5T4-226 | VH_CDR1 | GGSFSGYY |
| 49 | HC_5T4-226 | VH_CDR2 | IDHSGST |
| 50 | HC_5T4-226 | VH_CDR3 | AAWFGELWDYYYGMD V |
| 51 | LC_5T4-226 | VL | EIVLTQSPATLSLSP GERATLSCRASQSVS SFLAWYQQKPGQAPR LLIYDASNRATGIPA RFSGSGSGTDFTLTI SSLEPEDFAVYYCQQ RSNWPLTFGQGTRLE IK |
| 52 | LC_5T4-226 LC_5T4-226 | VL_CDR1 VL_CDR2 | QSVSSF DAS |
| 53 | LC_5T4-226 | VL_CDR3 | QQRSNWPLT |
| 54 | VH_huCD3-H1L1_CDR1 | VH_CDR1 | GFTFNTYA |
| 55 | VH_huCD3-H1L1_CDR2 | VH_CDR2 | IRSKYNNYAT |
| 56 | VH_huCD3-H1L1_CDR3 | VH_CDR3 | VRHGNFGNSYVSWFA Y |
| 57 | VH_huCD3-H1L1 | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVSWFAYWGQGTL VTVSS |
| 58 | VL_huCD3-H1L1_CDR1 | VL_CDR1 | TGAVTTSNY |
| | VL_huCD3-H1L1_CDR2 | VL_CDR2 | GTN |
| 59 | VL_huCD3-H1L1_CDR3 | VL_CDR3 | ALWYSNLWV |
| 60 | VL_huCD3-H1L1 | VL | QAVVTQEPSFSVSPG GTVTLTCRSSTGAVT TSNYANWVQQTPGQA FRGLIGGTNKRAPGV |

| SEQ ID NO: | Name | Domain | Sequence |
|---|---|---|---|
| | | | PARFSGSLIGDKAAL TITGAQADDESIYFC ALWYSNLWVFGGGTK LTVL |
| 61 | VH_CDR1-T31P HC_T31PCDR1 | VH_CDR1 | GFTFNPYA |
| 62 | VH_T31P full length sequence HC_T31P | VH | EVKLVESGGGLVQPG GSLRLSCAASGFTFN PYAMNWVRQAPGKGL EWVARIRSKYNNYAT YYADSVKDRFTISRD DSKSSLYLQMNNLKT EDTAMYYCVRHGNFG NSYVSWFAYWGQGTL VTVSS |
| 63 | VH_CDR1-T31M HC_T31M_CDR1 | VH_CDR1 | GFTFNMYA |
| 64 | VH_T31M full length sequence HC_T31M | VH | EVKLVESGGGLVQPG GSLRLSCAASGFTFN MYAMNWVRQAPGKGL EWVARIRSKYNNYAT YYADSVKDRFTISRD DSKSSLYLQMNNLKT EDTAMYYCVRHGNFG NSYVSWFAYWGQGTL VTVSS |
| 65 | VH_CDR2-N57E HC_N57ECDR2 | VH_CDR2 | IRSKYNEYAT |
| 66 | VH_N57E full length sequence HC_N57E | VH | EVKLVESGGGLVQPG GSLRLSCAASGFTFN TYAMNWVRQAPGKGL EWVARIRSKYNEYAT YYADSVKDRFTISRD DSKSSLYLQMNNLKT EDTAMYYCVRHGNFG NSYVSWFAYWGQGTL VTVSS |
| 67 | VH_huCD3-H1L1-H101G_CDR3 HC_H101G_CDR3 | VH_CDR3 | VRGGNFGNSYVSWFA Y |
| 68 | VH_huCD3-H1L1-H101G HC_H101G | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRGGNFG NSYVSWFAYWGQGTL VTVSS |
| 69 | VH_CDR3-H101N HC_H101N_CDR3 | VH_CDR3 | VRNGNFGNSYVSWFA Y |
| 70 | VH_H101N_full length_sequence HC_H101N | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRNGNFG NSYVSWFAYWGQGTL VTVSS |
| 71 | VH_CDR3-G105P HC_G105P_CDR3 | VH_CDR3 | VRHGNFPNSYVSWFA Y |
| 72 | VH G105P full length sequence HC_G105P | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFP NSYVSWFAYWGQGTL VTVSS |
| 73 | VH CDR3-S110A HC S110A CDR3 | VH_CDR3 | VRHGNFGNSYVAWFA Y |
| 74 | VH S110A full length sequence HC_S110A | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVAWFAYWGQGTL VTVSS |
| 75 | VH CDR3-S110G HC_S110G CDR3 | VH_CDR3 | VRHGNFGNSYVGWFA Y |
| 76 | VH S110G full length sequence HC_S110G | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVGWFAYWGQGTL VTVSS |
| 77 | VH CDR3-Y114V HC_Y114VCDR3 | VH_CDR3 | VRHGNFGNSYVSWFA V |
| 78 | VH Y114V full length sequence HC_Y114V | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVSWFAVWGQGTL VTVSS |
| 79 | VH CDR3-Y114M | VH_CDR3 | VRHGNFGNSYVSWFA M |

| SEQ ID NO: | Name | Domain | Sequence |
|---|---|---|---|
| | HC_Y114M CDR3 | | |
| 80 | VH Y114M full length sequence HC_Y114M | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVSWFAMWGQGTL VTVSS |
| 81 | VH CDR3-Y114R HC_Y114RCDR3 | VH_CDR3 | VRHGNFGNSYVSWFA R |
| 82 | VH Y114R full length sequence HC_Y114R | VH | EVKLVESGGGLVQPG GSLRLSCAASGFTFN TYAMNWVRQAPGKGL EWVARIRSKYNNYAT YYADSVKDRFTISRD DSKSSLYLQMNNLKT EDTAMYYCVRHGNFG NSYVSWFARWGQGTL VTVSS |
| 83 | HC_5T4-A1 | VH | QIQLVQSGPELKKPG ETVKISCKASGYTFT NFGMNWVKQGPGEGL KWMGWINTNTGEPRY AEEFKGRFAFSLETT ASTAYLQINNLKNED TATYFCARDWDGAYF FDYWGQGTTLTVSS |
| 84 | LC_5T4-A1 | VL | SIVMTQTPKFLLVSA GDRVTITCKASQSVS NDVAWYQQKPGQSPK LLINFATNRYTGVPN RFTGSGYGTDFTFTI STVQAEDLALYFCQQ DYSSPWTFGGGTKLE IK |
| 85 | HC_5T4-A3 | VH | EVQLVESGGGLVQPK GSLKLSCAASGFTFN TYAMNWVRQAPGKGL EWVARIRSKSNNYAT YYADSVKDRFTISRD DSQSMLYLQMNNLKT EDTAMYYCVRQWDYD VRAMNYWGQGTSVTV SS |
| 86 | LC_5T4-A3 | VL | DIVMTQSHIFMSTSV GDRVSITCKASQDVD TAVAWYQQKPGQSPK LLIYWASTRLTGVPD RFTGSGSGTDFTLTI SNVQSEDLADYFCQQ YSSYPYTFGGGTKLE IK |
| 87 | HC_5T4-H8 | VH | EVQLQQSGPDLVKPG ASVKISCKASGYSFT GYYMHWVKQSHGKSL EWIGRINPNNGVTLY NQKFKDKAILTVDKS STTAYMELRSLTSED SAVYYCARSTMITNY VMDYWGQVTSVTVSS |
| 88 | LC_5T4-H8 | VL | SIVMTQTPTFLLVSA GDRVTITCKASQSVS NDVAWYQQKPGQSPT LLISYTSSRYAGVPD RFIGSGYGTDFTFTI STLQAEDLAVYFCQQ DYNSPPTFGGGTKLE IK |
| 89 | IgG1-Fc | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPELLGG PSVFLFPPKPKDTLM ISRTPEVTCVVVDVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFFLYSKLTVDKSRW QQGNVFSCSVMHEAL HNHYTQKSLSLSPGK |
| 90 | IgG1-Fc_F405L | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPELLGG PSVFLFPPKPKDTLM ISRTPEVTCVVVDVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFLLYSKLTVDKSRW QQGNVFSCSVMHEAL HNHYTQKSLSLSPGK |
| 91 | IgG1-Fc_FEA | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPEFEGG PSVFLFPPKPKDTLM ISRTPEVTCVVVAVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP |

| SEQ ID NO: | Name | Domain | Sequence |
|---|---|---|---|
| | | | ENNYKTTPPVLDSDG SFFLYSKLTVDKSRW QQGNVFSCSVMHEAL HNHYTQKSLSLSPGK |
| 92 | IgG1-Fc_FEAL | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPEFEGG PSVFLFPPKPKDTLM ISRTPEVTCVVVAVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFLLYSKLTVDKSRW QQGNVFSCSVMHEAL HNHYTQKSLSLSPGK |
| 93 | IgG1-Fc_FEAR | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPEFEGG PSVFLFPPKPKDTLM ISRTPEVTCVVVAVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFFLYSRLTVDKSRW QQGNVFSCSVMHEAL HNHYTQKSLSLSPGK |
| 94 | IgG1-Fc_K409R | Constant | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKRVEPKSCDK THTCPPCPAPELLGG PSVFLFPPKPKDTLM ISRTPEVTCVVVDVS HEDPEVKFNWYVDGV EVHNAKTKPREEQYN STYRVVSVLTVLHQD WLNGKEYKCKVSNKA LPAPIEKTISKAKGQ PREPQVYTLPPSREE MTKNQVSLTCLVKGF YPSDIAVEWESNGQP ENNYKTTPPVLDSDG SFFLYSRLTVDKSRW QQGNVFSCSVMHEAL HNHYTQKSLSLSPGK |
| 95 | Kappa | Constant | RTVAAPSVFIFPPSD EQLKSGTASVVCLLN NFYPREAKVQWKVDN ALQSGNSQESVTEQD SKDSTYSLSSTLTLS KADYEKHKVYACEVT HQGLSSPVTKSFNRG EC |
| 96 | Lambda | Constant | GQPKAAPSVTLFPPS SEELQANKATLVCLI SDFYPGAVTVAWKAD SSPVKAGVETTTPSK QSNNKYAASSYLSLT PEQWKSHRSYSCQVT HEGSTVEKTVAPTEC S |
| 97 | b12_VH | VH | QVQLVQSGAEVKKPG ASVKVSCQASGYRFS NFVIHWVRQAPGQRF EWMGWINPYNGNKEF SAKFQDRVTFTADTS ANTAYMELRSLRSAD TAVYYCARVGPYSWD DSPQDNYYMDVWGKG TTVIVSS |
| 98 | b12_VL | VL | EIVLTQSPGTLSLSP GERATFSCRSSHSIR SRRVAWYQHKPGQAP RLVIHGVSNRASGIS DRFSGSGSGTDFTLT ITRVEPEDFALYYCQ VYGASSYTFGQGTKL ERK |
| 99 | 5T4ECDHis | ORF | MPGGCSRGPAAGDGR LRLARLALVLLLGWVS SSSPTSSASSFSSSA PFLASAVSAQPPLPD QCPALCECSEAARTV KCVNRNLTEVPTDLP AYVRNLFLTGNQLAV LPAGAFARRPPLAEL AALNLSGSRLDEVRA GAFEHLPSLRQLDLS HNPLADLSPFAFSGS NASVSAPSPLVELIL NHIVPPEDERQNRSF EGMVVAALLAGRALQ GLRRLELASNHFLYL PRDVLAQLPSLRHLD LSNNSLVSLTYVSFR NLTHLESLHLEDNAL KVLHNGTLAELQGLP HIRVFLDNNPWVCDC HMADMVTWLKETEVV QGKDRLTCAYPEKMR NRVLLELNSADLDCD PILPPSLQTSHHHHH HH |
| 100 | 5T4ECD91-FcRbHis | ORF | MPGGCSRGPAAGDGR LRLARLALVLLLGWVS SSSPTSSASSFSSSA PFLASAVSAQPPLPD QCPALCECSEAARTV KCVNRNLTEVPTDLP AAPSTCSKPTCPPPE LLGGPSVFIFPPKPK DTLMISRTPEVTCVV |

-continued

| SEQ ID NO: | Name | Domain | Sequence |
|---|---|---|---|
| | | | VDVSQDDPEVQFTWY INNEQVRTARPPLRE QQFNSTIRVVSTLPI AHQDWLRGKEFKCKV HNKALPAPIEKTISK ARGQPLEPKVYTMGP PREELSSRSVSLTCM INGFYPSDISVEWEK NGKAEDNYKTTPAVL DSDGSYFLYSKLSVP TSEWQRGDVFTCSVM HEALHNHYTQKSISR SPGKHHHHHHHH |
| 101 | CD3E27-GSKa | ORF | MWWRLWWLLLLLLLL WPMVWAQDGNEEMGG ITQTPYKVSISGTTV ILTGGGGSGGGGSGG GGSEIVLTQSPATLS LSPGERATLSCRASQ SVSSYLAWYQQKPGQ APRLLIYDASNRATG IPARFSGSGSGTDFT LTISSLEPEDFAVYY CQQRSNWPITFGQGT RLEIKRTVAAPSVFI FPPSDEQLKSGTASV VCLLNNFYPREAKVQ WKVDNALQSGNSQES VTEQDSKDSTYSLSS TLTLSKADYEKHKVY ACEVTHQGLSSPVTK SFNRGE |
| 102 | HC_574-059 HC_5T4-207 HC_5T4-226 | VH-CDR3 C-term | YYGMDV |
| 103 | HC_5T4-207 HC_5T4-226 | VH-CDR-2 | IDHSX$_1$ST; X$_1$ is G or E |
| 104 | HC_5T4-207 HC_5T4-226 | VH-CDR-3 | AX$_2$WFGELX$_3$X$_4$YYYGMDV; X$_2$ is A or G, X$_3$ is W or Y, X$_4$ is D or H |
| 105 | HC_5T4-207 HC_5T4-226 | VL-CDR-1 | QSVSSX$_5$; X$_5$ is Y or F |

The present invention is further illustrated by the following examples which should not be construed as further limiting.

EXAMPLES

Example 1—Generation of 5T4 Antibodies and Screenings Materials

Expression Constructs for 5T4

The following codon-optimized constructs for expression of various full length 5T4 variants were generated: human (*Homo sapiens*) 5T4 (Uniprot accession no. Q13641), cynomolgus monkey (*Macaca fascicularis*) 5T4 (Uniprot accession no. Q4R8Y9), and chicken (*Gallus gallus*) 5T4 (Uniprot accession no. R4GM46). In addition, the following codon-optimized constructs for various 5T4 extracellular domain (ECD) variants were generated: the ECD of human 5T4 (aa 1-355 from Uniprot accession no. Q13641) with a C-terminal His tag (5T4ECDHis) (SEQ ID NO: 99), and the ECD of human 5T4 (aa 1-91) fused to rabbit Fc domain and C-terminal His-tag (5T4ECD91-FcRbHis). In SEQ ID NO: 99, amino acid residues 1-31 are a signal peptide; hence the mature 5T4ECDHis protein corresponds to amino acid residues 32-363 of SEQ ID NO: 99. Likewise, amino acid residues 1-31 of SEQ ID NO: 100 are a signal peptide and the mature 5T4ECD91-FcRbHis protein corresponds to amino acid residues 32-327 of SEQ ID NO: 100.

The constructs contained suitable restriction sites for cloning and an optimal Kozak (GCCGCCACC) sequence (Kozak, M., Gene 1999; 234(2):187-208). The full length human 5T4 and cynomolgus monkey 5T4 codon-optimized constructs were cloned in the mammalian expression vector pcDNA3.3 (Invitrogen). The full length chicken 5T4 codon-optimized constructs was cloned in pSB, a mammalian expression vector containing Sleeping Beauty inverter terminal repeats flanking an expression cassette consisting of a CMV promoter and HSV-TK polyA signal.

Generation of HEK-293F cell lines transiently expressing full length human, cynomolgus or chicken 5T4 Freestyle™ 293-F (a HEK-293 subclone adapted to suspension growth and chemically defined Freestyle medium [HEK-293F]) cells were obtained from Invitrogen (cat. no. R790-07) and transfected with the codon-optimized constructs described supra, using 293fectin (Invitrogen, cat. no. 12347-019) according to the manufacturer's instructions.

Purification of His-Tagged 5T4

5T4ECDHis (mature protein of SEQ ID NO: 99) was expressed in HEK-293F cells as described supra. 5T4ECD91-FcRbHis was expressed using the Expi293F expression platform (Thermo Fisher Scientific, Waltham, MA, USA, cat. no. A14527) essentially as described by the manufacturer.

The His-tag enables purification with immobilized metal affinity chromatography. In this process, a chelator fixed onto the chromatographic resin is charged with $Co^{2+}$ cations. Supernatants containing the His-tagged protein were incubated with the resin in batch mode (i.e. solution). The His-tagged protein binds strongly to the resin beads, while other proteins present in the culture supernatant do not bind or bind weakly compared to the His-tagged proteins. After incubation, the beads were retrieved from the supernatant and packed into a column. The column was washed in order to remove weakly bound proteins. The strongly bound His-tagged proteins were then eluted with a buffer containing imidazole, which competes with the binding of His to $Co^{2+}$. The eluent was removed by buffer exchange on a desalting column.

Immunization

For generation of antibodies IgG1-5T4-207 and IgG1-5T4-226, HCo17-BalbC transgenic mice (Bristol-Myers Squibb, New York, NY, USA) were immunized alternatingly intraperitoneally (IP) and subcutaneously (SC) with 20 μg of the 5T4ECDHis protein in Sigma adjuvant system (Sigma-Aldrich, St. Louis, MO, USA, cat. no. S6322) with an interval of 14 days. In total 8 immunizations were performed: 4 IP and 4 SC.

For generation of antibodies IgG1-5T4-076 and IgG1-5T4-059, HCo12-BalbC (IgG1-5T4-076) and HCo20-BalbC (IgG1-5T4-059) transgenic mice (Bristol-Myers Squibb) were immunized alternatingly IP and SC with 20 μg of the 5T4ECDHis protein in Sigma adjuvant system with an interval of 14 days. In total 8 immunizations were performed: 4 IP and 4 SC.

For generation of antibody IgG1-5T4-085, HCo17-BalbC transgenic mice were immunized alternatingly IP and SC with 20 μg of the 5T4ECDHis protein and 20 μg of the 5T4ECD91-FcRbHis mature protein in Sigma adjuvant system with an interval of 14 days. In total 8 immunizations were performed: 4 IP and 4 SC.

For generation of antibodies IgG1-5T4-106 and IgG1-5T4-127, HCo12-BalbC (IgG1-5T4-106) and HCo17-BalbC (IgG1-5T4-127) transgenic mice were immunized alternatingly IP and SC with 20 µg of the 5T4ECD91-FcRbHis mature protein in Sigma adjuvant system with an interval of 14 days. In total 8 immunizations were performed: 4 IP and 4 SC.

Mice with at least two sequential 5T4 specific antibody titers in the antigen specific screening Fluorometric Micro volume Assay Technology (FMAT) as described below, were boosted with 10 µg of 5T4ECDHis or 10 µg 5T4ECD91-FcRbHis (in PBS injected intravenously) and splenocytes and lymph node cells of these mice were fused 3-4 days later.

Homogeneous Antigen Specific Screening Assay

The presence of 5T4 antibodies in sera of immunized mice or HuMAb (human monoclonal antibody) hybridoma or transfectoma culture supernatant was determined by homogeneous antigen specific screening assays using FMAT (Applied Biosystems, Foster City, CA, USA). For this, a combination of 4 cell based assays was used.

Sera from immunized mice, or hybridoma or transfectoma culture supernatant samples were analyzed for binding of human antibodies to HEK-293F cells transiently expressing human 5T4, HEK-293F cells transiently expressing cynomolgus monkey 5T4, streptavidin-coated polystyrene particles (0.5% w/v; 6.7 µm; Spherotech, Lake Forest, IL, USA, cat. no. SVP-60-5) coated with 5T4ECD91-FcRBHis, and HEK-293 wild-type cells (negative control).

Samples were added to the cells to allow binding to 5T4. Subsequently, binding of HuMAb was detected using a fluorescent conjugate (AffiniPure Goat Anti-Human IgG Fc gamma-Alexa Fluor® 647; Jackson ImmunoResearch, cat no. 109-605-098). IgG1-5T4-H8-F405L was used as a positive control and ChromPure Human IgG, whole molecule (Jackson ImmunoResearch, cat no. 009-000-003) was used as negative control. The samples were scanned using an ImageXpress Velos (Molecular devices, LLC, Sunnyvale, CA, USA) and total fluorescence was used as read-out. Samples were stated positive when counts were higher than 50 and counts×fluorescence was at least three times higher than the negative control.

HuMAb Hybridoma Generation

HuMAb mice with sufficient antigen-specific titer development (described above) were sacrificed and the spleen and lymph nodes flanking the abdominal aorta and vena cava were collected. Fusion of splenocytes and lymph node cells to a mouse myeloma cell line (SP2.0 cells) was done by electrofusion using a CytoPulse CEEF 50 Electrofusion System (Cellectis, Paris, France), essentially according to the manufacturer's instructions. Next, the antigen-positive primary wells were sub-cloned using the ClonePix system (Genetix, Hampshire, UK). To this end, specific primary well hybridomas were seeded in semisolid medium made from 40% CloneMedia (Genetix, Hampshire, UK) and 60% HyQ 2× complete media (Hyclone, Waltham, USA). The subclones were retested for 5T4 binding according to the antigen-specific binding assay as described above and scanned using the IsoCyte system (Molecular Devices). IgG levels were measured using an Octet system (Fortebio, Menlo Park, USA) in order to select the best producing clone per primary well for further expansion. Further expansion and culturing of the resulting HuMAb hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Sequence Analysis of the 5T4 Antibody Variable Domains and Cloning in Expression Vectors Total RNA was prepared from 2 to 5×10$^6$ hybridoma cells and 5'-RACE-complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f and p33Kappa expression vectors (pcDNA3.3 based vectors with codon optimized human IgG1m(f) and Kappa constant domains, respectively), by ligation independent cloning (Aslanidis, C. and P. J. de Jong, Nucleic Acids Res 1990; 18(20): 6069-74). The variable domains from these expression vectors were sequenced and CDRs were annotated according to IMGT definitions (Lefranc M P. et al., Nucleic Acids Research, 27, 209-212, 1999 and Brochet X. Nucl. Acids Res. 36, W503-508 (2008)). Clones with a correct Open Reading Frame (ORF) were expressed and tested for binding to the antigen. A lead panel was ordered as codon optimized sequences (GeneArt, Thermo Fisher Scientific) and produced with the Expi293 expression system according to manufacturer's instructions (Thermo Fisher Scientific). The antibodies in these supernatants were purified and used for functional characterization. The sequences of the resulting lead clones are shown in the table above.

5T4 Control Antibodies

In some of the Examples comparison antibodies against 5T4 were used (IgG1-5T4-H8, IgG1-5T4-A3 and IgG1-5T4-A1) that have been previously described in WO2007/106744. The codon optimized antibody encoding sequences were synthesized and cloned in pCDNA3.3 expression vectors (Thermo Fisher Scientific).

IgG1-b12 Antibody

In some of the Examples the antibody b12, an HIV-1 gp120 specific antibody (Barbas, C F. J Mol Biol. 1993 Apr. 5; 230(3):812-23) was used as a negative control. The codon optimized antibody encoding sequences for this control antibody were synthesized and cloned into pCDNA3.3 expression vectors (Thermo Fisher Scientific). The sequence of the variable heavy chain (VH) region and the sequence of the variable light chain (VL) region are included herein as SEQ ID NOs.: 97 and 98, respectively.

Example 2—Determination of the Binding Affinities of 5T4 Specific Antibodies Using Biolayer Interferometry Affinities of the 5T4 antibodies for recombinant 5T4 protein were determined using label-free biolayer interferometry on an Octet HTX instrument (ForteBio, Portsmouth, UK). 5T4 antibodies (1 µg/mL) were immobilized for 600 seconds on anti-human IgG Fc Capture biosensors (ForteBio). After a baseline measurement (100 s), the association (200 s) and dissociation (1000 s) of human 5T4ECDHis (mature protein of SEQ ID NO: 99) or recombinant cynomolgus monkey 5T4 protein (Cusabio; cat. no. CSB-MP024093MOV) in Sample Diluent (ForteBio) was determined using a 2-fold dilution series (ranging from 100 nM to 1.56 nM) starting at 3.58 µg/mL (100 nM) human 5T4ECDHis or 3.99 µg/mL (100 nM) cynomolgus 5T4, while shaking at 1000 rpm at 30° C. Data were analyzed with Data Analysis Software v9.0.0.12 (ForteBio). Values of reference wells containing only Sample Diluent during the association and dissociation steps were subtracted from values of wells containing antigen, for each antibody separately. The Y-axis was aligned to the last 10 s of the baseline and Interstep Correction alignment to dissociation as well as Savitzky-Golay filtering was applied. Responses <0.05 nm were excluded from analysis. The data were fitted using the 1:1 model and a global full fit with 200 s association time and 1000 s or 50 s dissociation time as Window of Interest. The fit with the full dissociation time (1000 s) as Window of Interest was used by default. Based on the $R^2$ value and visual inspection of the fit, a dissociation time of 50 s was used as Window of Interest for IgG1-5T4-127-FEAR.

Table 1 shows the association rate constant $k_a$ (1/Ms), dissociation rate constant $k_d$ (1/s) and equilibrium dissociation constant $K_D$ (M) of the 5T4 antibodies for human 5T4ECDHis determined by biolayer interferometry. A range of affinities of the antibodies to human 5T4 was measured ranging from $1.3 \times 10^{-9}$–$2.7 \times 10^{-8}$ M. The response of IgG1-5T4-085-FEAR was lower than 0.05 nm, which prevented proper fitting of the data (low $R^2$ values for these fits). Furthermore, the response of IgG1-5T4-076-FEAR could not be fitted properly. These data are shown in italics.

Table 2 shows the association rate constant $k_a$ (1/Ms), dissociation rate constant $k_d$ (1/s) and equilibrium dissociation constant $K_D$ (M) for cynomolgus monkey 5T4 determined with biolayer interferometry. A range of affinities of the antibodies to cynomolgus monkey 5T4 was measured ranging from $1.1 \times 10^{-9}$–$4.1 \times 10^{-8}$ M. The responses of IgG1-5T4-085-FEAR, IgG1-5T4-106-FEAR and IgG1-5T4-H8-FEAR were lower than 0.05 nm, which prevented proper fitting of the data (low $R^2$ values for these fits). Furthermore, the response of IgG1-5T4-076-FEAR could not be fitted properly. These data are shown in italics.

TABLE 1

Binding affinities of monospecific, bivalent 5T4 antibodies to human 5T4 extracellular domain as determined by label-free biolayer interferometry.

| Antibody | On-rate $k_a$ (1/Ms) | Off-rate $k_d$ (1/s) | $K_D$ (M) |
|---|---|---|---|
| IgG1-5T4-059-FEAR | 2.1E+05 | 3.2E−04 | 1.5E−09 |
| *IgG1-5T4-076-FEAR* | | *No fit* | |
| *IgG1-5T4-085-FEAR* | | *Response <0.05 nm* | |
| IgG1-5T4-106-FEAR | 2.1E+05 | 1.2E−03 | 5.5E−09 |
| IgG1-5T4-127-FEAR | 5.8E+05 | 1.6E−02 | 2.7E−08 |
| IgG1-5T4-207-FEAR | 2.7E+05 | 6.8E−04 | 2.6E−09 |
| IgG1-5T4-226-FEAR | 3.3E+05 | 8.1E−04 | 2.5E−09 |
| IgG1-5T4-H8-FEAR | 2.2E+05 | 2.9E−04 | 1.3E−09 |

TABLE 2

Binding affinities of monospecific, bivalent 5T4 antibodies to cynomolgus monkey 5T4 extracellular domain as determined by label-free biolayer interferometry.

| Antibody | On-rate $k_a$ (1/Ms) | Off-rate $k_d$ (1/s) | $K_D$ (M) |
|---|---|---|---|
| IgG1-5T4-059-FEAR | 1.6E+05 | 2.8E−04 | 1.8E−09 |
| *IgG1-5T4-076-FEAR* | | *No fit* | |
| *IgG1-5T4-085-FEAR* | | *Response <0.05 nm* | |
| *IgG1-5T4-106-FEAR* | | *Response <0.05 nm* | |
| IgG1-5T4-127-FEAR | 3.7E+05 | 1.5E−02 | 4.1E−08 |
| IgG1-5T4-207-FEAR | 1.4E+05 | 8.7E−04 | 6.3E−09 |
| IgG1-5T4-226-FEAR | 1.4E+05 | 1.5E−03 | 1.1E−08 |
| *IgG1-5T4-H8-FEAR* | | *Response <0.05 nm* | |

Example 3—Cross-Block of 5T4 Antibodies Determined by Biolayer Interferometry Antibody cross-block analysis (epitope binning) was performed using biolayer interferometry on an Octet HTX instrument (ForteBio). 5T4 antibodies (20 µg/mL in 10 mM sodium acetate buffer pH 6.0, ForteBio) were immobilized on Amine-Reactive 2nd Generation (AR2G) biosensors (ForteBio) according to the manufacturer's instructions. After a baseline measurement (100 s) in Sample Diluent (ForteBio), biosensors containing immobilized antibodies were loaded for 500 s with human 5T4ECDHis (mature protein of SEQ ID NO: 99) 100 nM (3.6 µg/mL). Next, the association response of a second 5T4 antibody (10 µg/mL) was determined for 500 s. Biosensors were regenerated by 3 times 5 s exposure to 10 mM glycine pH 2.5 followed by Sample Diluent, and the measurement was repeated with a new set of second 5T4 antibodies starting from the baseline step. Each biosensor was used four times. Measurements were performed at 30° C. using a shaker speed of 1000 rpm. Data were analyzed using Data Analysis Software v9.0.0.12 (ForteBio). The Y-axis was aligned to the association step and Savitzky-Golay filtering was applied. The response of Sample Diluent during the association step was subtracted from the association response of the second antibody in order to correct for the dissociation of 5T4ECDHis from the immobilized antibody. The corrected association responses were plotted in a matrix format. In general, responses >0.1 nm were considered non-blocking antibody pairs (white), while responses between −0.1 and 0.1 nm were considered to be blocking antibody pairs (dark grey). For some antibody pairs the second antibody showed an initial positive response, followed by a decrease in signal. This was considered to be antibody displacement (light grey), i.e. the second antibody displacing the interaction between the first antibody and the antigen (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi:10.1371/journal.pone.0169535). In some cases, the data curves needed visual inspection by an expert to assign blocking, non-blocking or displacement properties to antibody pairs.

Cross-block experiments were performed for antibodies IgG1-5T4-059-FEAR, IgG1-5T4-076-FEAR, IgG1-5T4-085-FEAR, IgG1-5T4-106-FEAR, IgG1-5T4-127-FEAR, IgG1-5T4-207-FEAR, IgG1-5T4-226-FEAR, and prior art antibodies IgG1-5T4-H8-FEAR, IgG1-5T4-A1-F405L and IgG1-5T4-A3-F405L. The results are summarized in Table 3.

None of the antibodies (except IgG1-5T4-A1-F405L itself) blocked binding of IgG1-5T4-A1-F405L to 5T4ECDHis. Antibodies IgG1-5T4-076-FEAR, IgG1-5T4-085-FEAR, IgG1-5T4-127-FEAR, IgG1-5T4-106-FEAR, IgG1-5T4-059-FEAR, IgG1-5T4-207-FEAR and IgG1-5T4-226-FEAR (as well as IgG1-5T4-H8-FEAR itself) blocked binding of IgG1-5T4-H8-FEAR to 5T4ECDHis. Antibodies IgG1-5T4-076-FEAR, IgG1-5T4-085-FEAR, and IgG1-5T4-127-FEAR (as well as IgG1-5T4-A3-F405L itself) also blocked binding of IgG1-5T4-A3-F405L to 5T4ECDHis, while antibodies IgG1-5T4-106-FEAR and IgG1-5T4-H8-FEAR did not block binding of IgG1-5T4-A3-F405L to 5T4ECDHis. Antibodies IgG1-5T4-059-FEAR, IgG1-5T4-207-FEAR and IgG1-5T4-226-FEAR showed antibody displacement in combination with IgG1-5T4-A3-F405L, which is described in more detail in Example 4.

TABLE 3

Antibody cross-block as determined by biolayer interferometry.
The first column shows the immobilized antibodies and the first row shows the antibodies in solution. Corrected association responses of the antibodies in solution are shown. Cross-block of antibodies is indicated by italics and underlining, displacing antibody combinations are indicated by an asterisk. Non-blocking antibody combinations are unmarked.

|     | A1 | A3 | 076 | 085 | 127 | 106 | H8 | 059 | 207 | 226 |
| --- | --- | --- | --- | --- | --- | --- | --- | --- | --- | --- |
| A1  | *-0.01* | 0.76 | 0.36 | 0.72 | 0.87 | 0.85 | 0.89 | 0.91 | 0.86 | 0.86 |
| A3  | 0.69 | *0.01* | *0.00* | *0.00* | *0.01* | 0.57 | 0.50 | * | * | * |
| 076 | 0.04 | *0.00* | *-0.01* | *-0.02* | *-0.02* | -0.02 | *0.00* | -0.02 | 0.05 | 0.05 |
| 085 | 0.07 | *-0.01* | *-0.01* | *-0.01* | *0.00* | *-0.01* | *-0.01* | *-0.04* | 0.08 | 0.07 |
| 127 | 0.15 | *-0.01* | *-0.02* | *-0.01* | *-0.01* | *-0.01* | *-0.02* | *-0.05* | 0.16 | 0.16 |
| 106 | 0.79 | 0.56 | *-0.03* | *-0.04* | *-0.02* | *-0.02* | *-0.02* | *-0.03* | *-0.03* | *-0.02* |
| H8  | 0.64 | 0.49 | *-0.02* | *-0.02* | *-0.01* | *-0.01* | *0.00* | *-0.02* | *-0.01* | *-0.01* |
| 059 | 0.96 | * | *0.00* | *-0.02* | *-0.10* | *0.01* | *0.01* | *0.01* | *0.02* | *0.01* |
| 207 | 1.29 | * | 1.22 | 1.03 | 1.29 | *-0.01* | *-0.01* | *-0.02* | *-0.02* | *-0.02* |
| 226 | 1.56 | * | 1.47 | 1.35 | 1.51 | *-0.02* | *-0.01* | *-0.02* | *-0.02* | *-0.02* |

Example 4—Antibody Displacement of IgG1-5T4-059-FEAR, IgG1-5T4-207-FEAR and IgG1-5T4-226-FEAR in Combination with IgG1-5T4-A3-F405L Antibody displacement was demonstrated using biolayer interferometry on an Octet HTX instrument (ForteBio). IgG1-5T4-A3-F405L (20 µg/mL in 10 mM sodium acetate buffer pH 6.0, ForteBio) was immobilized on Amine-Reactive 2nd Generation (AR2G) biosensors (ForteBio) according to the manufacturer's instructions. After a baseline measurement (100 s) in Sample Diluent (ForteBio), biosensors containing immobilized IgG1-5T4-A3-F405L antibodies were loaded for 500 s with human 5T4ECDHis (mature protein of SEQ ID NO: 99) 100 nM (3.6 µg/mL). Next, the association response of a second 5T4 antibody (IgG1-5T4-059-FEAR, IgG1-5T4-207-FEAR or IgG1-5T4-226-FEAR; 10 µg/mL) or Sample Diluent (buffer control) was determined for 500 s. The experiment was performed at 30° C. using a shaker speed of 1000 rpm. Data was analyzed using Data Analysis Software v9.0.0.12 (ForteBio). The buffer control response was subtracted from the responses of the second antibodies to correct for the dissociation of human 5T4ECDHis from the immobilized IgG1-5T4-A3-F405L, the Y-axis was aligned to the association step and Savitzky-Golay filtering was applied.

Figure 1B:
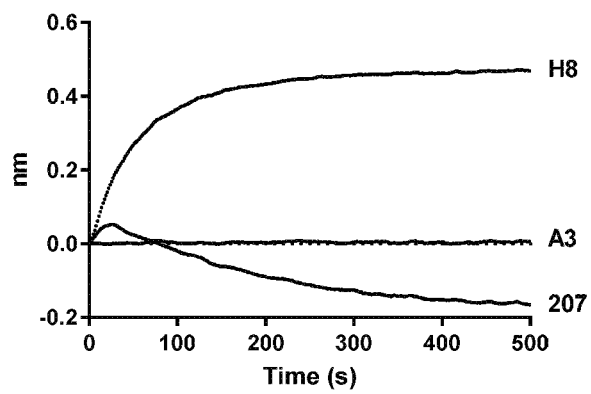
Figure 1C:
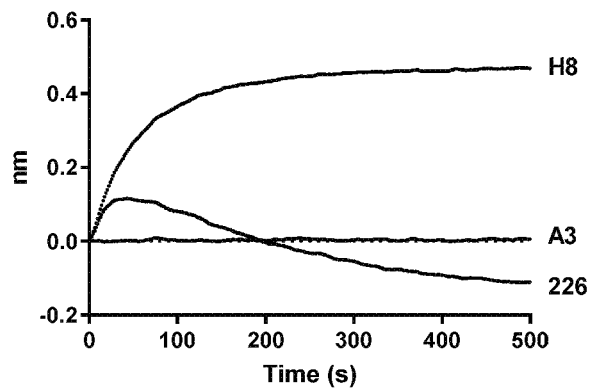

As shown in FIG. 1, IgG1-5T4-A3-F405L did not show binding, indicating cross-block (self-block) with IgG1-5T4-A3-F405L. IgG1-5T4-H8-FEAR showed binding to 5T4ECDHis and hence no cross-block with IgG1-5T4-A3-F405L. IgG1-5T4-059-FEAR, IgG1-5T4-207-FEAR and IgG1-5T4-226-FEAR initially showed a positive response (indicating binding to the IgG1-5T4-A3-F405L-5T4ECDHis complex instead of cross-blocking with IgG1-5T4-A3-F405L), followed by a decrease in response that dropped below the self-block response of IgG1-5T4-A3-F405L. This demonstrates loss of mass from the IgG1-5T4-A3-F405L-5T4ECDHis complex, indicating that IgG1-5T4-059-FEAR, IgG1-5T4-207-FEAR and IgG1-5T4-226-FEAR induce dissociation of human 5T4ECDHis from IgG1-5T4-A3-F405L upon binding to the complex. This phenomenon has been described as antibody displacement and indicates that the epitopes are closely adjacent or minimally overlapping (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi:10.1371/journal.pone.0169535)). This indicates that antibodies IgG1-5T4-059-FEAR, IgG1-5T4-207-FEAR and IgG1-5T4-226-FEAR bind to a distinct epitope on 5T4 as compared to IgG1-5T4-A3-F405L.

Example 5—Simultaneous Binding of 5T4 Antibodies to Membrane-Bound 5T4 Measured with Flow Cytometry Binding of IgG1-5T4-207-FEAR and IgG1-5T4-226-FEAR antibodies to membrane-bound 5T4 in the presence of IgG1-5T4-A1-F405L and IgG1-5T4-A3-F405L was assessed by flow cytometry. IgG1-5T4-H8-FEAR, IgG1-5T4-207-FEAR and IgG1-5T4-226-FEAR were conjugated to fluorescein isothiocyanate (FITC, Thermo Fisher Scientific) according to manufacturer's instructions. SK-OV-3 cells (50,000 cells per condition), which express approximately 20,000 5T4 molecules/cell, were incubated with mixtures of 10 µg/mL unconjugated 5T4 antibodies (IgG1-5T4-H8-FEAR, IgG1-5T4-A1-F405L, IgG1-5T4-A3-F405L, IgG1-b12, IgG1-5T4-207-FEAR or IgG1-5T4-226-FEAR) and 2 µg/mL FITC-conjugated 5T4 antibodies (IgG1-5T4-H8-FEAR-FITC, IgG1-5T4-207-FEAR-FITC and IgG1-5T4-226-FEAR-FITC). Table 4 shows an overview of the tested combinations. After 30 min incubation at 4° C., cells were centrifuged at 1200 RPM for 5 min, and the supernatant was discarded. The cells were resuspended in 100 µL FACS-buffer supplemented with 1:4000 Topro-3-iodine (Molecular Probes). Mean fluorescence intensity (MFI) of the FITC signal was measured using a flow cytometer (FACS Fortessa, BD Biosciences). Percentage of binding was calculated using the following formula:

$$\frac{\left([MFI \text{ of cells with } Ab\text{-}FITC \text{ and unconjugated } Ab - MFI \text{ of cells without } Ab\text{-}FITC \text{ or unconjugated } Ab]\right) * 100}{\left(MFI \text{ of cells with } Ab\text{-}FITC \text{ and isotype control} - MFI \text{ of cells without } Ab\text{-}FITC \text{ or unconjugated } Ab\right)}$$

FIG. 2 shows that binding of IgG1-5T4-H8-FEAR-FITC, IgG1-5T4-207-FEAR-FITC and IgG1-5T4-226-FEAR-FITC was blocked in presence of their unconjugated counterpart. However, binding of IgG1-5T4-207-FEAR-FITC and IgG1-5T4-226-FEAR-FITC to membrane-bound 5T4 was still observed in the presence of unconjugated IgG1-5T4-A1-F405L, IgG1-5T4-A3-F405L or IgG1-b12, and was comparable to binding of IgG1-5T4-H8-FEAR-FITC to membrane-bound 5T4 in the presence of unconjugated IgG1-5T4-A1-F405L, IgG1-5T4-A3-F405L or IgG1-b12. This demonstrates that antibodies IgG1-5T4-H8-FEAR, IgG1-5T4-207-FEAR and IgG1-5T4-226-FEAR bind to a distinct epitope on 5T4 as compared to antibodies IgG1-5T4-A1-F405L and IgG1-5T4-A3-F405L.

TABLE 4

Overview of antibody combinations used in flow cytometry experiment.

|   | FITC-labeled antibody (2 µg/mL) | Unconjugated antibody (10 µg/mL) |
|---|---|---|
| 1 | IgG1-5T4-H8-FEAR-FITC | IgG1-5T4-H8-FEAR |
| 2 | IgG1-5T4-H8-FEAR-FITC | IgG1-5T4-A3-F405L |
| 3 | IgG1-5T4-H8-FEAR-FITC | IgG1-5T4-207-FEAR |
| 4 | IgG1-5T4-H8-FEAR-FITC | IgG1-5T4-226-FEAR |
| 5 | IgG1-5T4-H8-FEAR-FITC | IgG1-5T4-A1-F405L |
| 6 | IgG1-5T4-H8-FEAR-FITC | IgG1-b12 |
| 7 | IgG1-5T4-207-FEAR-FITC | IgG1-5T4-H8-FEAR |
| 8 | IgG1-5T4-207-FEAR-FITC | IgG1-5T4-A3-F405L |
| 9 | IgG1-5T4-207-FEAR-FITC | IgG1-5T4-207-FEAR |
| 10 | IgG1-5T4-207-FEAR-FITC | IgG1-5T4-226-FEAR |
| 11 | IgG1-5T4-207-FEAR-FITC | IgG1-5T4-A1-F405L |
| 12 | IgG1-5T4-207-FEAR-FITC | IgG1-b12 |
| 13 | IgG1-5T4-226-FEAR-FITC | IgG1-5T4-H8-FEAR |
| 14 | IgG1-5T4-226-FEAR-FITC | IgG1-5T4-A3-F405L |
| 15 | IgG1-5T4-226-FEAR-FITC | IgG1-5T4-207-FEAR |
| 16 | IgG1-5T4-226-FEAR-FITC | IgG1-5T4-226-FEAR |
| 17 | IgG1-5T4-226-FEAR-FITC | IgG1-5T4-A1-F405L |
| 18 | IgG1-5T4-226-FEAR-FITC | IgG1-b12 |

Example 6—Binding of 5T4 Antibodies to HEK-293 Cells Transfected with Human or Chicken 5T4

Binding of 5T4 antibodies to HEK-293 cells transiently transfected with full length human or chicken 5T4 (generated as described in Example 1) was analyzed by flow cytometry. Cells (5×10$^4$ cells/well) were incubated in polystyrene 96-well round-bottom plates (Greiner bio-one, cat. no. 650180) with serial dilutions of 5T4 antibodies (range 0.01 to 10 µg/mL in 3-fold dilution steps) in 50 µL PBS/0.1% BSA/0.02% azide (staining buffer) at 4° C. for 30 min. After washing twice in staining buffer, cells were incubated in 50 µL R-Phycoerythrin (PE)-conjugated goat-anti-human IgG F(ab')$_2$ (1:500 in staining buffer; Jackson ImmunoResearch Laboratories, Inc., West Grove, PA, cat. no. 109-116-098) at 4° C. for 30 min. Cells were washed twice in staining buffer, re-suspended in 20 µL staining buffer and analyzed on an iQue screener (Intellicyt Corporation, USA). Binding curves were analyzed by non-linear regression (sigmoidal dose-response with variable slope) using GraphPad Prism V7.02 software (GraphPad Software, San Diego, CA, USA).

Figure 3A:
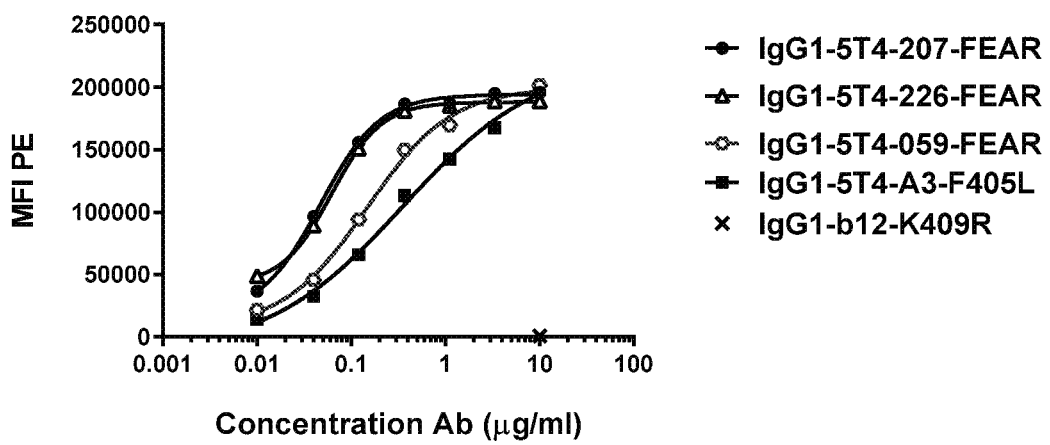
FIGS. 3A and 3B: Binding of 5T4 antibodies to HEK-293 cells transfected with full length human and chicken 5T4. HEK-293 cells transiently transfected with full length human 5T4 (SEQ ID NO: 1) (FIG. 3A) or chicken 5T4 (SEQ ID NO: 3) (FIG. 3B) were incubated with various concentrations of IgG1-5T4-A3-F405L, IgG1-5T4-059-FEAR, IgG1-5T4-207-FEAR or IgG1-5T4-226-FEAR antibodies. After incubation with R-Phycoerythrin (PE)-conjugated goat-anti-human IgG F(ab')2, the mean fluorescence intensity (MFI) was determined by flow cytometry. As negative control, IgG1-b12-K409R (10 µg/mL) was included.
Figure 3B:
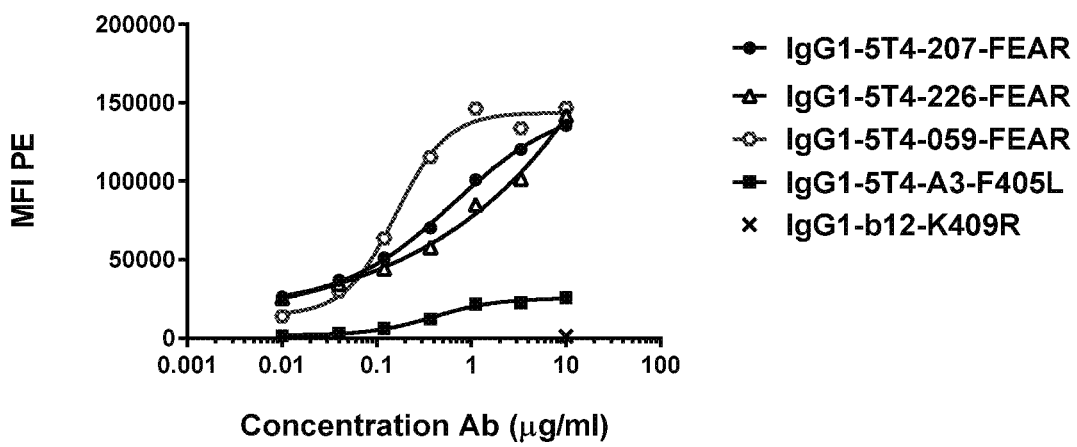

FIG. 3A shows dose-dependent binding of IgG1-5T4-207-FEAR, IgG1-5T4-226-FEAR, IgG1-5T4-059-FEAR and IgG1-5T4-A3-F405L to HEK-293 cells transfected with full length human 5T4. FIG. 3B shows that while dose-dependent binding of IgG1-5T4-207-FEAR, IgG1-5T4-226-FEAR and IgG1-5T4-059-FEAR to HEK-293 cells transfected with full length chicken 5T4 was observed, IgG1-5T4-A3-F405L showed minimal binding to HEK-293 cells transfected with full length chicken 5T4. The negative control antibody, IgG1-b12-K409R, did not show binding to HEK-293 cells transfected with full length human or chicken 5T4 at a concentration of 10 µg/mL.

Example 7—Internalization Capacity of 5T4 Antibodies in Tumor Cells

Experiments were performed to characterize the internalization capacity of monovalent 5T4 antibodies. Intracellular payload delivery and resulting cytotoxicity were used as a read out for internalization of the 5T4 antibodies upon target binding. Bispecific, toxin-conjugated antibodies that recognize 5T4 with one Fab-arm while recognizing an irrelevant antigen (HIV-1 gp120, which is not expressed on tumor cells) with the second Fab-arm, were generated by controlled Fab-arm exchange of unconjugated 5T4 antibodies with (HIV-1 gp120-specific) IgG1-b12 antibodies that had been conjugated with the microtubule-disrupting agent Duostatin-3. The resulting bispecific Duostatin-3 conjugated antibodies carry 1 toxin molecule per antibody (drug-antibody ratio 1). Serial dilutions (0.00152-10 µg/mL, 3-fold) of Duostatin-3 conjugated bispecific antibodies that monovalently bind 5T4, were added to MDA-MB-468 (mammary cancer cell line, ATCC, clone HTB-132) or HCC1954 (mammary cancer cell line, ATCC, clone CRL-2338) cells seeded in flat-bottom 96-well tissue culture plates (5,000 cells/well; Greiner-bio-one, The Netherlands, cat. no. 655180). The cells were incubated for 5 days at 37° C., after which cell viability was assessed using a CellTiter-Glo Luminescent Cell Viability Assay (Promega, USA, cat. no. G7570) according to manufacturer's instructions. Cytotoxicity curves were analyzed using non-linear regression (sigmoidal dose-response with variable slope) using GraphPad Prism V7.02 software (Graph Pad Software, San Diego, CA, USA).

Figure 4A:
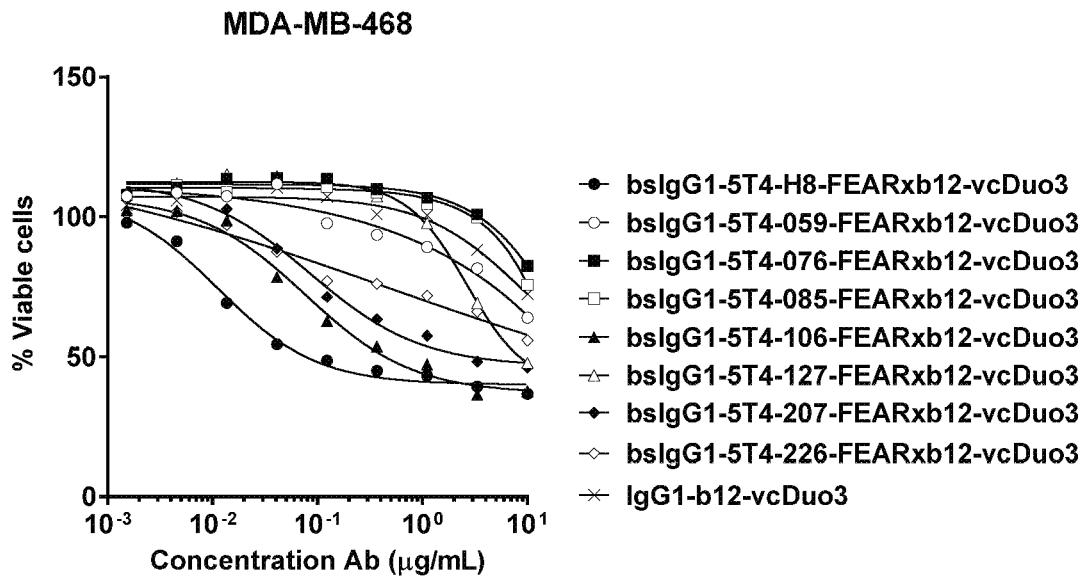
FIGS. 4A and 4B: Internalization capacity of monovalent 5T4 antibodies. Bispecific, toxin-conjugated antibodies that recognize 5T4 with one Fab-arm while recognizing an irrelevant antigen (HIV-1 gp120, which is not expressed on tumor cells) with the second Fab-arm, were generated by controlled Fab-arm exchange of unconjugated 5T4 antibodies with (HIV-1 gp120-specific) IgG1-b12 antibodies that had been conjugated with one Duostatin-3 molecule per antibody. MDA-MB-468 (FIG. 4A) and HCC1954 (FIG. 4B) cells were incubated with increasing concentrations of antibodies, as indicated. Cell viability was measured after 5 days. Data are presented as mean percentage viable cells of three replicate experiments. As negative control, monospecific, bivalent IgG1-b12 conjugated with Duostatin-3 (IgG1-b12-vcDuo3) was included.
Figure 4B:
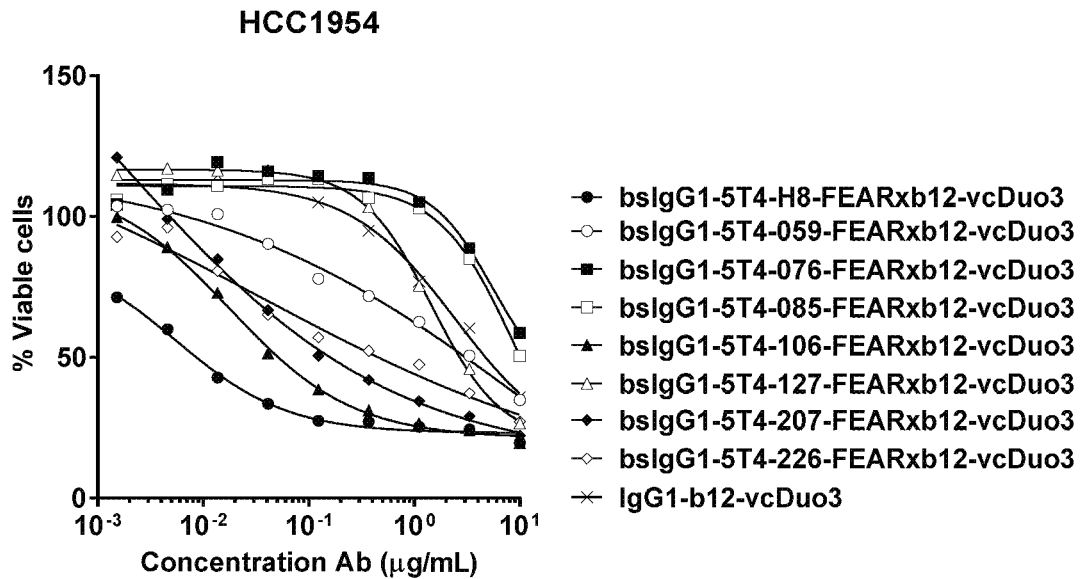
Figure 5A:
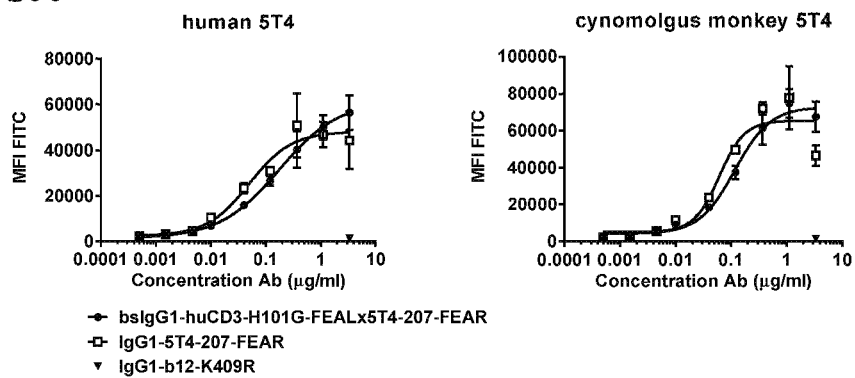
FIGS. 5A-5D: Binding of CD3×5T4 bispecific antibodies to full length human and cynomolgus monkey 5T4 transfected into HEK-293 cells. Binding of monovalent and bivalent 5T4 antibodies was analysed using HEK-293 cells transiently transfected with full length human (left panels) or cynomolgus monkey 5T4 (right panels). Cells were incubated with increasing concentrations of antibodies, as indicated. After secondary labelling with FITC conjugated goat-anti-human IgG F(ab')2, binding was analysed by flow cytometry. As negative control antibody, IgG1-b12-K409R (3 µg/mL) was included. Data are presented as mean fluorescence intensity (MFI) values of two technical replicates±SD.
Figure 5B:
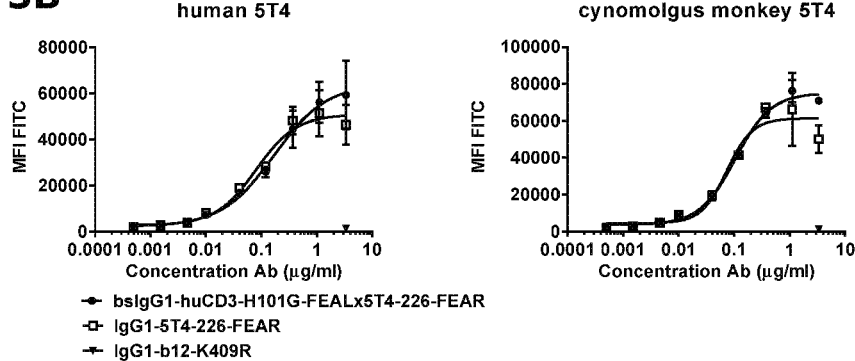
Figure 5C:
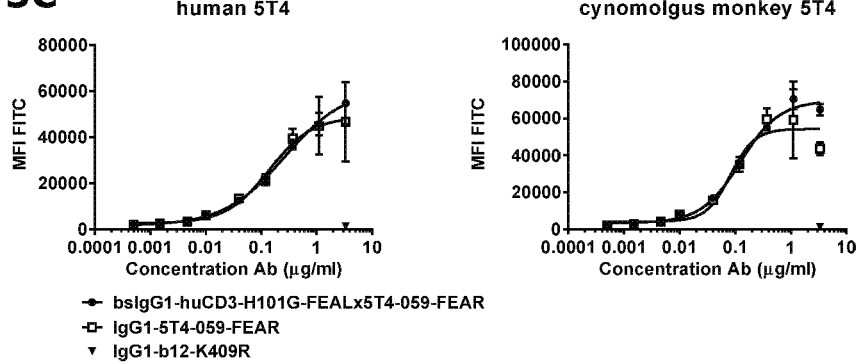
Figure 5D:
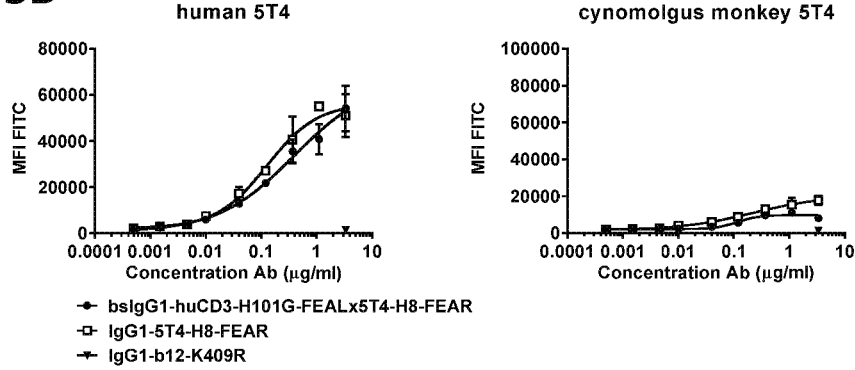
Figure 5E:
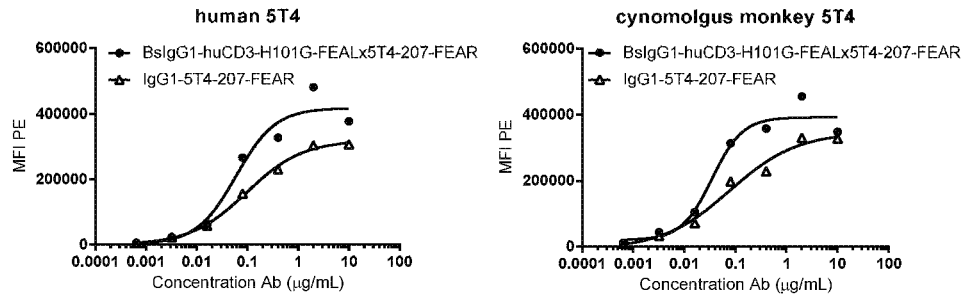
FIGS. 5E-5M: Binding of bispecific CD3×5T4 antibodies to cynomolgus monkey and human 5T4 transfected into HEK-293 cells. Mono- and bivalent binding of 5T4 antibodies was analysed using HEK-293 cells transiently transfected with human 5T4 (left panels) or with cynomolgus monkey 5T4 (right panels). Cells were incubated with increasing concentrations of antibodies, as indicated. After secondary labelling with phycoerythrin (PE)-conjugated goat-anti-human IgG F(ab')2, binding was analysed by flow cytometry.
Figure 5F:
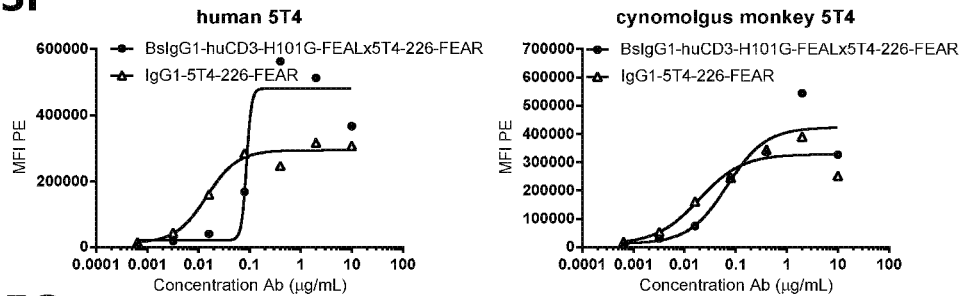
Figure 5G:
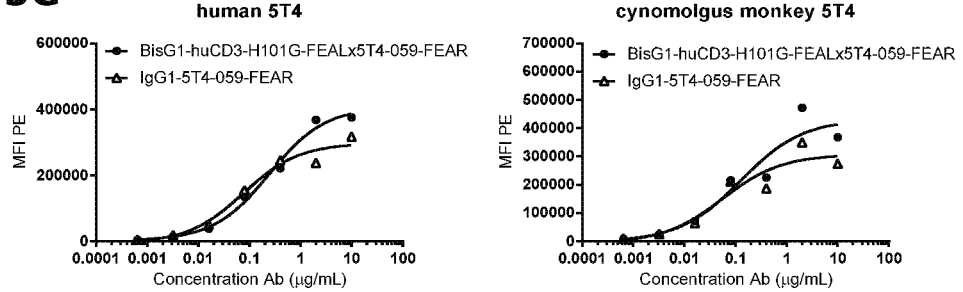
Figure 5H:
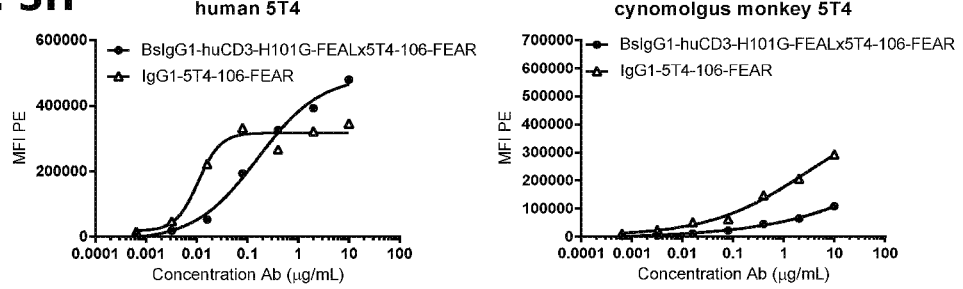
Figure 5I:
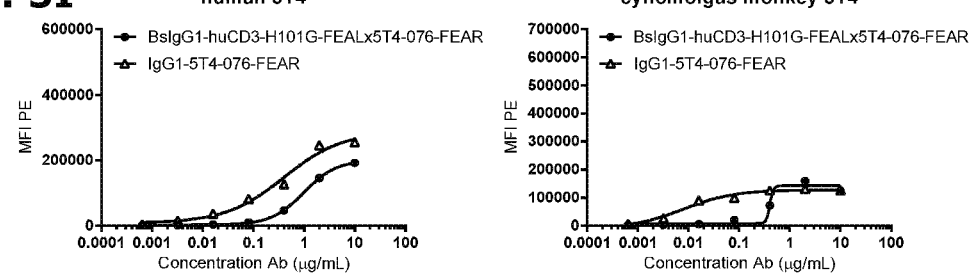
Figure 5J:
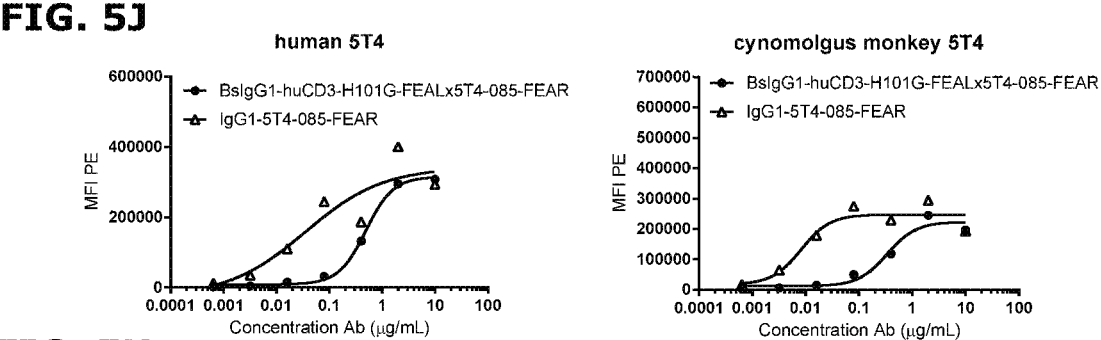
Figure 5K:
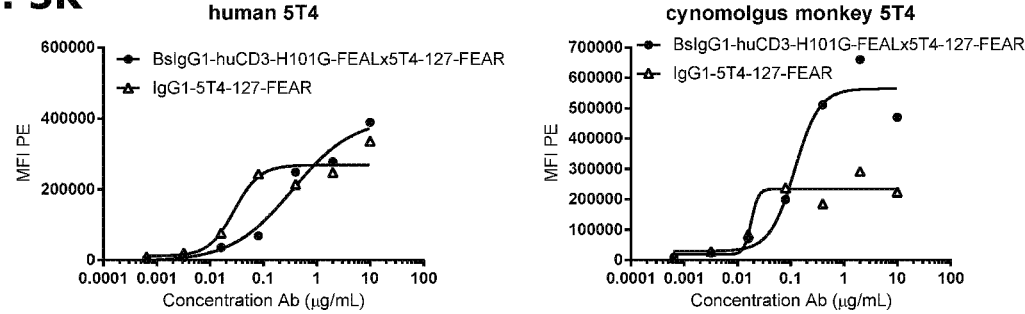
Figure 5L:
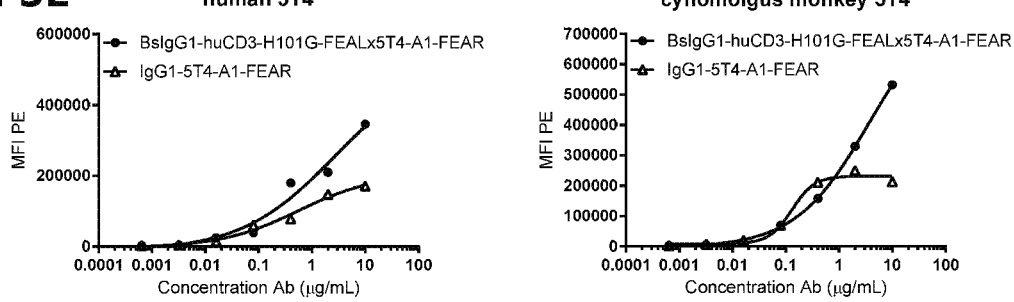
Figure 5M:
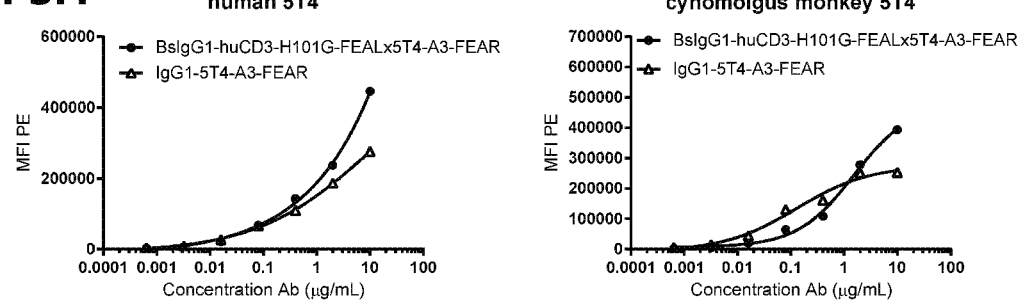

FIG. 4 shows the cytotoxic capacity of Duostatin-3 conjugated bispecific antibodies that monovalently bind 5T4 in MDA-MB-468 (A) or HCC1954 cells (B). BsIgG1-5T4-H8-FEAR×b12-vcDuo3 was highly capable of inducing cytotoxicity, indicative of an effective internalization capacity of the antibody. In contrast, bsIgG1-5T4-076-FEAR×b12-vcDuo3, bsIgG1-5T4-085-FEAR×b12-vcDuo3 and bsIgG1-5T4-127-FEAR×b12-vcDuo3 did not induce any cytotoxicity; dose response curves were similar to that of the non-binding IgG1-b12-vcDuo3 control antibody. This indicates poor internalization of those antibodies upon binding to membrane-bound 5T4. BsIgG1-5T4-059-FEAR×b12-vcDuo3, bsIgG1-5T4-106-FEAR×b12-vcDuo3, bsIgG1-5T4-207-FEAR×b12-vcDuo3, and bsIgG1-5T4-226-FEAR×b12-vcDuo3 induced intermediate cytotoxicity in both tested cell lines, indicating that these monovalent 5T4 antibodies induced internalization but to a lesser extent than bsIgG1-5T4-H8-FEAR×b12-vcDuo3.

Example 8—Humanized CD3 Antibodies for the Generation of CD3×5T4 Bispecific Antibodies The generation of humanized antibody IgG1-huCD3-H1L1 is described in Example 1 of WO2015/001085. IgG1-huCD3-H1L1 is referred to herein as 'IgG1-huCD3'. Antibody IgG1-huCD3-H1L1-FEAL is a variant hereof with amino acid substitutions in the Fc domain that prevent interactions with IgG Fc receptors (Fc gamma receptors [FcγR]) and complement, in addition to a mutation that allows the generation of bispecific antibodies through controlled Fab-arm exchange: L234F, L235E, D265A and F405L, as described herein above. It has previously been demonstrated that these mutation have no effect on target binding of the antibodies in which they are introduced (see e.g. US 2015/0337049)

The generation of humanized antibody IgG1-huCD3-H1L1-H101G is described in Example 2 of WO2017/009442. IgG1-huCD3-H1L1-H101G will be referred to as 'IgG1-huCD3-H101G'. Antibody IgG1-huCD3-H101G-FEAL is a variant hereof with amino acid substitutions L234F, L235E, D265A and F405L, as described herein above.

Example 9—CD3 Binding Affinity Determination Using Biolayer Interferometry

Binding affinities of selected CD3 antibodies, including IgG1-huCD3 and IgG1-huCD3-H101G, were determined as described in Example 7 of WO2017/009442.

In short, binding affinities of selected CD3 antibodies in an IgG1-huCD3-FEAL format to for recombinant soluble CD3ε (CD3E27-GSKa) (mature protein of SEQ ID NO: 101) were determined using biolayer interferometry on a ForteBio Octet HTX (ForteBio). Anti-human Fc capture biosensors (ForteBio, cat. no. 18-5060) were loaded for 600 s with hIgG (1 mg/mL). After a baseline measurement (200 s), the association (1000 s) and dissociation (2000 s) of CD3E27-GSKa was determined, using a CD3E27-GSKa concentration range of 27.11 μg/mL–0.04 μg/mL (1000 nM-1.4 nM) with three-fold dilution steps (sample diluent, ForteBio, cat. no. 18-5028). For calculations, the theoretical molecular mass of CD3E27-GSKa based on the amino acid sequence was used, i.e. 27.11 kDa. Experiments were carried out while shaking at 1000 rpm and at 30° C. Each antibody was tested in at least two independent experiments. Data was analyzed with ForteBio Data Analysis Software v8.1, using the 1:1 model and a global full fit with 1000 s association time and 100 s dissociation time. Data traces were corrected by subtraction of a reference curve (antibody on biosensor, measurement with sample diluent only), the Y-axis was aligned to the last 10 s of the baseline, and interstep correction as well as Savitzky-Golay filtering was applied. Data traces with a response <0.05 nm were excluded from analysis.

Table 5 shows the association rate constant $k_a$ (1/Ms), dissociation rate constant $k_d$ (1/s) and equilibrium dissociation constant $K_D$ (M) for recombinant CD3ε determined by biolayer interferometry. IgG1-huCD3-FEAL showed a relatively high ($K_D$: 15 nM) binding affinity to recombinant CD3ε compared to IgG1-huCD3-H101G-FEAL ($K_D$: 638 nM).

TABLE 5

Binding affinities of monospecific, bivalent CD3 antibodies to recombinant CD3ε as determined by label-free biolayer interferometry

| Antibody | On-rate $k_a$ (1/Ms) | Off-rate $k_d$ (1/s) | $K_D$ (nM) |
|---|---|---|---|
| IgG1-huCD3-FEAL | 2.7E+05 | 4.0E−03 | 15 |
| IgG1-huCD3-H101G-FEAL | 3.0E+04 | 2.0E−02 | 683 |

Example 10—Generation of Bispecific Antibodies by 2-MEA-Induced Fab-Arm Exchange Bispecific antibodies were generated in vitro using the DuoBody® platform technology, i.e. 2-MEA-induced Fab-arm exchange as described in WO2011147986, WO2011131746 and WO2013060867 (Genmab) and Labrijn et al. (Labrijn et al., PNAS 2013, 110: 5145-50; Gramer et al., MAbs 2013, 5: 962-973). To enable the production of bispecific antibodies by this method, IgG1 molecules carrying a single mutation in the CH3 domain were generated: in one parental IgG1 antibody the F405L mutation (i.e. the CD3 antibodies), in the other parental IgG1 antibody the K409R mutation (i.e. the 5T4 or control, HIV-1 gp120-specific, antibodies). In addition to these mutations, the parental IgG1 antibodies included substitutions that result in a Fc domain that is unable to interact with IgG Fc receptors (Fc gamma receptors) and complement: L234F, L235E, D265A (FEA).

To generate bispecific antibodies, the two parental antibodies were mixed in equal mass amounts in PBS buffer (Phosphate Buffered Saline; 8.7 mM $HPO_4^{2-}$, 1.8 mM $H_2PO_4^-$, 163.9 mM $Na^+$, 140.3 mM $Cl^-$, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer carriages (Thermo Fisher Scientific) according to the manufacturer's protocol in order to allow re-oxidation of the inter-chain disulfide bonds and formation of intact bispecific antibodies.

The following antibodies were used in the examples:
CD3 Antibodies
IgG1-huCD3-FEAL (having the VH and VL sequences set forth in SEQ ID NO: 57 and SEQ ID NO: 60).
IgG1-huCD3-H101G-FEAL (having the VH and VL sequences set forth in SEQ ID NO: 68 and SEQ ID NO: 60)
5T4 Antibodies
IgG1-5T4-207-FEAR (having the VH and VL sequences set forth in SEQ ID NO: 40 and SEQ ID NO: 44)
IgG1-5T4-226-FEAR (having the VH and VL sequences set forth in SEQ ID NO: 47 and SEQ ID NO: 51)
IgG1-5T4-059-FEAR (having the VH and VL sequences set forth in SEQ ID NO: 5 and SEQ ID NO: 9)
IgG1-5T4-076-FEAR (having the VH and VL sequences set forth in SEQ ID NO: 12 and SEQ ID NO: 16)
IgG1-5T4-085-FEAR (having the VH and VL sequences set forth in SEQ ID NO: 19 and SEQ ID NO: 23)
IgG1-5T4-106-FEAR (having the VH and VL sequences set forth in SEQ ID NO: 26 and SEQ ID NO: 30)
IgG1-5T4-127-FEAR (having the VH and VL sequences set forth in SEQ ID NO: 33 and SEQ ID NO: 37)
IgG1-5T4-H8-FEAR (based on 5T4 antibody H8 from Wyeth (WO 2007/106744 and US2010/0173382); having the VH and VL sequences set forth in SEQ ID NO: 87 and SEQ ID NO: 88)
IgG1-5T4-A1-F405L (based on 5T4 antibody A1 from Wyeth (WO 2007/106744 and U.S. Pat. No. 8,044,178); having the VH and VL sequences set forth in SEQ ID NO: 83 and SEQ ID NO: 84)
IgG1-5T4-A1-FEAR (based on 5T4 antibody A1 from Wyeth (WO 2007/106744 and U.S. Pat. No. 8,044,178); having the VH and VL sequences set forth in SEQ ID NO: 83 and SEQ ID NO: 84)
IgG1-5T4-A3-F405L (based on 5T4 antibody A3 from Wyeth (WO 2007/106744 and U.S. Pat. No. 8,759,495); having the VH and VL sequences set forth in SEQ ID NO: 85 and SEQ ID NO: 86)
IgG1-5T4-A3-FEAR (based on 5T4 antibody A3 from Wyeth (WO 2007/106744 and U.S. Pat. No. 8,759,495); having the VH and VL sequences set forth in SEQ ID NO: 85 and SEQ ID NO: 86)
Bispecific Antibodies
bsIgG1-huCD3-H101G-FEAL×5T4-207-FEAR
bsIgG1-huCD3-H101G-FEAL×5T4-226-FEAR bsIgG1-huCD3-H101G-FEALx5T4-059-FEAR
bsIgG1-huCD3-H101G-FEALx5T4-106-FEAR
bsIgG1-huCD3-H101G-FEALx5T4-076-FEAR
bsIgG1-huCD3-H101G-FEALx5T4-085-FEAR
bsIgG1-huCD3-H101G-FEALx5T4-127-FEAR
bsIgG1-huCD3-H101G-FEALx5T4-A1-FEAR
bsIgG1-huCD3-H101G-FEALx5T4-A3-FEAR
bsIgG1-huCD3-H101G-FEALx5T4-H8-FEAR
bsIgG1-huCD3-H101G-FEALxb12-FEAR
bsIgG1-huCD3-FEALx5T4-207-FEAR
bsIgG1-huCD3-FEALx5T4-226-FEAR
bsIgG1-huCD3-FEALx5T4-059-FEAR
bsIgG1-huCD3-FEALx5T4-106-FEAR
bsIgG1-huCD3-FEALx5T4-H8-FEAR
bsIgG1-huCD3-FEALx5T4-A1-FEAR
bsIgG1-huCD3-FEALx5T4-A3-FEAR
bsIgG1-b12-FEALx5T4-207-FEAR Fluorescein Isothiocyanate (FITC)-Labeled Bispecific Antibodies bsIgG1-b12-FEALx5T4-059-FEAR-FITC
bsIgG1-b12-FEALx5T4-207-FEAR-FITC
bsIgG1-b12-FEALx5T4-226-FEAR-FITC
bsIgG1-5T4-A1-F405Lxb12-FEAR-FITC
bsIgG1-5T4-A3-F405Lxb12-FEAR-FITC Duostatin-3 Conjugated Bispecific Antibodies BsIgG1-5T4-H8-FEARxb12-vcDuo3
bsIgG1-5T4-076-FEARxb12-vcDuo3
bsIgG1-5T4-085-FEARxb12-vcDuo3
bsIgG1-5T4-127-FEARxb12-vcDuo3
BsIgG1-5T4-059-FEARxb12-vcDuo3
bsIgG1-5T4-106-FEARxb12-vcDuo3
bsIgG1-5T4-207-FEARxb12-vcDuo3
bsIgG1-5T4-226-FEARxb12-vcDuo3.

Non-Binding Control Antibodies

IgG-b12 is a HIV-1 gp120 specific antibody (Barbas, C F. J Mol Biol. 1993 Apr. 5; 230(3):812-23) that is used in some of the examples as negative, non-binding, control second arm for bispecific antibodies.

IgG1-b12-F405L is a variant hereof with the substitution F405L.

IgG1-b12-FEAL is a variant hereof with substitutions that result in a Fc domain that is unable to interact with IgG Fc receptors (Fc gamma receptors) and complement, in addition to a mutation that allows the generation of bispecific antibodies through controlled Fab-arm exchange: L234F, L235E, D265A and F405L.

IgG1-b12-K409R is a variant hereof with the substitution K409R.

IgG1-b12-FEAR is a variant hereof with substitutions that result in a Fc domain that is unable to interact with IgG Fc receptors (Fc gamma receptors) and complement, in addition to a mutation that allows the generation of bispecific antibodies through controlled Fab-arm exchange: L234F, L235E, D265A and K409R.

Example 11—Binding of CD3x5T4 Bispecific Antibodies to Cynomolgus Monkey and Human 5T4 Expressed in HEK-293 Cells Binding of bispecific, monovalent CD3x5T4 antibodies and monospecific, bivalent 5T4 antibodies to the plasma membrane of HEK-293 cells transiently transfected with human 5T4 or with cynomolgus monkey (*Macaca fascicularis*) 5T4 (generated as described in Example 1) was analyzed by flow cytometry.

Cells ($3 \times 10^4$ cells/well) were incubated in polystyrene 96-well round-bottom plates (Greiner bio-one, cat. no. 650180) with serial dilutions of antibodies (ranging from 0.0137 to 10 µg/mL in 3-fold dilution steps) in 100 µL PBS/0.1% BSA/0.02% azide (staining buffer) at 4° C. for 30 min. Experiments were performed in technical duplicate. After washing twice in staining buffer, cells were incubated in 50 µL secondary antibody at 4° C. for 30 min. As a secondary antibody, FITC-conjugated goat-anti-human IgG F(ab')$_2$ (Southern Biotech, USA, cat. no. 2043-02) diluted 1:200 in staining buffer, was used in all experiments. Cells were washed twice in staining buffer, re-suspended in 30 µL staining buffer and analyzed on an iQue Screener (Intellicyt Corporation, USA). Binding curves were analyzed using non-linear regression (sigmoidal dose-response with variable slope) using GraphPad Prism V7.02 software (GraphPad Software, San Diego, CA, USA).

FIGS. 5A-5D (left panels) show that bispecific antibodies bsIgG1-huCD3-H101G-FEALx5T4-207-FEAR (FIG. 5A), bsIgG1-huCD3-H101G-FEALx5T4-226-FEAR (FIG. 5B), bsIgG1-huCD3-H101G-FEALx5T4-059-FEAR (FIG. 5C) and bsIgG1-huCD3-H101G-FEALx5T4-H8-FEAR (FIG. 5D), that monovalently bind 5T4, display dose-dependent binding to HEK-293 cells transfected with human 5T4, which was comparable to binding of monospecific, bivalent 5T4 antibodies IgG1-5T4-207-FEAR, IgG1-5T4-226-FEAR, IgG1-5T4-059-FEAR and IgG1-5T4-H8-FEAR, respectively.

FIGS. 5A-5D (right panels) show that bispecific antibodies bsIgG1-huCD3-H101G-FEALx5T4-207-FEAR (FIG. 5A), bsIgG1-huCD3-H101G-FEALx5T4-226-FEAR (FIG. 5B), and bsIgG1-huCD3-H101G-FEALx5T4-059-FEAR (FIG. 5C), that monovalently bind 5T4, display dose-dependent binding to HEK-293 cells transfected with cynomolgus monkey 5T4, which was comparable to binding of monospecific, bivalent 5T4 antibodies IgG1-5T4-207-FEAR, IgG1-5T4-226-FEAR and IgG1-5T4-059-FEAR, respectively. BsIgG1-huCD3-H101G-FEALx5T4-H8-FEAR and IgG1-5T4-H8-FEAR show poor binding to cynomolgus monkey 5T4, which is in line with Example 2 and experiments described in WO2007/106744. As negative control, IgG1-b12-K409R (3 µg/mL) was included in these experiments, which showed no binding to HEK-293 cells transfected with either human or cynomolgus monkey 5T4.

In a second experiment, the staining was performed as described above with minor adjustments. The cells were incubated with serial dilutions of antibodies ranging from 0.000128 to 10 µg/mL, in 5-fold dilution steps. As a secondary antibody, Phycoerythrin (PE)-conjugated goat-anti-human IgG F(ab')2 (Jackson Immunoresearch, UK, cat. no. 109-116-098) diluted 1:200 in staining buffer, was used.

FIGS. 5E-5M show that antibodies bsIgG1-huCD3-H101G-FEALx5T4-207-FEAR and IgG1-5T4-207-FEAR (FIG. 5E), bsIgG1-huCD3-H101G-FEALx5T4-226-FEAR and IgG1-5T4-226-FEAR (FIG. 5F), bsIgG1-huCD3-H101G-FEALx5T4-059-FEAR and IgG1-5T4-059-FEAR (FIG. 5G), bsIgG1-huCD3-H101G-FEALx5T4-106-FEAR and IgG1-5T4-106-FEAR (FIG. 5H), bsIgG1-huCD3-H101G-FEALx5T4-076-FEAR and IgG1-5T4-076-FEAR (FIG. 5I), bsIgG1-huCD3-H101G-FEALx5T4-085-FEAR and IgG1-5T4-085-FEAR (FIG. 5J), bsIgG1-huCD3-H101G-FEALx5T4-127-FEAR and IgG1-5T4-127-FEAR (FIG. 5K), bsIgG1-huCD3-H101G-FEALx5T4-A1-FEAR and IgG1-5T4-A1-FEAR (FIG. 5L), bsIgG1-huCD3-H101G-FEALx5T4-A3-FEAR and IgG1-5T4-A3-FEAR (FIG. 5M) display dose-dependent binding to HEK-293 cells transfected with human 5T4 (left panels) as well as HEK-293 cells with cynomolgus monkey 5T4 (right panels). Again, the binding curves of the bivalent, monospecific and bispecific, monovalent antibodies display a similar trend between human and cynomolgus 5T4.

Example 12—Binding of CD3×5T4 Bispecific Antibodies to 5T4-Positive Human Tumor Cells Binding of CD3×5T4 bispecific antibodies to the 5T4-expressing human tumor cell lines HeLa (cervix adenocarcinoma; ATCC, cat. no. CCL-2) and MDA-MB-231 (breast adenocarcinoma; ATCC, cat. no. HTB-26) cell line was analyzed by flow cytometry. Neither HeLa nor MDA-MB-231 cells express CD3.

Cells ($3\times10^4$ cells/well) were incubated in polystyrene 96-well round-bottom plates (Greiner bio-one, cat. no. 650180) with serial dilutions of antibodies (range 0.000152 to 3 µg/mL in 3-fold dilution steps) in 100 µL PBS/0.1% BSA/0.02% azide (staining buffer) at 4° C. for 30 min. After washing twice in staining buffer, cells were incubated in 50 µL secondary antibody at 4° C. for 30 min. As a secondary antibody, Fluorescein isothiocyanate (FITC)-conjugated goat-anti-human IgG F(ab')$_2$ (Southern Biotech, USA, cat. no. 2043-02) diluted 1:400 in staining buffer, was used for the first experiment. Next, cells were washed twice in staining buffer, re-suspended in 120 µL staining buffer and analyzed on a BD LSRFortessa FACS (BD Biosciences, USA). Binding curves were analyzed using non-linear regression (sigmoidal dose-response with variable slope) using GraphPad Prism V7.02 software (GraphPad Software, San Diego, CA, USA).

Figure 6D:
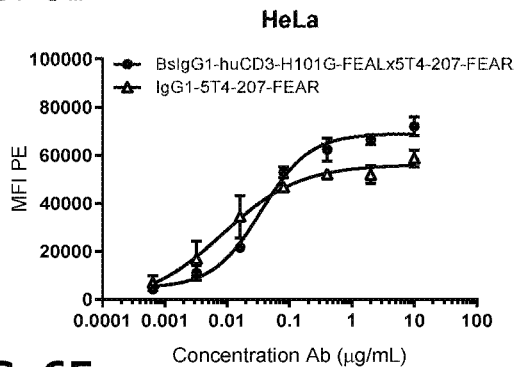
FIGS. 6D-6K: Binding of CD3×5T4 bispecific and 5T4 monospecific antibodies to HeLa cells. Mono- and bivalent binding of 5T4 antibodies to HeLa cells was determined by flow cytometry. Cells were incubated with increasing concentrations of antibodies. After secondary labelling with Phycoerythrin (PE)-conjugated goat-anti-human IgG F(ab')2, the mean fluorescence intensity (MFI) was determined by flow cytometry.
Figure 6E:
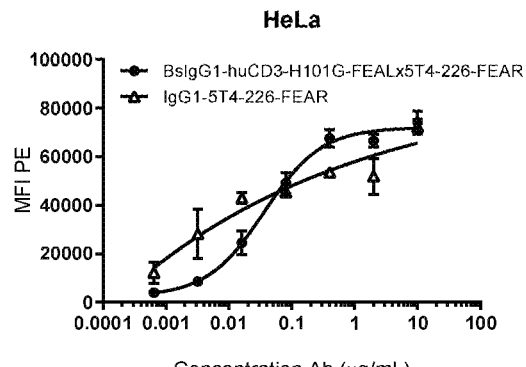
Figure 6F:
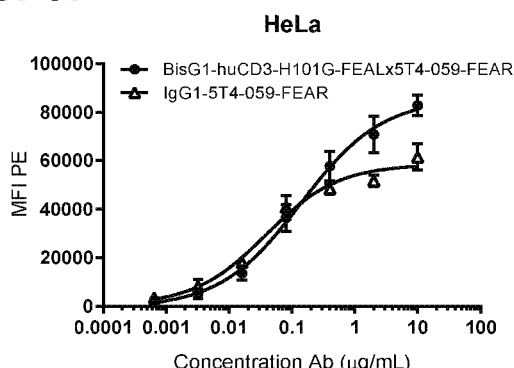
Figure 6G:
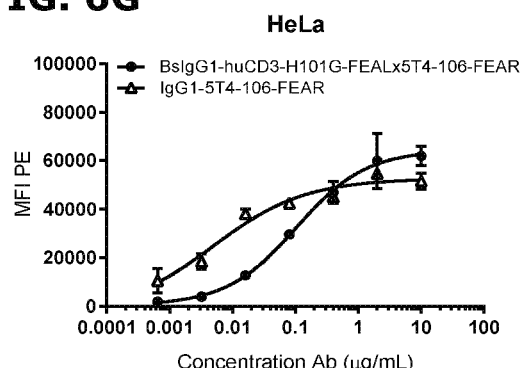
Figure 6H:
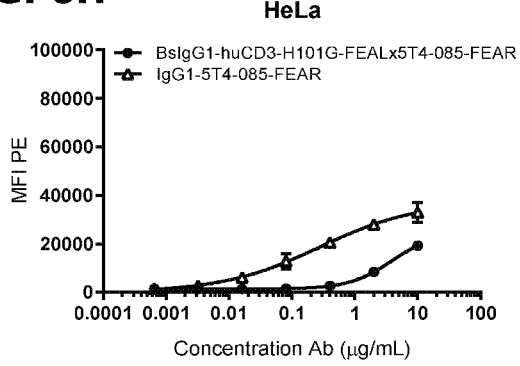
Figure 6I:
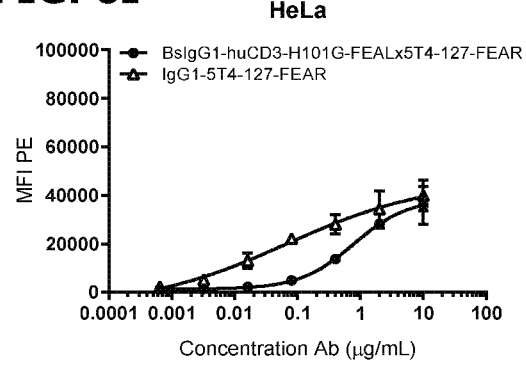
Figure 6J:
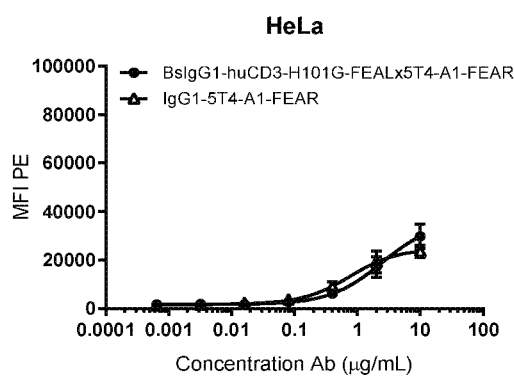
Figure 6K:
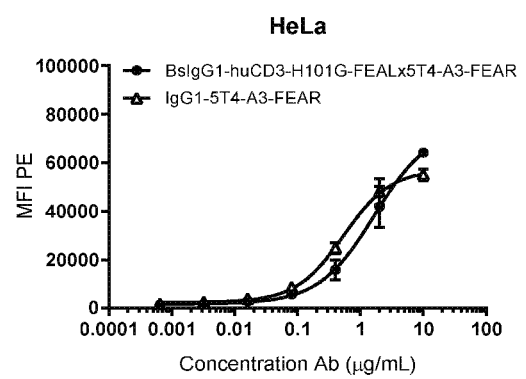
Figure 6L:
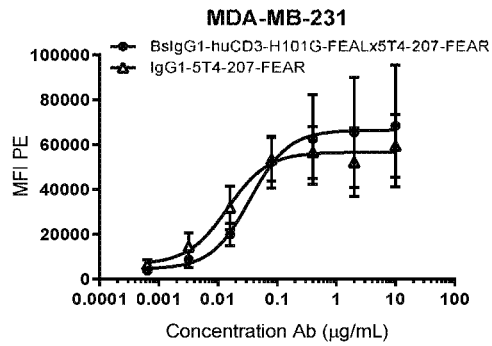
FIGS. 6L-6S: Binding of CD3x5T4 bispecific and 5T4 monospecific antibodies to MDA-MB-231 cells. Mono- and bivalent binding of 5T4 antibodies to MDA-MB-231 cells was determined by flow cytometry. Cells were incubated with increasing concentrations of antibodies. After secondary labelling with PE-conjugated goat-anti-human IgG F(ab')2, the mean fluorescence intensity (MFI) was determined by flow cytometry.
Figure 6M:
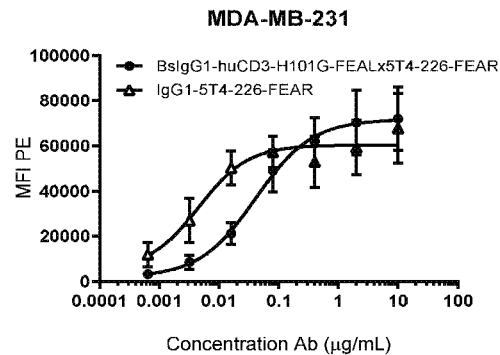
Figure 6N:
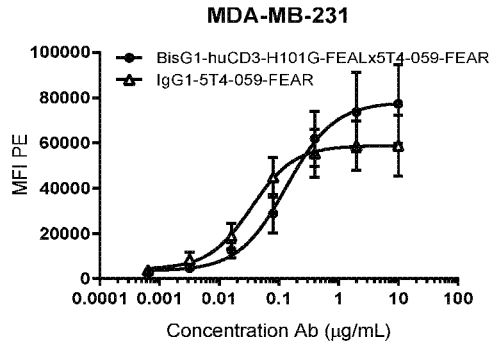
Figure 6O:
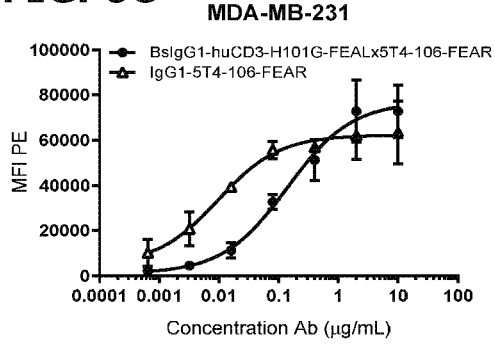
Figure 6P:
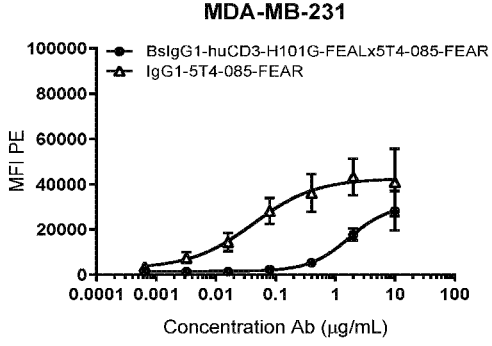
Figure 6Q:
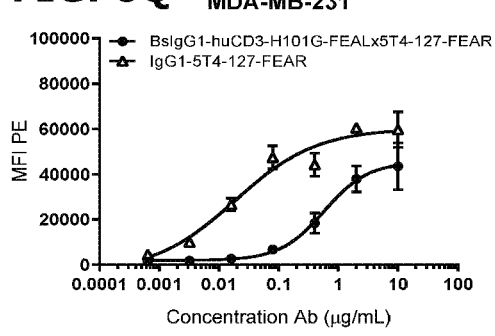
Figure 6R:
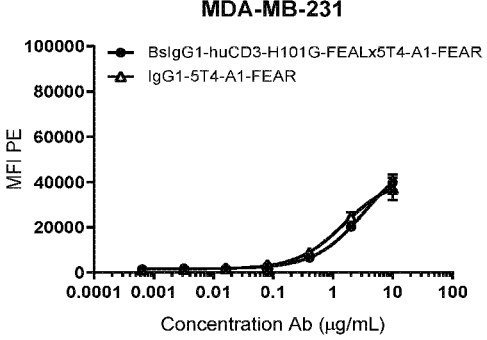
Figure 6S:
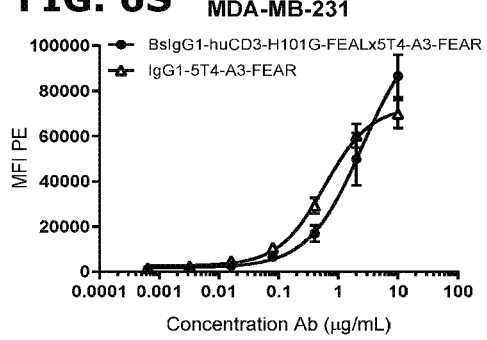

FIGS. 6A-6C (left panels) show that the CD3×5T4 bispecific antibodies bsIgG1-huCD3-H101G-FEAL×5T4-207-FEAR (FIG. 6A) and bsIgG1-huCD3-H101G-FEAL×5T4-059-FEAR (FIG. 6B) display dose-dependent binding to HeLa cells, with higher maximum binding than the monospecific, bivalent 5T4 antibodies IgG1-5T4-207-FEAR and IgG1-5T4-059-FEAR. For bsIgG1-huCD3-H101G-FEAL×5T4-226-FEAR (FIG. 6C) the maximum binding was similar to that of the monospecific, bivalent 5T4 antibody IgG1-5T4-226-FEAR on HeLa cells.

FIGS. 6A-6C (right panels) show that the CD3×5T4 bispecific antibodies bsIgG1-huCD3-H101G-FEAL×5T4-207-FEAR (FIG. 6A), bsIgG1-huCD3-H101G-FEAL×5T4-059-FEAR (FIG. 6B) and bsIgG1-huCD3-H101G-FEAL×5T4-226-FEAR (FIG. 6C) display dose-dependent binding to MDA-MB-231 cells, with higher maximum binding than the monospecific, bivalent 5T4 antibodies IgG1-5T4-207-FEAR, IgG1-5T4-226-FEAR and IgG1-5T4-059-FEAR. The negative control antibody that was included in these experiments, IgG1-b12-K409R (3 µg/mL), did not show binding to HeLa and MDA-MB-231 cells.

In a second experiment, the staining was performed as described above with minor adjustments. The cells were incubated with serial dilutions of antibodies, ranging from 0.000128 to 10 µg/mL, in 5-fold dilution steps. As a secondary antibody, Phycoerythrin (PE)-conjugated goat-anti-human IgG F(ab')2 (Jackson Immunoresearch, UK, cat. no. 109-116-098) diluted 1:200 in staining buffer, was used.

FIGS. 6D-6K and 6L-6S show that antibodies bsIgG1-huCD3-H101G-FEAL×5T4-207-FEAR and IgG1-5T4-207-FEAR, bsIgG1-huCD3-H101G-FEAL×5T4-226-FEAR and IgG1-5T4-226-FEAR, bsIgG1-huCD3-H101G-FEAL×5T4-059-FEAR and IgG1-5T4-059-FEAR, bsIgG1-huCD3-H101G-FEAL×5T4-106-FEAR and IgG1-5T4-106-FEAR, bsIgG1-huCD3-H101G-FEAL×5T4-085-FEAR and IgG1-5T4-085-FEAR, bsIgG1-huCD3-H101G-FEAL×5T4-127-FEAR and IgG1-5T4-127-FEAR, bsIgG1-huCD3-H101G-FEAL×5T4-A1-FEAR and IgG1-5T4-A1-FEAR, bsIgG1-huCD3-H101G-FEAL×5T4-A3-FEAR and IgG1-5T4-A3-FEAR display dose-dependent binding to HeLa and MDA-MB-231 tumor cells. In general, bsIgG1-huCD3-H101G-FEAL×5T4-207-FEAR, bsIgG1-huCD3-H101G-FEAL×5T4-226-FEAR, bsIgG1-huCD3-H101G-FEAL×5T4-059-FEAR, bsIgG1-huCD3-H101G-FEAL×5T4-106-FEAR, IgG1-5T4-207-FEAR, IgG1-5T4-226-FEAR, IgG1-5T4-059-FEAR, IgG1-5T4-106-FEAR, IgG1-5T4-085-FEAR and IgG1-5T4-127-FEAR display binding at lower antibody concentrations compared to bsIgG1-huCD3-H101G-FEAL×5T4-A1-FEAR, bsIgG1-huCD3-H101G-FEAL×5T4-A3-FEAR, IgG1-5T4-A1-FEAR and IgG1-5T4-A3-FEAR.

Example 13—Induction of T-Cell Activation, Cytokine Release and Cytotoxicity In Vitro by CD3×5T4 Bispecific Antibodies Using Purified T Cells as Effector Cells CD3×5T4 bispecific antibodies were tested in an in vitro cytotoxicity assay using 5T4-positive tumor cell lines as target cells and purified T cells as effector cells. T cells were derived from healthy human donor buffy coats (Sanquin, Amsterdam, The Netherlands) and isolated using the RosetteSep human T cell enrichment cocktail (Stemcell Technologies, France, cat. no. 15061) according to the manufacturer's instructions. To determine the percentage of viable T cells after isolation (either total T cells, CD4$^+$ T cells or CD8$^+$ T cells), a sample of the isolated T cells ($2.5\times10^5$ cells per condition) was stained for 30 min at 4° C. in a U-well 96-well plate (Cellstar, cat. no. 650180) using the following antibodies: Pacific Blue-anti-CD3 (eBiosciences, clone OKT3), APC-Cy-anti-CD4 (eBiosciences, clone OKT4), AF700-anti-CD8 (Biolegend, clone RPA-T8) and viability marker FVS 510 (BD Biosciences) in 100 µL PBS/0.1% BSA/0.02% azide (staining buffer). Next, cells were washed twice in staining buffer, re-suspended in 120 µL staining buffer and analyzed on a BD LSRFortessa FACS (BD Biosciences, USA). The percentages of CD3$^+$, CD3$^+$CD4$^+$ and CD3$^+$CD8$^+$ T cells for each of the donors used in the cytotoxicity experiment are described in Table 6.

TABLE 6

| Ratio CD3$^+$, CD4$^+$ and CD8$^+$ T cells per donor | | | |
| --- | --- | --- | --- |
| Donor | % CD3+ of viable cells | % CD4+ within CD3+ cells | % CD8+ within CD3+ cells |
| A | 91.2 | 84.2 | 11.8 |
| B | 77.8 | 78.3 | 18 |
| C | 97.6 | 78.1 | 19.6 |
| D | 92.6 | 77.3 | 15.5 |
| E | 99.2 | 78.4 | 20.3 |

MDA-MB-231 cells (16,000 cells/well) were seeded into flat bottom 96-well plates (Greiner-bio-one, The Netherlands, cat. no. 655180) and left to adhere for 4 hours at 37° C. T cells were added to tumor cells at an E:T ratio=8:1. Serial dilutions of bispecific CD3×5T4 antibodies or monospecific, bivalent 5T4 antibodies were added (final concentration ranging from 1000 to 0.0128 ng/mL; 5-fold dilutions) and plates were incubated for 72 hours at 37° C. Next, 110 µL supernatants containing T cells were transferred to U-bottom 96 Well culture plates (CellStar, cat. no. 650180). Plates were centrifuged (300×g) for 3 min at 4° C., after which 75 µL of supernatant was transferred to a new plate for cytokine production measurement, and T cells were kept to assess T cell activation markers (described below). Cytokine production induced by 0.2 μg/mL CD3×5T4 bispecific antibodies was analyzed by a multiplex U-plex assay (MeSo Scale Discovery, USA, cat. no. K15049K) according to manufacturer's instructions.

T cells were stained for T-cell markers CD3 (1:200; eBioscience, clone OKT3, conjugated to eFluor450), CD4 (1:50; eBioscience, clone OKT4, conjugated to APC-eFluor780), CD8 (1:100; Biolegend, clone RPA-T8, conjugated to AF700) and T-cell activation markers CD69 (1:50; BD Biosciences, clone AB2439, conjugated to APC), CD25 (1:50; eBioscience, clone BC96, conjugated to PE-Cy7) and CD279/PD1 (1:50; Biolegend, clone EH12.2H7, conjugated to BV605). Single stained samples with Ultracomp beads (5 μL; Invitrogen, cat. no. 01-2222-42) were used for compensation adjustments of the flow cytometer. After 30 min of incubation at 4° C., plates were washed three times with PBS/0.1% BSA/0.02% azide (staining buffer). Cells were resuspended in 120 μL staining buffer and analyzed using a FACS Fortessa (BD Biosciences). Data were processed using FlowJo (BD Biosciences).

In parallel, the viability of the tumor cells was assessed using Resazurin (7-Hydroxy-3H-phenoxazin-3-one 10-oxide). The adherent tumor cells were washed twice with PBS and incubated with 10% Resazurin (150 μL; Life Technologies, The Netherlands, cat. no. DAL1100) in RPMI-1640 (Lonza, Switzerland, cat. no. BE12-115F) medium containing 10% donor bovine serum with iron (Life Technologies, The Netherlands, cat. no. 10371-029) and pen/strep (Lonza, cat. no. DE17-603E) for 4 h at 37° C. The absorbance was measured with an Envision multilabel plate reader (PerkinElmer, US). The absorbance of staurosporine-treated (Sigma-Aldrich, US, cat. no. S6942) tumor cell samples was set as 0% viability and the absorbance of untreated tumor cell samples was set as 100% viability. The 'percentage viable cells' was calculated as follows:

% viable cells=([absorbance sample−absorbance staurosporine-treated target cells]/[absorbance untreated target cells−absorbance staurosporine treated target cells])×100.

Dose-response curves, EC50 and IC50 values were analyzed using non-linear regression (sigmoidal dose-response with variable slope) using GraphPad Prism V7.02 software (GraphPad Software, San Diego, CA, USA).

FIGS. 7A-7C show that bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR and bsIgG1-huCD3-H101G-FEAL×5T4-059-FEAR induced dose-dependent cytotoxicity (shown as decrease in % viable cells) in the 5T4-positive tumor cell line MDA-MB-231. Donor-to-donor variation was observed, but T cells of both donors induced maximum kill in the presence of 1 μg/mL CD3×5T4 bispecific antibody. Monospecific, bivalent antibodies IgG1-5T4-207-FEAR, IgG1-5T4-226-FEAR and IgG1-5T4-059-FEAR did not induce cytotoxicity. $IC_{50}$ values calculated from the graphs are presented in FIG. 7D. The $IC_{50}$ value of bsIgG1-huCD3-FEAL×5T4-207-FEAR and bsIgG1-huCD3-FEAL×5T4-059-FEAR were lower compared to bsIgG1-huCD3-H101G-FEAL×5T4-207-FEAR and bsIgG1-huCD3-H101G-FEAL×5T4-059-FEAR, respectively. In contrast, the $IC_{50}$ value of bsIgG1-huCD3-FEAL×5T4-226-FEAR was comparable to bsIgG1-huCD3-H101G-FEAL×5T4-226-FEAR.

Figure 8A:
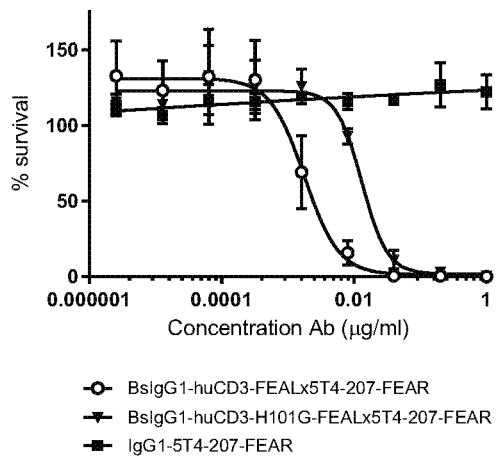
FIGS. 8A-8F: Induction of cytotoxicity by CD3x5T4 bispecific antibodies in MDA-MB-231 cells using T cells as effector cells in vitro. MDA-MB-231 cells were incubated with increasing concentrations of CD3x5T4 bispecific antibodies or 5T4 homodimers and isolated T cells as effector cells in an E:T ratio of 8:1. Three different donors were used for this experiment. Data shown are mean % survival±standard error of the mean (SEM) of three donors tested.
Figure 8B:
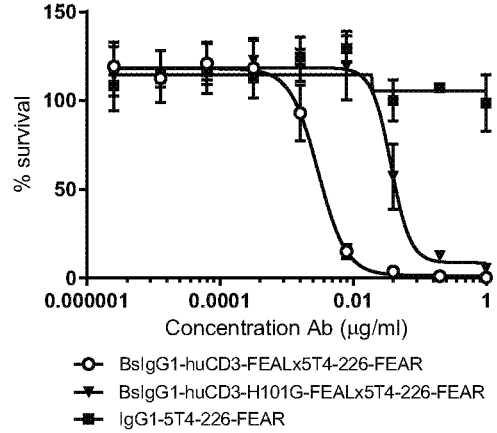
Figure 8C:
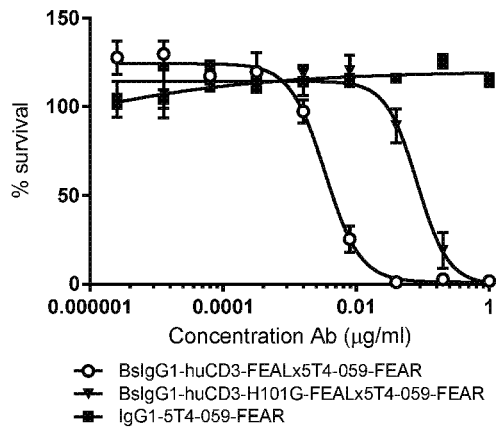
Figure 8D:
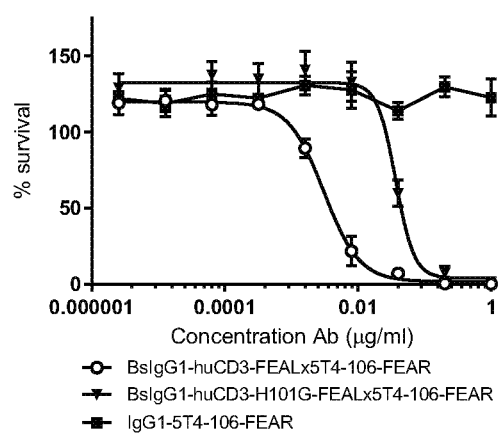
Figure 8E:
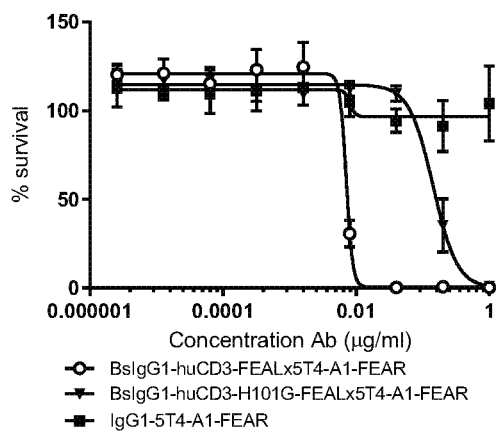
Figure 8F:
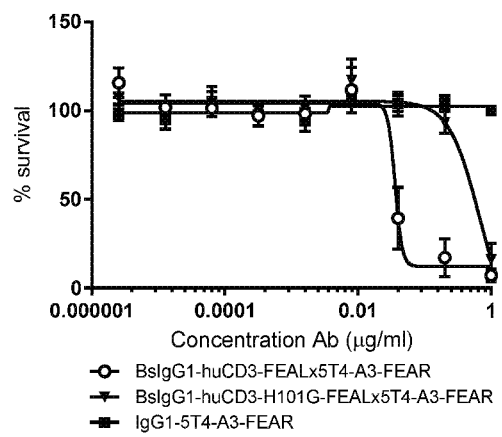
Figure 8G:
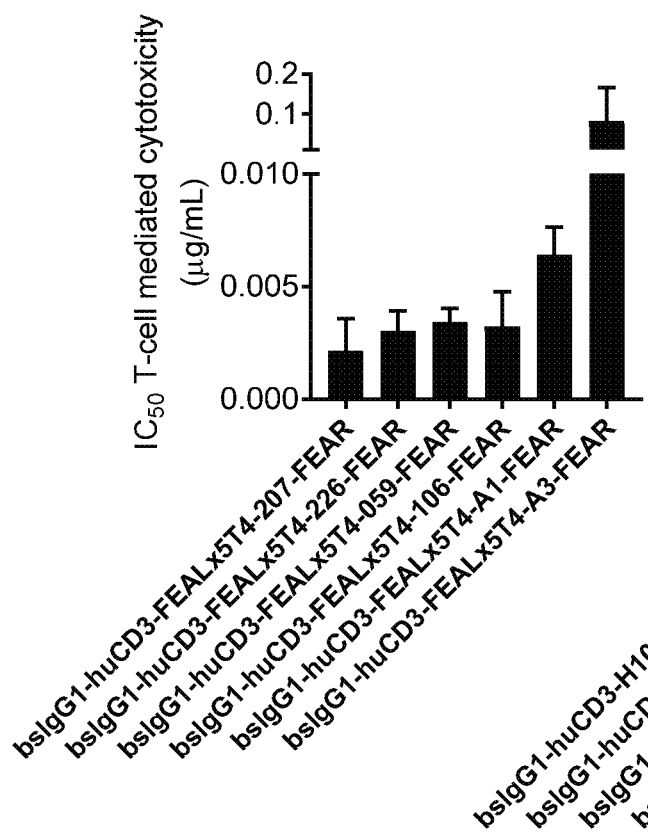
FIGS. 8G-8H: IC50 values of cytotoxicity induced by CD3x5T4 bispecific antibodies in MDA-MB-231 cells using T cells as effector cells in vitro. IC50 values of the T-cell-mediated cytotoxicity induced CD3x5T4 bispecific antibodies in MDA-MB-231 cells were analyzed using GraphPad Prism V7.02 software. Data are presented as mean IC50 values of three different donors±SD.
Figure 8H:
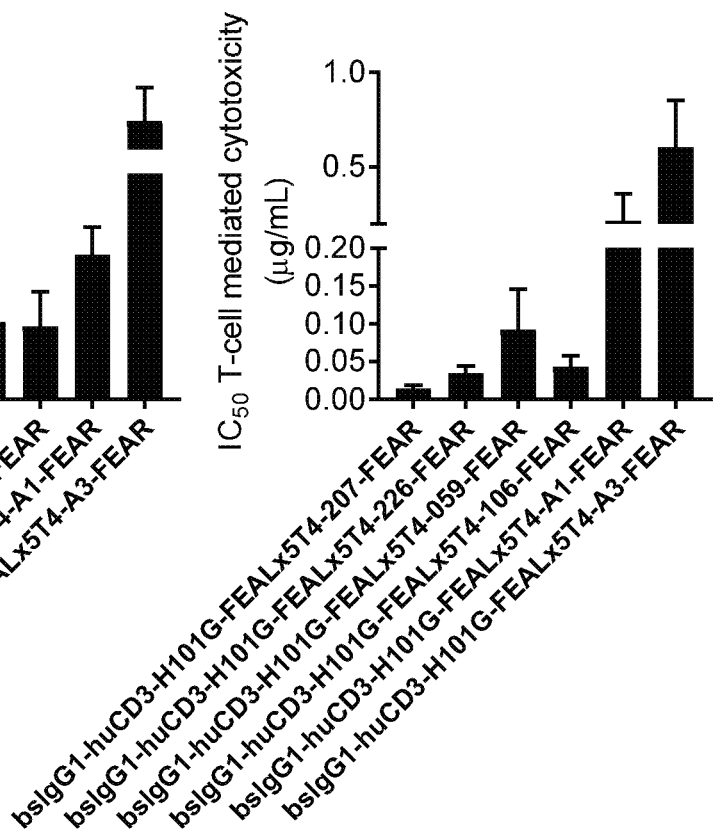

FIGS. 8A-8F show that bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR, bsIgG1-huCD3-H101G-FEAL×5T4-059-FEAR, bsIgG1-huCD3-FEAL×5T4-106-FEAR, bsIgG1-huCD3-H101G-FEAL×5T4-106-FEAR, bsIgG1-huCD3-FEAL×5T4-A1-FEAR, bsIgG1-huCD3-H101G-FEAL×5T4-A1-FEAR, bsIgG1-huCD3-FEAL×5T4-A3-FEAR and bsIgG1-huCD3-H101G-FEAL×5T4-A3-FEAR induced T-cell mediated cytotoxicity (shown as decrease in tumor cell survival) in MDA-MB-231 cell line. Bivalent, monospecific antibodies IgG1-5T4-207-FEAR, IgG1-5T4-226-FEAR, IgG1-5T4-059-FEAR, IgG1-5T4-106-FEAR, IgG1-5T4-A1-FEAR and IgG1-5T4-A3-FEAR did not induce T-cell-mediated cytotoxicity. IC50 values calculated from the graphs are presented in FIGS. 8G-8H. IC50 values of the T-cell mediated cytotoxicity induced by bsIgG1-huCD3-FEAL×5T4-207-FEAR, bsIgG1-huCD3-FEAL×5T4-226-FEAR, bsIgG1-huCD3-FEAL×5T4-059-FEAR and bsIgG1-huCD3-FEAL×5T4-106-FEAR are lower than the IC50 values of bsIgG1-huCD3-FEAL×5T4-A1-FEAR and bsIgG1-huCD3-FEAL×5T4-A3-FEAR. Also, IC50 values of the T-cell mediated cytotoxicity induced by bsIgG1-huCD3-H101G-FEAL×5T4-207-FEAR, bsIgG1-huCD3-H101G-FEAL×5T4-226-FEAR, bsIgG1-huCD3-H101G-FEAL×5T4-059-FEAR and bsIgG1-huCD3-H101G-FEAL×5T4-106-FEAR are lower than the IC50 values of bsIgG1-huCD3-H101G-FEAL×5T4-A1-FEAR and bsIgG1-huCD3-H101G-FEAL×5T4-A3-FEAR.

Figure 9A:
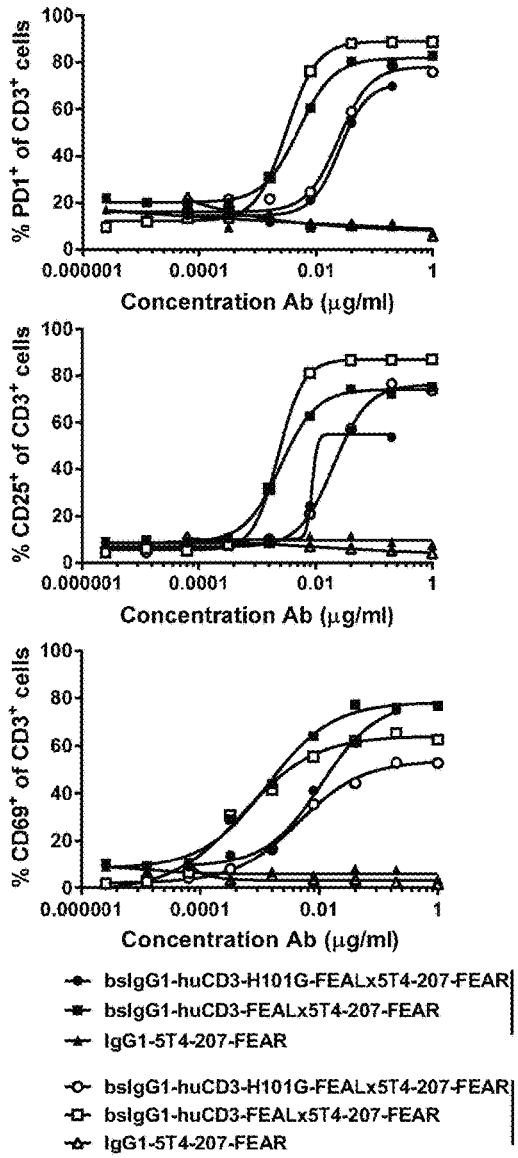
FIGS. 9A-9C: In vitro T-cell activation by CD3x5T4 bispecific antibodies in the presence of MDA-MB-231 cells. MDA-MB-231 cells were incubated with increasing concentrations of CD3x5T4 bispecific antibodies and monospecific, bivalent 5T4 antibodies, as indicated, and isolated T cells as effector cells in an E:T ratio of 8:1. The expression of three T cell activation markers (PD1 [upper panels], CD25 [middle panels] and CD69 [lower panels]) was analyzed by flow cytometry. Two different donors were used for this experiment, donor A (closed symbols) and donor B (open symbols).
Figure 9B:
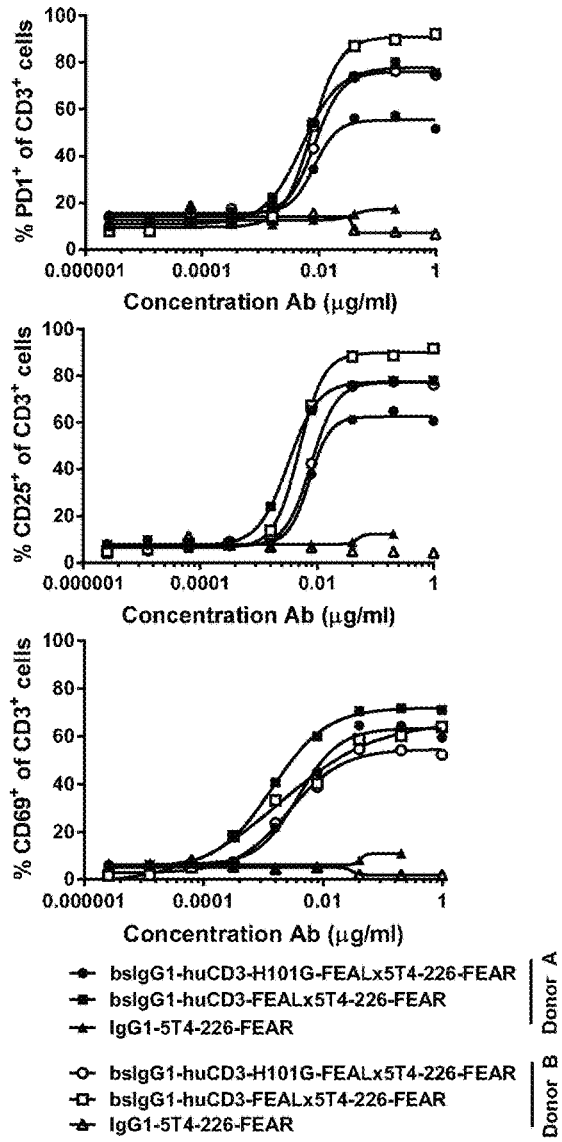
Figure 9C:
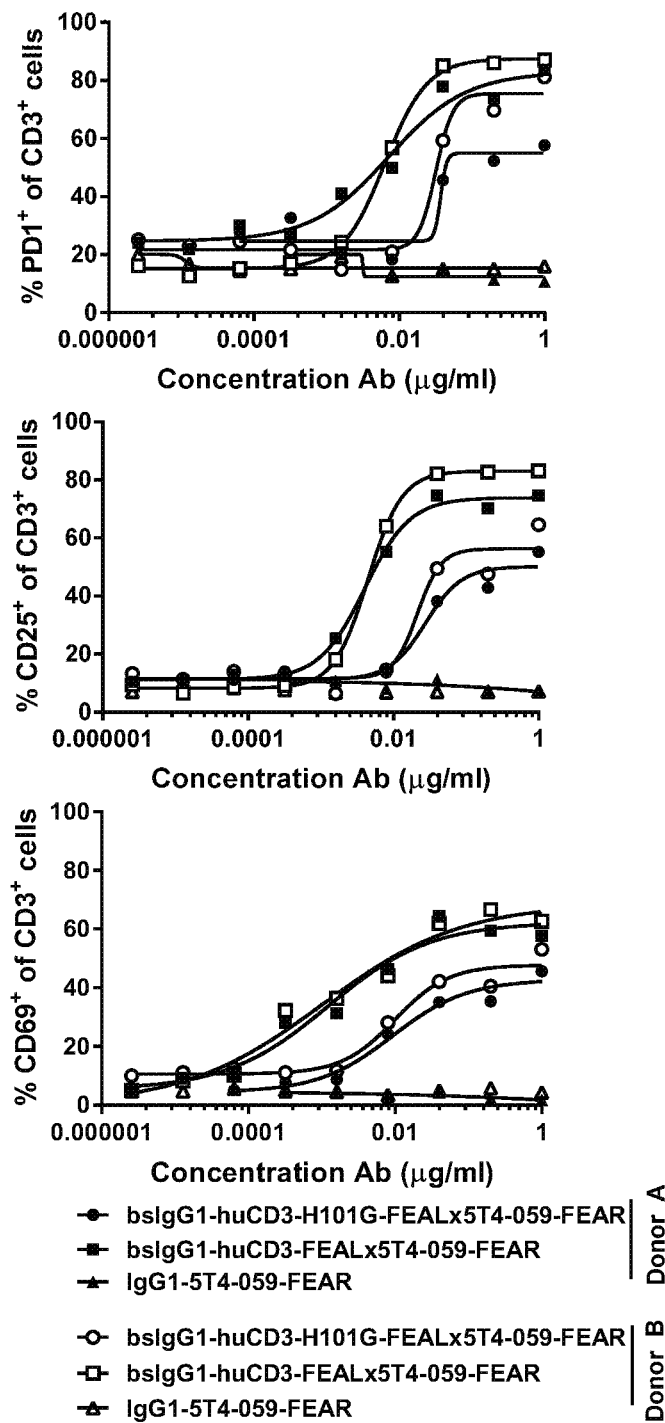
Figure 9D:
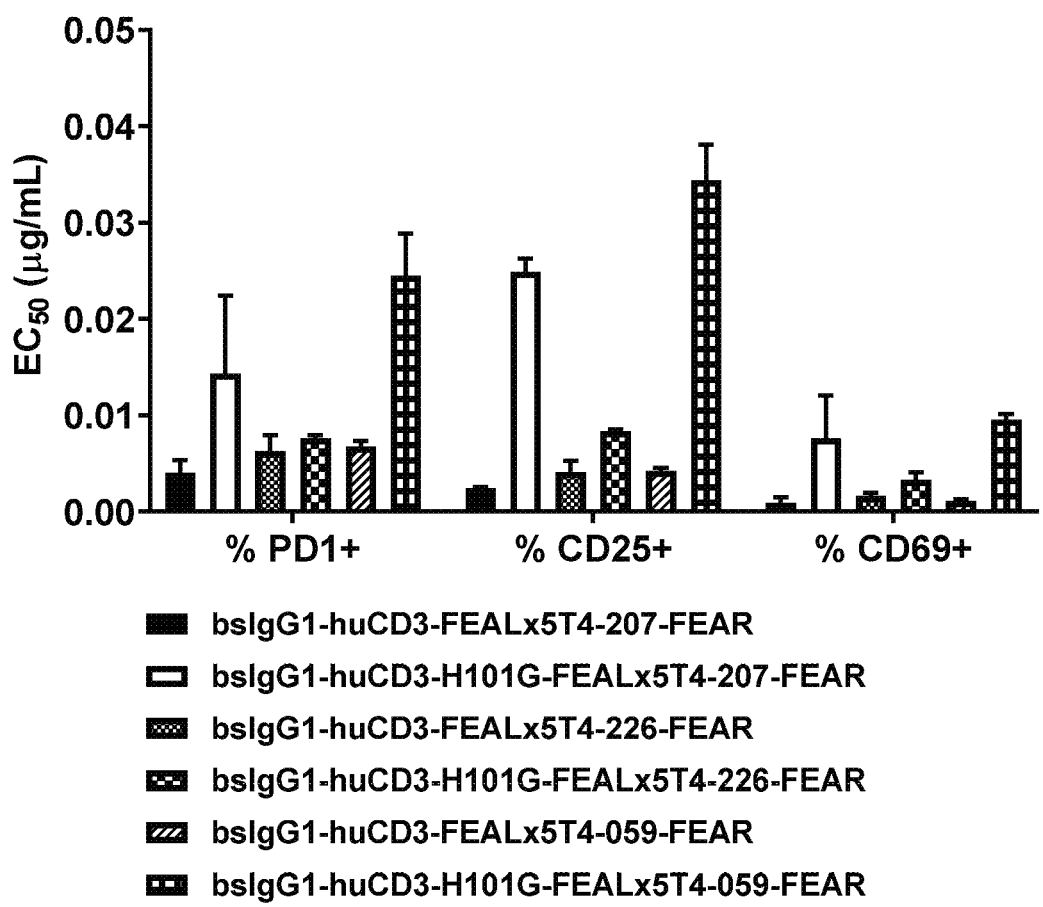
FIG. 9D: EC50 values of in vitro T-cell activation by CD3×5T4 bispecific antibodies in the presence of MDA-MB-231 cells. EC50 values of in vitro T-cell activation markers (PD1, CD25 and CD69) induced by bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR or bsIgG1-huCD3-H101G-FEAL×5T4-059-FEAR in the presence of MDA-MB-231 cells were analyzed using GraphPad Prism V7.02 software. Data are presented as mean of two different donors±SD.
Figure 10G:
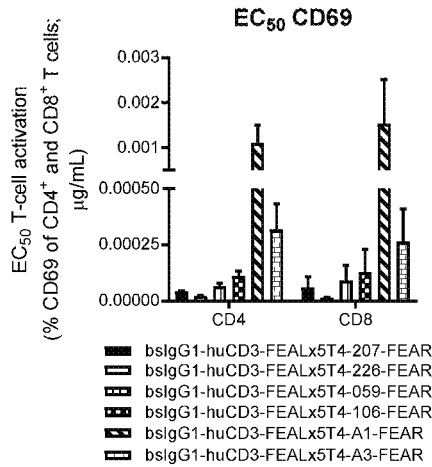
FIGS. 10G-10L: $EC_{50}$ values of in vitro T-cell activation by CD3×5T4 bispecific antibodies in the presence of MDA-MB-231 cells. $EC_{50}$ values of T-cell activation markers (increase in % of CD69$^+$ [FIGS. 10G-10H], CD25$^+$ [FIGS. 10I-10J] and PD1$^+$ [FIGS. 10K-10L], CD25 and CD69 cells within the CD4$^+$ and CD8$^+$ T cell populations) induced in vitro by CD3×5T4 bispecific antibodies in the presence of MDA-MB-231 cells were analyzed using GraphPad Prism V7.02 software. Data are presented as mean of three different donors±SD.
Figure 10H:
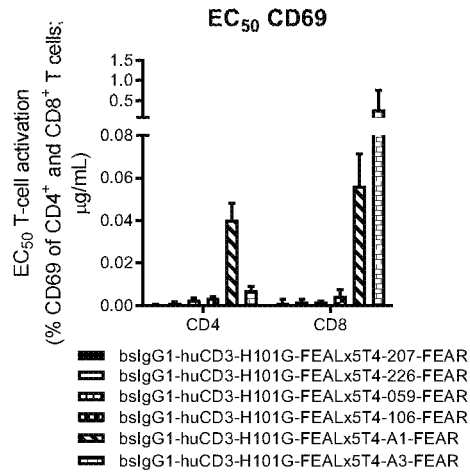
Figure 10I:
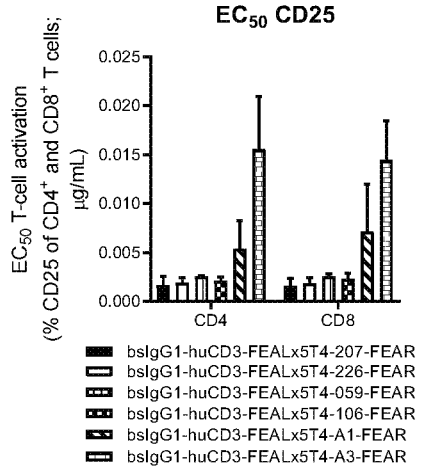
Figure 10J:
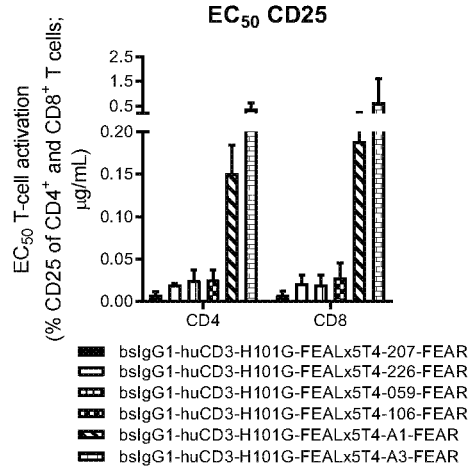
Figure 10K:
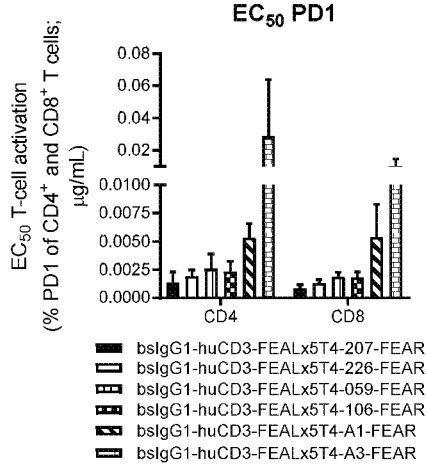
Figure 10L:
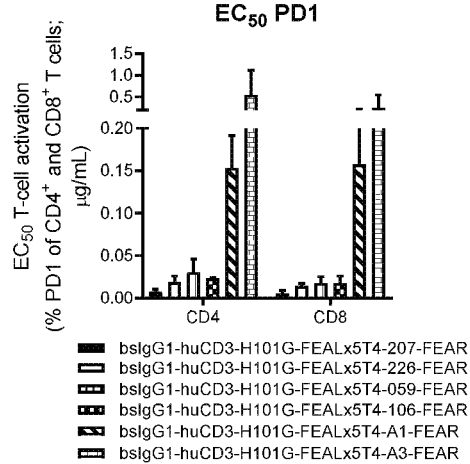

T-cell activation was determined by flow cytometry through staining for activation markers PD1, CD25 and CD69 (FIGS. 9A-9C). Monospecific, bivalent antibodies IgG1-5T4-207-FEAR, IgG1-5T4-226-FEAR and IgG1-5T4-059-FEAR did not induce upregulation of these T-cell activation markers, while bispecific antibodies bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR and bsIgG1-huCD3-H101G-FEAL×5T4-059-FEAR induced dose-dependent upregulation of PD1, CD25 and CD69. $EC_{50}$ values calculated from the graphs are represented in FIG. 9D. The $EC_{50}$ values for upregulation of PD1, CD25 and CD69 by bsIgG1-huCD3-FEAL×5T4-207-FEAR and bsIgG1-huCD3-FEAL×5T4-059-FEAR were lower compared to bsIgG1-huCD3-H101G-FEAL×5T4-207-FEAR and bsIgG1-huCD3-H101G-FEAL×5T4-059-FEAR, respectively. The $EC_{50}$ values for upregulation of CD25 and CD69 by bsIgG1-huCD3-FEAL×5T4-226-FEAR were lower compared to bsIgG1-huCD3-H101G-FEAL×5T4-226-FEAR, while the $EC_{50}$ value for PD1 upregulation was comparable between bsIgG1-huCD3-FEAL×5T4-226-FEAR and bsIgG1-huCD3-H101G-FEAL×5T4-226-FEAR.

FIGS. 10A-10F show that bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR, bsIgG1-huCD3-H101G-FEAL×5T4-059-FEAR, bsIgG1-huCD3-FEAL×5T4-106-FEAR, bsIgG1-huCD3-H101G-FEAL×5T4-106-FEAR, bsIgG1-huCD3-FEAL×5T4-A1-FEAR, bsIgG1-huCD3-H101G-FEAL×5T4-A1-FEAR, bsIgG1-huCD3-FEAL×5T4-A3-FEAR and bsIgG1-huCD3-H101G-FEAL×5T4-A3-FEAR induced T-cell activation (exemplified in FIGS. 10A-10F by increase in % $CD69^+$ T cells within the $CD4^+$ and $CD8^+$ T cell populations) when incubated with the MDA-MB-231 cell line, while the bivalent, monospecific antibodies IgG1-5T4-207-FEAR, IgG1-5T4-226-FEAR, IgG1-5T4-059-FEAR, IgG1-5T4-106-FEAR, IgG1-5T4-A1-FEAR and IgG1-5T4-A3-FEAR did not induce T-cell activation. EC50 values of three T-cell activation markers are shown in FIGS. 10G-10L. In general, the EC50 values of the T-cell activation (increase in % CD69$^+$, CD25$^+$ and PD1$^+$ cells within the CD4$^+$ and CD8$^+$ T cell populations) induced by bsIgG1-huCD3-FEALx5T4-207-FEAR, bsIgG1-huCD3-FEALx5T4-226-FEAR, bsIgG1-huCD3-FEALx5T4-059-FEAR and bsIgG1-huCD3-FEALx5T4-106-FEAR are lower than the EC50 values of bsIgG1-huCD3-FEALx5T4-A1-FEAR and bsIgG1-huCD3-FEALx5T4-A3-FEAR. Also, EC50 values of T-cell activation (increase in % of CD69$^+$, CD25$^+$ and PD1$^+$ T cells within the CD4$^+$ and CD8$^+$ T cell populations) induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR and bsIgG1-huCD3-H101G-FEALx5T4-106-FEAR are lower than the EC50 values of bsIgG1-huCD3-H101G-FEALx5T4-A1-FEAR and bsIgG1-huCD3-H101G-FEALx5T4-A3-FEAR.

Figure 11A:
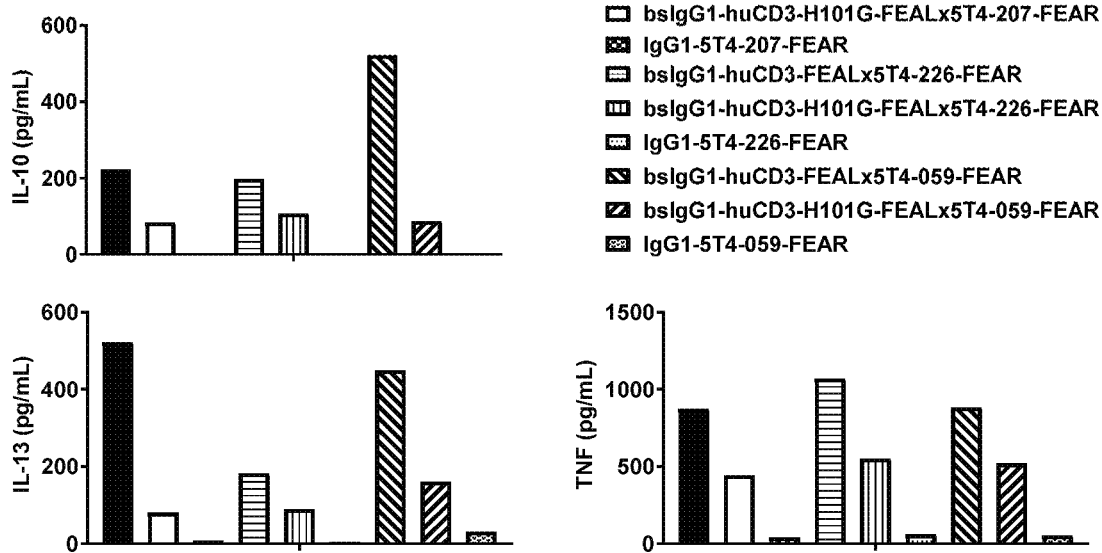
FIGS. 11A and 11B: T cell cytokine release induced by CD3×5T4 bispecific antibodies in the presence of 5T4-positive tumor cells. MDA-MB-231 cells were incubated with 0.2 μg/mL CD3×5T4 bispecific antibodies (bsIgG1-huCD3-FEAL×5T4-207-FEAR, bsIgG1-huCD3-H101G-FEAL×5T4-207-FEAR, bsIgG1-huCD3-FEAL×5T4-226-FEAR, bsIgG1-huCD3-H101G-FEAL×5T4-226-FEAR, bsIgG1-huCD3-FEAL×5T4-059-FEAR or bsIgG1-huCD3-H101G-FEAL×5T4-059-FEAR) and 5T4 monospecific antibodies (IgG1-5T4-207-FEAR, IgG1-5T4-226-FEAR or IgG1-5T4-059-FEAR) and isolated T cells as effector cells in an E:T ratio of 8:1. Release of cytokines was analyzed by U-PLEX assay.
Figure 11B:
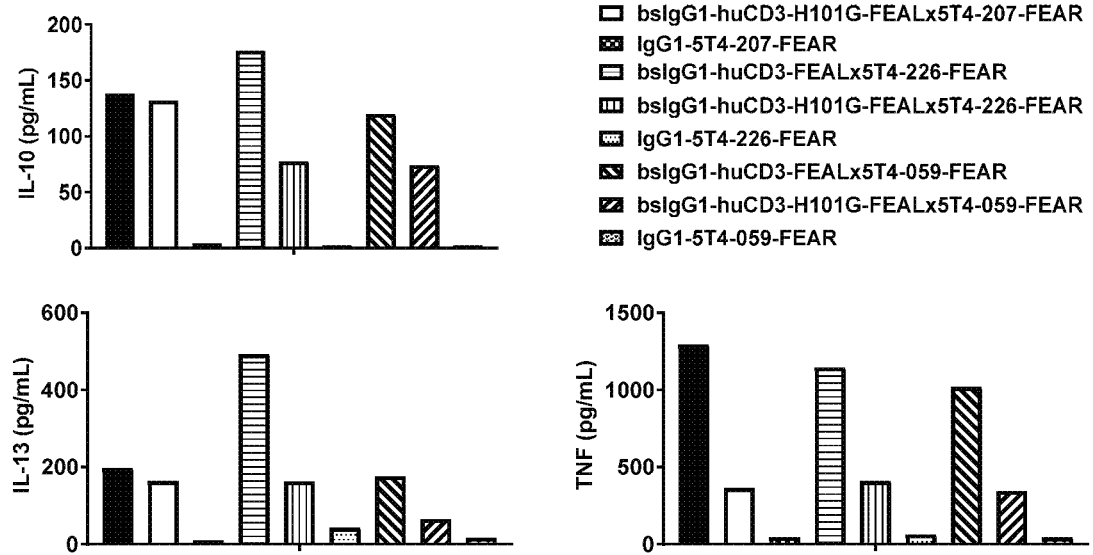

Production of the cytokines IL-10, IL-13 and TNF after exposure of co-cultures of T cells and MDA-MB-231 cells to 0.2 μg/mL CD3x5T4 bispecific antibodies was measured in culture supernatant, by multiplex U-plex assay. FIG. 11 shows the cytokine levels in the supernatant of T cell-tumor cell co-cultures, after incubation with bispecific antibodies. Experiments were performed using T cells from two different healthy donors; FIG. 11A shows the results from co-cultures with T cells derived from donor A, FIG. 11B shows the results from co-cultures with T cells derived donor B. Bispecific antibodies bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR and bsIgG1-huCD3-H101G-FEALx5T4-059-FEAR all induced cytokine release, although the cytokine levels in T cell-tumor cell co-cultures incubated with CD3x5T4 bispecific antibodies containing a IgG1-huCD3-H101G-FEAL-derived CD3-specific Fab-arm were lower than cytokine levels in co-cultures that had been incubated with bispecific antibodies containing a IgG1-huCD3-FEAL-derived CD3-specific Fab-arm. The monospecific antibodies IgG1-5T4-207-FEAR, IgG1-5T4-226-FEAR and IgG1-5T4-059-FEAR did not induce any cytokine release.

Example 14—Induction of Cytotoxicity In Vitro by CD3x5T4 Bispecific Antibodies Using PBMCs or Purified T Cells as Effector Cells at Varying Effector to Target Ratios To determine the efficiency of the T-cell-mediated kill of bispecific antibodies bsIgG1-huCD3-H101G-FEALx5T4-207-FEAR and bsIgG1-huCD3-H101G-FEALx5T4-207-FEAR in more detail, a cytotoxicity assay was performed as described in Example 13, with varying effector to target cell (E:T) ratios. In addition, either peripheral blood mononuclear cells (PBMCs) or isolated T cells were used as effector cells. The ovarian cancer cell line SK-OV-3 (9,000 cells/well, ATCC, cat. no. HTB-77) was used as target cell line. PBMCs were isolated from 40 mL of buffy coat of human blood (Sanquin) using a Ficoll gradient (Lonza; lymphocyte separation medium, cat. no. 17-829E) according to the manufacturer's instructions. T cells were isolated as described in Example 13. For PBMCs, the following E:T ratios were used: 1:2, 1:1, 2:1, 4:1, 8:1 and 12:1. For isolated T cells, the following E:T ratios were used: 1:2, 1:1, 2:1, 4:1 and 8:1. In each experiment, effector cells from two separate donors were used. Table 7 provides an overview of the percentage of CD3$^+$, CD3$^+$CD4$^+$ and CD3$^+$CD8$^+$ T cells in the PMBC or T-cell isolates for each of the donors (determined as described in Example 13).

TABLE 7

| | Ratio CD3$^+$, CD4$^+$ and CD8$^+$ T cells per donor. | | |
|---|---|---|---|
| Donor | % CD3 with viable cell population | % CD4$^+$ within CD3$^+$ cells | % CD8$^+$ within CD3$^+$ cells |
| C (PBMCs) | 75 | 56.8 | 28.9 |
| D (PBMCs) | 60 | 63.2 | 32 |
| E (T cells) | 98.3 | 59.6 | 31.6 |
| F (T cells) | 97.2 | 70 | 26.4 |

Figure 12A:
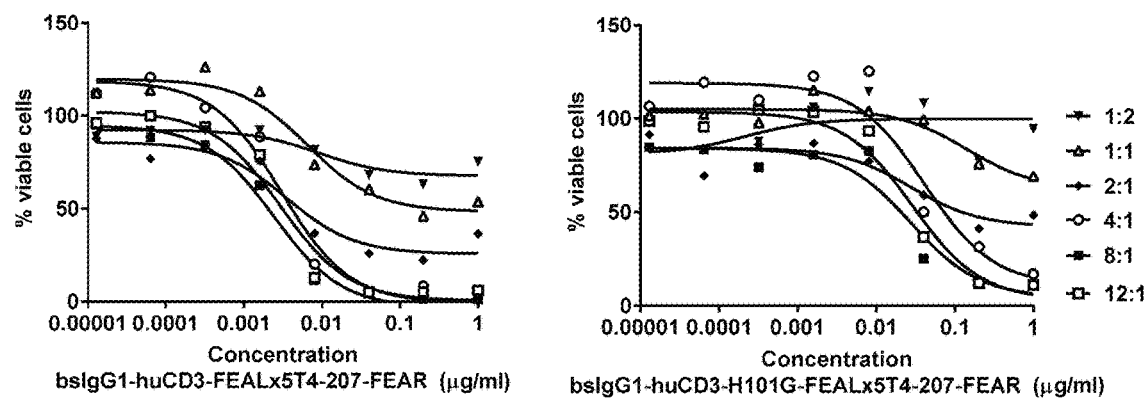
FIGS. 12A and 12B: Induction of cytotoxicity in vitro by CD3×5T4 bispecific antibodies in SK-OV-3 cells using PBMCs as effector cells at varying E:T ratios. SK-OV-3 cells were incubated with increasing concentrations of bsIgG1-huCD3-FEAL×5T4-207-FEAR (left panels) or bsIgG1-huCD3-H101G-FEAL×5T4-207-FEAR (right panels) and PBMCs as effector cells in an E:T ratio of 1:2, 1:1, 2:1, 4:1, 8:1 and 12:1. Cytotoxicity was determined by measuring the percentage of viable SK-OV-3 cells after 72 h of incubation (% viable cells=[absorbance sample−absorbance staurosporine-treated target cells]/[absorbance untreated target cells−absorbance staurosporine-treated target cells]×100). PBMCs from two different donors were used for this experiment.
Figure 12B:
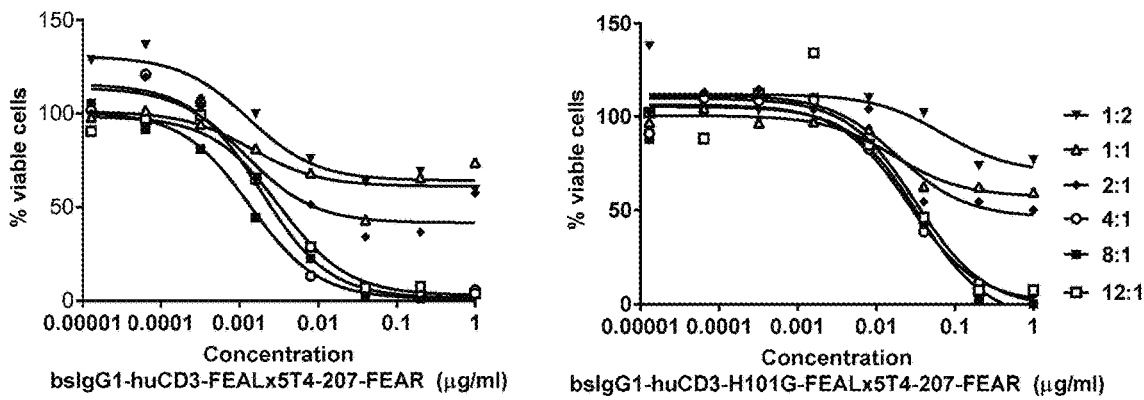

As shown in FIG. 12, using effector cells from two different donors, E:T ratios from 4:1 to 12:1 resulted in efficient PBMC-mediated kill of the SK-OV-3 cells in the presence of bsIgG1-huCD3-FEALx5T4-207-FEAR or bsIgG1-huCD3-H101G-FEALx5T4-207-FEAR. At E:T ratios of 2:1 and lower, maximum kill of the SK-OV-3 cells was not achieved at the highest antibody concentration used (1000 ng/mL). A similar result was observed when isolated T cells were used as effector cells (FIG. 13). Using effector cells from two different donors, an E:T ratio of 4:1 and 8:1 resulted in maximum T-cell-mediated kill of the SK-OV-3 cells in the presence of bsIgG1-huCD3-FEALx5T4-207-FEAR or bsIgG1-huCD3-H101G-FEALx5T4-207-FEAR at the highest antibody concentration used (1000 ng/mL), whereas lower E:T ratios were not sufficient to induce maximum kill. The efficacy of the T-cell-mediated kill induced by bsIgG1-huCD3-FEALx5T4-207-FEAR and bsIgG1-huCD3-H101G-FEALx5T4-207-FEAR is thus dependent on a sufficiently high E:T ratio.

Example 15—Anti-Tumor Activity of CD3x5T4 Bispecific Antibodies in a Humanized Immune System Mouse Xenograft Model The in vivo anti-tumor efficacy of the CD3x5T4 bispecific antibodies bsIgG1-huCD3-FEALx5T4-207-FEAR and bsIgG1-huCD3-H101G-FEALx5T4-207-FEAR was evaluated in humanized (tail vein injected CD34+ hematopoietic stem cells [HSC] at an age of 3-4 weeks) NOD.Cg-Prkdc$^{scid}$ Il2rg$^{tm1Wjl}$/SzJ (NSG-HIS) mice (obtained from The Jackson Laboratory) that were inoculated subcutaneously with human MDA-MB-231 tumor cells. Humanization of the immune system of NSG-HIS mice was confirmed 16 weeks post-engraftment by flow cytometry. Subsequently, NSG-HIS mice were randomized in three groups (8 mice per group), based on HSC donor (#5239 or #2328) and the percentage of human CD3$^+$ T cells within the human CD45$^+$ population in peripheral blood (mean % hCD45$^+$ and % hCD3$^+$ cells respectively; 42% hCD45$^+$ and 39% hCD3$^+$ for the PBS group, 34% hCD45$^+$ and 25% hCD3$^+$ for the bsIgG1-huCD3-FEALx5T4-207-FEAR group, and 36% hCD45$^+$ and 29% hCD3$^+$ for the bsIgG1-huCD3-H101G-FEALx5T4-207-FEAR). 5x10$^6$ MDA-MB-231 cells (in 100 μL PBS) were injected subcutaneously (SC) in the flank of the mice; this was indicated as day 0 in the study. At day 14, 18, 21 and 25, the mice were injected intravenously (IV) with either 0.5 mg/kg antibody or PBS. Treatment groups are shown in Table 8. Tumor growth was evaluated twice per week (starting at day 14) using a caliper. Tumor volumes (mm$^3$) were calculated from caliper measurements as 0.52x (length)x(width)$^2$.

Figure 14A:
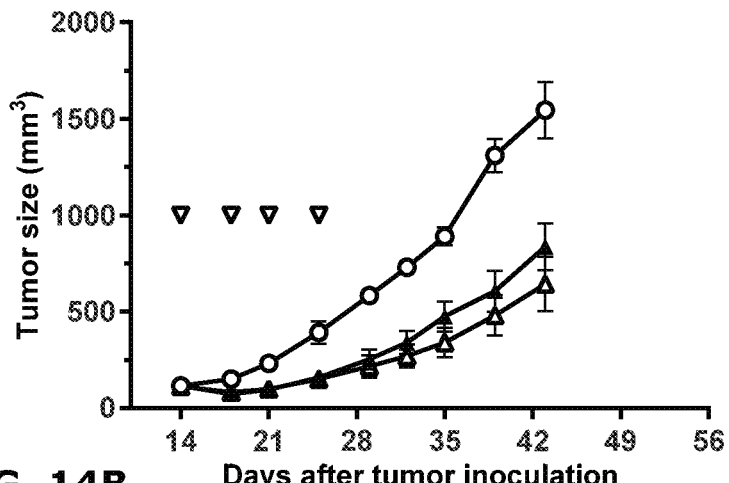
FIGS. 14A and 14B: Anti-tumor activity of CD3×5T4 bispecific antibodies in a MDA-MB-231 xenograft model in NSG-HIS mice.
Figure 14B:
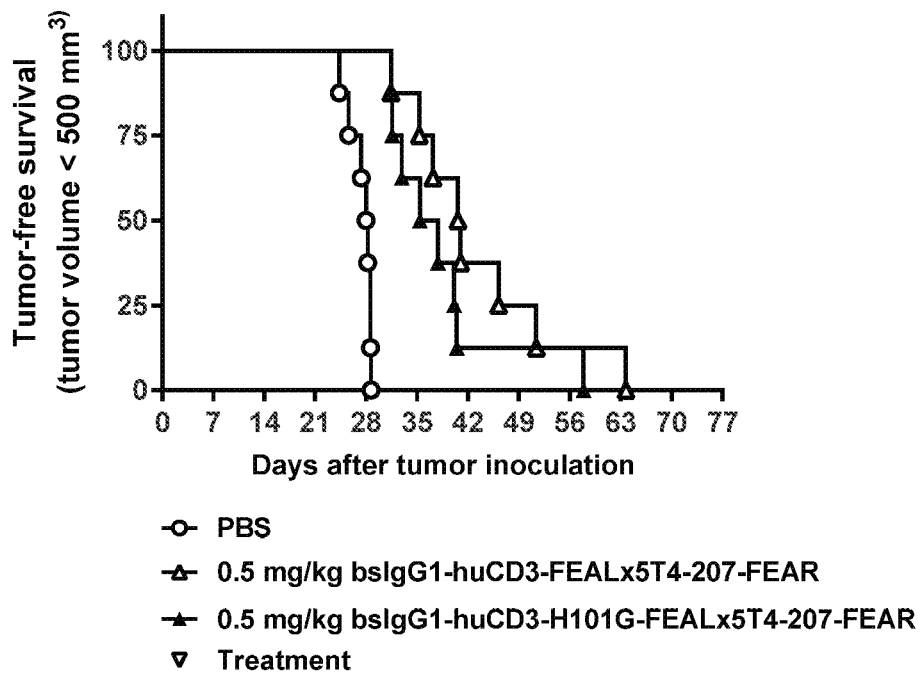
Figure 15A:
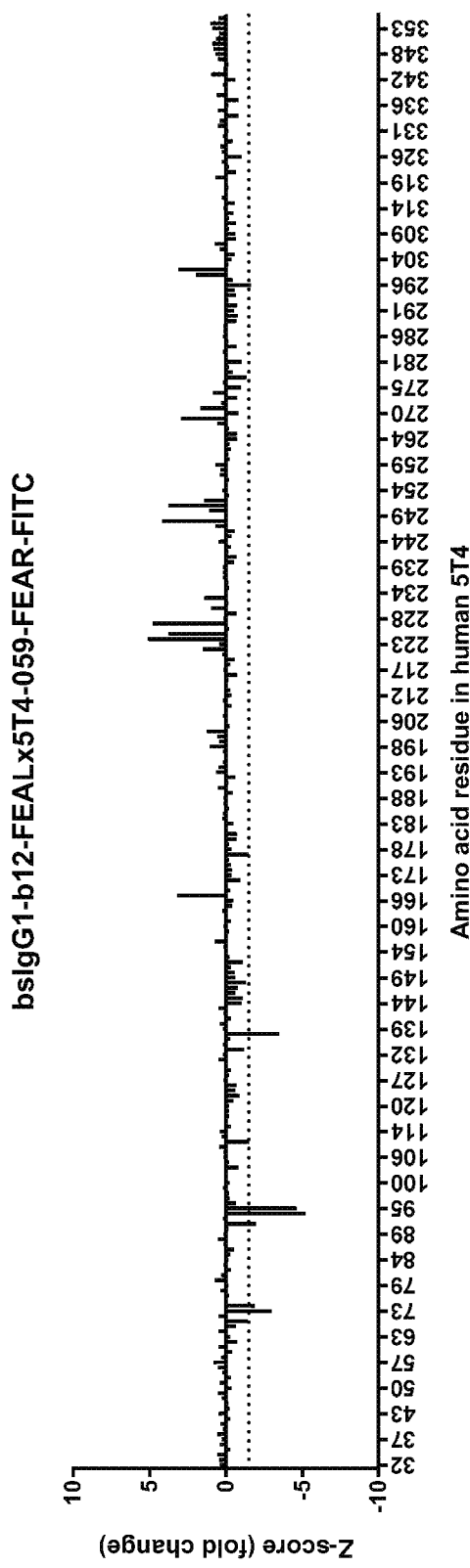
FIGS. 15A-15D: Binding of directly FITC-labeled 5T4-specific antibodies to human 5T4 variants with single alanine mutations at positions 32 to 355 of human 5T4 ECD, as determined by flow cytometry. Binding was expressed as Z-score (fold change), as a measure for change in binding compared to a non-cross blocking 5T4-specific control antibody (bsIgG1-5T4-A1-F405L×b12-FEAR-FITC) used for normalization. The number on the x-axis refers to the amino acid positions in human 5T4 (SEQ ID: 1). Residues where the Z-score in binding was lower than −1.5 (indicated by the dotted line) were considered 'loss of binding mutants'. Residues with a positive Z-score in binding are loss of binding residues for the non-cross blocking 5T4 specific control antibody (bsIgG1-5T4-A1-67F-F405L×b12-FEAR-FITC). Residues on aa position 38, 45, 49, 51, 54, 62, 64, 66, 68, 71, 72, 77, 91, 104, 108, 110, 112, 118, 121, 122, 135, 137, 155, 161, 167, 171, 201, 202, 205, 208, 218, 231, 269, 279, 298, 300, 303, 323, 324, 340 and 344 were not evaluated, as these positions contained either endogenous alanines or cysteines. Data shown are Z-scores for binding of (FIG. 15A) bsIgG1-b12-FEAL×5T4-059-FEAR-FITC, (FIG. 15B) bsIgG1-b12-FEAL×5T4-207-FEAR-FITC, (FIG. 15C) bsIgG1-b12-FEAL×5T4-226-FEAR-FITC, and (FIG. 15D) bsIgG1-5T4-A3-F405L×b12-FEAR-FITC. Buried residues with a Z-score just below −1.5 that were predicted to be spatially separated from the majority of surface-exposed loss of binding residues were excluded (for bsIgG1-b12-FEAL×5T4-207-FEAR-FITC: L281 [Z-score: −1.57] and P326 [Z-score: −1.54]; and for bsIgG1-b12-FEAL×5T4-226-FEAR-FITC: L273 [Z-score: −1.58], L281 [Z-score: −1.65], N294 [Z-score: −1.57], L309 [Z-score: −1.63] and P326 [Z-score: −1.67]).
Figure 15B:
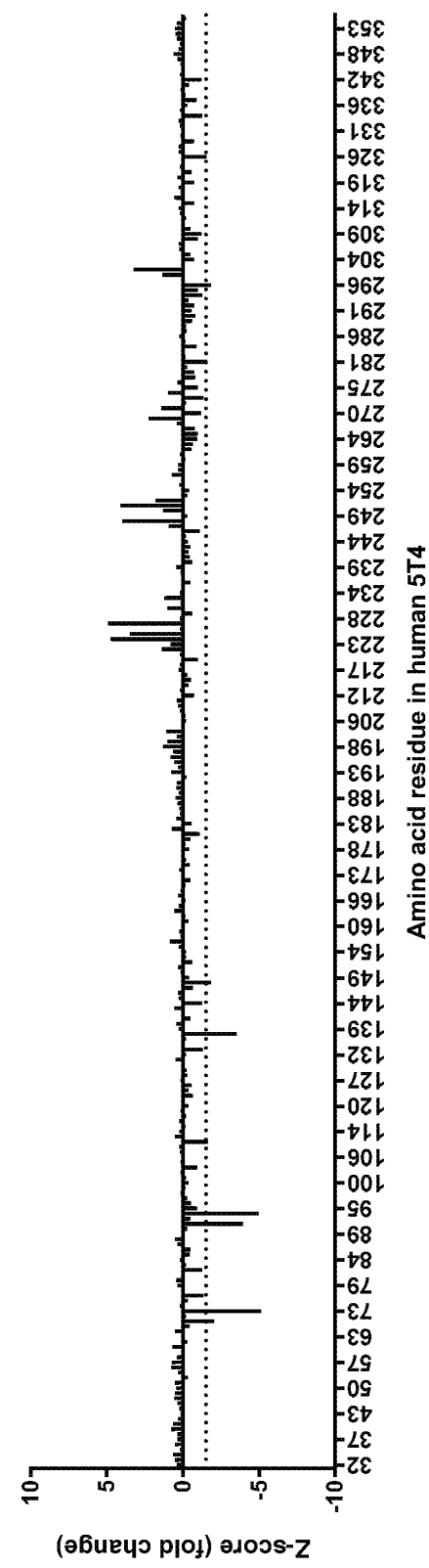
Figure 15C:
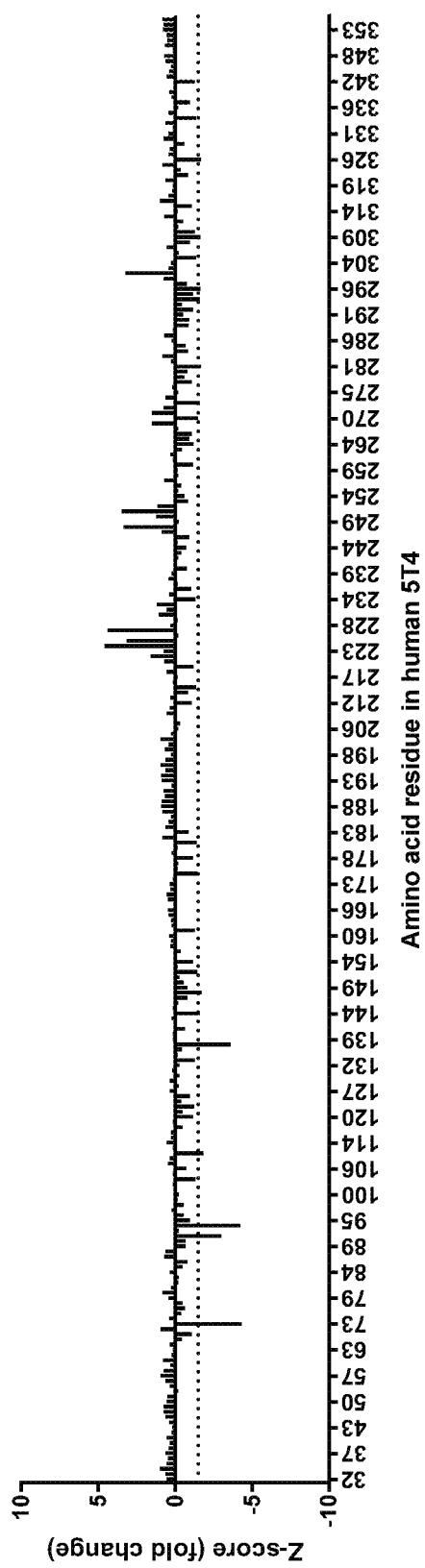
Figure 15D:
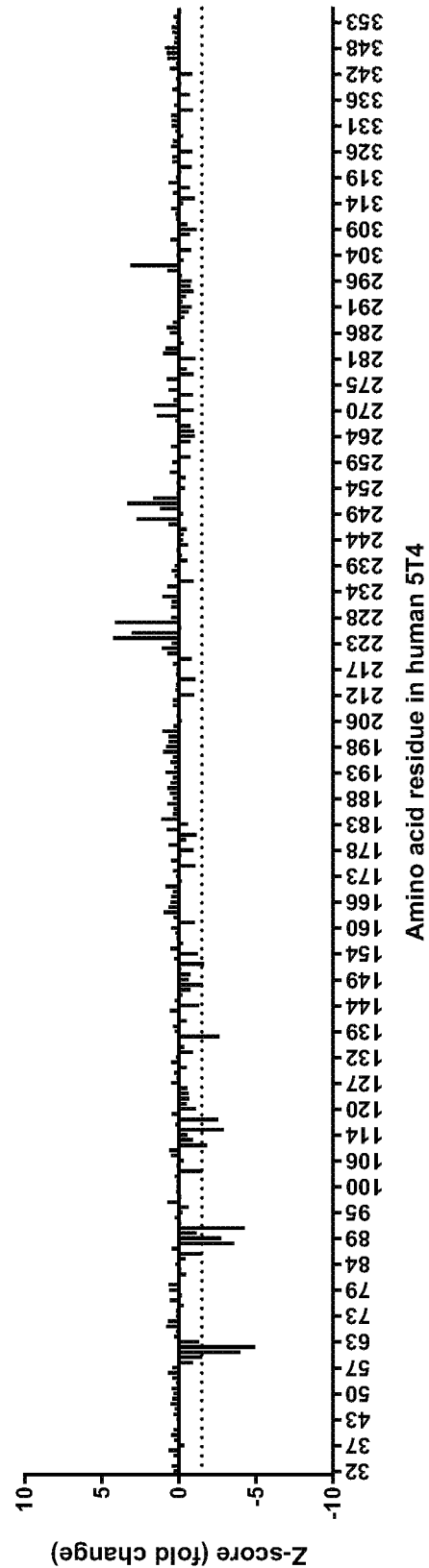

The results are shown in FIG. 14. FIG. 14A shows that both bsIgG1-huCD3-FEALx5T4-207-FEAR (p<0.01) and bsIgG1-huCD3-H101G-FEALx5T4-207-FEAR (p<0.05) efficiently inhibited tumor growth based on Mann-Whitney statistical analysis at day 43 compared to the control group. Furthermore, statistical analysis of the tumor-free survival curves (Kaplan Meier plot, using a tumor size <500 mm$^3$ as a cut-off) using a Mantel Cox test demonstrated that the difference in tumor-free survival was statistically different, showing increased tumor-free survival in animals treated with bsIgG1-huCD3-FEALx5T4-207-FEAR (p<0.001) or bsIgG1-huCD3-H101G-FEALx5T4-207-FEAR (p<0.001) compared to the untreated animals (FIG. 14B).

TABLE 8

Treatment groups.

| Antibody | Dose | Treatment days | Animals per group |
|---|---|---|---|
| PBS | — | 14, 18, 21, 25 | 8 |
| bsIgG1-huCD3-FEALx5T4-207-FEAR | 0.5 mg/kg | 14, 18, 21, 25 | 8 |
| bsIgG1-huCD3-H101G-FEALx5T4-207-FEAR | 0.5 mg/kg | 14, 18, 21, 25 | 8 |

Example 16—Determination of the Contribution of 5T4 Amino Acid Residues to Antibody Binding Using Alanine Scanning Library Design A human 5T4 (Uniprot ID Q13641) single residue alanine library was synthesized (GeneArt, Thermo Fisher Scientific), in which all amino acid residues in the extracellular domain of human 5T4 were individually mutated to alanine, except for positions already containing an alanine or cysteine. To minimize the chance of structural disruption of the antigen, cysteines were not mutated. The library was cloned in the pMAC expression vector containing a CMV/TK-polyA expression cassette, an Ampicillin resistance gene and a pBR322 replication origin.

Library Production and Screening

The wild type 5T4 and alanine mutants were expressed individually in FreeStyle HEK293 cells according to the manufacturer's instructions (Thermo Fisher Scientific, cat. no. 12347-019). One day post transfection, the cells were harvested. Approximately 80,000 cells were incubated with 20 μL FITC-conjugated antibody (3 μg/mL; in FACS buffer (PBS [Lonza, cat. no. BE17-517]+0.1% [w/v] BSA [Roche, cat. no. 10735086001]+0.02% [w/v] sodium azide [NaN$_3$; EMELCA Bioscience, cat. no. 41920044-3]); Table 9) at room temperature for 40 min. Subsequently, cells were washed twice by centrifugation using 150-180 μL FACS buffer. Cells were resuspended in 30 μL FACS buffer and stored at 4° C. until analysis by flow cytometry using an iQue screener (Intellicyt Corporation).

The entire experiment was performed twice yielding duplicate measurements.

TABLE 9

Antibodies used in determination of the contribution of 5T4 amino acid residues in antibody binding using alanine scanning. Antibodies monovalently binding to 5T4 were labeled with FITC (Thermo Fisher Scientific, cat. no. 46425), prior to performing the experiment. IgG1-5T4-A1-F405L and IgG1-5T4-A3-F405L are surrogate A1 and A3 antibodies, respectively, that were cloned into the human IgG1 backbone containing the F405L mutations. Hence, the surrogate A1 antibody has a variable region identical to that of the A1 antibody disclosed in WO2007106744. Likewise, the A3 surrogate antibody has a variable region identical to that of the A3 antibody disclosed in WO2007106744. In both antibodies, the Fc domain carries the F405L substitution.

| Antibody | Test or control antibody |
|---|---|
| bsIgG1-b12-FEALx5T4-059-FEAR-FITC | Test antibody |
| bsIgG1-b12-FEALx5T4-207-FEAR-FITC | Test antibody |
| bsIgG1-b12-FEALx5T4-226-FEAR-FITC | Test antibody |
| bsIgG1-5T4-A3-F405Lxb12-FEAR-FITC | Test antibody |
| bsIgG1-5T4-A1-F405Lxb12-FEAR-FITC | Control antibody used for normalization |

Data Analysis

For every sample, the average amount of antibody bound per cell was determined as the geometric mean of the fluorescence intensity (gMFI) for the viable, single cell population. The gMFI is influenced by the affinity of the antibody for the 5T4 mutant and the expression level of the 5T4 mutant per cell. Since specific alanine mutations can impact the surface expression level of the mutant 5T4, and to correct for expression differences for each 5T4 mutant in general, data for each test antibody were normalized against the binding intensity of a non-cross blocking 5T4-specific control antibody, using the following equation:

$$\text{Normalized } gMFI_{aa\ position} = \text{Log}_{10}\left(\frac{gMFI_{Test\ Ab}}{gMFI_{Control\ Ab}}\right)$$

In which 'aa position' refers to the position that was mutated into an alanine; and the Z-score was calculated to express loss or gain of binding of the antibodies, according to the following calculation:

$$Z\text{-score(fold change)} = \frac{\text{Normalized } gMFI_{aa\ position} - \mu}{\sigma}$$

Where μ and σ are the mean and standard deviation of the Normalized gMFI calculated from all mutants.

If the gMFI of the control antibody for a particular 5T4 mutant was lower than the mean gMFIControl Ab−2.5×SD of the mean gMFIControl Ab (from all mutants), data were excluded from analysis (it was assumed that expression levels for those 5T4 mutants were not sufficient to draw conclusions). This was the case for amino acid W at position 296 (SEQ ID NO: 1).

Results

FIG. 15 shows the binding results of the tested antibodies to human 5T4 variants with single alanine mutations in the ECD: positions 32 to 355 (according to SEQ ID NO: 1). The results indicate that antibody bsIgG1-b12-FEALx5T4-059-FEAR-FITC showed loss of binding when aa R at position 73, T at position 74, Y at position 92, R at position 94, N at position 95 or F at position 138 of human 5T4 were mutated to an alanine. This suggests that binding of antibody IgG1-5T4-059-04-FEAR is at least dependent on aa R73, T74, Y92, R94, N95, F138 of human 5T4 (SEQ ID NO: 1), antibody bsIgG1-b12-FEALx5T4-207-FEAR-FITC showed loss of binding when aa S at position 69, R at position 73, Y at position 92, R at position 94, F at position 111, F at position 138, D at position 148 of human 5T4 were mutated to an alanine. This suggests that binding of antibody IgG1-5T4-207-FEAR is at least dependent on aa S69, R73, Y92, R94, F111, F138 and D148 of human 5T4 (SEQ ID NO: 1), antibody bsIgG1-b12-FEALx5T4-226-FEAR-FITC showed loss of binding when aa R at position 73, Y at position 92, R at position 94, F at position 111, F at position 138, L at position 144 or D at position 148 of human 5T4 were mutated to an alanine. This suggests that binding of antibody IgG1-5T4-226-FEAR is at least dependent on aa R73, Y92, R94, F111, F138, L144 and D148 of human 5T4 (SEQ ID NO: 1), antibody bsIgG1-5T4-A3-F405Lxb12-FEAR-FITC showed loss of binding when aa D at position 60, Q at position 61, D at position 88, L at position 89, Y at position 92, F at position 111, P at position 115, L at position 117, F at position 138, D at position 148 or N at position 152 of human 5T4 were mutated to an alanine. This suggests that binding of antibody IgG1-5T4-A3-FEAR is at least dependent on aa D60, Q61, D88, L89, Y92, F111, P115, L117, F138, D148 and N152 of human 5T4 (SEQ ID NO: 1).

Some amino acids might be indirectly involved in binding. For example, mutating a hydrophobic residue to alanine might impact the local folding and affect the positioning of directly interacting residues (Zhao et al., 2014 Structure 22, 612-620). Based on structural data (human 5T4 crystal structure 4cnm; RCSB protein databank) the following residues are buried and therefore expected to indirectly contribute to binding to:

antibody bsIgG1-b12-FEALx5T4-059-04-FEAR-FITC: F138,
antibody bsIgG1-b12-FEALx5T4-207-FEAR-FITC: F111, F138, D148,
antibody bsIgG1-b12-FEALx5T4-226-FEAR-FITC: F111, F138, L144, D148,
antibody bsIgG1-5T4-A3-F405Lxb12-FEAR-FITC: L89, F111, L117, F138, D148, N152.

Since only surface-exposed residues can directly interact with the antibody, the following residues are expected to directly interact with:

antibody bsIgG1-b12-FEALx5T4-059-04-FEAR-FITC: R73, T74, Y92, R94 and N95,
antibody bsIgG1-b12-FEALx5T4-207-FEAR-FITC: S69, R73, Y92 and R94,
antibody bsIgG1-b12-FEALx5T4-226-FEAR-FITC: R73, Y92 and R94,
antibody bsIgG1-5T4-A3-F405Lxb12-FEAR-FITC: D60, Q61, D88, Y92 and P115.

Together, these results propose that antibodies IgG1-5T4-059, IgG1-5T4-207 and IgG1-5T4-226 all bind by direct interaction with amino acid residues R73, Y92 and R94. The results also indicate that antibodies IgG1-5T4-059, IgG1-5T4-207 and IgG1-5T4-226 each bind to a epitope which is different from but partially overlapping with the epitope bound by IgG1-5T4-A3. This is in line with the displacement behavior described in Example 3 and 4.

Example 17—Induction of T-Cell Activation and Cytotoxicity by CD3x5T4 Bispecific Antibodies in Cell Lines of Different Indications In Vitro CD3x5T4 bispecific antibodies were tested in an in vitro cytotoxicity assay using tumor cell lines of pancreas and cervical cancer as target cells and purified T cells as effector cells. For each indication (pancreas cancer and cervical cancer) two representative cell lines were selected. The tumor cell lines used in the in vitro cytotoxicity assay are summarized in Table 10. T cells were derived from human donor buffy coats (Sanquin, Amsterdam, The Netherlands) and isolated using the RosetteSep human T cell enrichment cocktail (Stemcell Technologies, France, cat. no. 15061) according to manufacturer's instructions. For each cell line, at least three different donors were tested in the in vitro cytotoxicity assay and T-cell activation analysis, as summarized in Table 10.

TABLE 10

Tumor cell lines used for in vitro cytotoxicity assay

| Tumor cell line | Indication | ATCC clone no. | cytotox (n) | T-cell activation (n) |
|---|---|---|---|---|
| BxPC-3 | Pancreas | CRL-1687 | 3 | 3 |
| PANC-1 | Pancreas | CRL-1469 | 9 | 4 |
| Ca Ski | Cervical | CRL-1550 | 5 | 3 |
| SiHa | Cervical | HTB-35 | 3 | 3 |

Tumor cells (16,000 cells/well) were seeded into flat-bottom 96-well plates (Greiner Bio-One, The Netherlands, cat. no. 655180) and left to adhere at 37° C. for 4 h. T cells were added to tumor cells at an E:T ratio=4:1. Serial dilutions of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) were added (final concentration ranging from 5000 to 0.0128 ng/mL; 5-fold dilutions) and plates were incubated at 37° C. for 72 h. Next, 110 μL supernatants containing T cells were transferred to round-bottom 96-well culture plates (CellStar, cat. no. 650180) and centrifuged (300xg) at 4° C. for 3 min. T cells were stained for T-cell markers by incubation with CD3-eFluor450 (1:200; eBioscience, clone OKT3), CD4-APC-eFluor780 (1:50; eBioscience, clone OKT4), CD8-AF700 (1:100; Biolegend, clone RPA-T8) and T-cell activation markers CD69-APC (1:50; BD Biosciences, clone AB2439), CD25-PE-Cy7 (1:50; eBioscience, clone BC96) and CD279/PD1-BV605 (1:50; Biolegend, clone EH12.2H7) diluted in 50 μL PBS/0.1% BSA/0.02% azide (staining buffer). Single stained samples with Ultracomp beads (5 μL; Invitrogen, cat. no. 01-2222-42) were used for compensation adjustments of the flow cytometer. After 30 min of incubation at 4° C., plates were washed three times with staining buffer. Cells were resuspended in 120 μL staining buffer and analyzed using a FACS Fortessa (BD Biosciences). Data were processed using FlowJo (version 10, BD Biosciences).

In parallel, the viability of the tumor cells was assessed using Resazurin (7-Hydroxy-3H-phenoxazin-3-one 10-oxide). The adherent tumor cells were washed twice with PBS and incubated with 10% Resazurin (150 μL; Life Technologies, The Netherlands, cat. no. DAL1100) in RPMI-1640 medium (Lonza, Switzerland, cat. no. BE12-115F) supplemented with 10% donor bovine serum with iron (Life Technologies, The Netherlands, cat. no. 10371-029) and pen/strep (Lonza, cat. no. DE17-603E) at 37° C. for 4 h. The absorbance was measured with an Envision multilabel plate reader (PerkinElmer, US). The absorbance of staurosporine-treated (Sigma-Aldrich, US, cat. no. S6942) cells were set as 0% viability and the absorbance of untreated cells were set as 100% viability. The 'percentage viable cells' was calculated as follows:

% viable cells=([absorbance sample−absorbance staurosporine-treated target cells]/[absorbance untreated target cells−absorbance staurosporine treated target cells])×100.

Cytotoxicity curves, T-cell activation curves, IC50 (cytotoxicity) and EC50 (T-cell activation) values were analyzed using non-linear regression (sigmoidal dose-response with variable slope) using GraphPad Prism V7.02 software (Graph Pad Software, San Diego, CA, USA).

Figure 16A:
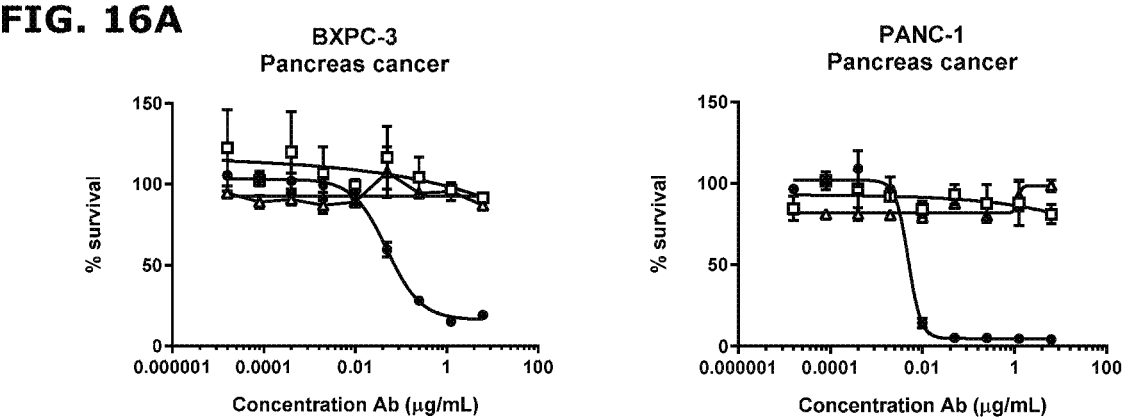
FIGS. 16A and 16B: Induction of cytotoxicity in vitro by CD3×5T4 bispecific antibodies in tumor cells of different indications using T cells as effector cells. Tumor cells were incubated with increasing concentrations of bsIgG1-huCD3-H101G-FEAL×5T4-207-FEAR or control antibodies (bsIgG1-huCD3-H101G-FEAL×b12-FEAR, bsIgG1-b12-FEAL×5T4-207-FEAR) and isolated T cells as effector cells in an E:T ratio of 4:1. Cytotoxicity (decrease in survival) was determined by measuring the percentage of viable tumor cells after 72 h of incubation. Data shown are mean % survival±SEM of duplicate wells from one representative donor out of at least three donors tested.
Figure 16B:
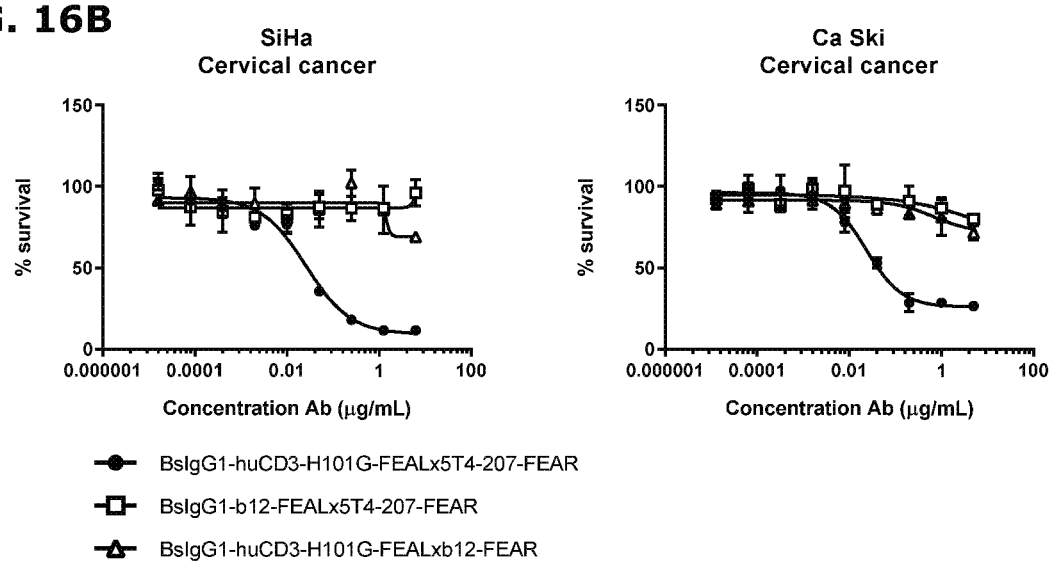
Figure 16C:
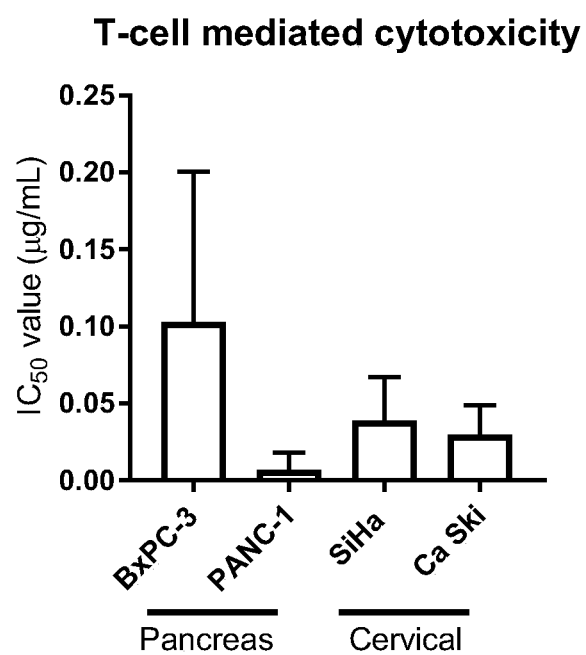
FIG. 16C: IC50 values of cytotoxicity induced in vitro by CD3×5T4 bispecific antibodies in tumor cell lines of different indications using T cells as effector cells. IC50 values of the T-cell-mediated cytotoxicity induced by bsIgG1-huCD3-H101G-FEAL×5T4-207-FEAR in tumor cells of the indicated indications were analyzed using GraphPad Prism V7.02 software. Data are presented as mean IC50 values of at least three different donors (see Table 10)±SD.
Figure 17A:
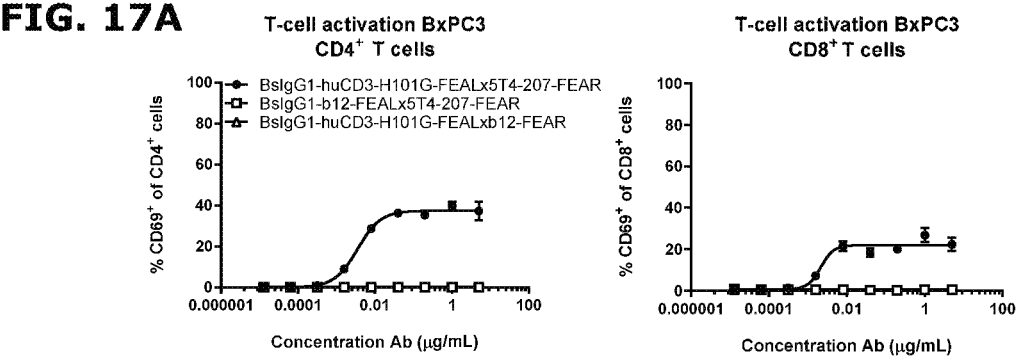
FIGS. 17A-17D: In vitro T-cell activation by CD3×5T4 bispecific antibodies in the presence of tumor cells of different indications. Tumor cells were incubated with increasing concentrations of bsIgG1-huCD3-H101G-FEAL×5T4-207-FEAR or control antibodies (bsIgG1-huCD3-H101G-FEAL×b12-FEAR, bsIgG1-b12-FEAL×5T4-207-FEAR and isolated T cells as effector cells in an E:T ratio of 4:1 for 72 h. T-cell activation was measured by the upregulation of CD69 (% of CD69+ cells) within CD4$^+$ (left panels) and CD8$^+$ (right panels) T-cell populations. Data shown are mean % CD69+ cells±SD of duplicate wells from one representative donor out of at least three donors tested.
Figure 17B:
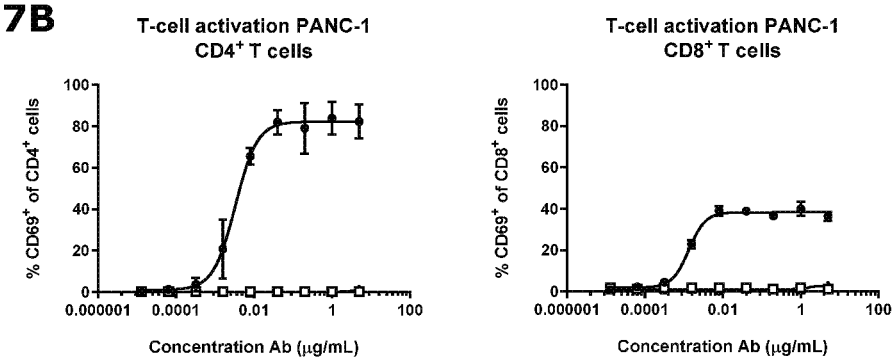
Figure 17C:
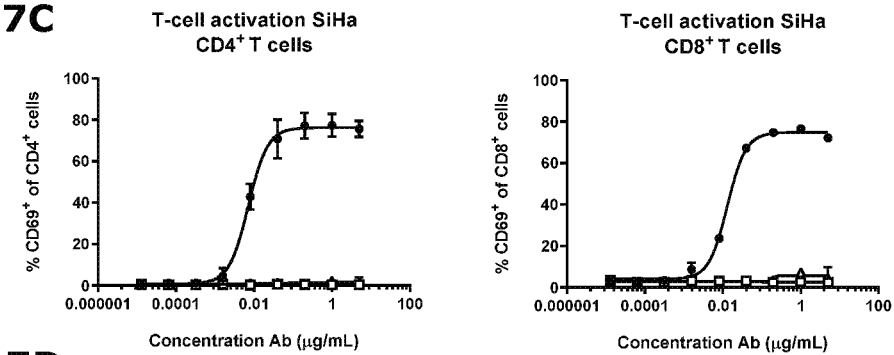
Figure 17D:
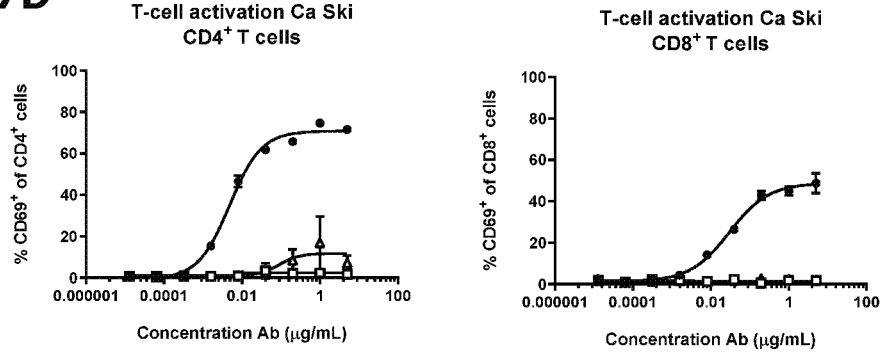
Figure 17E:
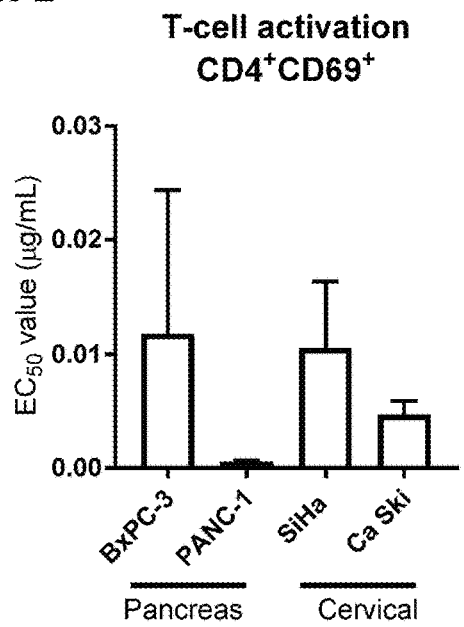
FIGS. 17E-17F: EC50 values of in vitro T-cell activation by CD3×5T4 bispecific antibodies in with the presence of tumor cell lines of different indications. EC50 values of the T-cell activation (% of CD69+ cells within CD4$^+$ and CD8$^+$ T-cell populations) induced by bsIgG1-huCD3-H101G-FEAL×5T4-207-FEAR in co-culture with tumor cell lines of the different indications were analyzed using GraphPad Prism V7.02 software. Data are presented as mean EC50 values of at least three different donors (see Table 10)±SD.
Figure 17F:
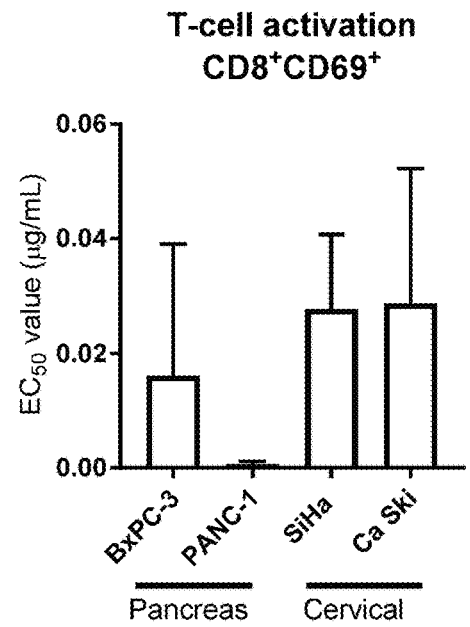

FIGS. 16A-16B show that bsIgG1-huCD3-H101G-FEAL×5T4-207-FEAR induced cytotoxicity in a range of cell lines of different indications, while the control bispecific antibodies (bsIgG1-huCD3-H101G-FEAL×b12-FEAR, bsIgG1-b12-FEAL×5T4-207-FEAR) targeting only the tumor cells or the T cells did not show any cytotoxicity. FIG. 16C shows the mean $IC_{50}$ values for each of the cell lines tested with different donors (at least n=3). FIGS. 17A-17D show the T-cell activation induced by bsIgG1-huCD3-H101G-FEAL×5T4-207-FEAR in a range of cell lines of different indications as measured by the upregulation of CD69 on $CD4^+$ and $CD8^+$ T cells (% of $CD69^+$ cells within the $CD4^+$ or $CD8^+$ population). The control bispecific antibodies (bsIgG1-huCD3-H101G-FEAL×b12-FEAR, bsIgG1-b12-FEAL×5T4-207-FEAR) targeting only the tumor cells or the T cells, did not induce any T-cell activation. FIGS. 17E-17F show the mean $EC_{50}$ values for each of the cell lines tested with different donors (at least n=3).

These data indicate that bsIgG1-huCD3-H101G-FEAL×5T4-207-FEAR can specifically induce T-cell mediated cytotoxicity and T-cell activation in pancreas and cervical cancer, while control bispecific antibodies bsIgG1-huCD3-H101G-FEAL×b12-FEAR and bsIgG1-b12-FEAL×5T4-207-FEAR do not induce T-cell activation and T-cell mediated cytotoxicity.

REFERENCES

1. Zhao et al., 2014 Structure 22, 612-620
2. Southall et al., 1990 Br J Cancer 61, 89-95
3. Stern and Harrop, 2017 Cancer Immunol Immunother 66, 415-426; Southall et al., 1990 Br J Cancer 61, 89-95
4. Damelin et al., 2011 Cancer Res 71, 4236-4246; Carsberg et al., 1996 Int J Cancer 68, 84-92
5. Carsberg et al., 1996 Int J Cancer 68, 84-92
6. Kagermeier-Schenk et al., 2011 Dev Cell 21, 1129-1143
7. Eisen, et al., 2014 Curr Oncol Rep 16, 370
8. Stern and Harrop, 2017 Cancer Immunol Immunother 66, 415-426; Scurr et al., 2017 JAMA Oncol 12, 10
9. Scurr et al., 2017 JAMA Oncol 12, 10)
10. WO2007106744
11. WO03038098
12. WO2011048369
13. WO2013041687
14. WO2017072207
15. Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi: 10.1371/journal.pone.0169535)
16. WO 2007/059782; Genmab A/S
17. Ward et al., Nature 341, 544-546 (1989)
18. Holt et al; Trends Biotechnol. 2003 November; 21(11): 484-90
19. Revets et al; Expert Opin Biol Ther. 2005 January; 5(1):111-24
20. Bird et al., Science 242, 423-426 (1988)
21. Huston et al., PNAS USA 85, 5879-5883 (1988)
22. Fundamental Immunology Ch. 7 (Paul, W., ed., 2nd ed. Raven Press, N.Y. (1989)
23. Lefranc M P. et al., Nucleic Acids Research, 27, 209-212, 1999
24. Brochet X. Nucl. Acids Res. 36, W503-508 (2008)
25. Abdiche Y N, Malashock D S, Pinkerton A, Pons J. Exploring blocking assays using Octet, ProteOn, and Biacore biosensors. Anal Biochem. 2009; 386(2): 172-180)
26. WO92/22653
27. EP0629240
28. Kabat, E. A. et al., Sequences of proteins of immunological interest. 5th Edition—US Department of Health and Human Services, NIH publication No. 91-3242, pp 662, 680, 689 (1991)
29. Rice et al., 2000, Trends Genet. 16: 276-277
30. WO2007106744
31. Shaw et al. (2002), Biochem. J. 363: 137-45, WO98/55607
32. WO06/031653
33. Wu et al., Generation and Characterization of a Dual Variable Domain Immunoglobulin (DVD-Ig™) Molecule, In: Antibody Engineering, Springer Berlin Heidelberg (2010)
34. WO 2011/131746; Genmab A/S
35. WO/2002/020039; Trion Pharma/Fresenius Biotech
36. WO9850431; Genetech
37. WO2011117329; Roche
38. EP1870459; Amgen
39. WO2009089004; Amgen
40. US201000155133; Chugai
41. WO2010129304; Oncomed
42. WO2007110205; EMD Serono
43. WO 2010/015792; Regeneron
44. WO11143545; Pfizer/Rinat
45. WO2012058768; Zymeworks/Merck
46. WO2011028952; Xencor
47. WO 2009/080254; Roche
48. WO2008003116; F-Star
49. U.S. Pat. No. 7,262,028; Crucell/Merus
50. U.S. Pat. No. 7,612,181; Abbott
51. WO20100226923; Unilever, Sanofi Aventis
52. US007951918; Biogen Idec
53. CN 102250246; Changzhou Adam Biotech Inc
54. WO2012025525; Roche
55. WO2012025530; Roche
56. WO2008157379; Macrogenics
57. WO2010/080538; Macrogenics
58. WO 2008/119353
59. WO 2011/131746
60. WO2015001085
61. Shields et al., 2001, J. Biol. Chem. (276):6591-604)
62. Sykes and Johnston, Nat Biotech 17, 355-59 (1997)
63. U.S. Pat. No. 6,077,835
64. WO 00/70087
65. Schakowski et al., Mol Ther 3, 793-800 (2001)
66. WO 00/46147
67. Benvenisty and Reshef, PNAS USA 83, 9551-55 (1986)
68. Wigler et al., Cell 14, 725 (1978)
69. Coraro and Pearson, Somatic Cell Genetics 7, 603 (1981)
70. U.S. Pat. No. 5,589,466
71. U.S. Pat. No. 5,973,972
72. Van Heeke & Schuster, J Biol Chem 264, 5503-5509 (1989)
73. Remington: The Science and Practice of Pharmacy, 19th Edition, Gennaro, Ed., Mack Publishing Co., Easton, PA, 1995

74. Sustained and Controlled Release Drug Delivery Systems, J. R. Robinson, ed., Marcel Dekker, Inc., New York, 1978
75. U.S. Pat. No. 4,699,880
76. Kozak, M., Gene 1999; 234(2):187-208)
77. Coligan J. E., Bierer, B. E., Margulies, D. H., Shevach, E. M. and Strober, W., eds. Current Protocols in Immunology, John Wiley & Sons, Inc., 2006)
78. Aslanidis, C. and P. J. de Jong, Nucleic Acids Res 1990; 18(20): 6069-74
79. Lefranc M P. et al., Nucleic Acids Research, 27, 209-212, 1999
80. Brochet X. Nucl. Acids Res. 36, WS03-508 (2008)
81. WO2007/106744
82. WO2015/001085
83. WO2017/009442
84. WO2011147986,
85. WO2011131746
86. WO2013060867
87. Labrijn et al., PNAS 2013, 110: 5145-50
88. Gramer et al., MAbs 2013, 5: 962-973
89. Barbas, C F. J Mol Biol. 1993 Apr. 5; 230(3):812-23
90. WO2007/106744
91. US 2015/0337049

The invention claimed is:

1. A nucleic acid construct, or combination of nucleic acid constructs, encoding an antibody which binds to human 5T4 and comprises a heavy chain variable (VH) region and a light chain variable (VL) region, wherein the VH region comprises the CDR1, CDR2, and CDR3 sequences set forth in SEQ ID NOs: 41, 42, and 43, respectively, and the VL region comprises the CDR1, CDR2, and CDR3 sequences set forth in SEQ ID NO: 45, the sequence DAS, and SEQ ID NO: 46, respectively.

2. The nucleic acid construct, or combination of nucleic acid constructs, of claim 1, wherein the antibody comprises a VH region comprising the amino acid sequence set forth in SEQ ID NO: 40 and a VL region comprising the amino acid sequence set forth in SEQ ID NO: 44.

3. An expression vector comprising the nucleic acid construct, or combination of nucleic acid constructs, of claim 2.

4. A host cell comprising the nucleic acid construct, or combination of nucleic acid constructs, of claim 2.

5. A method of producing an antibody that binds to human 5T4, the method comprising the steps of:
(a) culturing the host cell of claim 4 in culture medium; and
(b) purifying the antibody from the culture medium.

6. The nucleic acid construct, or combination of nucleic acid constructs, of claim 1, wherein the antibody is a monoclonal antibody.

7. The nucleic acid construct, or combination of nucleic acid constructs, of claim 1, wherein the antibody is a full length antibody.

8. The nucleic acid construct, or combination of nucleic acid constructs, of claim 1, wherein the antibody comprises a human IgG1 constant region.

9. The nucleic acid construct, or combination of nucleic acid constructs, of claim 1, wherein the antibody comprises a kappa light chain constant region or lambda light chain constant region.

10. An expression vector comprising the nucleic acid construct, or combination of nucleic acid constructs, of claim 1.

11. A host cell comprising the nucleic acid construct, or combination of nucleic acid constructs, of claim 1.

12. A method of producing an antibody that binds to human 5T4, the method comprising the steps of:
 (a) culturing the host cell of claim 11 in culture medium; and
 (b) purifying the antibody from the culture medium.

13. A method of producing a bispecific antibody that binds to both human 5T4 and human CD3, the method comprising the steps of:
 (a) providing an antibody capable of binding to 5T4 by culturing the host cell of claim 11 under conditions allowing expression of the antibody capable of binding to 5T4, and purifying the antibody capable of binding to 5T4 from the culture medium;
 (b) providing an antibody capable of binding to CD3 by culturing a host cell comprising:
  (i) a nucleic acid construct encoding a heavy chain sequence of an antibody comprising an antigen-binding region capable of binding to CD3, wherein the heavy chain comprises a variable heavy chain (VH) region comprising the CDR1, CDR2, and CDR3 sequences set forth in SEQ ID NOs: 54, 55 and 67, respectively, and
  (ii) a nucleic acid construct encoding a light chain sequence of an antibody comprising an antigen-binding region capable of binding to CD3, wherein the light chain comprises a variable light chain (VL) region comprising the CDR1, CDR2, and CDR3 sequences set forth in SEQ ID NO: 58, the sequence GTN, and SEQ ID NO: 59, respectively;
 under conditions allowing expression of the antibody capable of binding to CD3, and purifying the antibody capable of binding to CD3 from the culture medium;
 (c) incubating the antibody capable of binding to 5T4 together with the antibody capable of binding to CD3 under reducing conditions sufficient to allow cysteines in the hinge region to undergo disulfide-bond isomerization, and
 (d) obtaining the bispecific antibody.

14. The method of claim 13, wherein the antibody capable of binding to 5T4 comprises a VH region comprising the amino acid sequence of SEQ ID NO: 40 and a VL region comprising the amino acid sequence of SEQ ID NO: 44, and/or the antibody capable of binding to CD3 comprises a VH region comprising the amino acid sequence of SEQ ID NO: 68 and a VL region comprising the amino acid sequence of SEQ ID NO: 60.

15. A nucleic acid construct, or combination of nucleic acid constructs, encoding a bispecific antibody comprising (a) a first heavy chain and a first light chain comprising a first antigen-binding region corresponding to an antigen binding region of the antibody defined in claim 1, and (b) a second heavy chain and a second light chain comprising a second antigen-binding region.

16. The nucleic acid construct, or combination of nucleic acid constructs, of claim 15, wherein the second antigen-binding region binds to human CD3.

17. The nucleic acid construct, or combination of nucleic acid constructs, of claim 16, wherein the second antigen-binding region comprises a VH region comprising the CDR1, CDR2, and CDR3 sequences set forth in SEQ ID NOs: 54, 55 and 67, respectively, and a VL region comprising the CDR1, CDR2, and CDR3 sequences set forth in SEQ ID NO: 58, the sequence GTN, and SEQ ID NO: 59, respectively.

18. The nucleic acid construct, or combination of nucleic acid constructs, of claim 17, wherein the second antigen-binding region comprises a VH region comprising the amino acid sequence set forth in SEQ ID NO: 68 and a VL region comprising the amino acid sequence set forth in SEQ ID NO: 60.

19. The nucleic acid construct, or combination of nucleic acid constructs, of claim 17, wherein the first antigen-binding region comprises a VH region comprising the amino acid sequence of SEQ ID NO: 40 and a VL region comprising the amino acid sequence of SEQ ID NO: 44, and the second antigen-binding region comprises a VH region comprising the amino acid sequence of SEQ ID NO: 68 and a VL region comprising the amino acid sequence of SEQ ID NO: 60.

20. The nucleic acid construct, or combination of nucleic acid constructs, of claim 19, wherein the bispecific antibody is a full length antibody.

21. The nucleic acid construct, or combination of nucleic acid constructs, of claim 20, wherein the bispecific antibody comprises a human IgG1 constant region.

22. A nucleic acid construct, or combination of nucleic acid constructs, encoding a bispecific antibody comprising (a) a first heavy chain and a first light chain comprising a first antigen-binding region corresponding to an antigen binding region of the antibody defined in claim 2, and (b) a second heavy chain and a second light chain comprising a second antigen-binding region.

23. The nucleic acid construct, or combination of nucleic acid constructs, claim 22, wherein the second antigen-binding region binds to human CD3.

24. A nucleic acid construct, or combination of nucleic acid constructs, encoding a bispecific antibody comprising a first heavy chain and a first light chain comprising a first antigen-binding region which binds to human 5T4, and a second heavy chain and a second light chain comprising a second antigen-binding region which binds to human CD3, wherein:
 (a) the first antigen-binding region comprises a variable heavy chain (VH) region comprising the amino acid sequence set forth in SEQ ID NO: 40 and a variable light chain (VL) region comprising the amino acid sequence set forth in SEQ ID NO: 44, and
 (b) the second antigen-binding region comprises a VH region comprising the amino acid sequence set forth in SEQ ID NO: 68 and a VL region comprising the amino acid sequence set forth in SEQ ID NO: 60,
 wherein the bispecific antibody comprises a human IgG1 Fc region, and wherein the first heavy chain comprises a constant region wherein the amino acid residues corresponding to L234, L235, D265 and F405 in a human IgG1 heavy chain according to EU numbering are F, E, A and L, respectively, and the second heavy chain comprises a constant region wherein the amino acid residues corresponding to L234, L235, D265 and K409 in a human IgG1 heavy chain according to EU numbering are F, E, A and R, respectively, and wherein the first light chain and second light chain comprise light chain constant regions comprising the amino acid sequences set forth in SEQ ID NOs: 95 and 96, respectively.

25. An expression vector comprising the nucleic acid construct, or combination of nucleic acid constructs, of claim 24.

26. A host cell comprising the nucleic acid construct, or combination of nucleic acid constructs, of claim 24.

27. A method of producing a bispecific antibody that binds to both human 5T4 and human CD3 comprising the steps of:
 (a) culturing the host cell of claim 26 in culture medium; and
 (b) purifying the antibody from the culture medium.

28. A nucleic acid construct, or combination of nucleic acid constructs, encoding a bispecific antibody comprising a first heavy chain and a first light chain comprising a first antigen-binding region which binds to human 5T4, and a second heavy chain and a second light chain comprising a second antigen-binding region which binds to human CD3, wherein:
 (a) the first antigen-binding region comprises a variable heavy chain (VH) region comprising the amino acid sequence set forth in SEQ ID NO: 40 and a variable light chain (VL) region comprising the amino acid sequence set forth in SEQ ID NO: 44, and
 (b) the second antigen-binding region comprises a VH region comprising the amino acid sequence set forth in SEQ ID NO: 68 and a VL region comprising the amino acid sequence set forth in SEQ ID NO: 60, wherein the bispecific antibody comprises a human IgG1 Fc region, and wherein the first heavy chain comprises a constant region wherein the amino acid residues corresponding to L234, L235, D265 and K409 in a human IgG1 heavy chain according to EU numbering are F, E, A and R, respectively, and the second heavy chain comprises a constant region wherein the amino acid residues corresponding to L234, L235, D265 and F405 in a human IgG1 heavy chain according to EU numbering are F, E, A and L, respectively, and wherein the first light chain and second light chain comprise light chain constant regions comprising the amino acid sequences set forth in SEQ ID NOs: 95 and 96, respectively.

29. An expression vector comprising the nucleic acid construct, or combination of nucleic acid constructs, of claim 28.

30. A host cell comprising the nucleic acid construct, or combination of nucleic acid constructs, of claim 28.

31. A method of producing a bispecific antibody that binds to both human 5T4 and human CD3 comprising the steps of:
 (a) culturing the host cell of claim 30 in culture medium; and
 (b) purifying the antibody from the culture medium.

* * * * *

SEQUENCE LISTING

```
<160> NUMBER OF SEQ ID NOS: 105

<210> SEQ ID NO 1
<211> LENGTH: 420
<212> TYPE: PRT
<213> ORGANISM: Homo Sapiens

<400> SEQUENCE: 1

Met Pro Gly Gly Cys Ser Arg Gly Pro Ala Gly Asp Gly Arg Leu
1               5                   10                  15

Arg Leu Ala Arg Leu Ala Leu Val Leu Leu Gly Trp Val Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285
```

```
Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
                340                 345                 350

Gln Thr Ser Tyr Val Phe Leu Gly Ile Val Leu Ala Leu Ile Gly Ala
                355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 2
<211> LENGTH: 420
<212> TYPE: PRT
<213> ORGANISM: Macaca Fascicularis

<400> SEQUENCE: 2

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Ser Thr Ser Ser Ala Ser Ser Ser Ser Ser Ala Pro Phe Leu
                35                  40                  45

Ala Ser Ala Ala Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Leu Tyr Val Arg Asn Leu
                85                  90                  95

Phe Leu Thr Gly Asn Gln Leu Ala Val Leu Pro Ala Gly Ala Phe Ala
                100                 105                 110

Arg Arg Pro Pro Leu Ala Glu Leu Ala Ala Leu Asn Leu Ser Gly Ser
                115                 120                 125

Arg Leu Asp Glu Val Arg Gly Gly Ala Phe Glu His Leu Pro Ser Leu
    130                 135                 140

Arg Gln Leu Asp Leu Ser His Asn Pro Leu Ala Tyr Leu Ser Pro Phe
145                 150                 155                 160

Ala Phe Ser Gly Ser Asn Ala Ser Ile Ser Ala Pro Ser Pro Leu Val
                165                 170                 175

Glu Leu Ile Leu Asn His Ile Val Pro Pro Asp Asp Lys Arg Gln Asn
                180                 185                 190

Arg Ser Phe Glu Gly Met Val Ala Ala Leu Val Ala Gly Arg Ala
                195                 200                 205

Leu Gln Gly Leu His Leu Leu Glu Leu Ala Ser Asn His Phe Leu Tyr
    210                 215                 220

Leu Pro Arg Asp Val Leu Ala Gln Leu Pro Ser Leu Arg Tyr Leu Asp
```

```
              225                 230                 235                 240
Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
                260                 265                 270

Leu His Asn Gly Thr Leu Ala Glu Leu Gln Gly Leu Pro His Val Arg
                275                 280                 285

Val Phe Leu Asp Asn Asn Pro Trp Val Cys Asp Cys His Met Ala Asp
                290                 295                 300

Met Val Thr Trp Leu Lys Gln Thr Gly Val Val Gln Gly Lys Asp Arg
305                 310                 315                 320

Leu Thr Cys Ala Phe Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
                340                 345                 350

Gln Thr Ser Tyr Val Phe Leu Gly Ile Val Leu Ala Leu Ile Gly Ala
                355                 360                 365

Ile Phe Leu Leu Val Leu Tyr Leu Asn Arg Lys Gly Ile Lys Lys Trp
                370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
                420

<210> SEQ ID NO 3
<211> LENGTH: 379
<212> TYPE: PRT
<213> ORGANISM: Gallus Gallus

<400> SEQUENCE: 3

Met Pro Gly Arg Glu Ala Glu Arg Arg Gly Ala Leu Cys Leu Gly Leu
1               5                   10                  15

Leu Leu His Ala Leu Leu Gly Cys Gly Ser Ala Gln Pro Pro Ala Ala
                20                  25                  30

Cys Pro Ala Pro Cys Glu Cys Ser Glu Ala Ala Lys Thr Val Lys Cys
                35                  40                  45

Val Asn Lys Asn Leu Thr Glu Val Pro Pro Asp Leu Pro Pro Tyr Val
50                  55                  60

Arg Asn Leu Phe Ile Thr Gly Asn Arg Leu Gly Arg Leu Pro Ala Gly
65                  70                  75                  80

Ala Leu Ser Ala Pro Arg Leu Ala Glu Leu Gly Ser Leu Asn Leu Ser
                85                  90                  95

Gly Asn His Leu Arg Ala Val Glu Ala Gly Ala Leu Ala Ala Leu Pro
                100                 105                 110

Ala Leu Arg Gln Leu Asp Leu Gly Gly Asn Pro Leu Ala Glu Leu Ser
                115                 120                 125

Pro Leu Ala Phe Gly Arg Ala Ser Pro Leu Glu Glu Leu Ala Leu Arg
                130                 135                 140

Gly Ala Leu Arg Glu Gln Gly Ala Leu Leu Gly Leu Ala Asp Leu Leu
145                 150                 155                 160

Gln Ala Gly Ala Leu Arg Asn Leu Ser Arg Leu Glu Leu Ala Asp Asn
                165                 170                 175
```

```
Gly Leu Leu Leu Leu Pro Thr Gly Met Leu Gly Ala Leu Pro Ala Leu
            180                 185                 190

Arg His Leu Asp Leu Ser Asn Asn Ser Leu Val Gly Leu Arg Asn Val
        195                 200                 205

Ser Phe Gln Gly Leu Val Arg Leu Gln Ser Leu Asn Leu Ser Asp Asn
    210                 215                 220

Ser Leu Gly Val Leu Arg Asn Gly Thr Leu Ala Gln Trp Arg Gly Leu
225                 230                 235                 240

Pro Ala Leu Arg Arg Ile Ser Leu Ser His Asn Thr Trp Val Cys Asp
                245                 250                 255

Cys Ala Ile Glu Asp Met Val Ala Trp Leu Lys Glu Ser Asp Gln Val
            260                 265                 270

Glu Gly Lys Glu Ala Leu Ser Cys Ala Phe Pro Glu Lys Met Ala Gly
        275                 280                 285

Arg Ala Leu Leu Lys Leu Asn Thr Ser Glu Leu Asn Cys Ser Ala Pro
    290                 295                 300

Val Asp Val Pro Ser Gln Leu Gln Thr Ser Tyr Val Phe Leu Gly Ile
305                 310                 315                 320

Val Leu Ala Leu Ile Gly Ala Ile Phe Leu Leu Val Leu Tyr Leu Asn
                325                 330                 335

Arg Lys Gly Ile Lys Lys Trp Met His Asn Ile Arg Asp Ala Cys Arg
            340                 345                 350

Asp His Met Glu Gly Tyr His Tyr Arg Tyr Glu Ile Asn Ala Asp Pro
        355                 360                 365

Arg Leu Thr Asn Leu Ser Ser Asn Ser Asp Val
    370                 375

<210> SEQ ID NO 4
<211> LENGTH: 186
<212> TYPE: PRT
<213> ORGANISM: Homo Sapiens

<400> SEQUENCE: 4

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
    130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175
```

```
Leu Tyr Ser Gly Leu Asn Gln Arg Arg Ile
            180                 185

<210> SEQ ID NO 5
<211> LENGTH: 125
<212> TYPE: PRT
<213> ORGANISM: Artificial sequence
<220> FEATURE:
<223> OTHER INFORMATION: Antibody variable domain

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Asp Met Asn Trp Val Arg Gln Ala Pro Gly Lys Gly Leu Glu Trp Val
        35                  40                  45

Thr Phe Ile Ser Tyr Asp Gly Ser Asn Lys Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Ser Arg Ser Trp Tyr Gly Asp Tyr Tyr Gly Met
            100                 105                 110

Asp Val Trp Gly Gln Gly Thr Thr Val Thr Val Ser Ser
        115                 120                 125

<210> SEQ ID NO 6
<211> LENGTH: 8
<212> TYPE: PRT
<213> ORGANISM: Artificial sequence
<220> FEATURE:
<223> OTHER INFORMATION: CDR sequence

<400> SEQUENCE: 6

Gly Phe Thr Phe Ser Ser Tyr Asp
1               5

<210> SEQ ID NO 7
<211> LENGTH: 8
<212> TYPE: PRT
<213> ORGANISM: Artificial sequence
<220> FEATURE:
<223> OTHER INFORMATION: CDR sequence

<400> SEQUENCE: 7

Ile Ser Tyr Asp Gly Ser Asn Lys
1               5

<210> SEQ ID NO 8
<211> LENGTH: 18
<212> TYPE: PRT
<213> ORGANISM: Artificial sequence
<220> FEATURE:
<223> OTHER INFORMATION: CDR sequence

<400> SEQUENCE: 8

Ala Arg Asp Ser Tyr Ser Arg Ser Trp Tyr Gly Asp Tyr Tyr Gly Met
1               5                   10                  15

Asp Val
```

<210> SEQ ID NO 9
<211> LENGTH: 107
<212> TYPE: PRT
<213> ORGANISM: Artificial sequence
<220> FEATURE:
<223> OTHER INFORMATION: Antibody variable domain

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 10
<211> LENGTH: 6
<212> TYPE: PRT
<213> ORGANISM: Artificial sequence
<220> FEATURE:
<223> OTHER INFORMATION: CDR sequence

<400> SEQUENCE: 10

```
Gln Gly Ile Ser Ser Trp
1               5
```

<210> SEQ ID NO 11
<211> LENGTH: 9
<212> TYPE: PRT
<213> ORGANISM: Artificial sequence
<220> FEATURE:
<223> OTHER INFORMATION: CDR sequence

<400> SEQUENCE: 11

```
Gln Gln Tyr Asn Ser Tyr Pro Leu Thr
1               5
```

<210> SEQ ID NO 12
<211> LENGTH: 121
<212> TYPE: PRT
<213> ORGANISM: Artificial sequence
<220> FEATURE:
<223> OTHER INFORMATION: Antibody variable domain

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60
```

```
Gln Gly Arg Val Thr Met Thr Thr Asp Thr Ser Thr Arg Thr Ala Tyr
 65                  70                  75                  80

Met Glu Leu Arg Ser Leu Arg Ser Asp Thr Ala Val Tyr Tyr Cys
                 85                  90                  95

Ala Arg Asp Pro Gly Tyr Phe Asp Trp Leu Tyr Gly Asp Tyr Trp Gly
            100                 105                 110

Gln Gly Thr Leu Val Thr Val Ser Ser
            115                 120

<210> SEQ ID NO 13
<211> LENGTH: 8
<212> TYPE: PRT
<213> ORGANISM: Artificial sequence
<220> FEATURE:
<223> OTHER INFORMATION: CDR sequence

<400> SEQUENCE: 13

Gly Tyr Thr Phe Thr Ser Tyr Gly
1               5

<210> SEQ ID NO 14
<211> LENGTH: 8
<212> TYPE: PRT
<213> ORGANISM: Artificial sequence
<220> FEATURE:
<223> OTHER INFORMATION: CDR sequence

<400> SEQUENCE: 14

Ile Ser Ala Tyr Asn Gly Asn Thr
1               5

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Ala Arg Asp Pro Gly Tyr Phe Asp Trp Leu Tyr Gly Asp Tyr
1               5                   10

<210> SEQ ID NO 16
<211> LENGTH: 107
<212> TYPE: PRT
<213> ORGANISM: Artificial sequence
<220> FEATURE:
<223> OTHER INFORMATION: Antibody variable region

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95
```

```
Thr Phe Gly Gln Gly Thr Lys Val Glu Ile Lys
                100                 105

<210> SEQ ID NO 17
<211> LENGTH: 6
<212> TYPE: PRT
<213> ORGANISM: Artificial sequence
<220> FEATURE:
<223> OTHER INFORMATION: CDR sequence

<400> SEQUENCE: 17

Gln Gly Ile Ser Ser Ala
1               5

<210> SEQ ID NO 18
<211> LENGTH: 9
<212> TYPE: PRT
<213> ORGANISM: Artificial sequence
<220> FEATURE:
<223> OTHER INFORMATION: CDR sequence

<400> SEQUENCE: 18

Gln Gln Phe Asn Ser Tyr Pro Arg Thr
1               5

<210> SEQ ID NO 19
<211> LENGTH: 121
<212> TYPE: PRT
<213> ORGANISM: Artificial sequence
<220> FEATURE:
<223> OTHER INFORMATION: Antibody variable region

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Asn Ala Asp Ser Val
    50                  55                  60

Lys Gly Arg Phe Thr Ile Phe Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Asp Pro Gly Tyr Asn Asn Val Glu Tyr Leu Asp His Trp Gly
            100                 105                 110

Gln Gly Thr Leu Val Thr Val Ser Ser
        115                 120

<210> SEQ ID NO 20
<211> LENGTH: 8
<212> TYPE: PRT
<213> ORGANISM: Artificial sequence
<220> FEATURE:
<223> OTHER INFORMATION: CDR sequence

<400> SEQUENCE: 20

Gly Phe Thr Phe Ser Ser Tyr Ala
1               5

<210> SEQ ID NO 21
<211> LENGTH: 8
```

```
<212> TYPE: PRT
<213> ORGANISM: Artificial sequence
<220> FEATURE:
<223> OTHER INFORMATION: CDR sequence

<400> SEQUENCE: 21

Ile Ser Gly Ser Gly Gly Ser Thr
1               5

<210> SEQ ID NO 22
<211> LENGTH: 14
<212> TYPE: PRT
<213> ORGANISM: Artificial sequence
<220> FEATURE:
<223> OTHER INFORMATION: CDR sequence

<400> SEQUENCE: 22

Ala Arg Asp Pro Gly Tyr Asn Asn Val Glu Tyr Leu Asp His
1               5                   10

<210> SEQ ID NO 23
<211> LENGTH: 107
<212> TYPE: PRT
<213> ORGANISM: Artificial sequence
<220> FEATURE:
<223> OTHER INFORMATION: Antibody variable region

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 24
<211> LENGTH: 6
<212> TYPE: PRT
<213> ORGANISM: Artificial sequence
<220> FEATURE:
<223> OTHER INFORMATION: CDR sequence

<400> SEQUENCE: 24

Gln Gly Ile Ser Ser Ala
1               5

<210> SEQ ID NO 25
<211> LENGTH: 9
<212> TYPE: PRT
<213> ORGANISM: Artificial sequence
<220> FEATURE:
<223> OTHER INFORMATION: CDR sequence

<400> SEQUENCE: 25

Gln Gln Phe Asn Ser Tyr Pro Leu Thr
1               5
```

```
<210> SEQ ID NO 26
<211> LENGTH: 115
<212> TYPE: PRT
<213> ORGANISM: Artificial sequence
<220> FEATURE:
<223> OTHER INFORMATION: Antibody variable region

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Ala Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Gly Met Tyr Tyr Cys
                85                  90                  95

Ala Arg Ser Val Leu Phe Asp Tyr Trp Gly Gln Gly Thr Leu Val Thr
            100                 105                 110

Val Ser Ser
        115

<210> SEQ ID NO 27
<211> LENGTH: 8
<212> TYPE: PRT
<213> ORGANISM: Artificial sequence
<220> FEATURE:
<223> OTHER INFORMATION: CDR sequence

<400> SEQUENCE: 27

Gly Tyr Arg Phe Thr Ser Tyr Trp
1               5

<210> SEQ ID NO 28
<211> LENGTH: 8
<212> TYPE: PRT
<213> ORGANISM: Artificial sequence
<220> FEATURE:
<223> OTHER INFORMATION: Antibody variable region

<400> SEQUENCE: 28

Ile Tyr Pro Gly Asp Ser Asp Ala
1               5

<210> SEQ ID NO 29
<211> LENGTH: 8
<212> TYPE: PRT
<213> ORGANISM: Artificial sequence
<220> FEATURE:
<223> OTHER INFORMATION: CDR sequence

<400> SEQUENCE: 29

Ala Arg Ser Val Leu Phe Asp Tyr
1               5

<210> SEQ ID NO 30
<211> LENGTH: 107
<212> TYPE: PRT
<213> ORGANISM: Artificial sequence
```

```
<220> FEATURE:
<223> OTHER INFORMATION: Antibody variable region

<400> SEQUENCE: 30

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Val Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 31
<211> LENGTH: 6
<212> TYPE: PRT
<213> ORGANISM: Artificial sequence
<220> FEATURE:
<223> OTHER INFORMATION: CDR sequence

<400> SEQUENCE: 31

Gln Gly Ile Ser Ser Ala
1               5

<210> SEQ ID NO 32
<211> LENGTH: 9
<212> TYPE: PRT
<213> ORGANISM: Artificial sequence
<220> FEATURE:
<223> OTHER INFORMATION: CDR sequence

<400> SEQUENCE: 32

Gln Gln Phe Asn Ser Tyr Pro His Thr
1               5

<210> SEQ ID NO 33
<211> LENGTH: 123
<212> TYPE: PRT
<213> ORGANISM: Artificial sequence
<220> FEATURE:
<223> OTHER INFORMATION: Antibody variable region

<400> SEQUENCE: 33

Glu Val Gln Leu Leu Glu Ser Arg Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Thr Tyr Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95
```

Ala Lys Asp Trp Gly Ser Gly Ser Tyr Pro Ala Glu Tyr Phe Gln His
            100                 105                 110

Trp Gly Gln Gly Thr Leu Val Thr Val Ser Ser
        115                 120

<210> SEQ ID NO 34
<211> LENGTH: 8
<212> TYPE: PRT
<213> ORGANISM: Artificial sequence
<220> FEATURE:
<223> OTHER INFORMATION: CDR sequence

<400> SEQUENCE: 34

Gly Phe Thr Phe Ser Ser Tyr Ala
1               5

<210> SEQ ID NO 35
<211> LENGTH: 8
<212> TYPE: PRT
<213> ORGANISM: Artificial sequence
<220> FEATURE:
<223> OTHER INFORMATION: CDR sequence

<400> SEQUENCE: 35

Ile Ser Gly Ser Gly Gly Ser Thr
1               5

<210> SEQ ID NO 36
<211> LENGTH: 16
<212> TYPE: PRT
<213> ORGANISM: Artificial sequence
<220> FEATURE:
<223> OTHER INFORMATION: CDR sequence

<400> SEQUENCE: 36

Ala Lys Asp Trp Gly Ser Gly Ser Tyr Pro Ala Glu Tyr Phe Gln His
1               5                   10                  15

<210> SEQ ID NO 37
<211> LENGTH: 108
<212> TYPE: PRT
<213> ORGANISM: Artificial sequence
<220> FEATURE:
<223> OTHER INFORMATION: Antibody variable region

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Met
                85                  90                  95

Tyr Thr Phe Gly Gln Gly Thr Lys Leu Glu Ile Lys
            100                 105

<210> SEQ ID NO 38

<211> LENGTH: 6
<212> TYPE: PRT
<213> ORGANISM: Artificial sequence
<220> FEATURE:
<223> OTHER INFORMATION: CDR sequence

<400> SEQUENCE: 38

Gln Ser Val Ser Ser Tyr
1               5

<210> SEQ ID NO 39
<211> LENGTH: 10
<212> TYPE: PRT
<213> ORGANISM: Artificial sequence
<220> FEATURE:
<223> OTHER INFORMATION: Synthetic

<400> SEQUENCE: 39

Gln Gln Arg Ser Asn Trp Leu Met Tyr Thr
1               5                   10

<210> SEQ ID NO 40
<211> LENGTH: 122
<212> TYPE: PRT
<213> ORGANISM: Artificial Sequence
<220> FEATURE:
<223> OTHER INFORMATION: Synthetic

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Asp His Ser Glu Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Trp Phe Gly Glu Leu Tyr His Tyr Tyr Gly Met Asp Val Trp
            100                 105                 110

Gly Gln Gly Thr Thr Val Thr Val Ser Ser
        115                 120

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Gly Gly Ser Phe Ser Gly Tyr Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic

```
<400> SEQUENCE: 42

Ile Asp His Ser Glu Ser Thr
1               5

<210> SEQ ID NO 43
<211> LENGTH: 16
<212> TYPE: PRT
<213> ORGANISM: Artificial Sequence
<220> FEATURE:
<223> OTHER INFORMATION: Synthetic

<400> SEQUENCE: 43

Ala Gly Trp Phe Gly Glu Leu Tyr His Tyr Tyr Tyr Gly Met Asp Val
1               5                   10                  15

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Gln Ser Val Ser Ser Tyr
1               5

<210> SEQ ID NO 46
<211> LENGTH: 9
<212> TYPE: PRT
<213> ORGANISM: Artificial sequence
<220> FEATURE:
<223> OTHER INFORMATION: CDR sequence

<400> SEQUENCE: 46

Gln Gln Arg Ser Asn Trp Pro Leu Thr
1               5

<210> SEQ ID NO 47
<211> LENGTH: 122
<212> TYPE: PRT
```

```
<213> ORGANISM: Artificial sequence
<220> FEATURE:
<223> OTHER INFORMATION: Antibody variable region

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ala Trp Phe Gly Glu Leu Trp Asp Tyr Tyr Gly Met Asp Val Trp
            100                 105                 110

Gly Gln Gly Thr Thr Val Thr Val Ser Ser
        115                 120

<210> SEQ ID NO 48
<211> LENGTH: 8
<212> TYPE: PRT
<213> ORGANISM: Artificial sequence
<220> FEATURE:
<223> OTHER INFORMATION: CDR sequence

<400> SEQUENCE: 48

Gly Gly Ser Phe Ser Gly Tyr Tyr
1               5

<210> SEQ ID NO 49
<211> LENGTH: 7
<212> TYPE: PRT
<213> ORGANISM: Artificial sequence
<220> FEATURE:
<223> OTHER INFORMATION: CDR sequence

<400> SEQUENCE: 49

Ile Asp His Ser Gly Ser Thr
1               5

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Ala Ala Trp Phe Gly Glu Leu Trp Asp Tyr Tyr Gly Met Asp Val
1               5                   10                  15

<210> SEQ ID NO 51
<211> LENGTH: 107
<212> TYPE: PRT
<213> ORGANISM: Artificial sequence
<220> FEATURE:
<223> OTHER INFORMATION: Antibody variable region

<400> SEQUENCE: 51
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Arg Leu Glu Ile Lys
            100                 105
```

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

```
Gln Ser Val Ser Ser Phe
1               5
```

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

```
Gln Gln Arg Ser Asn Trp Pro Leu Thr
1               5
```

<210> SEQ ID NO 54
<211> LENGTH: 8
<212> TYPE: PRT
<213> ORGANISM: Artificial sequence
<220> FEATURE:
<223> OTHER INFORMATION: CDR sequence

<400> SEQUENCE: 54

```
Gly Phe Thr Phe Asn Thr Tyr Ala
1               5
```

<210> SEQ ID NO 55
<211> LENGTH: 10
<212> TYPE: PRT
<213> ORGANISM: Artificial sequence
<220> FEATURE:
<223> OTHER INFORMATION: CDR sequence

<400> SEQUENCE: 55

```
Ile Arg Ser Lys Tyr Asn Asn Tyr Ala Thr
1               5                   10
```

<210> SEQ ID NO 56
<211> LENGTH: 16
<212> TYPE: PRT
<213> ORGANISM: Artificial Sequence
<220> FEATURE:

<223> OTHER INFORMATION: Synthetic

<400> SEQUENCE: 56

Val Arg His Gly Asn Phe Gly Asn Ser Tyr Val Ser Trp Phe Ala Tyr
1               5                   10                  15

<210> SEQ ID NO 57
<211> LENGTH: 125
<212> TYPE: PRT
<213> ORGANISM: Artificial Sequence
<220> FEATURE:
<223> OTHER INFORMATION: Synthetic

<400> SEQUENCE: 57

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 9
<212> TYPE: PRT
<213> ORGANISM: Artificial sequence
<220> FEATURE:
<223> OTHER INFORMATION: CDR sequence

<400> SEQUENCE: 58

Thr Gly Ala Val Thr Thr Ser Asn Tyr
1               5

<210> SEQ ID NO 59
<211> LENGTH: 9
<212> TYPE: PRT
<213> ORGANISM: Artificial sequence
<220> FEATURE:
<223> OTHER INFORMATION: CDR sequence

<400> SEQUENCE: 59

Ala Leu Trp Tyr Ser Asn Leu Trp Val
1               5

<210> SEQ ID NO 60
<211> LENGTH: 109
<212> TYPE: PRT
<213> ORGANISM: Artificial sequence
<220> FEATURE:
<223> OTHER INFORMATION: Antibody variable region

<400> SEQUENCE: 60

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Gly Phe Thr Phe Asn Pro Tyr Ala
1               5

<210> SEQ ID NO 62
<211> LENGTH: 125
<212> TYPE: PRT
<213> ORGANISM: Artificial Sequence
<220> FEATURE:
<223> OTHER INFORMATION: Synthetic

<400> SEQUENCE: 62

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Pro Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Gly Phe Thr Phe Asn Met Tyr Ala
1               5

-continued

<210> SEQ ID NO 64
<211> LENGTH: 125
<212> TYPE: PRT
<213> ORGANISM: Artificial Sequence
<220> FEATURE:
<223> OTHER INFORMATION: Synthetic

<400> SEQUENCE: 64

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Met Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Ile Arg Ser Lys Tyr Asn Glu Tyr Ala Thr
1               5                   10

<210> SEQ ID NO 66
<211> LENGTH: 125
<212> TYPE: PRT
<213> ORGANISM: Artificial sequence
<220> FEATURE:
<223> OTHER INFORMATION: Antibody variable region

<400> SEQUENCE: 66

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Glu Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser

```
<210> SEQ ID NO 67
<211> LENGTH: 16
<212> TYPE: PRT
<213> ORGANISM: Artificial Sequence
<220> FEATURE:
<223> OTHER INFORMATION: Synthetic

<400> SEQUENCE: 67

Val Arg Gly Gly Asn Phe Gly Asn Ser Tyr Val Ser Trp Phe Ala Tyr
1               5                   10                  15

<210> SEQ ID NO 68
<211> LENGTH: 125
<212> TYPE: PRT
<213> ORGANISM: Artificial Sequence
<220> FEATURE:
<223> OTHER INFORMATION: Synthetic

<400> SEQUENCE: 68

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Gly Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 69
<211> LENGTH: 16
<212> TYPE: PRT
<213> ORGANISM: Artificial Sequence
<220> FEATURE:
<223> OTHER INFORMATION: Synthetic

<400> SEQUENCE: 69

Val Arg Asn Gly Asn Phe Gly Asn Ser Tyr Val Ser Trp Phe Ala Tyr
1               5                   10                  15

<210> SEQ ID NO 70
<211> LENGTH: 125
<212> TYPE: PRT
<213> ORGANISM: Artificial Sequence
<220> FEATURE:
<223> OTHER INFORMATION: Synthetic

<400> SEQUENCE: 70

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

```
                35                  40                  45
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
 65                 70                  75                  80

Leu Tyr Leu Gln Met Asn Asn Leu Lys Thr Glu Asp Thr Ala Met Tyr
                85                  90                  95

Tyr Cys Val Arg Asn Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 71
<211> LENGTH: 16
<212> TYPE: PRT
<213> ORGANISM: Artificial Sequence
<220> FEATURE:
<223> OTHER INFORMATION: Synthetic

<400> SEQUENCE: 71

Val Arg His Gly Asn Phe Pro Asn Ser Tyr Val Ser Trp Phe Ala Tyr
 1               5                  10                  15

<210> SEQ ID NO 72
<211> LENGTH: 125
<212> TYPE: PRT
<213> ORGANISM: Artificial Sequence
<220> FEATURE:
<223> OTHER INFORMATION: Synthetic

<400> SEQUENCE: 72

Glu Val Lys Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
 65                 70                  75                  80

Leu Tyr Leu Gln Met Asn Asn Leu Lys Thr Glu Asp Thr Ala Met Tyr
                85                  90                  95

Tyr Cys Val Arg His Gly Asn Phe Pro Asn Ser Tyr Val Ser Trp Phe
                100                 105                 110

Ala Tyr Trp Gly Gln Gly Thr Leu Val Thr Val Ser Ser
        115                 120                 125

<210> SEQ ID NO 73
<211> LENGTH: 16
<212> TYPE: PRT
<213> ORGANISM: Artificial Sequence
<220> FEATURE:
<223> OTHER INFORMATION: Synthetic

<400> SEQUENCE: 73

Val Arg His Gly Asn Phe Gly Asn Ser Tyr Val Ala Trp Phe Ala Tyr
 1               5                  10                  15

<210> SEQ ID NO 74
```

<211> LENGTH: 125
<212> TYPE: PRT
<213> ORGANISM: Artificial Sequence
<220> FEATURE:
<223> OTHER INFORMATION: Synthetic

<400> SEQUENCE: 74

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ala Trp Phe
            100                 105                 110

Ala Tyr Trp Gly Gln Gly Thr Leu Val Thr Val Ser Ser
        115                 120                 125

<210> SEQ ID NO 75
<211> LENGTH: 16
<212> TYPE: PRT
<213> ORGANISM: Artificial Sequence
<220> FEATURE:
<223> OTHER INFORMATION: Synthetic

<400> SEQUENCE: 75

Val Arg His Gly Asn Phe Gly Asn Ser Tyr Val Gly Trp Phe Ala Tyr
1               5                   10                  15

<210> SEQ ID NO 76
<211> LENGTH: 125
<212> TYPE: PRT
<213> ORGANISM: Artificial Sequence
<220> FEATURE:
<223> OTHER INFORMATION: Synthetic

<400> SEQUENCE: 76

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Gly Trp Phe
            100                 105                 110

Ala Tyr Trp Gly Gln Gly Thr Leu Val Thr Val Ser Ser
        115                 120                 125

```
<210> SEQ ID NO 77
<211> LENGTH: 16
<212> TYPE: PRT
<213> ORGANISM: Artificial Sequence
<220> FEATURE:
<223> OTHER INFORMATION: Synthetic

<400> SEQUENCE: 77

Val Arg His Gly Asn Phe Gly Asn Ser Tyr Val Ser Trp Phe Ala Val
1               5                   10                  15

<210> SEQ ID NO 78
<211> LENGTH: 125
<212> TYPE: PRT
<213> ORGANISM: Artificial Sequence
<220> FEATURE:
<223> OTHER INFORMATION: Synthetic

<400> SEQUENCE: 78

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Val Trp Gly Gln Gly Thr Leu Val Thr Val Ser Ser
        115                 120                 125

<210> SEQ ID NO 79
<211> LENGTH: 16
<212> TYPE: PRT
<213> ORGANISM: Artificial Sequence
<220> FEATURE:
<223> OTHER INFORMATION: Synthetic

<400> SEQUENCE: 79

Val Arg His Gly Asn Phe Gly Asn Ser Tyr Val Ser Trp Phe Ala Met
1               5                   10                  15

<210> SEQ ID NO 80
<211> LENGTH: 125
<212> TYPE: PRT
<213> ORGANISM: Artificial Sequence
<220> FEATURE:
<223> OTHER INFORMATION: Synthetic

<400> SEQUENCE: 80

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Met Trp Gly Gln Gly Thr Leu Val Thr Val Ser Ser
                115                 120                 125
```

<210> SEQ ID NO 81
<211> LENGTH: 16
<212> TYPE: PRT
<213> ORGANISM: Artificial Sequence
<220> FEATURE:
<223> OTHER INFORMATION: Synthetic

<400> SEQUENCE: 81

```
Val Arg His Gly Asn Phe Gly Asn Ser Tyr Val Ser Trp Phe Ala Arg
 1                   5                  10                  15
```

<210> SEQ ID NO 82
<211> LENGTH: 125
<212> TYPE: PRT
<213> ORGANISM: Artificial Sequence
<220> FEATURE:
<223> OTHER INFORMATION: Synthetic

<400> SEQUENCE: 82

```
Glu Val Lys Leu Val Glu Ser Gly Gly Gly Leu Val Gln Pro Gly Gly
 1                   5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Arg Trp Gly Gln Gly Thr Leu Val Thr Val Ser Ser
                115                 120                 125
```

<210> SEQ ID NO 83
<211> LENGTH: 119
<212> TYPE: PRT
<213> ORGANISM: Homo Sapiens

<400> SEQUENCE: 83

```
Gln Ile Gln Leu Val Gln Ser Gly Pro Glu Leu Lys Lys Pro Gly Glu
 1                   5                  10                  15

Thr Val Lys Ile Ser Cys Lys Ala Ser Gly Tyr Thr Phe Thr Asn Phe
                 20                  25                  30

Gly Met Asn Trp Val Lys Gln Gly Pro Gly Glu Gly Leu Lys Trp Met
                 35                  40                  45
```

-continued

```
Gly Trp Ile Asn Thr Asn Thr Gly Glu Pro Arg Tyr Ala Glu Phe
    50                  55                  60

Lys Gly Arg Phe Ala Phe Ser Leu Glu Thr Thr Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Asp Trp Asp Gly Ala Tyr Phe Phe Asp Tyr Trp Gly Gln Gly
            100                 105                 110

Thr Thr Leu Thr Val Ser Ser
            115

<210> SEQ ID NO 84
<211> LENGTH: 107
<212> TYPE: PRT
<213> ORGANISM: Homo Sapiens

<400> SEQUENCE: 84

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Phe Ala Thr Asn Arg Tyr Thr Gly Val Pro Asn Arg Phe Thr Gly
    50                  55                  60

Ser Gly Tyr Gly Thr Asp Phe Thr Phe Thr Ile Ser Thr Val Gln Ala
 65                  70                  75                  80

Glu Asp Leu Ala Leu Tyr Phe Cys Gln Gln Asp Tyr Ser Ser Pro Trp
                 85                  90                  95

Thr Phe Gly Gly Gly Thr Lys Leu Glu Ile Lys
            100                 105

<210> SEQ ID NO 85
<211> LENGTH: 122
<212> TYPE: PRT
<213> ORGANISM: Homo Sapiens

<400> SEQUENCE: 85

Glu Val Gln Leu Val Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser
            115                 120

<210> SEQ ID NO 86
<211> LENGTH: 107
```

```
<212> TYPE: PRT
<213> ORGANISM: Homo Sapiens

<400> SEQUENCE: 86

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 87
<211> LENGTH: 120
<212> TYPE: PRT
<213> ORGANISM: Homo Sapiens

<400> SEQUENCE: 87

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Val Thr Ser Val Thr Val Ser Ser
        115                 120

<210> SEQ ID NO 88
<211> LENGTH: 107
<212> TYPE: PRT
<213> ORGANISM: Homo Sapiens

<400> SEQUENCE: 88

Ser Ile Val Met Thr Gln Thr Pro Thr Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Thr Leu Leu Ile
        35                  40                  45

Ser Tyr Thr Ser Ser Arg Tyr Ala Gly Val Pro Asp Arg Phe Ile Gly
50                  55                  60

Ser Gly Tyr Gly Thr Asp Phe Thr Phe Thr Ile Ser Thr Leu Gln Ala
```

```
            65                  70                  75                  80
Glu Asp Leu Ala Val Tyr Phe Cys Gln Gln Asp Tyr Asn Ser Pro Pro
                    85                  90                  95

Thr Phe Gly Gly Gly Thr Lys Leu Glu Ile Lys
                100                 105

<210> SEQ ID NO 89
<211> LENGTH: 330
<212> TYPE: PRT
<213> ORGANISM: Homo Sapiens

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 90
<211> LENGTH: 330
<212> TYPE: PRT
<213> ORGANISM: Artificial Sequence
<220> FEATURE:
<223> OTHER INFORMATION: Synthetic

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 91
<211> LENGTH: 330
<212> TYPE: PRT
<213> ORGANISM: Artificial Sequence
<220> FEATURE:
```

<223> OTHER INFORMATION: Synthetic

<400> SEQUENCE: 91

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 92
<211> LENGTH: 330
<212> TYPE: PRT
<213> ORGANISM: Artificial Sequence
<220> FEATURE:
<223> OTHER INFORMATION: Synthetic

<400> SEQUENCE: 92

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 93
<211> LENGTH: 330
<212> TYPE: PRT
<213> ORGANISM: Artificial Sequence
<220> FEATURE:
<223> OTHER INFORMATION: Synthetic

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 330
<212> TYPE: PRT
<213> ORGANISM: Artificial Sequence
<220> FEATURE:
<223> OTHER INFORMATION: Synthetic

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 107
<212> TYPE: PRT
<213> ORGANISM: Homo Sapiens

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 96
<211> LENGTH: 106
<212> TYPE: PRT
<213> ORGANISM: Homo Sapiens

<400> SEQUENCE: 96

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 97
<211> LENGTH: 127
<212> TYPE: PRT
<213> ORGANISM: Homo Sapiens

<400> SEQUENCE: 97

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125

<210> SEQ ID NO 98
<211> LENGTH: 108
<212> TYPE: PRT
<213> ORGANISM: Homo Sapiens

<400> SEQUENCE: 98

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60
```

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 99
<211> LENGTH: 363
<212> TYPE: PRT
<213> ORGANISM: Artificial Sequence
<220> FEATURE:
<223> OTHER INFORMATION: Synthetic

<400> SEQUENCE: 99

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

```
Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser His His His His His His His
        355                 360

<210> SEQ ID NO 100
<211> LENGTH: 327
<212> TYPE: PRT
<213> ORGANISM: Artificial Sequence
<220> FEATURE:
<223> OTHER INFORMATION: Synthetic

<400> SEQUENCE: 100

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
        50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Ala Pro Ser Thr Cys
                85                  90                  95

Ser Lys Pro Thr Cys Pro Pro Glu Leu Leu Gly Gly Pro Ser Val
                100                 105                 110

Phe Ile Phe Pro Pro Lys Pro Lys Asp Thr Leu Met Ile Ser Arg Thr
            115                 120                 125

Pro Glu Val Thr Cys Val Val Val Asp Val Ser Gln Asp Asp Pro Glu
        130                 135                 140

Val Gln Phe Thr Trp Tyr Ile Asn Asn Glu Gln Val Arg Thr Ala Arg
145                 150                 155                 160

Pro Pro Leu Arg Glu Gln Gln Phe Asn Ser Thr Ile Arg Val Val Ser
                165                 170                 175

Thr Leu Pro Ile Ala His Gln Asp Trp Leu Arg Gly Lys Glu Phe Lys
            180                 185                 190

Cys Lys Val His Asn Lys Ala Leu Pro Ala Pro Ile Glu Lys Thr Ile
        195                 200                 205

Ser Lys Ala Arg Gly Gln Pro Leu Glu Pro Lys Val Tyr Thr Met Gly
    210                 215                 220

Pro Pro Arg Glu Glu Leu Ser Ser Arg Ser Val Ser Leu Thr Cys Met
225                 230                 235                 240

Ile Asn Gly Phe Tyr Pro Ser Asp Ile Ser Val Glu Trp Glu Lys Asn
                245                 250                 255

Gly Lys Ala Glu Asp Asn Tyr Lys Thr Thr Pro Ala Val Leu Asp Ser
            260                 265                 270

Asp Gly Ser Tyr Phe Leu Tyr Ser Lys Leu Ser Val Pro Thr Ser Glu
        275                 280                 285

Trp Gln Arg Gly Asp Val Phe Thr Cys Ser Val Met His Glu Ala Leu
    290                 295                 300

His Asn His Tyr Thr Gln Lys Ser Ile Ser Arg Ser Pro Gly Lys His
305                 310                 315                 320
```

-continued

His His His His His His His
            325

<210> SEQ ID NO 101
<211> LENGTH: 276
<212> TYPE: PRT
<213> ORGANISM: Artificial Sequence
<220> FEATURE:
<223> OTHER INFORMATION: Synthetic

<400> SEQUENCE: 101

Met Trp Trp Arg Leu Trp Trp Leu Leu Leu Leu Leu Leu Leu Trp
1               5                   10                  15

Pro Met Val Trp Ala Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Gly Gly Gly Gly Ser Gly Gly Gly Ser Gly Gly Gly Ser Glu
    50                  55                  60

Ile Val Leu Thr Gln Ser Pro Ala Thr Leu Ser Leu Ser Pro Gly Glu
65                  70                  75                  80

Arg Ala Thr Leu Ser Cys Arg Ala Ser Gln Ser Val Ser Ser Tyr Leu
                85                  90                  95

Ala Trp Tyr Gln Gln Lys Pro Gly Gln Ala Pro Arg Leu Leu Ile Tyr
            100                 105                 110

Asp Ala Ser Asn Arg Ala Thr Gly Ile Pro Ala Arg Phe Ser Gly Ser
        115                 120                 125

Gly Ser Gly Thr Asp Phe Thr Leu Thr Ile Ser Ser Leu Glu Pro Glu
    130                 135                 140

Asp Phe Ala Val Tyr Tyr Cys Gln Gln Arg Ser Asn Trp Pro Ile Thr
145                 150                 155                 160

Phe Gly Gln Gly Thr Arg Leu Glu Ile Lys Arg Thr Val Ala Ala Pro
                165                 170                 175

Ser Val Phe Ile Phe Pro Pro Ser Asp Glu Gln Leu Lys Ser Gly Thr
            180                 185                 190

Ala Ser Val Val Cys Leu Leu Asn Asn Phe Tyr Pro Arg Glu Ala Lys
        195                 200                 205

Val Gln Trp Lys Val Asp Asn Ala Leu Gln Ser Gly Asn Ser Gln Glu
    210                 215                 220

Ser Val Thr Glu Gln Asp Ser Lys Asp Ser Thr Tyr Ser Leu Ser Ser
225                 230                 235                 240

Thr Leu Thr Leu Ser Lys Ala Asp Tyr Glu Lys His Lys Val Tyr Ala
                245                 250                 255

Cys Glu Val Thr His Gln Gly Leu Ser Ser Pro Val Thr Lys Ser Phe
            260                 265                 270

Asn Arg Gly Glu
        275

<210> SEQ ID NO 102
<211> LENGTH: 6
<212> TYPE: PRT
<213> ORGANISM: Artificial sequence
<220> FEATURE:
<223> OTHER INFORMATION: CDR consensus sequence

<400> SEQUENCE: 102

Tyr Tyr Gly Met Asp Val

```
<210> SEQ ID NO 103
<211> LENGTH: 7
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (5)..(5)
<223> OTHER INFORMATION: Xaa is G or E

<400> SEQUENCE: 103

Ile Asp His Ser Xaa Ser Thr
1               5

<210> SEQ ID NO 104
<211> LENGTH: 16
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (2)..(2)
<223> OTHER INFORMATION: Xaa is A or G
<220> FEATURE:
<221> NAME/KEY: Xaa
<222> LOCATION: (8)..(8)
<223> OTHER INFORMATION: Xaa is W or Y
<220> FEATURE:
<221> NAME/KEY: Xaa
<222> LOCATION: (9)..(9)
<223> OTHER INFORMATION: Xaa is D or H

<400> SEQUENCE: 104

Ala Xaa Trp Phe Gly Glu Leu Xaa Xaa Tyr Tyr Tyr Gly Met Asp Val
1               5                   10                  15

<210> SEQ ID NO 105
<211> LENGTH: 6
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (6)..(6)
<223> OTHER INFORMATION: Xaa is Y or F

<400> SEQUENCE: 105

Gln Ser Val Ser Ser Xaa
1               5
```